(12) United States Patent
Ackermann et al.

(10) Patent No.: US 12,728,260 B2
(45) Date of Patent: Sep. 8, 2026

(54) SYSTEMS AND METHODS FOR NERVE CONDUCTION BLOCK

(71) Applicant: Presidio Medical, Inc., South San Francisco, CA (US)

(72) Inventors: Douglas Michael Ackermann, Reno, NV (US); Kenneth Wu, San Francisco, CA (US); Aaron Hardinger, Reno, NV (US)

(73) Assignee: Presidio Medical, Inc., San Mateo, CA (US)

(*) Notice: Subject to any disclaimer, the term of this patent is extended or adjusted under 35 U.S.C. 154(b) by 34 days.

(21) Appl. No.: 18/465,043

(22) Filed: Sep. 11, 2023

(65) Prior Publication Data

US 2024/0198089 A1 Jun. 20, 2024

Related U.S. Application Data

(63) Continuation of application No. 17/255,882, filed as application No. PCT/US2019/040189 on Jul. 1, 2019, now Pat. No. 11,752,329.

(60) Provisional application No. 62/692,857, filed on Jul. 1, 2018.

(51) Int. Cl.

*A61N 1/05* (2006.01)
*A61N 1/36* (2006.01)
*A61N 1/40* (2006.01)

(52) U.S. Cl.

CPC ......... *A61N 1/0534* (2013.01); *A61N 1/0551* (2013.01); *A61N 1/36062* (2017.08); *A61N 1/36071* (2013.01); *A61N 1/36157* (2013.01); *A61N 1/40* (2013.01)

(58) Field of Classification Search

CPC ................ A61N 1/0534; A61N 1/0551; A61N 1/36062; A61N 1/36071; A61N 1/36157; A61N 1/40

See application file for complete search history.

(56) References Cited

U.S. PATENT DOCUMENTS 4,057,069 A 11/1977 Dorffer et al.
4,917,093 A 4/1990 Dufresne et al.
5,034,589 A 7/1991 Evans et al.
5,833,714 A 11/1998 Loeb (Continued)

FOREIGN PATENT DOCUMENTS

AU 2013273851 A1 1/2014
AU 2016201418 A1 3/2016

(Continued)

OTHER PUBLICATIONS

International Search Report and Written Opinion in PCT Application No. PCT/US2019/040189 mailed Sep. 20, 2019 in 16 pages.

(Continued)

*Primary Examiner* — Joseph M Dietrich

(74) *Attorney, Agent, or Firm* — Knobbe, Martens, Olson & Bear, LLP

(57) ABSTRACT

Disclosed herein are systems and methods for nerve conduction block. The systems and methods can utilize at least one rechargeable electrode. The methods can include delivering a first direct current with a first polarity to an electrode proximate nervous tissue sufficient to at least partially block conduction in the nervous tissue.

27 Claims, 103 Drawing Sheets

(56) References Cited

U.S. PATENT DOCUMENTS

| | | | |
|---|---|---|---|
| 5,868,743 | A | 2/1999 | Saul et al. |
| 6,139,545 | A | 10/2000 | Utley et al. |
| 6,189,536 | B1 | 2/2001 | Martinez et al. |
| 6,192,279 | B1 | 2/2001 | Barreras et al. |
| 6,205,359 | B1 | 3/2001 | Bovega |
| 6,293,266 | B1 | 9/2001 | Oetting |
| 6,366,813 | B1 | 4/2002 | DiLorenzo |
| 6,428,537 | B1 | 8/2002 | Swanson et al. |
| 6,442,424 | B1 | 8/2002 | Ben-Haim et al. |
| 6,600,956 | B2 | 7/2003 | Maschino et al. |
| 6,671,561 | B1 | 12/2003 | Moaddeb |
| 6,819,956 | B2 | 11/2004 | DiLorenzo |
| 6,895,280 | B2 | 5/2005 | Meadows et al. |
| 6,907,295 | B2 | 6/2005 | Gross et al. |
| 6,937,893 | B2 | 8/2005 | Danz et al. |
| 6,974,533 | B2 | 12/2005 | Zhou |
| 6,975,907 | B2 | 12/2005 | Zanakis et al. |
| 7,079,903 | B2 | 7/2006 | O'Brien |
| 7,216,001 | B2 | 5/2007 | Hacket et al. |
| 7,421,299 | B2 | 9/2008 | Frericks et al. |
| 7,428,438 | B2 | 9/2008 | Parramon et al. |
| 7,437,193 | B2 | 10/2008 | Parramon et al. |
| 7,502,652 | B2 | 3/2009 | Gaunt et al. |
| 7,519,428 | B1 | 4/2009 | Palmer |
| 7,587,241 | B2 | 9/2009 | Parramon et al. |
| 7,638,032 | B2 | 12/2009 | Zhou et al. |
| 7,691,252 | B2 | 4/2010 | Zhou et al. |
| 7,742,828 | B2 | 6/2010 | Gadsby et al. |
| 7,780,833 | B2 | 8/2010 | Hawkins et al. |
| 7,881,808 | B2 | 2/2011 | Borgaonkar et al. |
| 7,891,085 | B1 | 2/2011 | Kuzma et al. |
| 7,909,764 | B1 | 3/2011 | Wenzel et al. |
| 8,019,439 | B2 | 9/2011 | Kuzma et al. |
| 8,034,229 | B2 | 10/2011 | Zhou et al. |
| 8,121,703 | B1 | 2/2012 | Palmer |
| 8,135,478 | B2 | 3/2012 | Gross |
| 8,271,098 | B2 | 9/2012 | Swanson et al. |
| 8,359,102 | B2 | 1/2013 | Alataris et al. |
| 8,406,886 | B2 | 3/2013 | Gaunt et al. |
| 8,417,352 | B2 | 4/2013 | Carroll et al. |
| 8,509,903 | B2 | 8/2013 | York et al. |
| 8,644,933 | B2 | 2/2014 | Ozawa et al. |
| 8,646,172 | B2 | 2/2014 | Kuzma et al. |
| 8,650,747 | B2 | 2/2014 | Kuzma et al. |
| 8,712,533 | B2 | 4/2014 | Alataris et al. |
| 8,768,472 | B2 | 7/2014 | Fang et al. |
| 8,792,988 | B2 | 7/2014 | Alataris et al. |
| 8,897,895 | B2 | 11/2014 | Mashiach |
| 8,948,881 | B2 | 2/2015 | Fisk |
| 8,983,614 | B2 | 3/2015 | Kilgore et al. |
| 9,008,780 | B2 | 4/2015 | Nudo et al. |
| 9,008,781 | B2 | 4/2015 | Ahmed |
| 9,008,800 | B2 | 4/2015 | Ackermann et al. |
| 9,011,310 | B2 | 4/2015 | Ahmed |
| 9,037,248 | B2 | 5/2015 | Durand et al. |
| 9,072,886 | B2 | 7/2015 | Gaunt et al. |
| 9,119,966 | B2 | 9/2015 | Franke et al. |
| 9,205,265 | B2 | 12/2015 | Franke |
| 9,283,391 | B2 | 3/2016 | Ahmed |
| 9,327,125 | B2 | 5/2016 | Alataris et al. |
| 9,333,356 | B2 | 5/2016 | Franke et al. |
| 9,333,357 | B2 | 5/2016 | Alataris et al. |
| 9,364,661 | B2 | 6/2016 | Kilgore et al. |
| 9,370,664 | B2 | 6/2016 | Marnfeldt et al. |
| 9,381,350 | B2 | 7/2016 | Ahmed |
| 9,384,990 | B2 | 7/2016 | Musa |
| 9,387,322 | B2 | 7/2016 | Bhadra et al. |
| 9,393,423 | B2 | 7/2016 | Parramon et al. |
| 9,403,014 | B2 | 8/2016 | Kilgore et al. |
| 9,480,842 | B2 | 11/2016 | Alataris et al. |
| 9,492,665 | B2 | 11/2016 | Khalil et al. |
| 9,498,621 | B2 | 11/2016 | Ackermann et al. |
| 9,572,979 | B2 | 2/2017 | Fridman et al. |
| 9,694,181 | B2 | 7/2017 | Bhadra et al. |
| 9,707,390 | B2 | 7/2017 | Ahmed |
| 9,707,391 | B2 | 7/2017 | Ahmed |
| 9,782,593 | B2 | 10/2017 | Parramon et al. |
| 9,789,329 | B2 | 10/2017 | Ahmed |
| 9,821,157 | B2 | 11/2017 | Ahmed et al. |
| 9,844,668 | B2 | 12/2017 | Ahmed |
| 9,889,291 | B2 | 2/2018 | Bhadra et al. |
| 10,071,241 | B2 | 9/2018 | Bhadra et al. |
| 10,195,434 | B2 | 2/2019 | Bhadra et al. |
| 10,272,240 | B2 | 4/2019 | Ackermann et al. |
| 10,307,595 | B2 | 6/2019 | Shi et al. |
| 10,441,782 | B2 | 10/2019 | Bhadra et al. |
| 11,027,126 | B2 * | 6/2021 | Ackermann ............. A61N 1/20 |
| 11,607,548 | B1 * | 3/2023 | Vallejo ................... A61B 5/316 |
| 11,730,964 | B2 | 8/2023 | Faltys et al. |
| 11,752,329 | B2 | 9/2023 | Ackermann et al. |
| 11,813,459 | B2 | 11/2023 | Wu et al. |
| 11,918,803 | B2 | 3/2024 | Ackermann et al. |
| 12,268,865 | B2 | 4/2025 | Ackermann et al. |
| 2002/0015963 | A1 | 2/2002 | Keen |
| 2003/0040785 | A1 | 2/2003 | Maschino et al. |
| 2004/0181261 | A1 | 9/2004 | Manne |
| 2004/0215285 | A1 | 10/2004 | Pollock |
| 2005/0075709 | A1 | 4/2005 | Brennen et al. |
| 2006/0085048 | A1 | 4/2006 | Cory et al. |
| 2006/0095088 | A1 | 5/2006 | Ridder |
| 2006/0167527 | A1 | 7/2006 | Femano et al. |
| 2006/0184211 | A1 | 8/2006 | Gaunt et al. |
| 2006/0265027 | A1 | 11/2006 | Vaingast et al. |
| 2007/0027490 | A1 | 2/2007 | Ben-Haim et al. |
| 2007/0043400 | A1 | 2/2007 | Donders et al. |
| 2007/0060815 | A1 | 3/2007 | Martin et al. |
| 2007/0073354 | A1 | 3/2007 | Knudson et al. |
| 2007/0083193 | A1 | 4/2007 | Werneth et al. |
| 2007/0255319 | A1 | 11/2007 | Greenberg et al. |
| 2007/0291522 | A1 | 12/2007 | Toba et al. |
| 2008/0208287 | A1 | 8/2008 | Palermo et al. |
| 2008/0208300 | A1 | 8/2008 | Pasch et al. |
| 2008/0275439 | A1 | 11/2008 | Francischelli et al. |
| 2009/0149797 | A1 | 6/2009 | Dacey, Jr. et al. |
| 2009/0192567 | A1 | 7/2009 | Armstrong et al. |
| 2009/0254148 | A1 | 10/2009 | Borgens et al. |
| 2010/0241190 | A1 | 9/2010 | Kilgore et al. |
| 2011/0021943 | A1 | 1/2011 | Lacour et al. |
| 2011/0071590 | A1 | 3/2011 | Mounaim et al. |
| 2011/0077660 | A1 | 3/2011 | Janik et al. |
| 2011/0093042 | A1 | 4/2011 | Torgerson et al. |
| 2011/0137381 | A1 | 6/2011 | Lee et al. |
| 2011/0160798 | A1 | 6/2011 | Ackermann et al. |
| 2011/0190849 | A1 | 8/2011 | Faltys et al. |
| 2011/0192720 | A1 | 8/2011 | Blauw et al. |
| 2011/0221438 | A1 | 9/2011 | Goodwill et al. |
| 2012/0016226 | A1 | 1/2012 | Gertner |
| 2012/0053510 | A1 | 3/2012 | Peters et al. |
| 2012/0239108 | A1 | 9/2012 | Foutz et al. |
| 2012/0277830 | A1 | 11/2012 | Arfin et al. |
| 2013/0035745 | A1 | 2/2013 | Ahmed et al. |
| 2013/0053922 | A1 | 2/2013 | Ahmed et al. |
| 2013/0079645 | A1 | 3/2013 | Amirana et al. |
| 2013/0184779 | A1 | 7/2013 | Bikson et al. |
| 2013/0238048 | A1 | 9/2013 | Almendiger et al. |
| 2013/0274842 | A1 | 10/2013 | Guant et al. |
| 2014/0031905 | A1 | 1/2014 | Irazoqui et al. |
| 2014/0119480 | A1 | 5/2014 | Keegan |
| 2014/0128865 | A1 | 5/2014 | Gross |
| 2014/0135858 | A1 | 5/2014 | Ahmed et al. |
| 2014/0228837 | A1 | 8/2014 | Giovangrandi et al. |
| 2014/0324129 | A1 | 10/2014 | Franke et al. |
| 2015/0045675 | A1 | 2/2015 | Chernomorsky |
| 2015/0066108 | A1 | 3/2015 | Shi et al. |
| 2015/0073406 | A1 | 3/2015 | Molsberger |
| 2015/0165210 | A1 | 6/2015 | Kilgore et al. |
| 2015/0174397 | A1 | 6/2015 | Bhadra et al. |
| 2015/0182742 | A1 | 7/2015 | Ackermann et al. |
| 2015/0224326 | A1 | 8/2015 | Toth et al. |
| 2015/0238764 | A1 | 8/2015 | Franke |
| 2015/0258341 | A1 | 9/2015 | Ternes et al. |
| 2015/0293192 | A1 | 10/2015 | Schmidt et al. |
| 2015/0316499 | A1 | 11/2015 | Jacks et al. |
| 2016/0101286 | A1 | 4/2016 | Bhadra et al. |

(56) References Cited

U.S. PATENT DOCUMENTS

| | | | |
|---|---|---|---|
| 2016/0144183 | A1 | 5/2016 | Marnfeldt |
| 2016/0158542 | A1 | 6/2016 | Ahmed |
| 2016/0235969 | A1 | 8/2016 | Kilgore et al. |
| 2016/0235990 | A1 | 8/2016 | Mashiach |
| 2016/0243353 | A1 | 8/2016 | Ahmed |
| 2016/0256689 | A1 | 9/2016 | Vallejo et al. |
| 2016/0263381 | A1 | 9/2016 | Ahmed et al. |
| 2016/0271392 | A1 | 9/2016 | Vallejo et al. |
| 2016/0271413 | A1 | 9/2016 | Vallejo et al. |
| 2016/0303379 | A1 | 10/2016 | Ness et al. |
| 2016/0331326 | A1 | 11/2016 | Xiang et al. |
| 2016/0346533 | A1 | 12/2016 | Bhadra et al. |
| 2017/0028192 | A1 | 2/2017 | Ahmed et al. |
| 2017/0050024 | A1 | 2/2017 | Bhadra et al. |
| 2017/0080244 | A1 | 3/2017 | Chiel et al. |
| 2017/0100591 | A1 | 4/2017 | Nudo et al. |
| 2017/0136235 | A1 | 5/2017 | Molsberger |
| 2017/0136243 | A1 | 5/2017 | Lee et al. |
| 2017/0281099 | A1 | 10/2017 | Averina et al. |
| 2017/0312505 | A1 | 11/2017 | Ahmed |
| 2017/0326370 | A1 | 11/2017 | Grasse et al. |
| 2018/0028824 | A1 | 2/2018 | Pivonka et al. |
| 2018/0161573 | A1 | 6/2018 | Carbunaru et al. |
| 2018/0256886 | A1 | 9/2018 | Bhadra et al. |
| 2018/0280691 | A1 | 10/2018 | Ackermann et al. |
| 2018/0361155 | A1 | 12/2018 | Bhadra et al. |
| 2019/0060640 | A1 | 2/2019 | Bhadra et al. |
| 2019/0167996 | A1 | 6/2019 | Bhadra et al. |
| 2019/0184160 | A1 | 6/2019 | Franke et al. |
| 2019/0184172 | A1 | 6/2019 | Ardell et al. |
| 2019/0184173 | A1 | 6/2019 | Franke |
| 2019/0269921 | A1 | 9/2019 | Bhadra et al. |
| 2019/0314630 | A1 | 10/2019 | Ackermann et al. |
| 2020/0001073 | A1 | 1/2020 | Bhadra et al. |
| 2020/0001087 | A1 | 1/2020 | Parramon et al. |
| 2020/0086114 | A1 | 3/2020 | Willand et al. |
| 2020/0129767 | A1 | 4/2020 | Yoshida et al. |
| 2021/0038101 | A1 | 2/2021 | Wu et al. |
| 2022/0088374 | A1 | 3/2022 | Ackermann et al. |
| 2022/0096827 | A1 | 3/2022 | Ackermann et al. |
| 2022/0176130 | A1 | 6/2022 | Wu et al. |
| 2022/0409905 | A1 | 12/2022 | Faltys et al. |
| 2023/0008440 | A1 | 1/2023 | Ackermann et al. |
| 2024/0050751 | A1 | 2/2024 | Flores et al. |
| 2024/0181261 | A1 | 6/2024 | Faltys et al. |
| 2024/0216694 | A1 | 7/2024 | Wu et al. |
| 2024/0226572 | A1 | 7/2024 | Faltys et al. |
| 2024/0299747 | A1 | 9/2024 | Ackermann et al. |

FOREIGN PATENT DOCUMENTS

| | | | |
|---|---|---|---|
| DE | 4324185 | | 1/1995 |
| EP | 0281717 | | 9/1988 |
| EP | 2 942 023 | | 11/2015 |
| EP | 1981589 | B1 | 4/2016 |
| JP | 63-318958 | A | 12/1988 |
| JP | 2009-529352 | A | 8/2009 |
| JP | 2016-529039 | A | 9/2016 |
| WO | WO 1998/15317 | | 4/1998 |
| WO | WO 2007/082382 | | 7/2007 |
| WO | WO 2008/048321 | | 4/2008 |
| WO | WO 2008/140376 | | 11/2008 |
| WO | WO 2010/042750 | | 4/2010 |
| WO | WO 2013/188753 | | 12/2013 |
| WO | WO 2015/142838 | | 9/2015 |
| WO | 2015/170281 | A1 | 11/2015 |
| WO | 2015/179744 | A1 | 11/2015 |
| WO | WO 2017/044542 | | 3/2017 |
| WO | WO 2017/062272 | | 4/2017 |
| WO | WO 2017/106519 | | 6/2017 |
| WO | WO 2018/085611 | | 5/2018 |
| WO | WO 2018/187237 | | 10/2018 |
| WO | WO 2019/157285 | | 8/2019 |
| WO | WO 2019/164952 | | 8/2019 |
| WO | WO 2020/010020 | | 1/2020 |
| WO | WO 2021/102447 | | 5/2021 |
| WO | WO 2021/102448 | | 5/2021 |
| WO | 2022/251519 | A2 | 12/2022 |
| WO | 2022/251520 | A1 | 12/2022 |

OTHER PUBLICATIONS

Ackermann, Jr, D. Michael, et al. "Separated interface nerve electrode prevents direct current induced nerve damage." Journal of neuroscience methods 201.1 (2011): 173-176.

Bhadra, Niloy, and Kevin L. Kilgore. "Direct current electrical conduction block of peripheral nerve." IEEE Transactions on Neural Systems and Rehabilitation Engineering 12.3 (2004): 313-324.

Borsook, David. "A future without chronic pain: neuroscience and clinical research." Cerebrum: the Dana forum on brain science. vol. 2012. Dana Foundation, 2012.

Brummer, S.B. et al. "Electrical Stimulation of the Nervous System: The Principle of Safe Charge Injection with Noble Metal Electrodes." Bioelectrochemistry and Bioenergetics 2: (1975) 13-25.

Bussel, Catelijne M., Dirk L. Stronks, and Frank JPM Huygen. "Successful treatment of intractable complex regional pain syndrome type I of the knee with dorsal root ganglion stimulation: a case report." Neuromodulation: Technology at the Neural Interface 18.1 (2015): 58-61.

Cogan, S.F., et al. "In Vitro Comparison of the Charge-Injection Limits of Activated Iridium Oxide (AIROF) and Platinum-Iridium Microelectrodes", IEEE Transactions on Biomedical Engineering, 52.9 (2005): 1612-1614.

Cogan, S.F., et al. "Potential-Biased, Asymmetric Waveforms for Charge-Injection With Activated Iridium Oxide (AIROF) Neural Stimulation Electrodes." 2006: 53(2): 327-332.

Donaldson et al. "When are actively balanced biphasic ('Lilly') stimulating pulses necessary in a neurological prosthesis?" Medical & Biological Engineering & Computing Jan. 1986: 24: 41-49.

Elbasiouny, S., et al. Modulation of motoneuronal firing behavior after spinal cord injury using intraspinal microstimulation current pulses: a modeling study. J. Appl. Physiol. 103 (2007) 276-286.

Fridman, Gene Y., and Charles C. Della Santina. "Safe direct current stimulation to expand capabilities of neural prostheses." IEEE Transactions on Neural Systems and Rehabilitation Engineering 21.2 (2013): 319-328.

Fridman, Gene Y., and Charles C. Della Santina. "Safe direct current stimulator 2: concept and design." In Engineering in Medicine and Biology Society (EMBC), 2013 35th Annual International Conference of the IEEE, pp. 3126-3129. IEEE, 2013.

Gabrielsson, Erik O., et al. "A four diode full wave ionic current rectifier based on bipolar membranes: Overcoming the limit of electrode capacity." Advanced Materials 26.30 (2014): 5143-5147.

Hasegawa, G., et al. "Impact of Electrolyte on Pseudocapacitance and Stability of Porous Titanium Nitride (TiN) Monolithic Electrode", Journal of The Electrochemical Society, 162.1 (2015): A77-A85.

Hollingworth, Milo, et al. "Single Electrode Deep Brain Stimulation with Dual Targeting at Dual Frequency for the Treatment of Chronic Pain: A Case Series and Review of the Literature." Brain sciences 7.1 (2017): 1-11.

Holtzheimer, Paul E., and Helen S. Mayberg. "Deep brain stimulation for psychiatric disorders." Annual review of neuroscience 34 (2011): 289-307.

Huang, C. et al. "Electrical stimulation of the auditory nerve: direct current measurement in vivo." IEEE Transactions on Biomed. Eng. vol. 46 No. Apr. 4, 1999 at 461-470.

Hurlbert, R. John. "Dose-response study of the pathologic effects of chronically applied direct current stimulation on the normal rat spinal cord." J. Neurosurg. 79 (Dec. 1993) 905-916.

Keifer, Orion Paul, Jonathan P. Riley, and Nicholas M. Boulis. "Deep brain stimulation for chronic pain: intracranial targets, clinical outcomes, and trial design considerations." Neurosurgery Clinics 25.4 (2014): 671-692.

Krum, Henry, et al. "Catheter-based renal sympathetic denervation for resistant hypertension: a multicentre safety and proof-of-principle cohort study." The Lancet 373.9671 (2009): 1275-1281.

(56) References Cited

OTHER PUBLICATIONS

Kim et al. "Electrochemical studies on the alternating current corrosion of mild steel under cathodic protection condition in marine environments", Electrochimica Acta 51, 2006, p. 5259-5267.
Kumsa, D et al. Electrical neurostimulation with imbalanced waveform mitigates dissolution of platinum Electrodes. J. Neural Eng. 13 (2016): 1-5.
Kumsa, D et al. Electrical neurostimulation with imbalanced waveform mitigates dissolution of platinum electrodes. Neural Eng. (2018) 13(5): 1-8.
Kumsa, D.W., et al. "Electron transfer processes occurring on platinum neural stimulating electrodes: pulsing experiments for cathodic-first, charge-imbalanced, biphasic pulses for 0.566 ≤ k ≤ 2.3 in rat subcutaneous tissues", Journal of Neural Engineering, 16 (2019): 1-11.
Mchardy, J., et al., "An Approach to Corrosion Control during Electrical Stimulation", Annals of Biomedical Engineering, 5 (1977): 144-149.
Mendell, Lorne M. "Constructing and deconstructing the gate theory of pain." PAIN® 155.2 (2014): 210-216.
Merrill, Daniel R., Marom Bikson, and John GR Jefferys. "Electrical stimulation of excitable tissue: design of efficacious and safe protocols." Journal of neuroscience methods 141.2 (2005): 171-198.
Mortimer, J.T., et al., "Intramuscular Electrical Stimulation: Tissue Damage", Annals of Biomedical Engineering, 8 (1980): 235-244.
Nahin, Richard L. "Estimates of pain prevalence and severity in adults: United States, 2012." The Journal of Pain 16.8 (2015): 769-780.
Nakajima, H., et al. "Cervical angina: a seemingly still neglected symptom of cervical spine disorder?" Spinal cord 44.8 (2006): 509-513.
Neupane, M et al. Study of Anodic Oxide Films of Titanium Fabricated by Voltammetric Technique in Phosphate Buffer Media. Int. J. Electrochem. Sci., 4 (2009) 197-207.
Nielsen et al., "AC-Corrosion and Electrical Equivalent Diagrams", in: Proceedings of 5th International Congress, CeoCo, bruxelles, Belgium, 2000.
Schaldach, M, Fractal Coated Leads: Advanced Surface Technology of Genuine Sensing and Pacing, Progress in Biomedical Research, (2000): 259-272.
Scheiner, A., et al., "Imbalanced Biphasic Electrical Stimulation: Muscle Tissue Damage", Annals of Biomedical Engineering, 18 (1990): 407-425.
Specht, H. et al., Electrochemical properties and stability of PVD coatings for the application in cardiac and neurological stimulation, (2006).
Tjepkema Cloostermans, Marleen C., et al. "Effect of burst stimulation evaluated in patients familiar with spinal cord stimulation." Neuromodulation: Technology at the Neural Interface 19.5 (2016): 492-497.
Yang, Fei, et al. "Differential expression of voltage-gated sodium channels in afferent neurons renders selective neural block by ionic direct current." Science advances 4.4 (2018): eaaq1438 in 10 pages.
Ajijola et al., "Neural Remodeling and Myocardial Infarction—The Stellate Ganglion as a Double Agent", Journal of the American College of Cardiology, vol. 59, No. 10, pp. 962-964, 2012.
Clyburn et al., "What gets on the nerves of cardiac patients? Pathophysiological changes in cardiac innervation", J Physiol, vol. 600.3, pp. 451-461, 2022.
International Preliminary Report on Patentability dated Dec. 7, 2023 in Application No. PCT/US2022/031162 in 11 pages.
International Preliminary Report on Patentability issued Nov. 21, 2023 in Application No. PCT/US2022/031163 in 10 pages.
International Preliminary Report on Patentability, re PCT Application No. PCT/US18/025743, dated Oct. 17, 2019.
International Preliminary Report on Patentability, re PCT Application No. PCT/US19/017215, dated Aug. 20, 2020.
International Preliminary Report on Patentability, re PCT Application No. PCT/US19/018777, dated Sep. 3, 2020.
International Preliminary Report on Patentability, re PCT Application No. PCT/US19/040189, dated Jan. 14, 2021.
International Preliminary Report on Patentability, re PCT Application No. PCT/US20/062068, dated Jun. 2, 2022.
International Preliminary Report on Patentability, re PCT Application No. PCT/US20/062077, dated Jun. 2, 2022.
International Search Report and Written Opinion dated Oct. 18, 2022 in Application No. PCT/US2022/031162 in 20 pages.
International Search Report and Written Opinion dated Sep. 7, 2022 in Application No. PCT/US2022/031163 in 17 pages.
International Search Report and Written Opinion in PCT Application No. PCT/US2018/25743 dated Jun. 28, 2018 in 8 pages.
International Search Report and Written Opinion in PCT Application No. PCT/US2019/018777 dated Jun. 20, 2019 in 15 pages.
International Search Report and Written Opinion in PCT Application No. PCT/US2020/062077 dated Feb. 17, 2021 in 18 pages.
International Search Report and Written Opinion in PCT Application No. PCT/US19/17215 mailed Jun. 20, 2019.
International Search Report and Written Opinion in PCT Application No. PCT/US2020/062068 mailed Apr. 8, 2021 in 20 pages.
U.S. Appl. No. 18/421,709, filed Jan. 24, 2024.
U.S. Appl. No. 18/468,520, filed Sep. 15, 2023.
U.S. Appl. No. 18/563,859, filed Nov. 22, 2023.
U.S. Appl. No. 18/563,861, filed Nov. 22, 2024.
Zaman et al., "Sudden Cardiac Death Early After Myocardial Infarction—Pathogenesis, Risk Stratification, and Primary Prevention", Circulation, vol. 129, pp. 2426-2435, Jun. 10, 2014.

* cited by examiner 114
112
104
102
107
106
N
108
100
110
Region 1
Region 2
Region 3
Current amplitude and polarity delivered to electrode cell
+
0
-
Time
Water oxidation and decreased pH and electrode dissolution considerations / bounds
Ag/AgCl electrode: AgCl mass
m2
m1
0
Time
Water reduction and increased pH

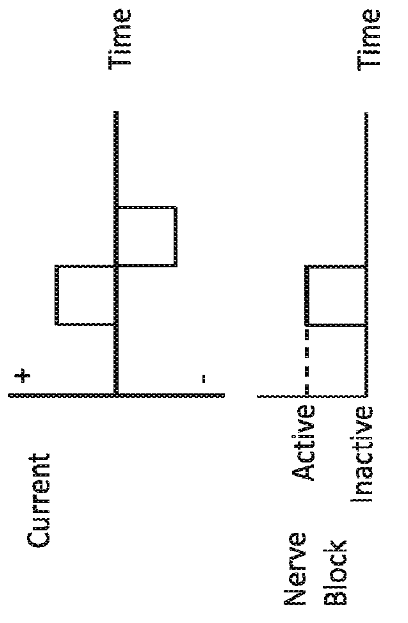
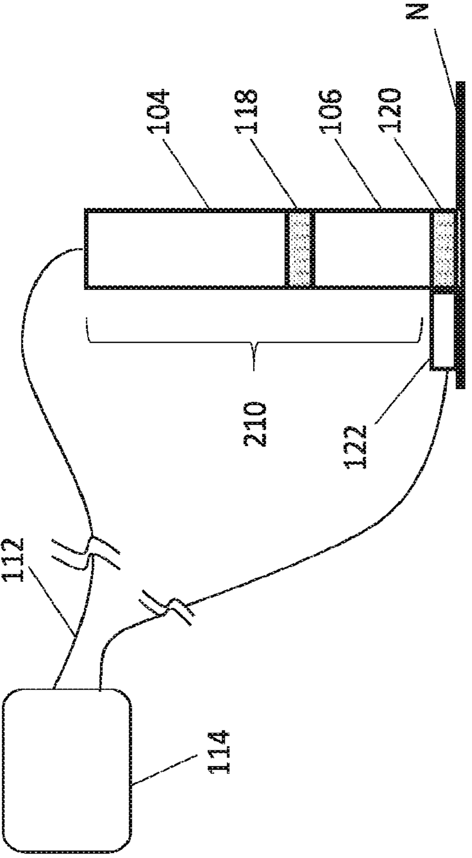
Fig. 1I

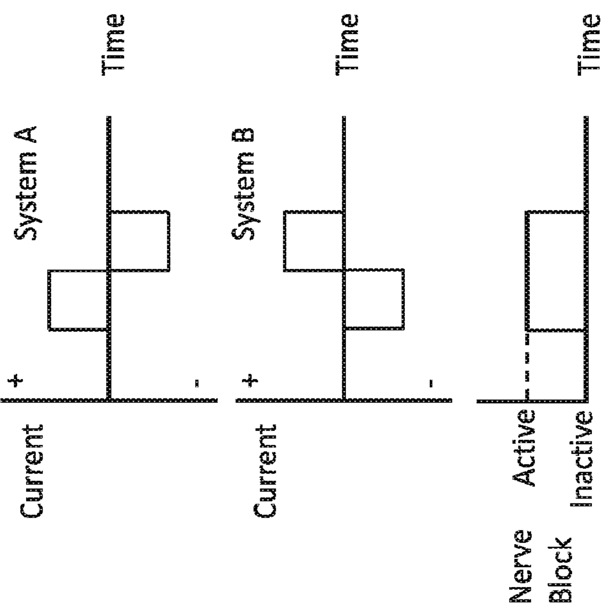
Fig. 3D
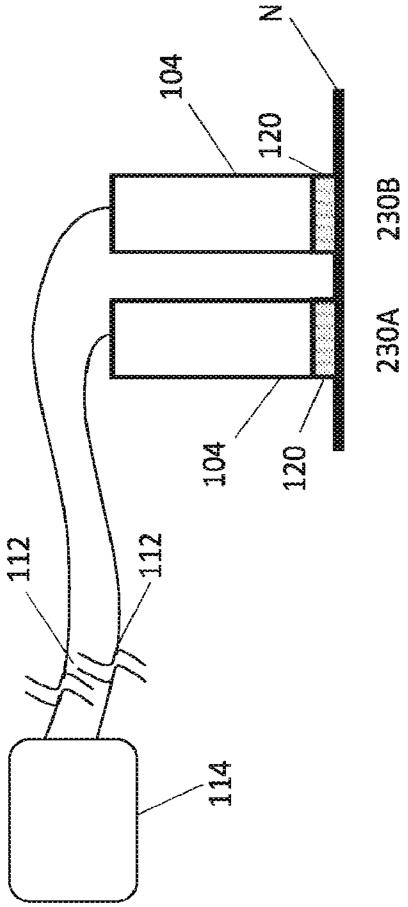
Fig. 3C

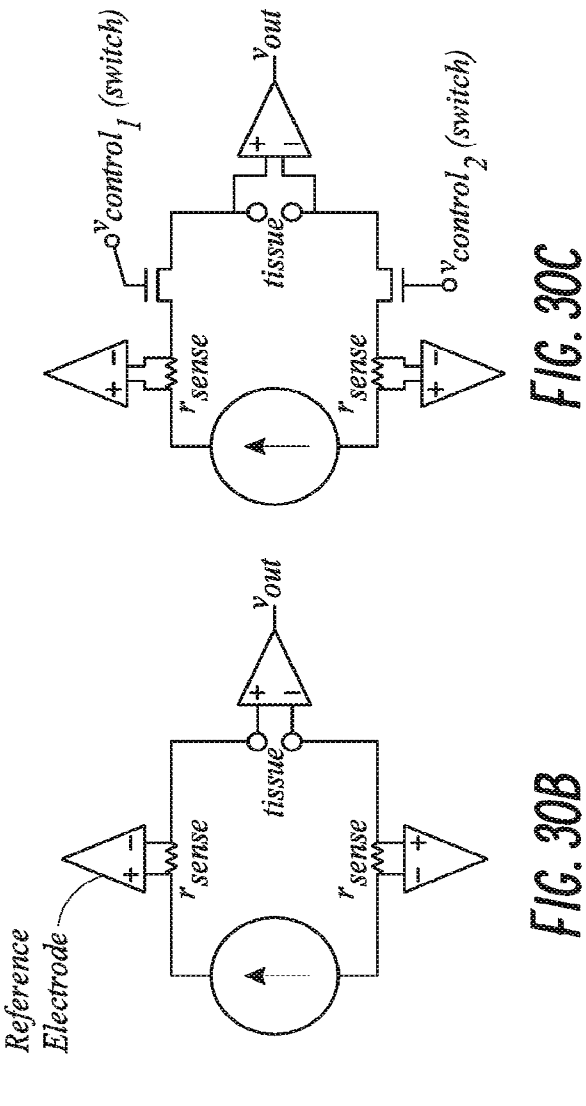
FIG. 30C
FIG. 30B
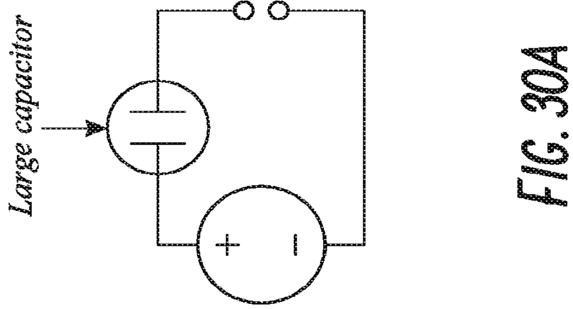
FIG. 30A

Model of electrode and body

Model of electrode and body at low frequencies when applying DC

2100 – electrode lead
2103 – to power source
2102 – insulated portion
2104 – ionically conductive portion
42B - cross section through 2102
2108 electrical connector
2106 - insulator 42C – cross section through 2104
2110 electrical connector connection to ionic current generator
2112 ionic current generator
2108 electrical connector
2106 - insulator

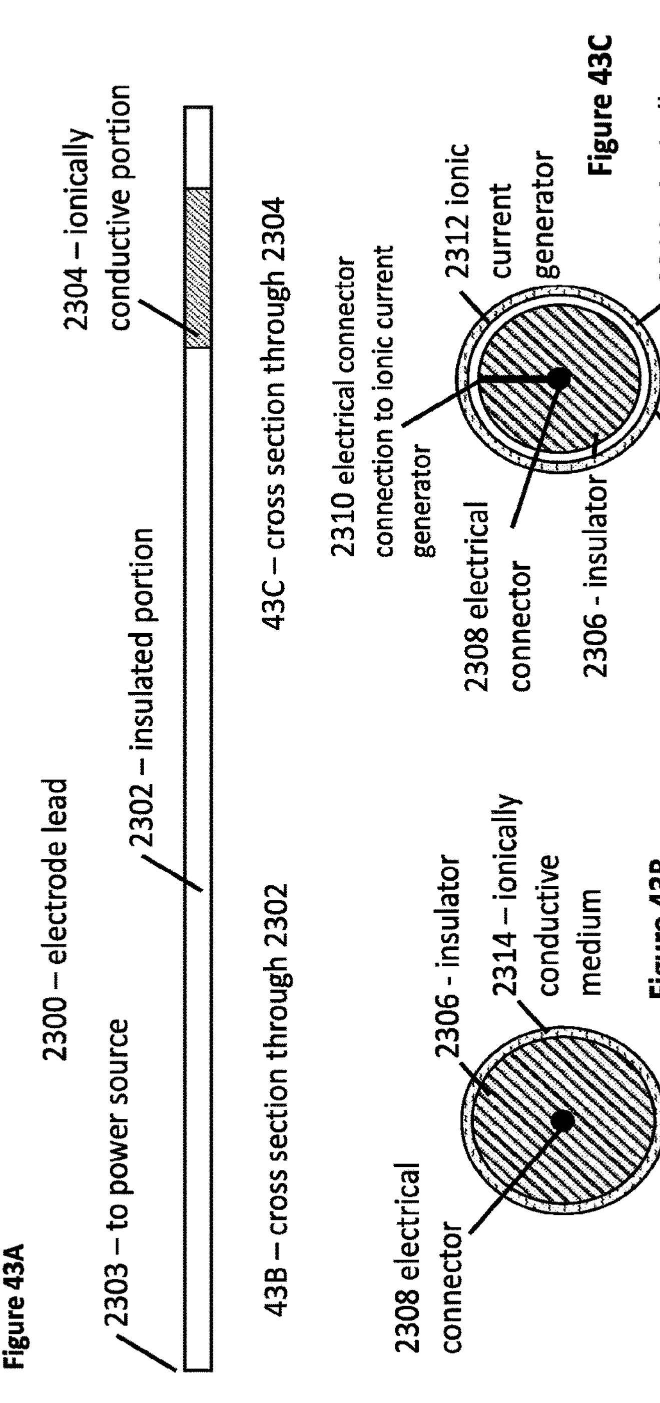
Figure 43A
2300 – electrode lead
2303 – to power source
2302 – insulated portion
2304 – ionically conductive portion
43B – cross section through 2302
43C – cross section through 2304
2308 electrical connector
2306 - insulator
2314 – ionically conductive medium
2316 – ionically selective membrane
Figure 43B
2310 electrical connector connection to ionic current generator
2312 ionic current generator
2308 electrical connector
2306 - insulator
2316 – ionically selective membrane
2314 – ionically conductive medium
Figure 43C

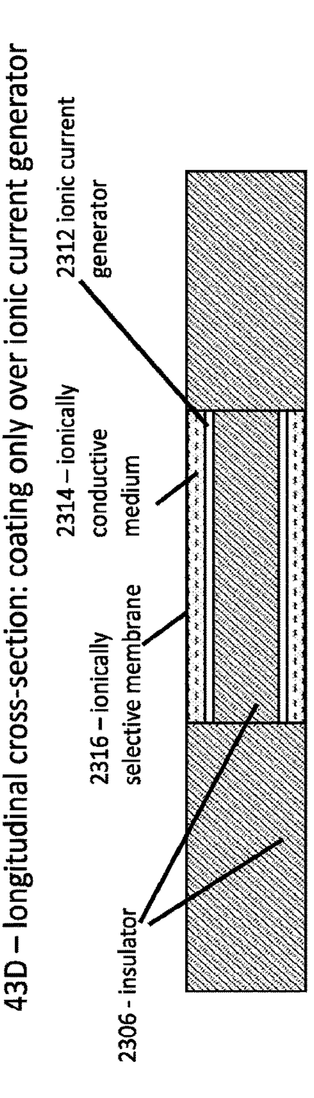
43D – longitudinal cross-section: coating only over ionic current generator
2306 - insulator
2316 – ionically selective membrane
2314 – ionically conductive medium
2312 ionic current generator
Figure 43D Figure 45A
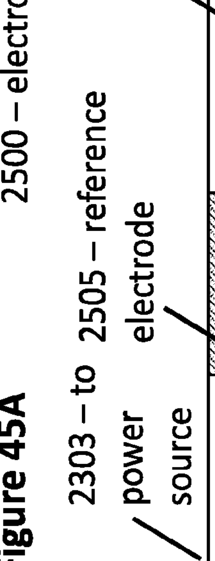
45B – cross section through 2302
Figure 45B
45C – cross section through 2304
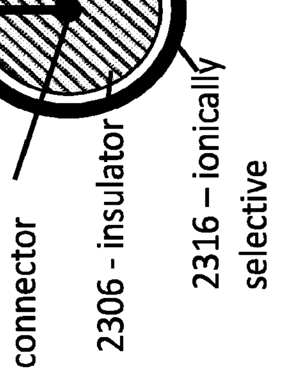
Figure 45C

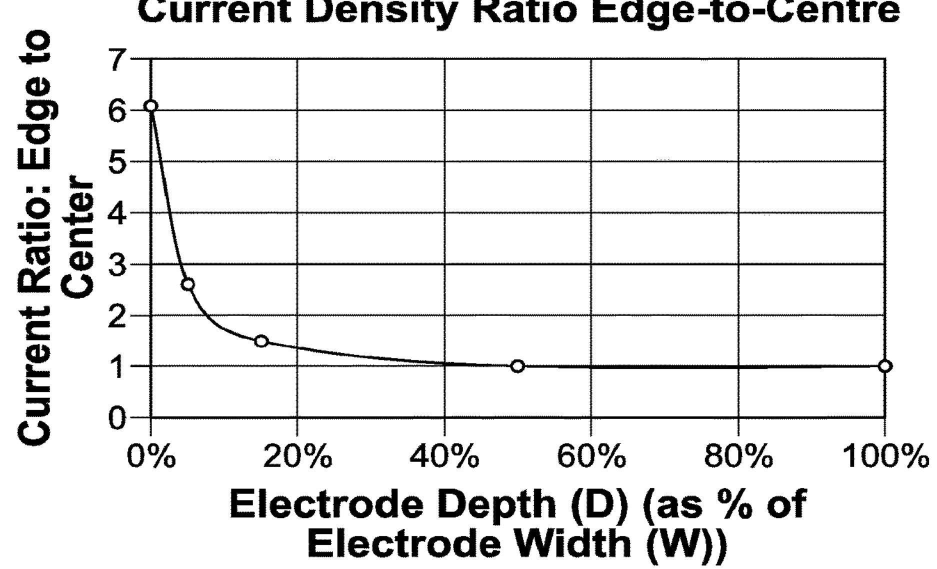
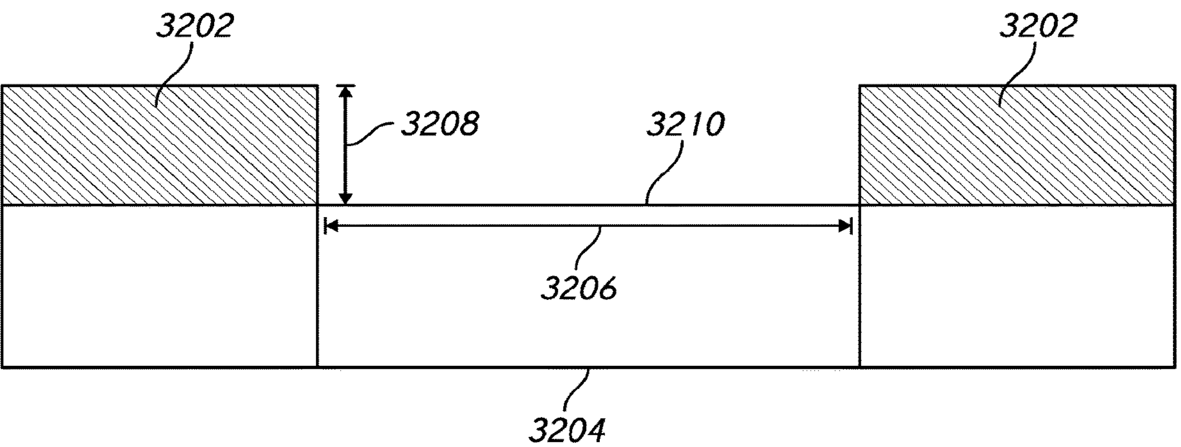
FIG. 52

3400
3402

3420
3402
3422

1604
1602
1606
1602
1602
1606
1602
1600

Examples of High Charge Density Materials

| Material | Published Charge Capacity(CSC) (mC/cm2) | Used in FDA-approved devices? | Robustness for use in literature | Evacuated Charge Capacity(CSC) Range (mC/cm2) | Surface Area Factor Example for Target 15-25 mC delivery |
|---|---|---|---|---|---|
| Pt / PtIr | 0.3 - 2 | ✓ | ✓ | 1.7-2[1] | 65 |
| Titanium | N/A | ✓ | ✓ | 1-2[2] | 65 |
| TiN | ~0.8-22 | ✓<br>✓ | ✓<br>✓ | ~0.4(smooth/gold)<br>12-14[3] (rough/back) | 325<br>10 |
| Tantalum | 0.5 | X | X | - | 260 |
| PEDOT | 5-38 | ✓* (CE Mark) | X | - | 13 |
| AIROF (IrOx) | 1-40 | X | ✓ | - | 13 |
| EIROF (IrOx) | 29-68 | X | ✓ | - | 6.5 |
| SIROF (IrOx) | 3-194 | X | ✓ | 45-53 | 2.6 |

FIG. 65B

Examples of Surface Area Technologies
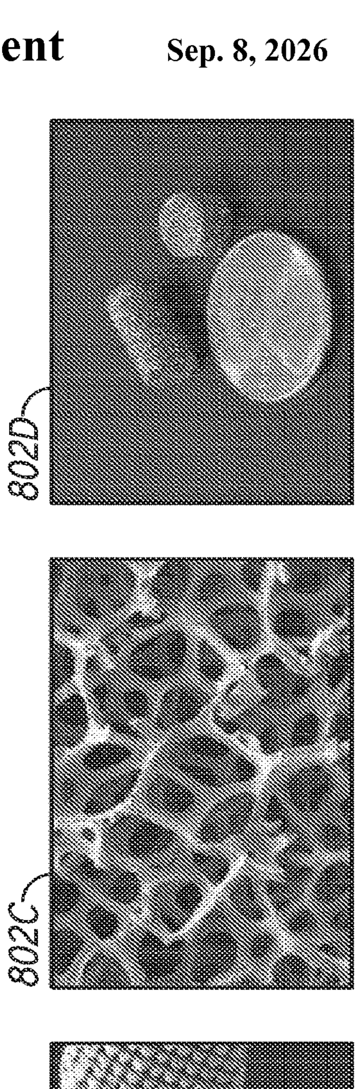
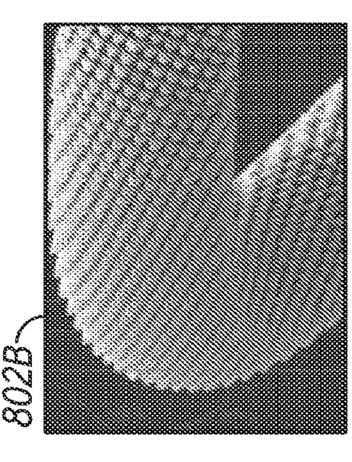
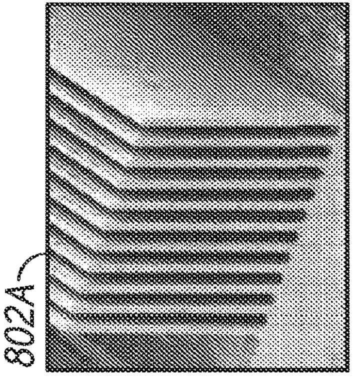
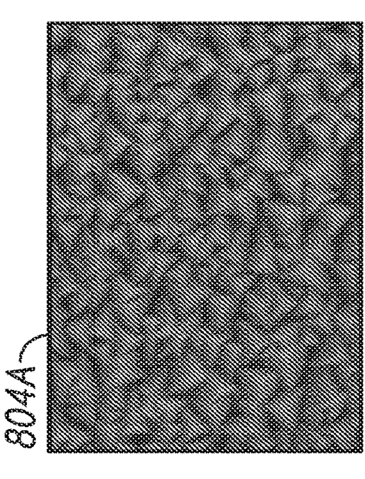
FIG. 65C Texturing of Rod / Tube a
a
c
806
b a. Surface Spacing
b. Channel Width
c. Channel Depth

Unidirectional or Bidirectional Channels a a c b a. Surface Spacing
b. Channel Width
c. Channel Depth 814
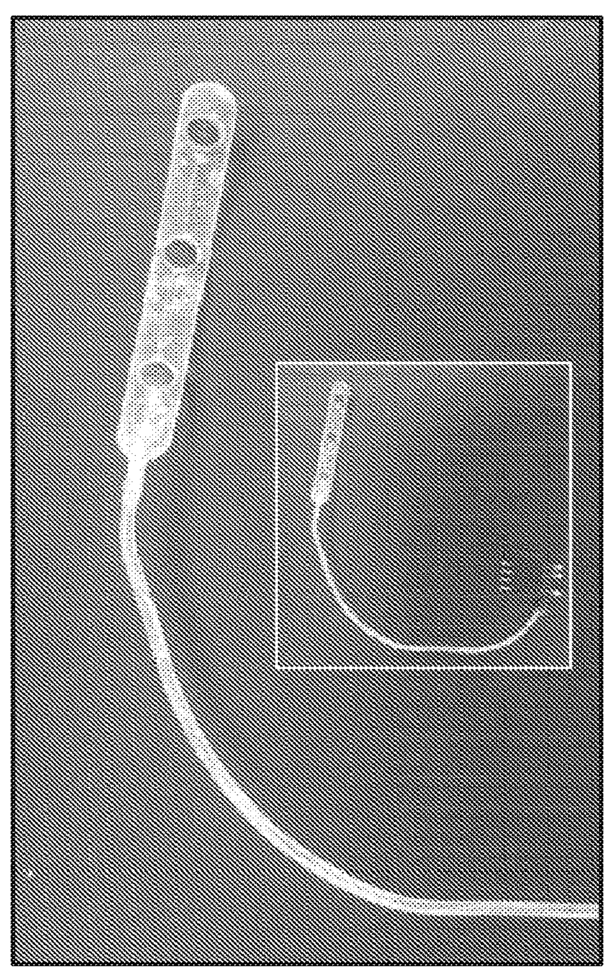
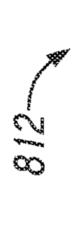
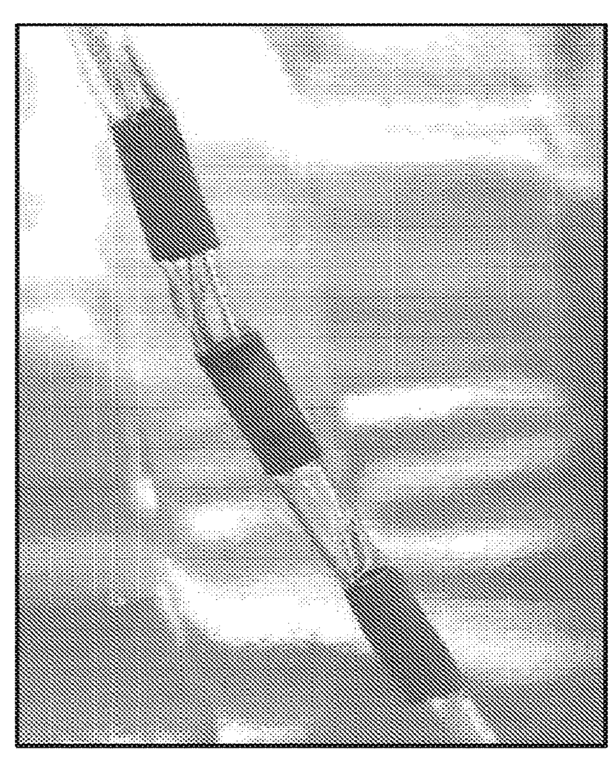
FIG. 66C

SYSTEMS AND METHODS FOR NERVE CONDUCTION BLOCK

INCORPORATION BY REFERENCE

This application is a continuation of U.S. application Ser. No. 17/255,882, filed Dec. 23, 2020, which is the U.S. National Phase under 35 U.S.C. § 371 of International Application No. PCT/US2019/040189, filed Jul. 1, 2019, which claims the benefit under 35 U.S.C. § 119(e) as a nonprovisional application of U.S. Prov. App. No. 62/692,857, filed on Jul. 1, 2018, which are each incorporated by reference in their entireties. This application claims the benefit under 35 U.S.C. § 119(e) as a nonprovisional application of U.S. Prov. App. No. 62/692,857 filed on Jul. 1, 2018 which is incorporated by reference in its entirety.

BACKGROUND

Field of the Invention

This application relates, in some embodiments, to facilitating block of biological signals through nerve tissue.

The gate control theory of pain was developed in the 1960s and led to the advent of stimulation-based pain management therapies to reduce pain inputs from reaching the brain by selectively stimulating non-nociceptive fibers (non-pain transmitting fibers) in the spinal cord to inhibit transmission of pain stimuli to the brain (See Mendell, Constructing and Deconstructing the Gate Theory of Pain, Pain, 2014 February 155(2): 210-216). Current stimulation systems for spinal cord stimulation (SCS), which act on this gate control theory to indirectly reduce pain, typically have relied on stimulation signals in the <100 Hz frequency range, and recently in the kHz frequency range. Stimulation of the dorsal root ganglia, DRG, in a similar frequency range has also been employed to reduce segmental pain through the same mechanism.

However, technologies based on this premise are not perfect as pain transmission inhibition is not complete and side effects such as paresthesia can be uncomfortable for patients. Therefore, it is desirable to have systems and methods of treating pain which directly block pain fibers from transmitting pain signals, rather than indirectly reducing pain signals through gate-theory activation of non-nociceptive fibers. Furthermore, block of neural tissue or neural activity has been implicated in not only affecting pain but also in the management of movement disorders, psychiatric disorders, cardiovascular health, as well as management of disease states such as diabetes.

SUMMARY

In some embodiments, a system to modulate the action potential transmission along a nerve body includes an electron to ion current conversion cell (EICCC) which comprises an electrode at which an electrochemical process occurs to generate current in the form of ions to change the electrical potential around the nerve and modulate the nerve membrane potential.

In some embodiments, a system to modulate the action potential transmission along a nerve body includes an electron to ion current conversion cell which comprises an electrode at which a capacitive charging process occurs to generate current in the form of ions to change the charge density around the nerve and modulate the nerve membrane potential.

In some embodiments, a system to modulate the stimulus transmission along a nerve body includes an electron to ion current conversion cell which comprises an electrode at which an electrochemical process occurs to generate current in the form of ions to change the charge density around the nerve and modulate the nerve membrane potential.

In some embodiments, a system to modulate the stimulus transmission along a nerve body includes an electron to ion current conversion cell which comprises an electrode at which an electrochemical process and capacitive charging process occur to generate current in the form of ions to change the charge density around the nerve and modulate the nerve membrane potential.

In some embodiments, the system modulates the electrical potential near the nerve to put the nerve tissue in a blocked state.

In some embodiments, the system puts the target nerve(s) in a state of acute nerve block.

In some embodiments, the system puts the target nerve(s) in a state of chronic nerve block.

In some embodiments, the system modulates the electrical potential to put the nerve tissue into a suppressed state.

In some embodiments, the system puts the target nerve(s) in a state of acute nerve suppression.

In some embodiments, the system puts the target nerve(s) in a state of nerve hypersuppression.

In some embodiments, the electrode comprises an electrode material of silver, silver-chloride (Ag/AgCl).

In some embodiments, the electrode comprises an electrode material of silver (Ag).

In some embodiments, the electrode comprises an electrode material of silver-chloride (AgCl).

In some embodiments, the masses of the electrode constituent materials are maintained in a specified range.

In some embodiments, the electrochemical processes which occur at the electrode are reversible.

In some embodiments, the electrode is sacrificial and cannot be restored.

In some embodiments, the system comprises an electrode immersed in electrolyte and fluidly and electronically coupled to an ion conductor in electrical contact with the nerve tissue.

In some embodiments, the ion conductor comprises a hydrogel material.

In some embodiments, the system comprises one or more current sources that are connected via a lead to the one or more electrodes.

In some embodiments, the ion conductor includes a proximal layer, e.g., screen or filter element to selectively sequester electrochemical process byproducts to the electrolyte volume.

In some embodiments, the ion conductor includes a distal screen or filter element to selectively sequester electrochemical process byproducts from the nerve tissue.

In some embodiments, the ion conductor includes multiple screen or filter elements to selectively sequester electrochemical process byproducts from the nerve tissue.

In some embodiments, the system comprises materials which come in contact with tissue that are biocompatible.

In some embodiments, two or more systems to modulate the stimulus transmission along a nerve body include electron to ion current conversion cells to change the electrical potential around the nerve and modulate the nerve membrane potential.

In some embodiments, a method using two or more systems to maintain a constant nerve block by delivering direct current in the form of ions includes operating one system in a blocking mode with current of one polarity while the other system or systems are run in a mode with current of the opposite polarity.

In some embodiments, a method of delivering a prolonged block to neural tissue includes an initial delivery of current in the form of ions proximal to the neural tissue to put the neural tissue into a suppressed state where block continues after current ceases.

In some embodiments, a method of delivering a prolonged block to neural tissue includes an initial delivery of current in the form of ions proximal to the neural tissue to put the neural tissue into a suppressed state where block continues after current ceases with subsequent current delivery to maintain the nerve in its suppressed state.

In some embodiments, a method of delivering a prolonged block to neural tissue includes an initial delivery of current in the form of ions proximal to the neural tissue to put the neural tissue into a suppressed state where block continues after current ceases with subsequent current delivery to maintain the nerve in its suppressed state whereby current of the opposite polarity between current delivery phases does not impact the nerve suppression state.

In some embodiments, a system for accessing and modulating the nerve signal transmission properties of a DRG includes an introducer needle comprising optionally radiopaque markers and a stylet and an electrode configured to fit within the needle bore. The electrode comprising stress-relief and securement features such as barbs and leads that provide electrical communication with a current source.

In some embodiments, a system for accessing and modulating the nerve signal transmission properties of the spinal cord includes an introducer needle comprising optionally radiopaque markers and a stylet and an electrode configured to fit within the needle bore. The electrode comprising stress-relief and securement features such as barbs and leads that provide electrical communication with a current source.

In some embodiments, a method for accessing and modulating the nerve signal transmission properties of a DRG includes insertion of an introducer needle into the body cavity to the nerve site, removing a stylet, inserting an electrode, securing the electrode at the desired tissue site, removing the needle, and connecting the EICCC electrode leads to a current source and delivering a current to put the nerve in a state of suppression.

In some embodiments, a method for accessing and modulating the nerve signal transmission properties of the spinal cord includes insertion of an introducer needle into the body cavity to the nerve site, removing a stylet, inserting an electrode, securing the electrode at the desired tissue site, removing the needle, and connecting the EICCC electrode leads to a current source and delivering a current to put the nerve in a state of suppression.

In some embodiments, the system includes an external current source.

In some embodiments, the system includes an implantable current source.

In some embodiments, the system includes a programmable current source.

In some embodiments, the system comprises a sensor proximal to the nerve tissue to monitor the nerve tissue membrane potential and provide a feedback measurement for the current source.

In some embodiments, the system comprises a sensor that is an electrode that serves as a reference electrode for the working electrode in the EICCC to monitor the electrode potential.

In some embodiments, a method for maintaining a nerve in a blocked state is disclosed wherein the nerve membrane potential is monitored and used as a signal to provide feedback to the current source and current source controller to enable modulation of the current source output to the electrode.

In some embodiments, the system for delivery of ion current to neural tissue comprises a current delivery source, a power supply, electrical connection to an EICCC with a connector element to which an ion conducting electrode may be connected wherein the system is hermetically sealed.

In some embodiments, the system for accessing and modulating the nerve signal transmission properties of the DRG is used to reduce pain due to neuralgias.

In some embodiments, the system for accessing and modulating the nerve signal transmission properties of the DRG or DRGs is used to reduce pain due to angina.

In some embodiments, the system for accessing and modulating the nerve signal transmission properties of the DRG or DRGs is used to reduce pain due to ischemic pain.

In some embodiments, the system for accessing and modulating the nerve signal transmission properties of the DRG or DRGs is used to reduce pain due to complex regional pain syndrome (CPRS).

In some embodiments, the system for accessing and modulating the nerve signal transmission properties of the DRG or DRGs is used to reduce pain in a specific region of the body.

In some embodiments, the system for accessing and modulating the nerve signal transmission properties of the DRG or DRGs is used to reduce pain in a specific limb of the body.

In some embodiments, the system for accessing and modulating the nerve signal transmission properties of the DRG or DRGs is used to reduce pain in a specific region of a limb of the body.

In some embodiments, the system for accessing and modulating the nerve signal transmission properties of the DRG or DRGs can delivery different current signals to different DRGs for improved pain reduction coverage.

In some embodiments, the system for accessing and modulating the nerve signal transmission properties of the spinal cord includes more than one electrode leads.

In some embodiments, the system for accessing and modulating the nerve signal transmission properties of the spinal cord includes more than one electrode leads which include one or more regions that contact tissue and deliver current to the tissue.

In some embodiments, the system for accessing and modulating the nerve signal transmission properties of the spinal cord includes more than one electrode leads at different levels along the spinal cord which include one or more regions that contact tissue and deliver current to the tissue.

In some embodiments, the system for accessing and modulating the nerve signal transmission properties of the spinal cord includes more than one electrode leads which include one or more regions that contact tissue and deliver current to the tissue and can be individually adjusted to deliver the desired current and electric field to the tissue.

In some embodiments, a method for accessing and modulating the nerve signal transmission properties of the spinal cord includes generating pain relief as part of a peri-procedural pain block.

In some embodiments, a method for accessing and modulating the nerve signal transmission properties of the spinal cord includes generating pain relief as part of a peri-procedural pain block that is quickly reversible.

In some embodiments, a method for accessing and modulating the nerve signal transmission properties of peripheral nerves to generate pain relief includes delivering direct current with an EICCC to peripheral nerve tissue to reduce focal pain.

In some embodiments, a method for accessing and modulating the nerve signal transmission properties of peripheral nerves to generate pain relief includes delivering direct current with an EICCC to peripheral nerve tissue to reduce phantom limb pain.

In some embodiments, a method for accessing and modulating the nerve signal transmission properties of peripheral nerves to generate pain relief includes delivering direct current with an EICCC to peripheral nerve tissue to reduce neuroma pain.

In some embodiments, a method for accessing and modulating the nerve signal transmission properties of peripheral nerves to generate pain relief includes delivering direct current with an EICCC to peripheral nerve tissue to reduce neuralgia pain.

In some embodiments, a method for accessing and modulating the nerve signal transmission properties of renal nerves includes reducing activity of the sympathetic nervous system to reduce hypertension.

In some embodiments, a method for accessing and modulating the nerve signal transmission properties of the sympathetic ganglia includes reducing activity of the sympathetic cervical ganglia to reduce heart failure progression.

In some embodiments, a method for accessing and modulating the nerve signal transmission properties of the sympathetic ganglia includes reducing activity of the sympathetic cervical ganglia to reduce or prevent tachycardia.

In some embodiments, a method for accessing and modulating the nerve signal transmission properties of the vagus nerve includes reducing activity of the vagus nerve to increase heart rate.

In some embodiments, a method for accessing and modulating the nerve signal transmission properties of the vagus nerves innervating the stomach includes reducing activity of the vagus nerve to increase satiety and satiation.

In some embodiments, a method for accessing and modulating the nerve signal transmission properties of hepatic nerves includes reducing activity of the sympathetic nervous system to increase insulin production.

In some embodiments, a method for accessing and modulating the nerve signal transmission properties of hepatic nerves includes reducing activity of the sympathetic nervous system to reduce insulin resistance.

In some embodiments, a method for accessing and modulating the nerve signal transmission properties of brain tissue includes accessing the desired region of the brain and reducing neural tissue activity to treat movement disorders.

In some embodiments, a method for accessing and modulating the nerve signal transmission properties of brain tissue includes accessing the desired region of the brain and reducing neural tissue activity to treat psychiatric disorders.

In some embodiments, a method for accessing and modulating the nerve signal transmission properties of brain tissue includes accessing the desired region of the brain and reducing neural tissue activity to treat chronic pain.

In some embodiments, disclosed herein is a system for nerve block of a patient utilizing a renewable electrode. The system can include a direct current generator, and/or at least one electrode comprising silver chloride. The system can also include a controller configured to signal the direct current generator to deliver a first direct current with a first polarity through the electrode sufficient to block conduction in a nerve, and/or decrease an amount of the silver chloride in the electrode thereby forming solid silver and chloride ions. The controller can also be configured to signal the direct current generator to deliver a second direct current with a second polarity through the electrode sufficient to increase the amount of the silver chloride, thereby renewing the electrode. The system can also include a nerve interface spaced apart from the electrode by a selective barrier. The selective barrier can also be configured to allow chloride ions through the barrier toward the nerve interface to block the nerve. The system can also include a sensor configured to determine whether a reaction, such as a predominantly silver/silver chloride reaction is occurring. The controller can be further configured to receive data from the sensor and discontinue or modulate at least one of the first direct current signal or the second direct current signal when water is being electrolyzed. The selective barrier can be further configured to prevent silver ions from passing through the barrier toward the nerve interface. The electrode can be housed in an insulated enclosure. The selective barrier can include an ion exchange membrane, and/or a hydrogel. The system can be devoid of any mechanically moving parts in some cases. The controller can be configured to deliver the first direct current such that the amount of silver chloride decreased is greater than a surface area of the electrode prior to delivery of the first direct current. The controller can also be configured to deliver the first direct current such that the amount of silver chloride decreased is greater than, such as about 1.25×, 1.5×, 2×, 3×, 4×, 5×, 10×, 15×, 20×, 50×, 100×, 1,000×, or more an amount capable of evenly covering a surface area, such as the entire functional surface area of the electrode prior to delivery of the first direct current, or ranges including any two of the aforementioned values.

In some embodiments, also disclosed herein is a system for nerve block of a patient utilizing a renewable electrode. The system can include one or more of: a direct current generator; at least one electrode comprising a solid component, an ionic component, and a nerve interface directly adjacent the ionic component; a controller configured to signal the direct current generator to: deliver a first direct current with a first polarity through the electrode sufficient to block conduction in a nerve and decrease an amount of the solid component; and/or deliver a second direct current with a second polarity through the electrode sufficient to increase the amount of the solid component, thereby renewing the electrode. The system can also include one or more sensors configured to determine whether a predominantly solid component/ionic component reaction is occurring. The controller can be further configured to receive data from the sensor and discontinue or modulate at least one of the first direct current signal or the second direct current signal when water is being electrolyzed. The electrode, or a plurality of electrodes, can be housed in an insulated enclosure, such as the same or a different enclosure. The electrode can also include a layer, such as a selective barrier spaced between the ionic component and the nerve. The layer can be configured to selectively allow negatively charged ions of the ionic component to pass through the layer and toward the nerve, and prevent positively charged ions of the ionic component from passing through the layer toward the nerve. The system can be devoid of any mechanically moving parts. The nerve interface can be spaced apart from the electrode by one or more of a gel, a hydrogel, and an ion conductive polymer. The electrode can be partially or completely surrounded by a solution, such as an electrolyte solution, e.g., isotonic saline. The solid component can include silver, and/or the ionic component can include silver chloride. The controller can be configured to deliver the first direct current such that the amount of solid component decreased is greater than a surface area of the solid component. The controller can also be configured to maintain the nerve in a hypersuppressed state at least partially preventing conduction of the nerve for at least about 10 minutes or more after cessation of delivering of the first direct current.

In some embodiments, also disclosed herein is a method for nerve block of a patient utilizing a renewable electrode. The method can include one or more of delivering a first direct current of a first polarity through an electrode comprising a first component proximate a nerve sufficient to block conduction in the nerve; and delivering a second direct current of a second polarity opposite the first polarity through the electrode. The first direct current can decrease an amount of the first component of the electrode thereby producing a second component different from the second component. The second direct current can increase the amount of the first component of the electrode and/or decreases the amount of the second component to renew the electrode. The method can also dynamically sensing the amount of the first component or the second component in the electrode while delivering the first direct current; and ceasing delivery of the first direct current when the amount of the first component is sensed to reach a pre-determined threshold value, and/or when water is electrolyzed.

Also disclosed herein is a method for extended nerve block utilizing a plurality of renewable electrodes. The method can deliver a first direct current with a first polarity through a first electrode proximate a nerve sufficient to block conduction in the nerve, the electrode comprising a solid component and an ionic component; delivering a second direct current with a second polarity opposite the first polarity through a second electrode spaced axially apart from the first electrode and proximate the nerve while the nerve is in the hypersuppressed state; and/or reversing the polarities of the first direct current and the second direct current, wherein reversing the polarities maintains the nerve in the hypersuppressed state.

In some embodiments, also disclosed herein is a method for extended nerve block utilizing at least one renewable electrode. The method can include delivering a first direct current with a first polarity to an electrode proximate a nerve sufficient to block conduction in the nerve. Delivering the first direct current can place the nerve in a hypersuppressed state at least partially preventing conduction of the nerve after cessation of delivering of the first direct current. The method can also include delivering a second direct current with a second polarity opposite the first polarity through the electrode entirely while the nerve remains in the hypersuppressed state. The electrode can be, for example, an electrochemical or capacitive electrode. A capacitive electrode can include tantalum or titanium, for example. The electrode can include silver and/or silver chloride in some cases. Delivering the first direct current can change the electrode from a first configuration to a second configuration, and delivering the second direct current transforms the electrode from the second configuration back to the first configuration, or at least closer to the first configuration. The second configuration can include a lower amount and/or a lower charge than a material than the first configuration.

Also disclosed herein is a method for nervous tissue block utilizing at least one renewable electrode. The method can include delivering a first direct current with a first polarity to an electrode proximate nervous tissue sufficient to block conduction in the nervous tissue. Delivering the first direct current can place the nervous tissue in a hypersuppressed state at least partially preventing conduction of the nervous tissue after cessation of delivering of the first direct current. The method can also include maintaining the nervous tissue in the hypersuppressed state for at least about 1 minute, 10 minutes, 1 hour, 24 hours, or more. The method can also include sensing the conduction ability of the nervous tissue, and/or maintaining the nervous tissue in a hypersuppressed state by delivering a third direct current through the electrode to the nervous tissue after sensing the conduction ability of the nervous tissue, wherein the third direct current has the same polarity as the first direct current. Sensing the conduction ability of the nervous tissue can include delivering a stimulus pulse to the nervous tissue and measuring a compound action potential signal, and/or measuring potential differences via a reference electrode. The nervous tissue could include one or more of a nerve, such as a spinal, cranial, or peripheral nerve, or brain tissue, dorsal root ganglia, tissue of the spinothalamic tract, autonomic nervous tissue, sympathetic nervous tissue, or parasympathetic nervous tissue. The direct current can be therapeutically effective to treat pain, such as acute or chronic pain and/or ischemic pain. The direct current can also be therapeutically effective to treat a psychiatric condition such as depression, anxiety, obsessive-compulsive disorder, PTSD, mania, or schizophrenia; a movement disorder such as Tourette's syndrome, Parkinson's disease, spasticity, or essential tremor; and/or a cardiopulmonary condition such as hypertension, congestive heart failure, ischemic cardiomyopathy, angina, or an arrhythmia.

Also disclosed herein is a system for extended nerve block utilizing a reversible electrode. The system can include one or more of a direct current generator; at least one electrode comprising a solid component, an ionic component, and a nerve interface adjacent the ionic component; a controller configured to signal the direct current generator to: deliver a first direct current with a first polarity through the electrode sufficient to block conduction in a nerve; maintain the nerve in a hypersuppressed state at least partially preventing conduction of the nerve after cessation of delivering of the first direct current; and/or deliver a second direct current with a second polarity through the electrode entirely while the nerve remains in the hypersuppressed state.

Also disclosed herein is a method for providing extended nerve block utilizing a renewable electrode. The method can include delivering a first direct current of a first polarity through an electrode proximate a nerve sufficient to block conduction in the nerve, the electrode comprising a first component and a second component; hypersuppressing the nerve to at least partially prevent conduction of the nerve after cessation of the first direct current; and/or delivering a second direct current of a second polarity opposite the first polarity through the electrode while the nerve is in the hypersuppressed state. The first direct current can decrease an amount of the first component and increase the amount of the second component. The second direct current can increase the amount of the first component and decreases the amount of the second component to renew the electrode. In some embodiments, the method does not fully deplete the first component. The method can also include sensing the amount of at least one of the first component and the second component; and ceasing delivering the first direct current when the amount of the first component reaches a predetermined minimum threshold value. A net charge delivered to the nerve after delivering the first direct current and the second direct current can be zero. The first direct current can be an anodic or cathodic current and the second direct current can be a cathodic or an anodic current. The method can also include sensing the conduction ability of the nerve, and/or maintaining the nerve in a hypersuppressed state by delivering a third direct current through the electrode to the nerve after sensing the conduction ability of the nerve, wherein the third direct current has the same polarity as the first direct current. Sensing the conduction ability of the nerve can include delivering a stimulus pulse to the nerve and measuring a compound action potential signal, and/or measuring potential differences via reference electrode. In some embodiments, there can be a current-free gap in time in between delivering the first direct current of the first polarity and delivering the second direct current of the second polarity.

The method can also include delivering at least one, two, or more additional cycles of direct current. One cycle can include delivering the first direct current of the first polarity and delivering the second direct current of the second polarity opposite the first polarity through the electrode. The method can also include implanting the electrode proximate the nerve, percutaneously positioning the electrode proximate the nerve, and/or transcutaneously positioning the electrode proximate the nerve. The nerve can be spaced apart from the electrode by a gel, a hydrogel, an ion conductive polymer, and/or a layer. The electrode can be partially or completely surrounded by an electrolyte solution, such as an isotonic saline solution.

In some embodiments, disclosed herein is a system for nerve block of a patient utilizing a capacitive rechargeable electrode. The system can include any number of: a current generator; at least one implantable electrode comprising titanium nitride, the at least one electrode configured to be in electrical communication with the current generator; a controller configured to signal the current generator to: generate a first current with a first polarity proximal to the at least one electrode sufficient to at least partially block conduction in a nerve, wherein an amount of stored charge in the at least one electrode decreases and generates current in an ionic component proximate the at least one electrode when the electrode is implanted within the patient; and generate a second current with a second polarity proximal to the at least one electrode sufficient to increase the amount of stored charge in the at least one electrode.

In some embodiments, the system can also include a sensor configured to determine the state of stored charge of the at least one electrode. The controller can be further configured to receive data from the sensor and discontinue at least one of the first current signal or the second current signal when an amount of water is being electrolyzed.

In some embodiments, the decrease and increase in amount of stored charge on the at least one electrode can be equal, or unequal.

In some embodiments, the at least one electrode is housed in an insulated enclosure.

In some embodiments, the titanium nitride comprises porous or fractal titanium nitride.

In some embodiments, the titanium nitride electrode can be configured to deliver at least about 5,000, 25,000 μC, or more of charge into excitable tissue without damaging the excitable tissue.

In some embodiments, the system is devoid of any mechanically moving parts.

In some embodiments, a system for nerve block of a patient utilizing a capacitive rechargeable electrode can include any number of the following features: a current generator; at least one implantable electrode comprising a high charge density material configured to be spaced apart from a nerve interface by an ionic component, the at least one implantable electrode configured to be in electrical communication with the current generator; and a controller configured to signal the current generator to: generate a first current with a first polarity proximal to the at least one implantable electrode sufficient to at least partially block conduction in a nerve, wherein an amount of stored charge in the at least one electrode decreases and generates current in an ionic component proximate the at least one electrode when the electrode is implanted within the patient; and generate a second current with a second polarity proximal to the at least one implantable electrode sufficient to increase the amount of stored charge of the at least one implantable electrode.

In some embodiments, a sensor can be configured to determine the state of charge of the at least one implantable electrode. The controller can be further configured to receive data from the sensor and discontinue at least one of the first current or the second current when an amount of water is being electrolyzed.

In some embodiments, the decrease and increase in amount of stored charge on the at least one electrode are not equal.

In some embodiments, the at least one implantable electrode is configured to deliver at least about 5,000 μC, 25,000 μC, or more of charge into excitable tissue without damaging the excitable tissue.

In some embodiments, the system is devoid of any mechanically moving parts.

In some embodiments, the at least one implantable electrode is at least partially surrounded by an electrolyte solution.

In some embodiments, the high charge density material comprises titanium nitride.

In some embodiments, the controller is configured to maintain the nerve in a hypersuppressed state at least partially preventing conduction of the nerve for at least about 10 minutes after cessation of delivering of the first current.

Also disclosed herein is a method for nerve block of a patient utilizing a rechargeable electrode. The method can include any number of: generating a first current of a first polarity through a titanium nitride implanted electrode proximate a nerve sufficient to at least partially block conduction in the nerve, wherein the electrode generates current in an ionic component proximate the at least one electrode sufficient to create at least a partial block in the nerve and decrease the amount of stored charge in the implanted electrode; and generating a second current of a second polarity opposite the first polarity through the implanted electrode. The second current can increase the amount of the stored charge of the implanted electrode to recharge the implanted electrode.

In some embodiments, a method can also include dynamically sensing the amount of the stored charge in the implanted electrode while delivering the first current; and ceasing delivery of the first current when the amount of the stored charge is sensed to reach a pre-determined threshold value.

In some embodiments, a method can also include discontinuing at least one of the first current signal or the second current signal when an amount of water is being electrolyzed.

In some embodiments, the decrease and increase in amount of stored charge on the at least one electrode are not equal.

In some embodiments, the decrease and increase in amount of stored charge on the at least one electrode are equal.

In some embodiments, the at least one electrode is housed in an insulated enclosure.

In some embodiments, the titanium nitride comprises porous or fractal titanium nitride.

In some embodiments, the titanium nitride electrode generates current sufficient to deliver at least about 5,000 μC, 25,000 μC, or more of charge into excitable tissue without damaging the excitable tissue.

In some embodiments, the titanium nitride electrode generates current sufficient to deliver at least about 25,000 μC of charge into excitable tissue without damaging the excitable tissue.

A method for nerve block of a patient utilizing a rechargeable electrode, comprising: generating a first current of a first polarity proximal to an implanted electrode comprising a high charge density material proximate a nerve sufficient to at least partially block conduction in the nerve, wherein the electrode generates current in an ionic component proximate the at least one electrode sufficient to create at least a partial block in the nerve and decrease the amount of stored charge in the implanted electrode; generating a second current of a second polarity opposite the first polarity through the implanted electrode, wherein the second current increases the amount of the stored charge of the implanted electrode to recharge the implanted electrode; and dynamically sensing the amount of the stored charge in the electrode while delivering the first current; and ceasing delivery of the first current when the amount of the stored charge is sensed to reach a pre-determined threshold value.

In some embodiments, the electrode is created by providing a substrate comprising a high charge density coating material on a surface thereof; and creating a microstructure within the substrate to increase an available electrochemical surface area of the high charge density coating material.

In some embodiments, the substrate comprises titanium or platinum-iridium.

In some embodiments, the coating material comprises porous titanium nitride.

In some embodiments, the high charge density coating material can include one or more of: iridium oxide, Poly(3,4-ethylenedioxythiophene)-poly(styrenesulfonate) (PEDOT), titanium nitride (TiN), fractal titanium nitride, porous titanium nitride, or a combination thereof.

In some embodiments, the high charge density coating material comprises titanium nitride.

In some embodiments, creating a microstructure comprises micromachining the substrate material.

In some embodiments, micromachining comprises electric discharge machining.

In some embodiments, creating a microstructure comprises using one or more of: material etching techniques, pattern masking and etching techniques, bead or grit blasting, and surface sanding.

In some embodiments, creating a microstructure comprises laser texturing.

In some embodiments, laser texturing comprises creating spaced-apart channels or grooves in the tubular member.

In some embodiments, the channels or grooves comprise a spiral or circumferential geometry with respect to a long axis of the tubular member.

In some embodiments, creating a microstructure comprises foaming.

In some embodiments, creating a microstructure comprises sintering.

In some embodiments, creating a microstructure comprises increasing an available electrochemical surface area by at least about 2×.

In some embodiments, creating a microstructure comprises increasing an available electrochemical surface area by at least about 5×.

In some embodiments, creating a microstructure comprises increasing an available electrochemical surface area by at least about 10×.

In some embodiments, the substrate comprises a tubular member.

In some embodiments, the substrate comprises a material sheet.

In some embodiments a current delivery system or method could include any number of features or combination of features as disclosed herein.

BRIEF DESCRIPTION OF THE DRAWINGS

FIG. 1I shows a similar configuration to FIG. 1H but also includes a feedback sensor that monitors the state of the nerve tissue and/or region proximal to the nerve N.

FIG. 1J illustrates current vs. time and nerve block status vs. time charts similar to FIG. 1I.

Figure 2B:
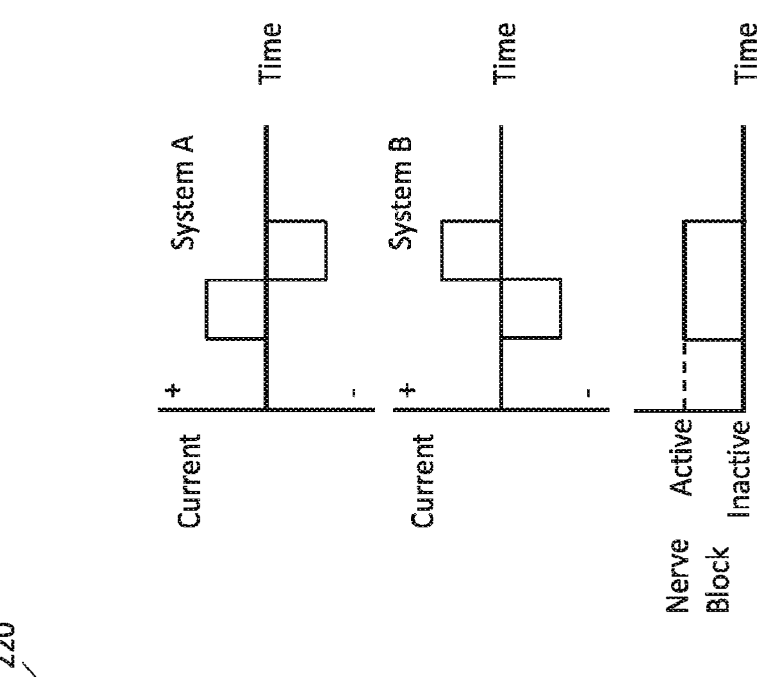
FIG. 2A shows a dual electrode system in which two EICCCs interface with a nerve, according to some embodiments.

As shown in the graphs of FIG. 2B, two electrodes are driven with currents of opposite polarities as a function of time such that when one is in an active blocking phase, the other is in an inactive non-blocking phase which resets the electrode for blocking once the current polarity is again reversed.

Figure 3B:
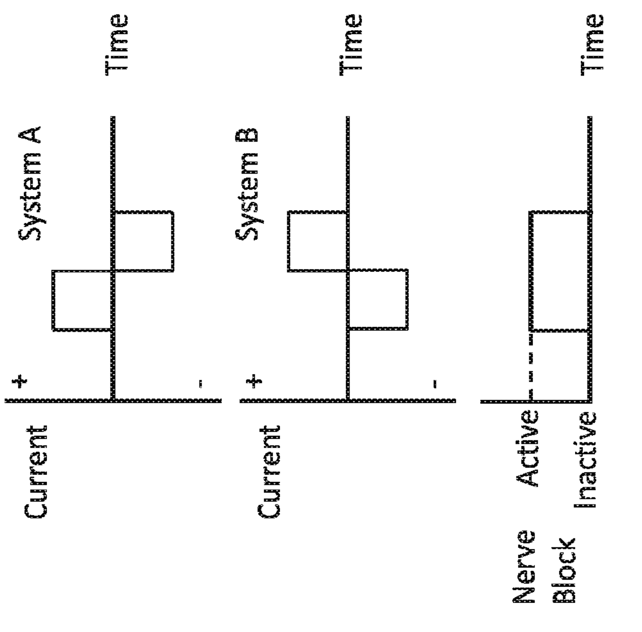
Figure 3A:
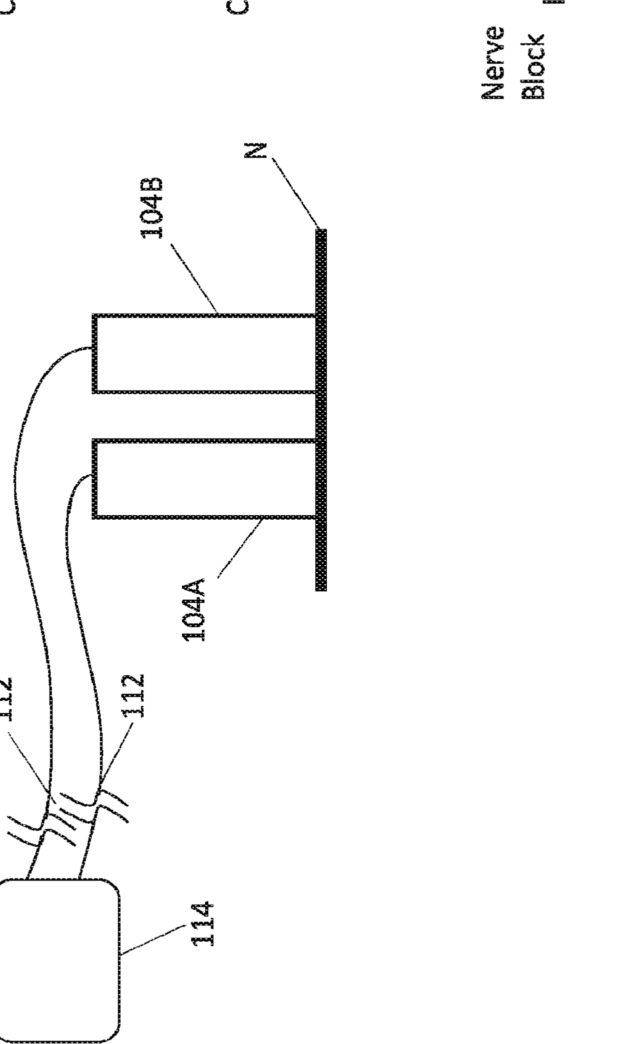

FIGS. 3A-B show an embodiment where dual traditional electrodes interface with a nerve but are driven from a current source via electrically insulated leads with currents of opposite polarities such that when one is in a blocking phase, the other is in a non-blocking phase which resets the electrode for blocking once the current polarity is again reversed.

FIGS. 3C-D show an embodiment where dual EICCCs interface with a nerve N but are driven with currents of opposite polarities such that when one is in a blocking phase, the other is in a non-blocking phase which resets the electrode for blocking once the current polarity is again reversed.

Figure 4A:
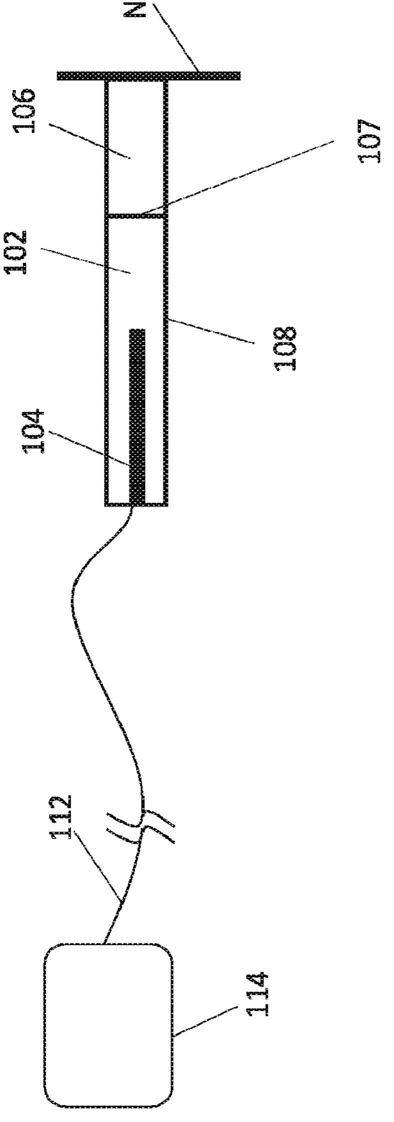

FIG. 4A shows an embodiment of an EICCC electrode in which an electrode is immersed in an electrolyte solution which fluidly in is contact with an ion-conductive material such as a hydrogel, gel or other polymer that electrically contacts the nerve tissue or area proximal to the nerve tissue.

Figures 4B, 4C:
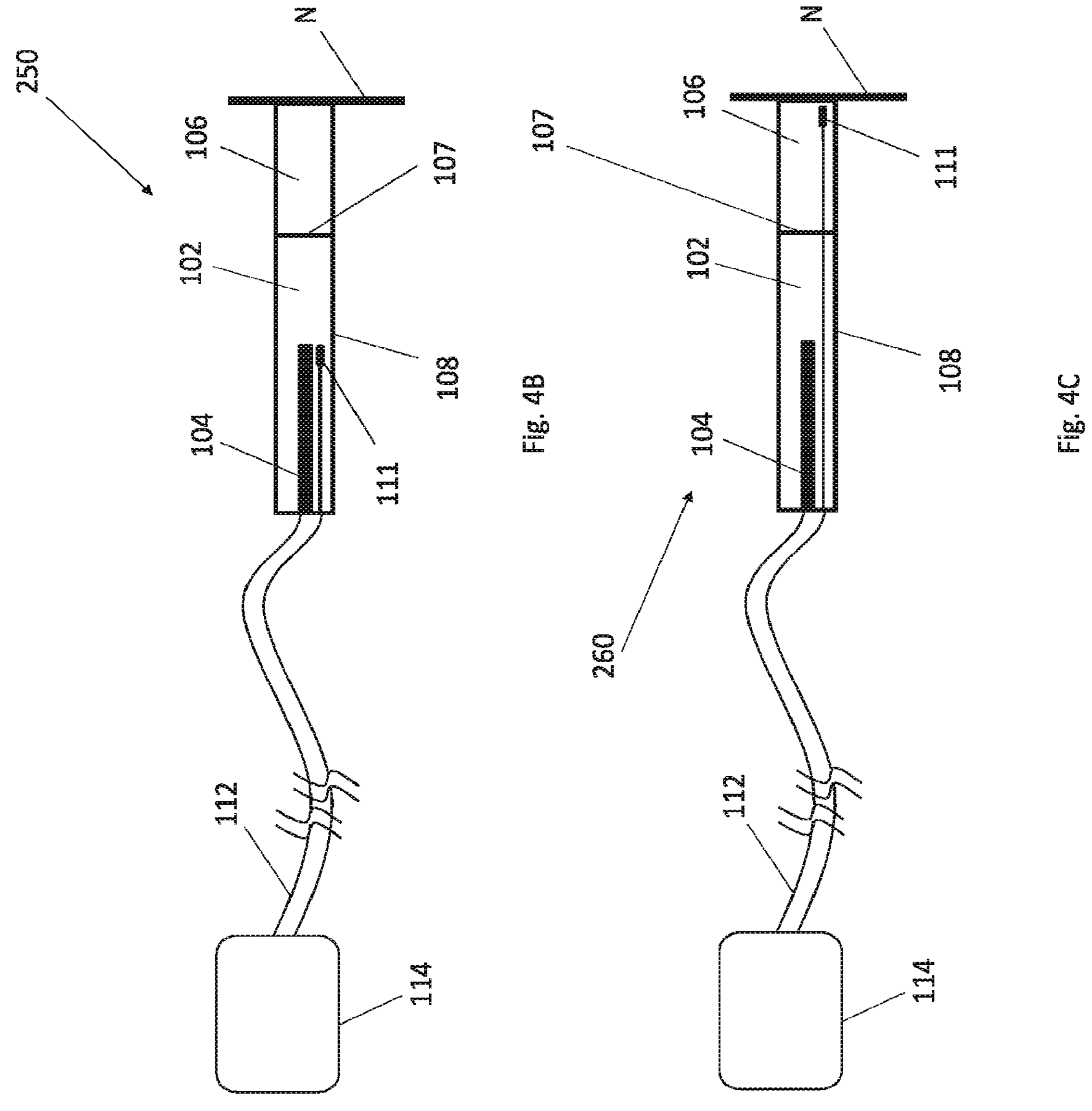

FIG. 4B shows a system similar to that shown in FIG. 4A with the addition of a reference electrode in proximity to the electrode (working electrode) to monitor voltage drop across the working electrode for EICCC monitoring purposes.

FIG. 4C shows a system similar to that shown in FIG. 4A with the addition of a reference electrode in proximity to the nerve tissue interface to monitor voltage drop across the EICCC to the nerve tissue for EICCC monitoring purposes.

Figures 4D, 4E, 4F:
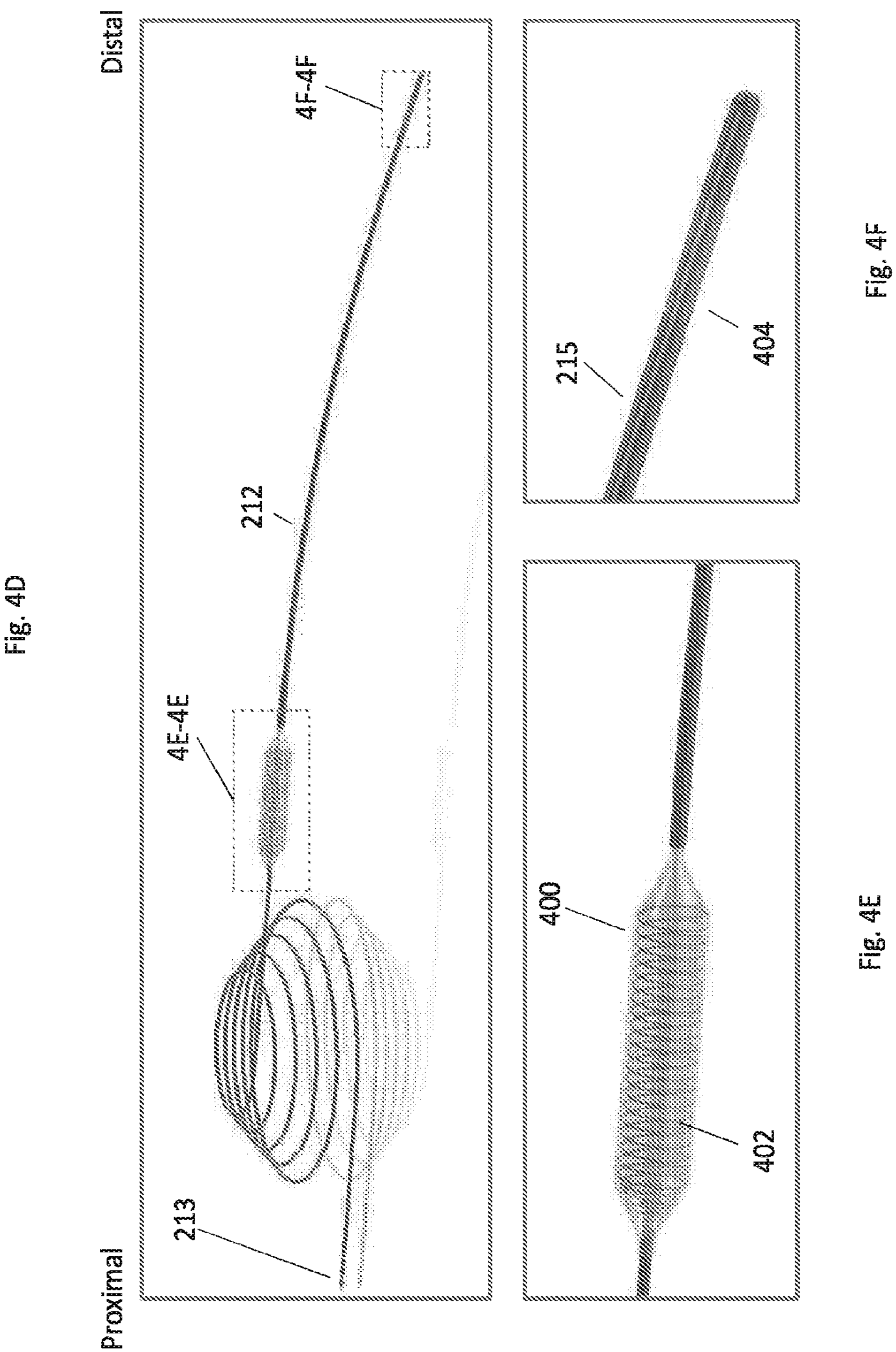

FIGS. 4D-4F show an embodiment of an electrode lead configured to plug into and extend from a current source (not shown, near end) that might take the form of conventional IPGs (implantable pulse generators).

Figure 4G:
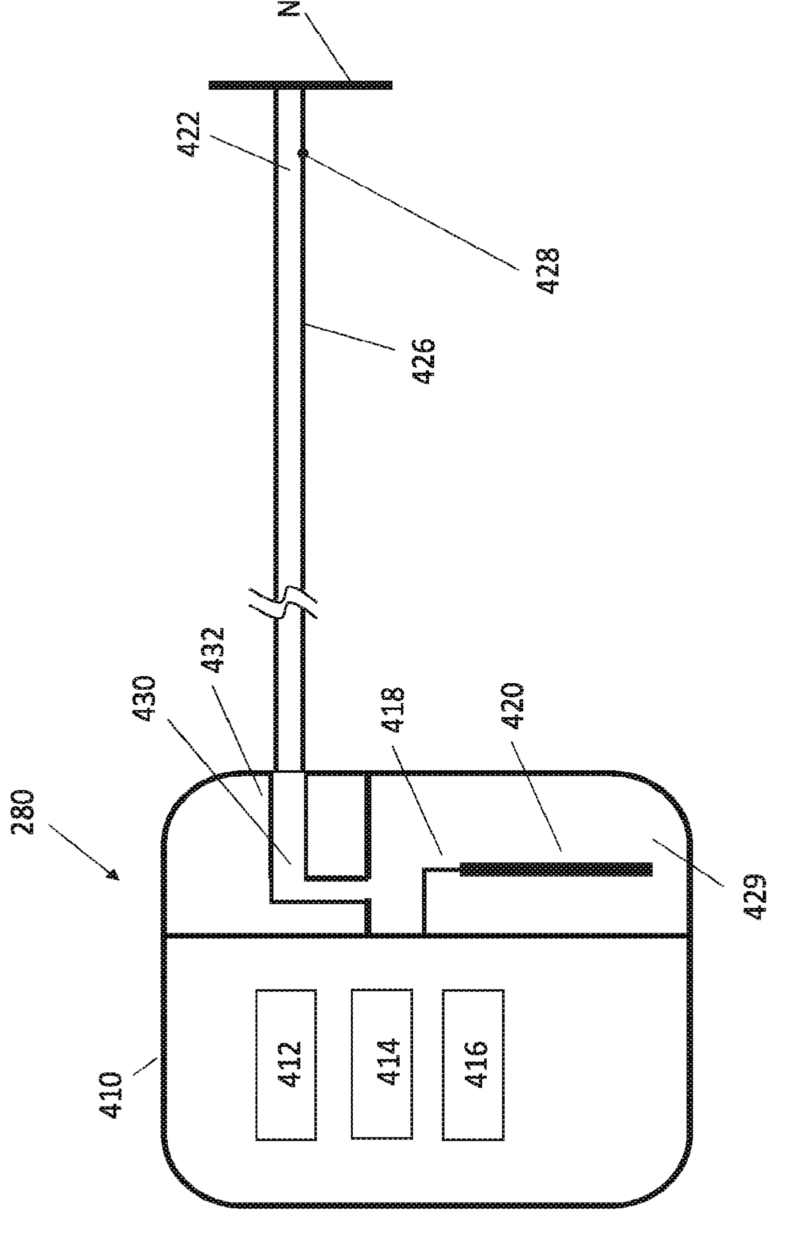

FIG. 4G shows a schematic embodiment of an EICCC integrated within a hermitically sealed enclosure which contains the current source, battery or power supply, and controller to drive the EICCC.

Figures 5A, 5B:
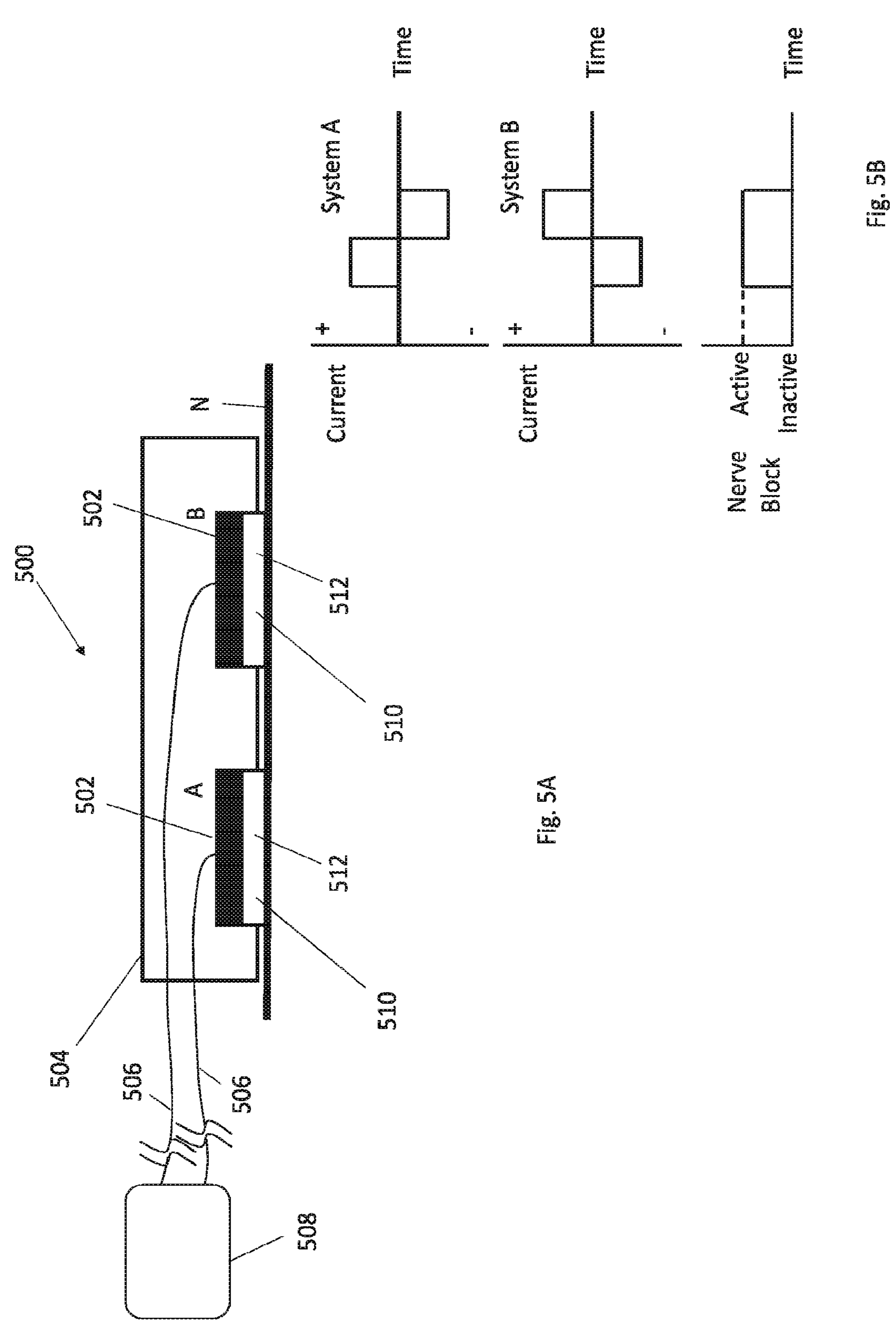

FIGS. 5A-B show an embodiment of an electrode configuration in which two electrode contacts are housed within the same electrically insulated enclosure.

Figure 6A:
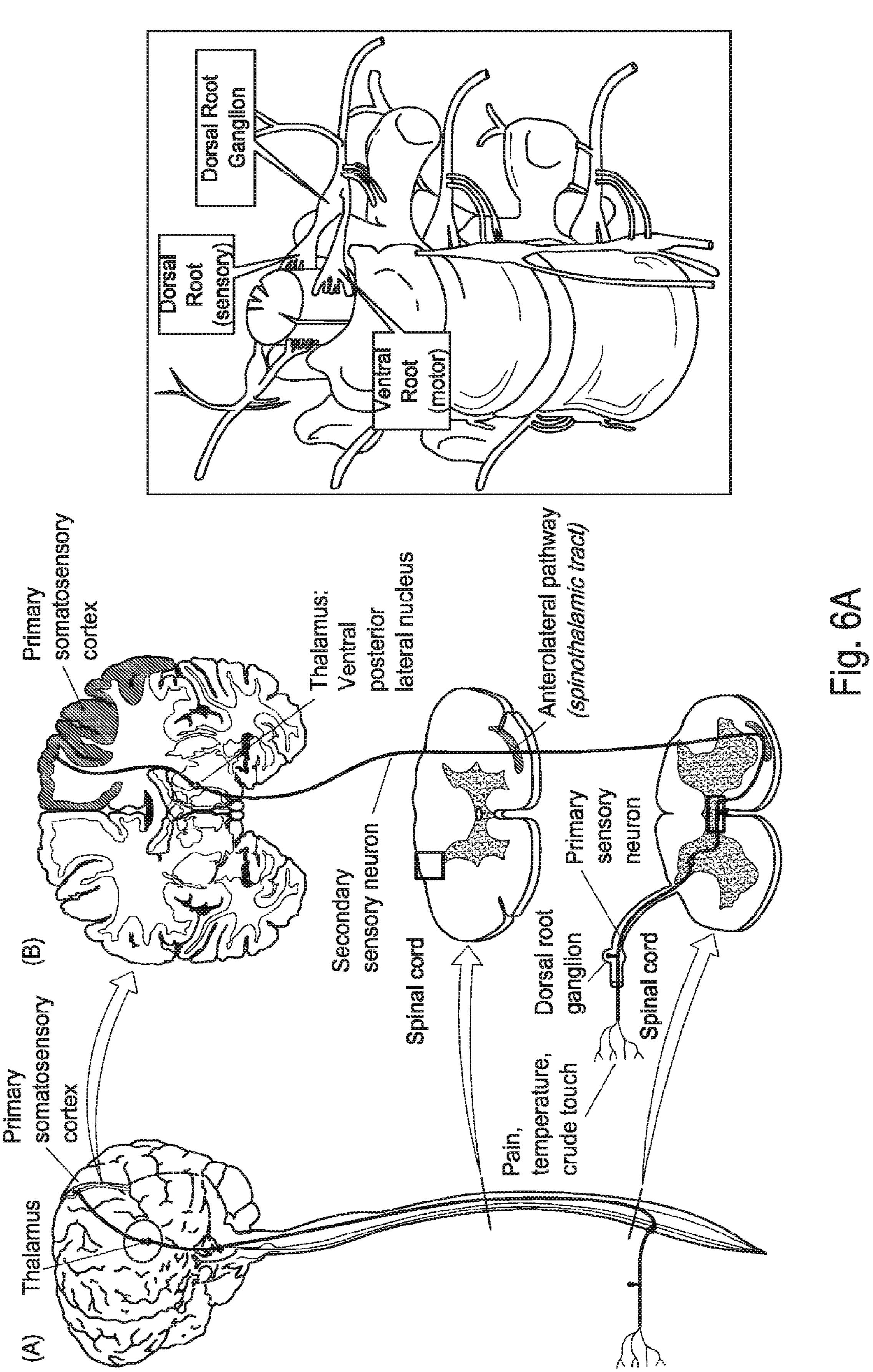

FIG. 6A illustrates a dorsal root, and/or dorsal root ganglion (DRG) through which pain signals pass.

Figure 6B:
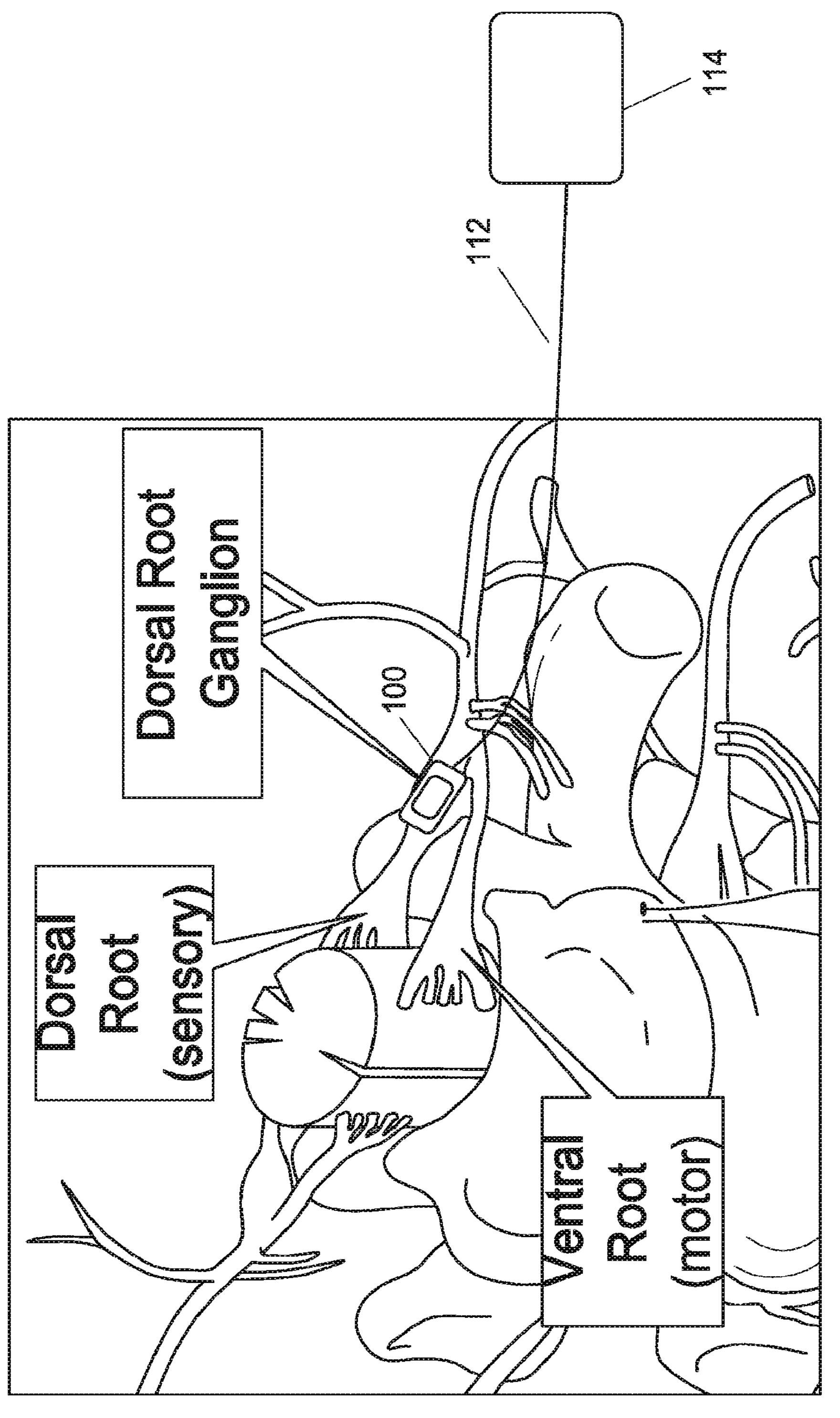

FIG. 6B shows an embodiment of a blocking electrode positioned along a DRG to facilitate nerve block along with lead and current source.

Figure 6C:
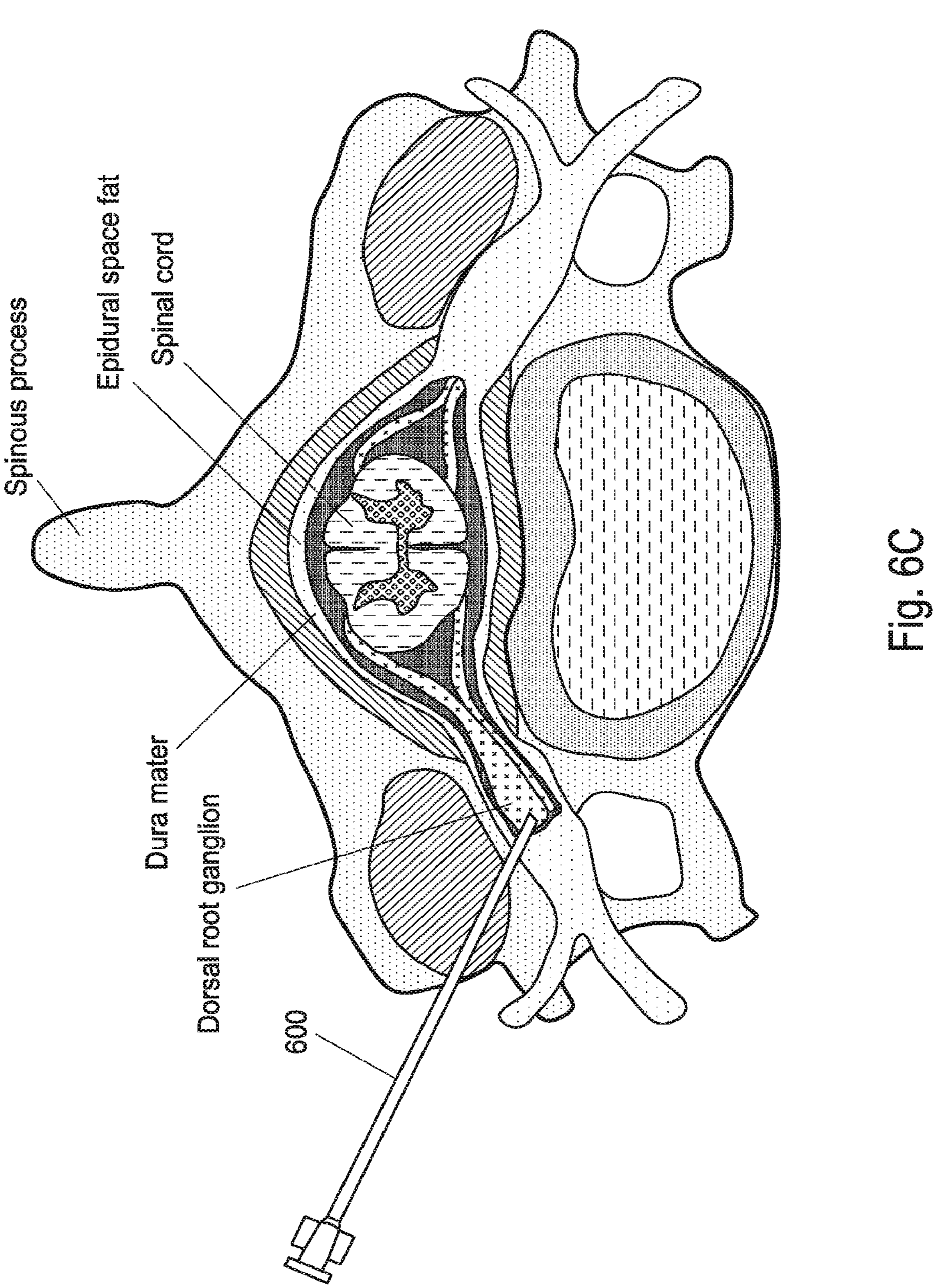

FIG. 6C illustrates that a DRG can be accessed with a needle, and the needle can be used to penetrate the dura mater as shown.

Figures 6D, 6E:
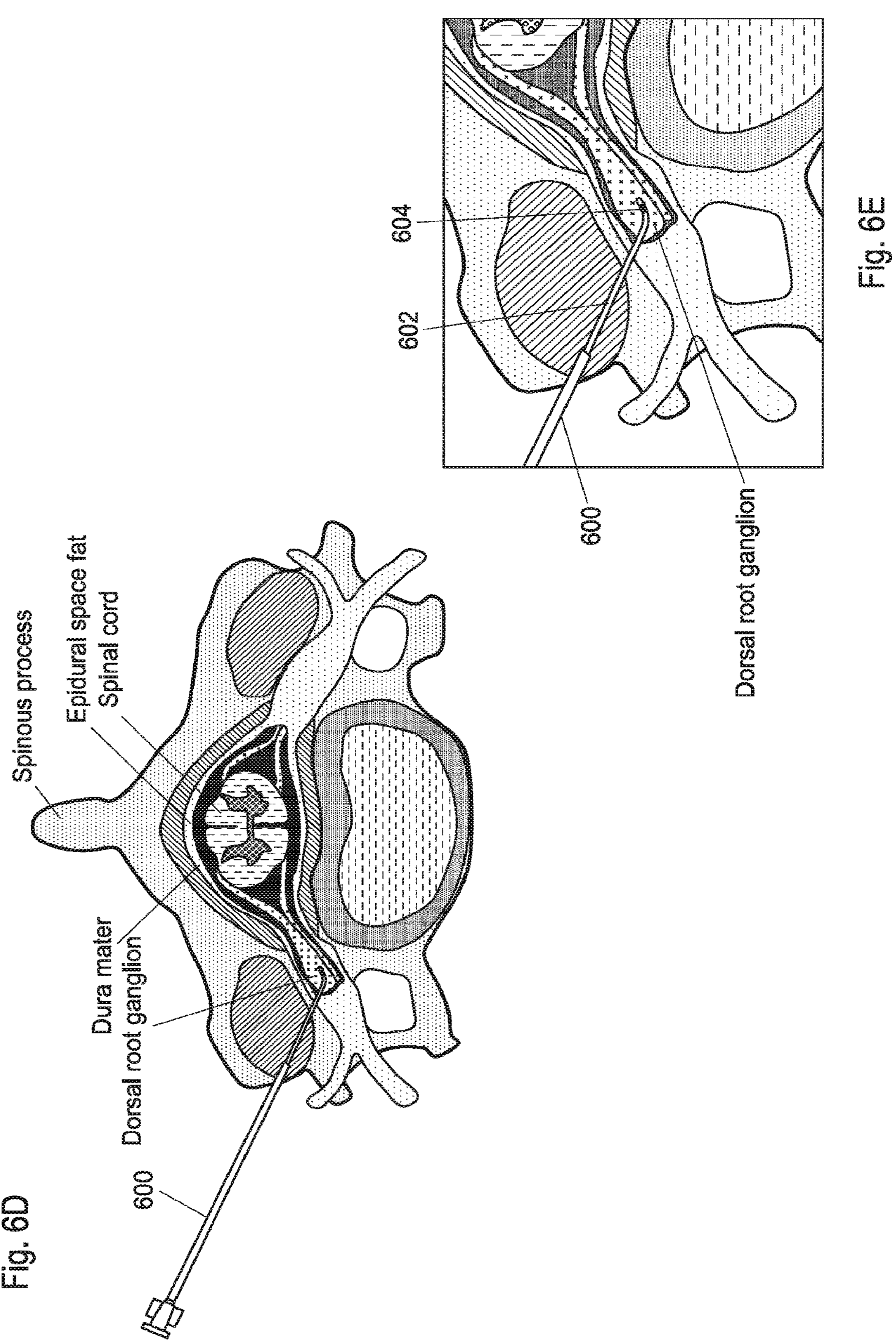

As shown in FIG. 6D and FIG. 6E, the electrode-nerve interface contacts can then be positioned in contact or proximal to the DRG and the introducing needle can be retracted to leave the electrode lead and nerve tissue interface in the desired position.

Figure 7:
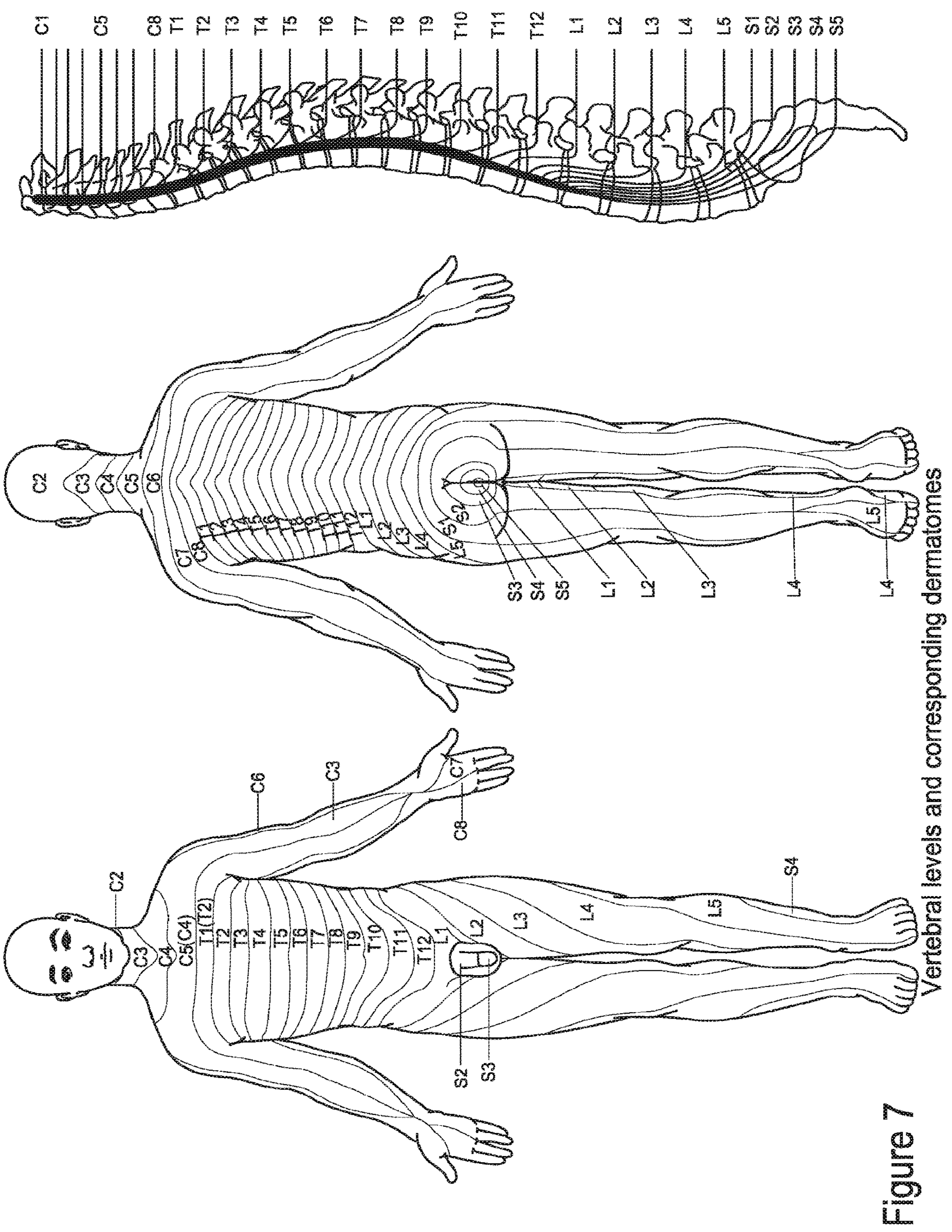

FIG. 7 shows associated dorsal root ganglia from each vertebral level correspond to specific dermatomes in the body, and blocking pain signals at the DRG level can reduce pain sensation at the innervated dermatome for that specific DRG.

Figure 8A:
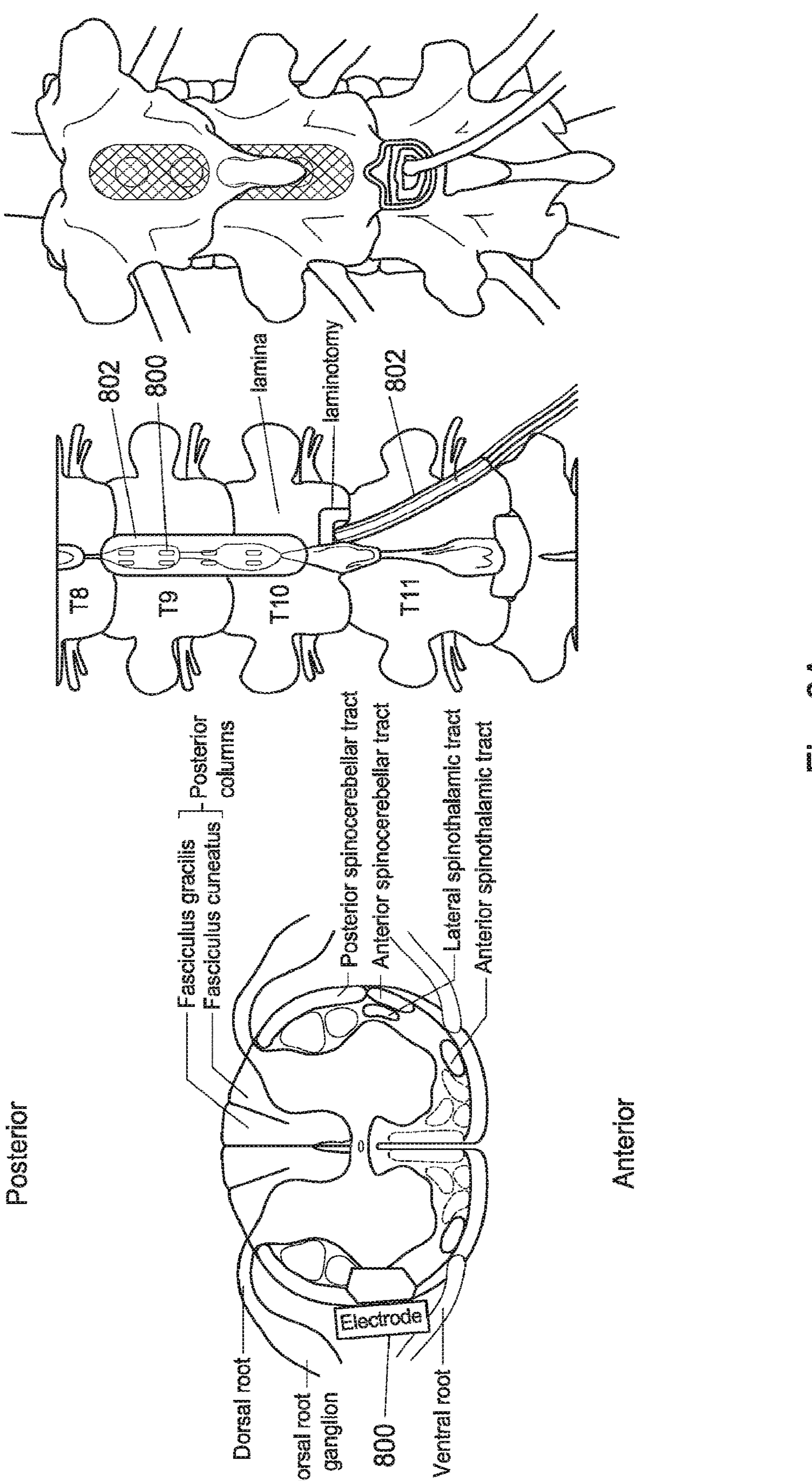

FIG. 8A illustrates placement of stimulating electrodes in proximity to the lateral spinothalamic tract (LT tract), which can leverage an EICCC to generate a nerve block at the desired level (and/or spinal levels distal (away from the head) to the EICCC since pain signals travel in the superior direction) and provide selective pain block depending on unilateral (left or right) or bilateral placement of electrodes.

Figure 8B:
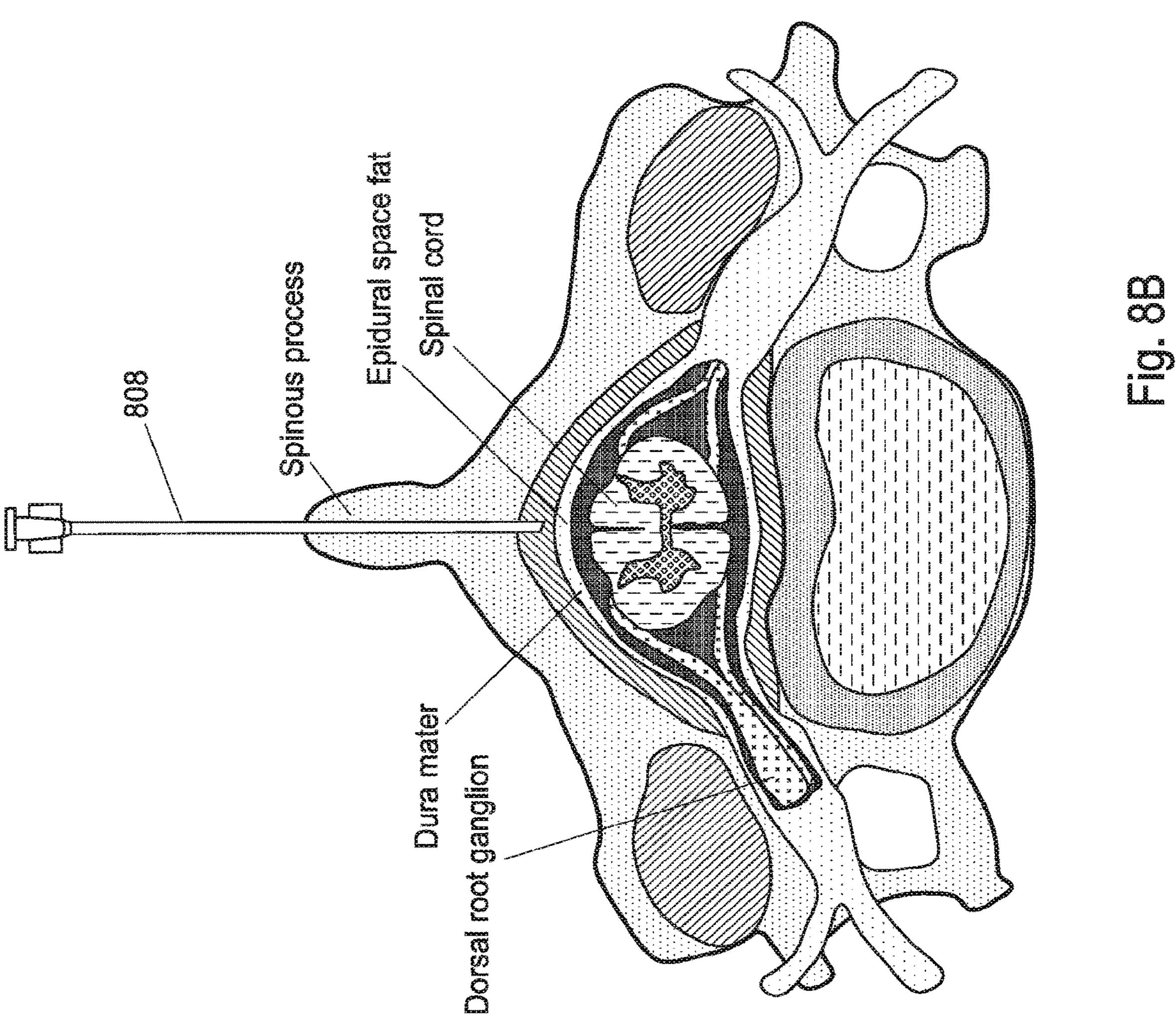

FIG. 8B illustrates a percutaneous placement procedure with or without fluoroscopic guidance such as by using a Tuohy or similar needle to introduce the electrode lead into the epidural space.

Figures 8C, 8D, 8E:
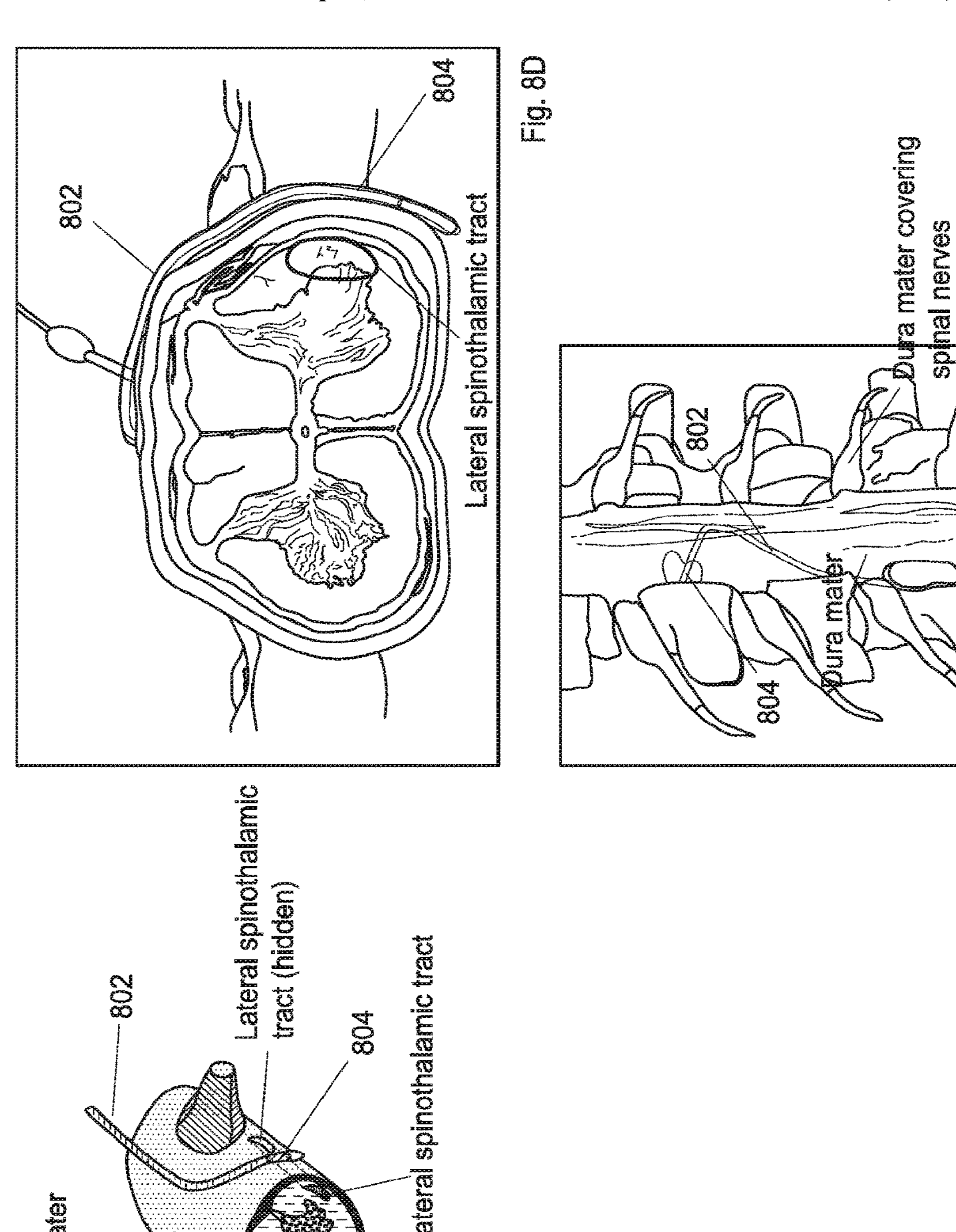

The leads can be directed along the spinal column within the epidural space such that the lead is between spinal nerve exit regions and the tissue interface is in proximity to the lateral spinothalamic tract as illustrated in FIGS. 8C-8E.

Figure 9A:
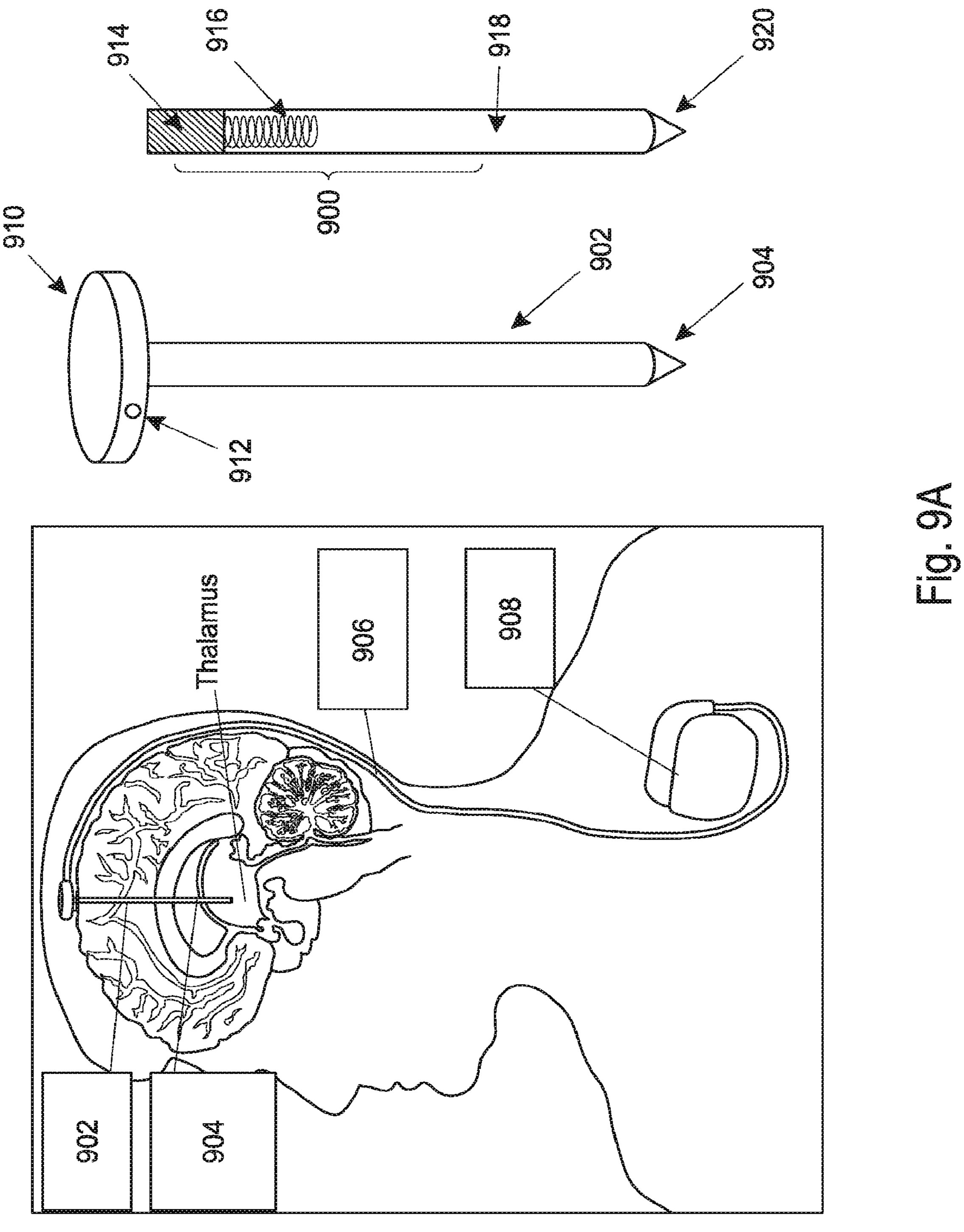

FIG. 9A shows an electron-ion current conversion cell (EICCC) electrode configured to interface with a deep brain block (DBB) target in the thalamus.

Figure 9B:
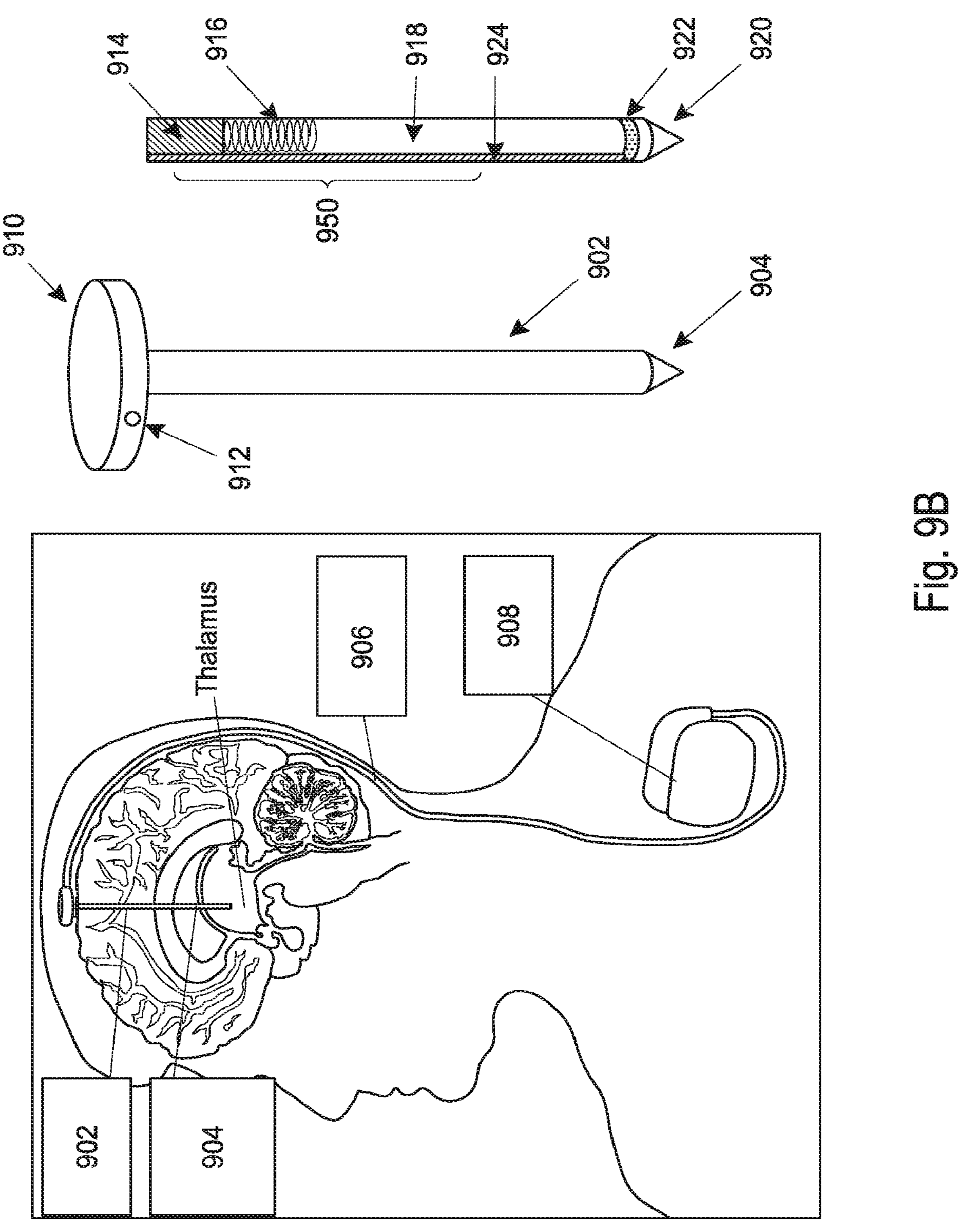

In FIG. 9B an embodiment of a blocking/suppressing electrode with an integrated sensing electrode is shown.

Figures 10A, 10B, 10C:
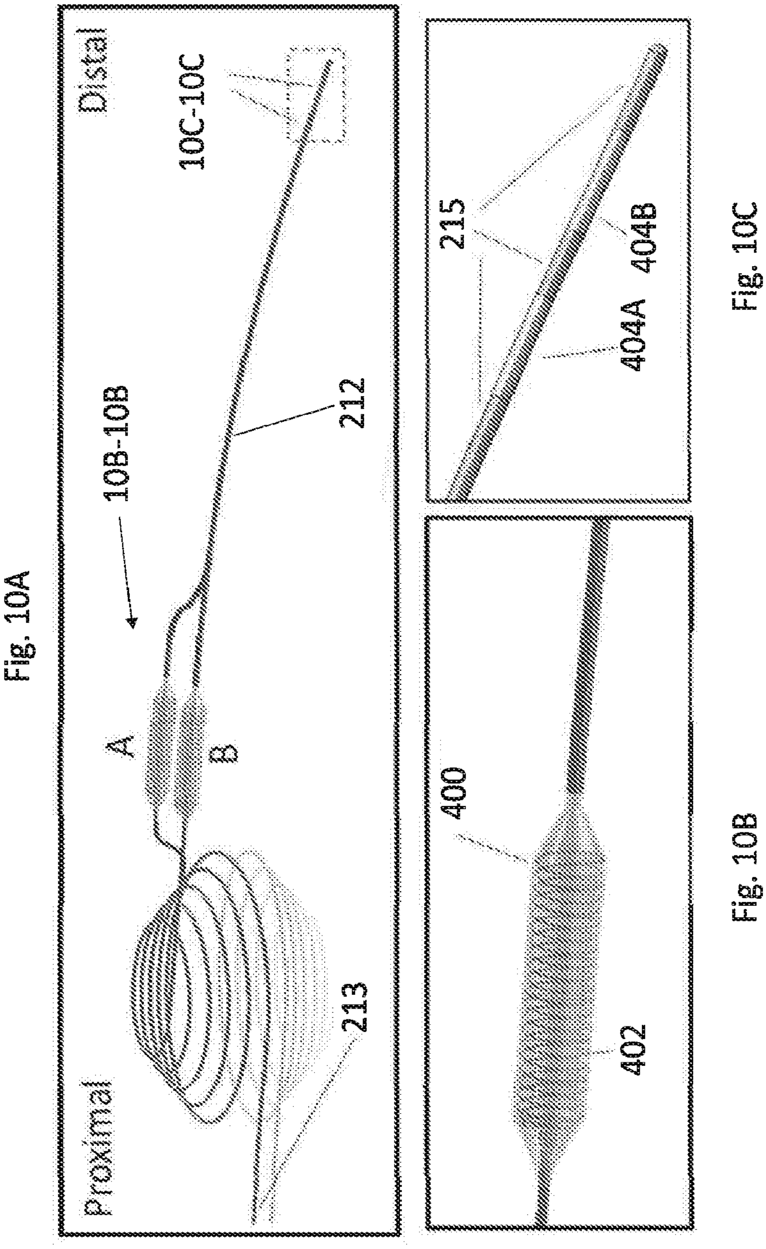

An embodiment of an EICCC electrode is shown in FIGS. 10A-10C in which multiple tissue interfaces are present on the electrode and are individually addressable.

FIG. 10B is a close-up view of 10B-10B of FIG. 10A.

FIG. 10C is a close-up view of 10C-10C of FIG. 10A.

Figure 11:
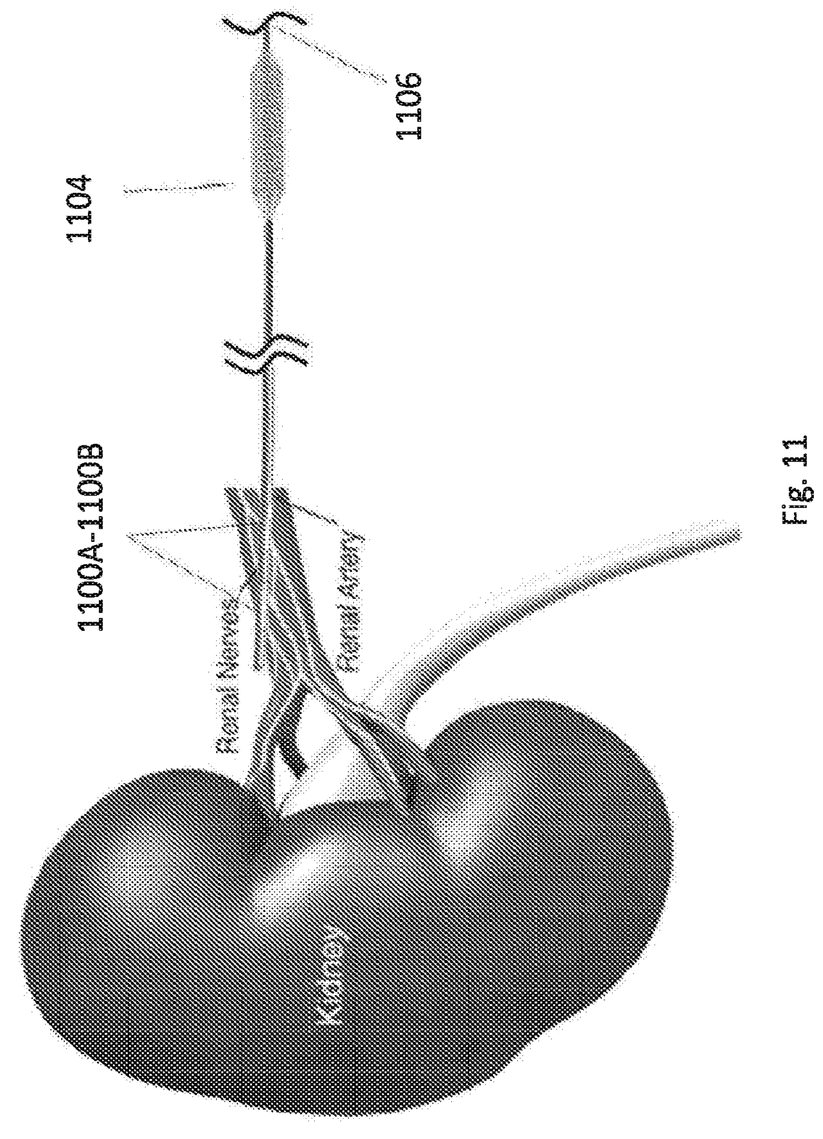

As shown in FIG. 11, the blocking electrode leads contact the renal nerves to facilitate a block or suppression Also systematically illustrated is EICCC openly connected at to current source (not shown).

Figure 12:
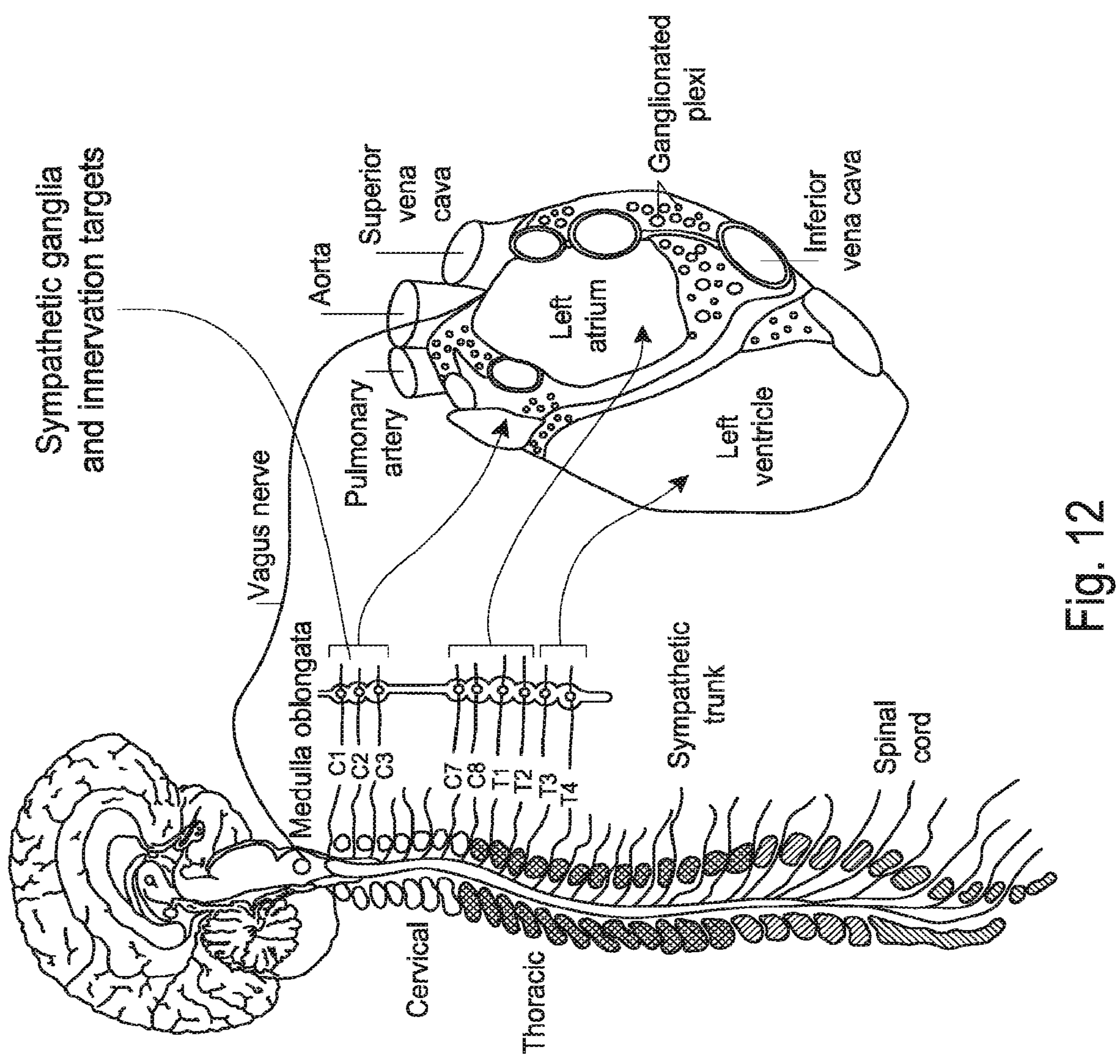

As shown in FIG. 12, the relevant sympathetic ganglia including the cervical and stellate (cervicothoracic) ganglia are shown along with their innervation targets in the heart.

Figures 13, 14:
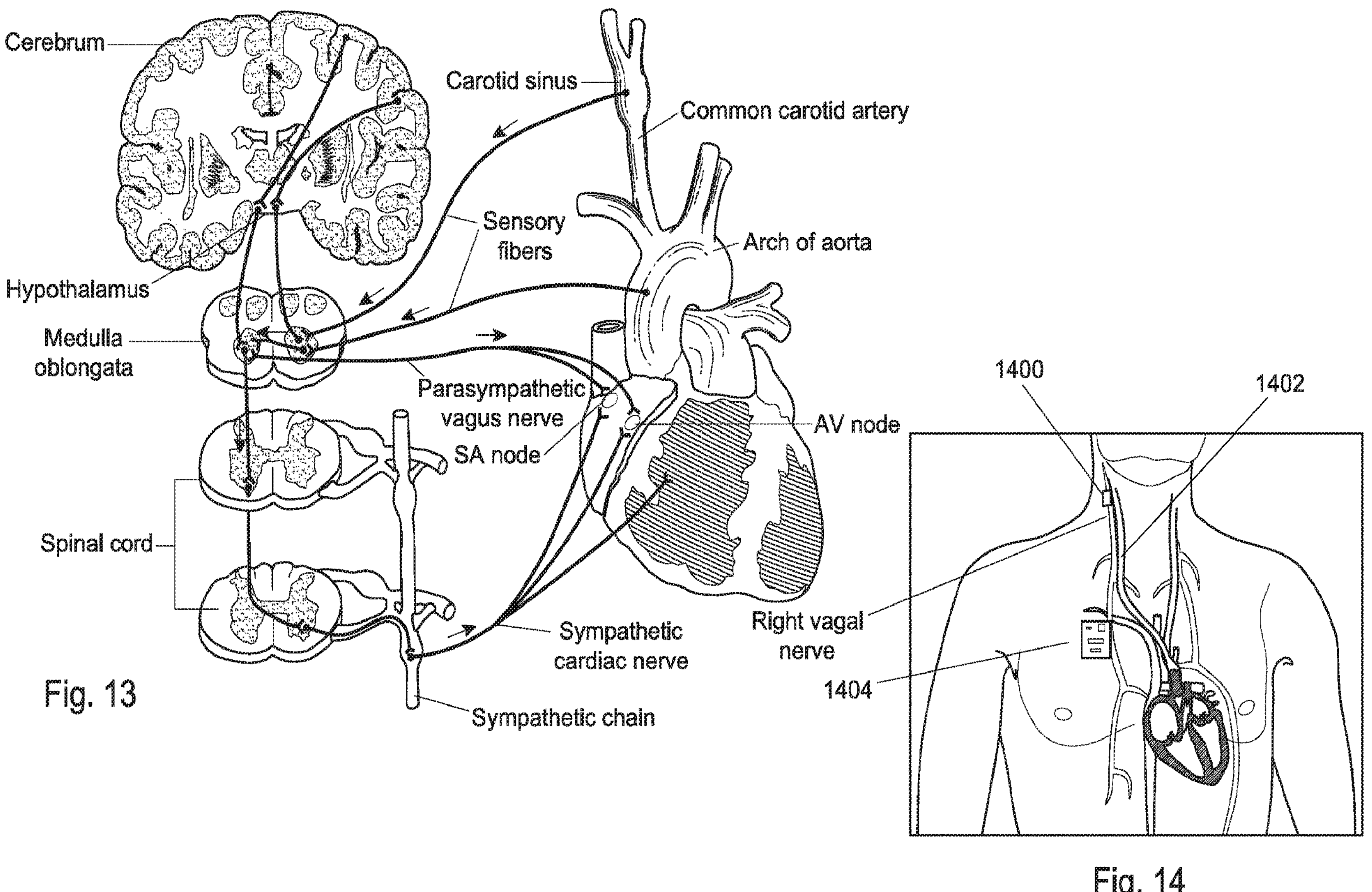

FIG. 13 illustrates select sympathetic nervous system-related anatomy.

FIG. 14 illustrates an embodiment of an EICCC electrode placed around or in proximity to the right (and/or left) vagus nerve within the right side of the neck and/or chest with an electrode lead running down toward an implantable current source shown in the right pectoral region.

Figures 15, 16:
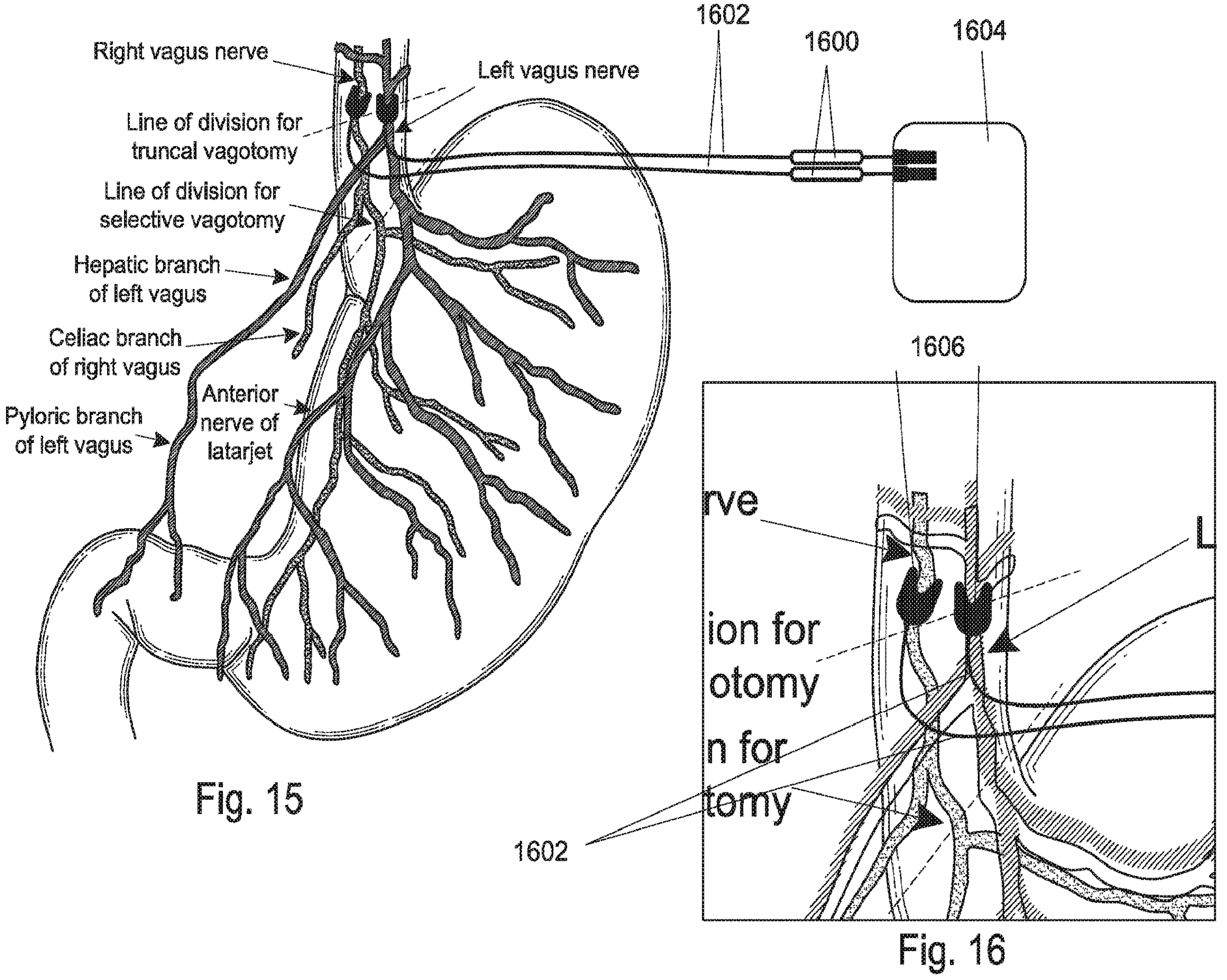

FIGS. 15-16 illustrate an embodiment of a dual EICCC system in which each vagus nerve is wrapped in a cuff-format tissue interface at which ionic current is deposited at the tissue site from the EICCCs.

Figures 17, 18:
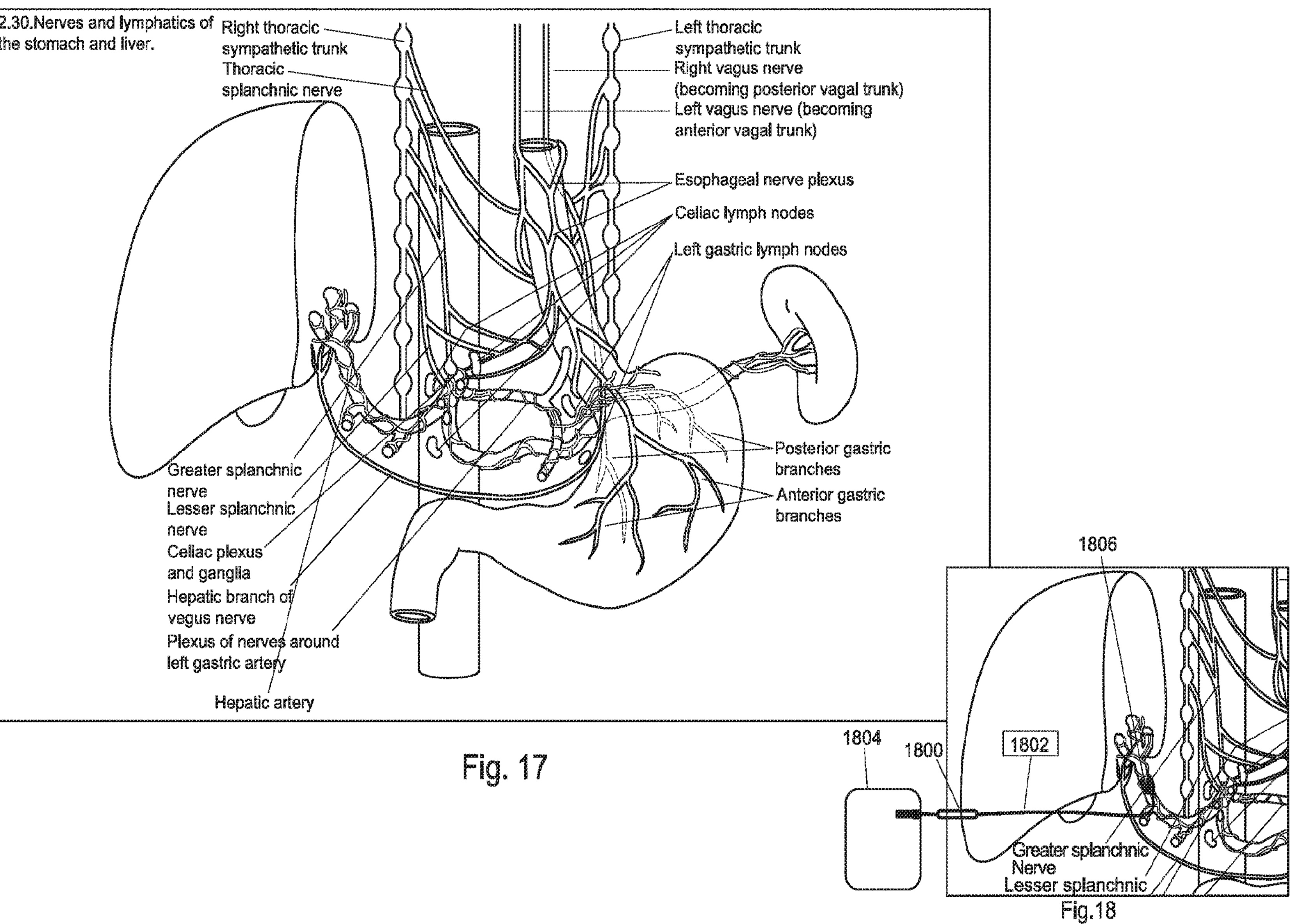

FIG. 17 schematically illustrates non-limiting anatomy where sympathetic nerve suppression or block can also be used to regulate hepatic function and influence glucose and insulin production.

FIG. 18 illustrates an EICCC system in which the nerves around the hepatic artery and the artery are surrounded by a cuff-format tissue interface, according to some embodiments of the invention.

Figure 19:
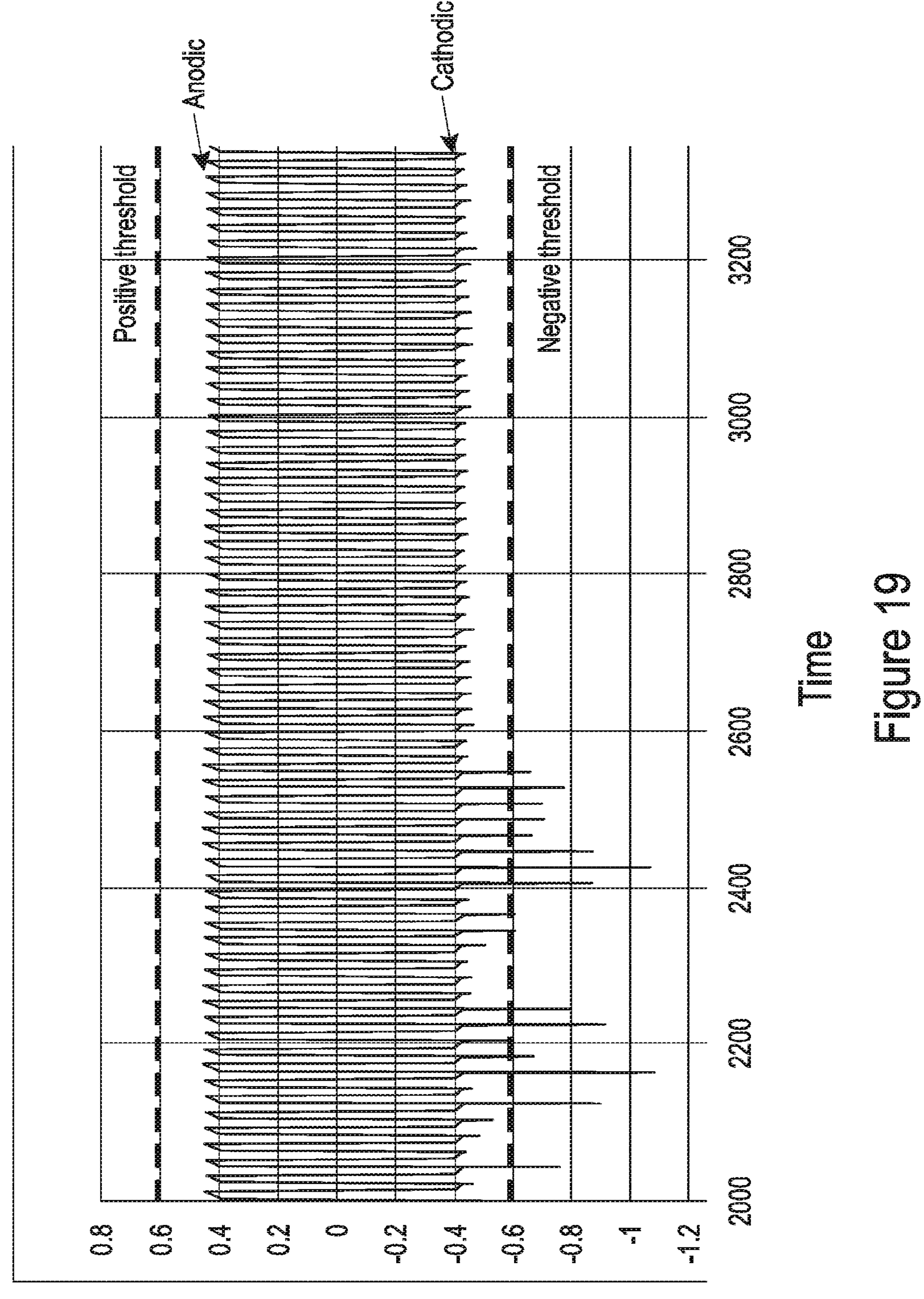

FIG. 19 illustrates a driving voltage waveform and positive and negative thresholds over a period of time.

Figure 20:
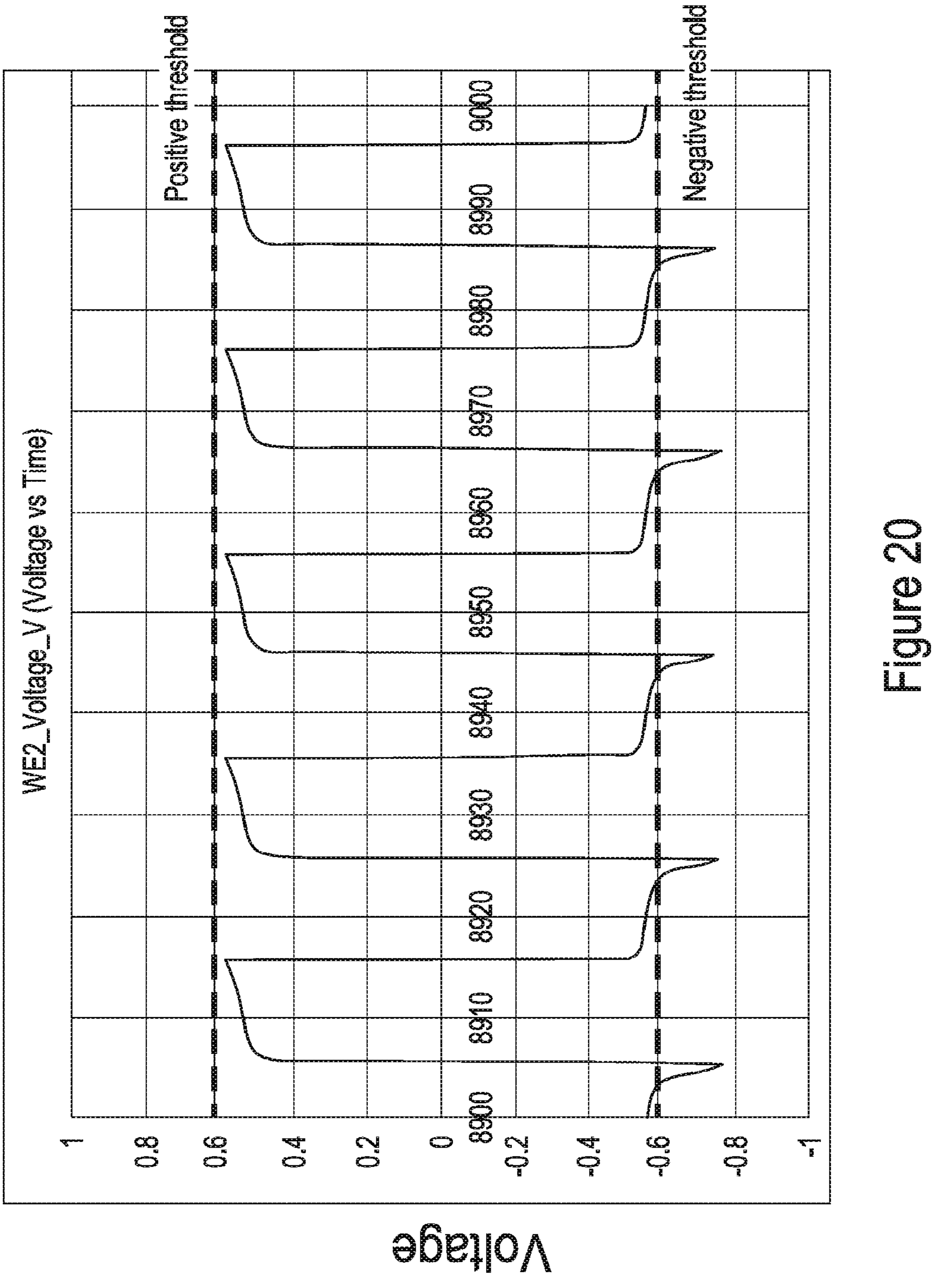

FIG. 20 illustrates a driving voltage waveform, and positive and negative thresholds over a period of time.

Figure 21:
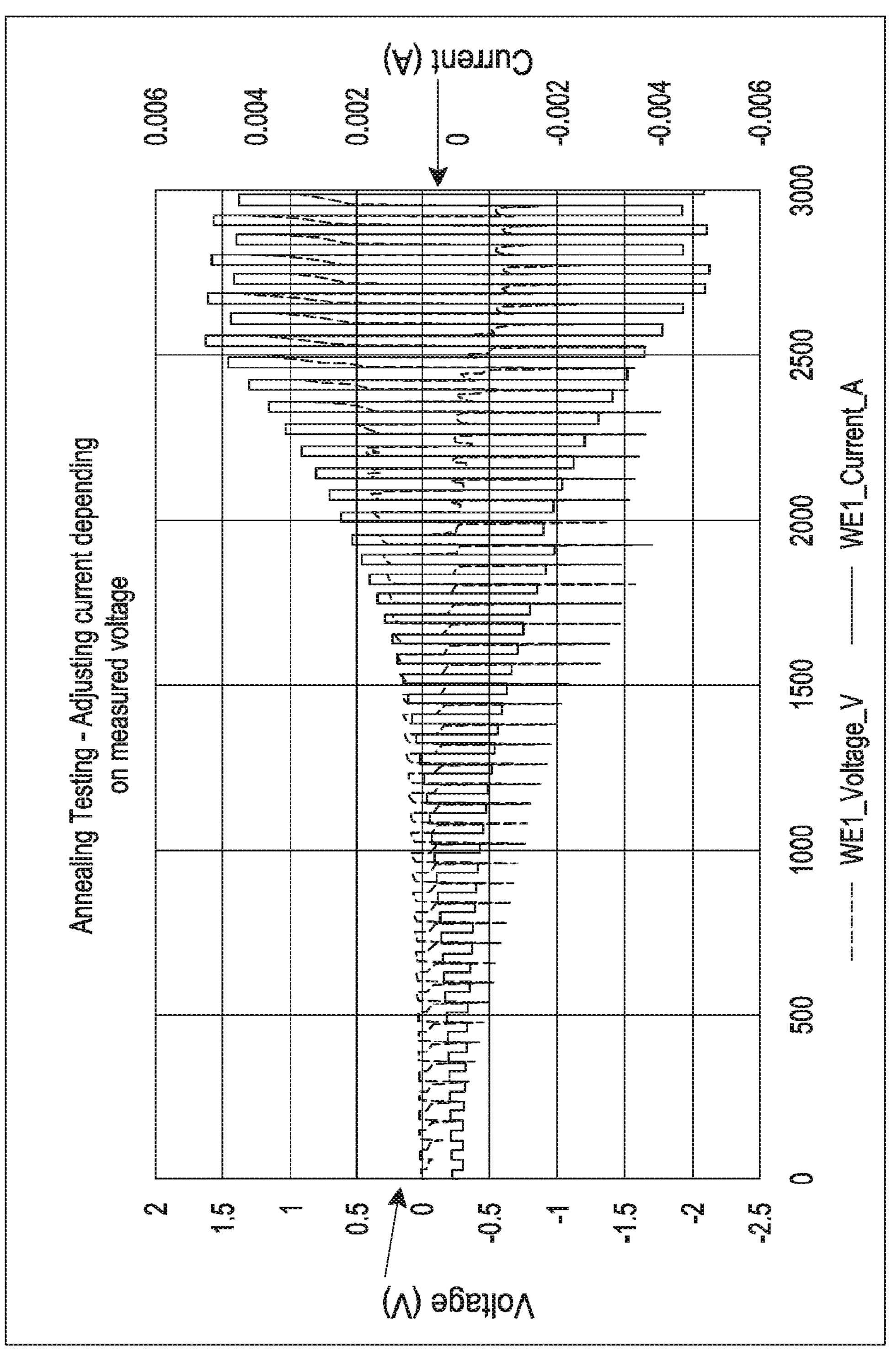

FIG. 21 illustrates schematically a voltage and current versus time graph illustrating an electrode annealing process in which the current amplitude is being ramped to a set target while the driving voltage is held below a set threshold.

Figure 22:
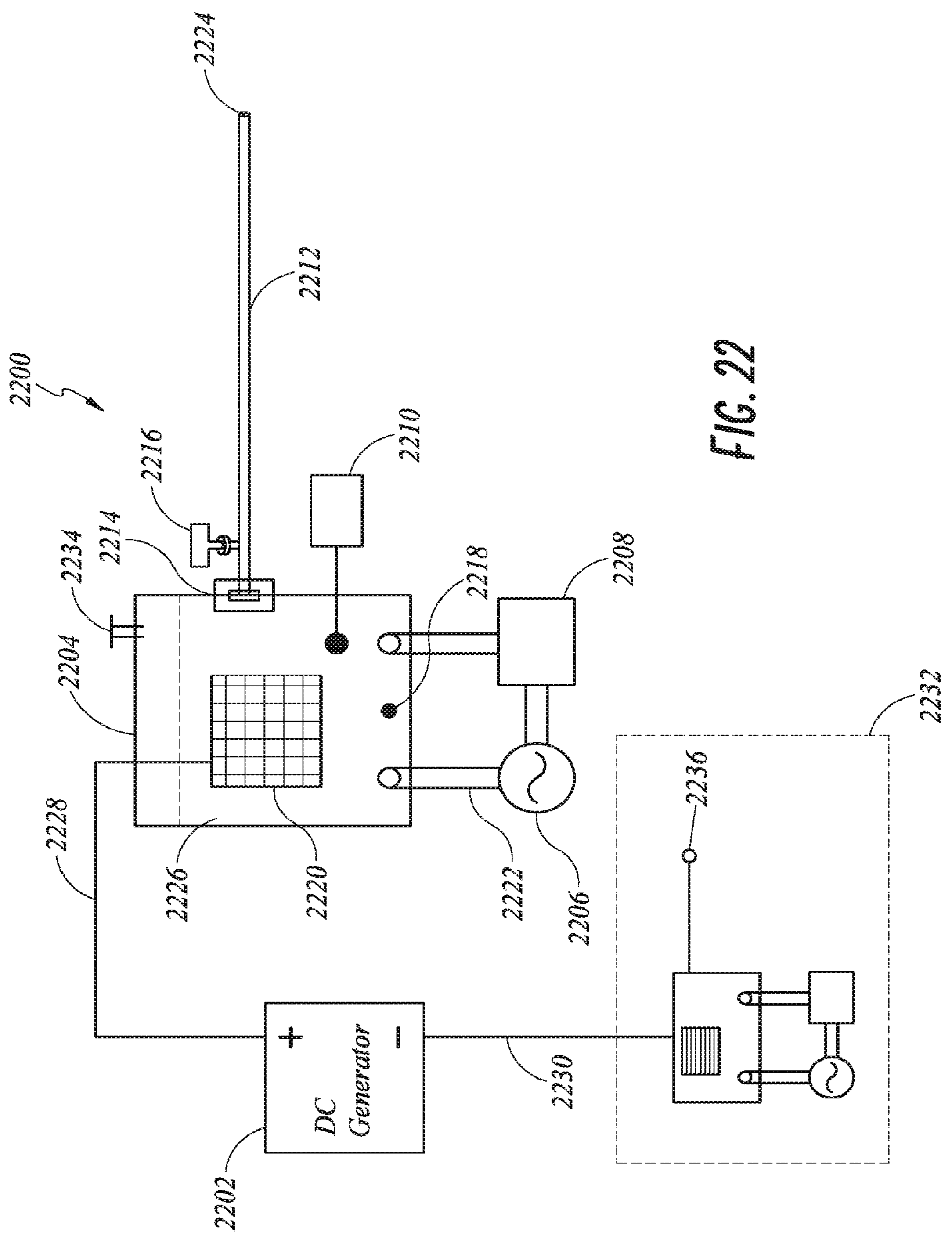

FIG. 22 illustrates a system that can include a nerve-tissue interface operably connected to a catheter configured to hold a liquid.

Figures 23A, 23B:
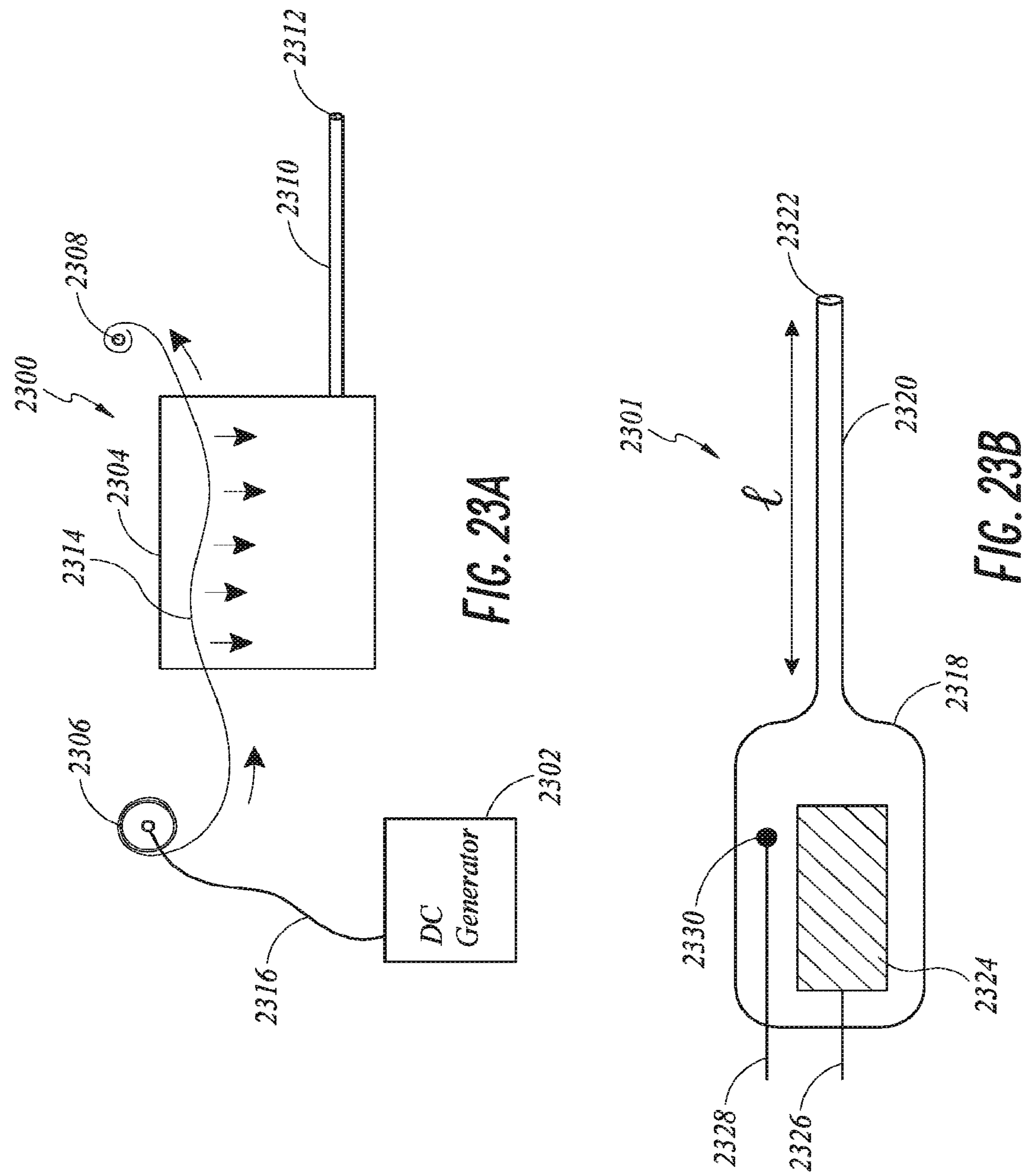

FIG. 23A illustrates a system including a reaction chamber including a reaction material.

FIG. 23B illustrates a separated interface nerve electrode that can include an integrated sensor for detecting the electrochemical status of a reaction/working electrode.

Figure 24:
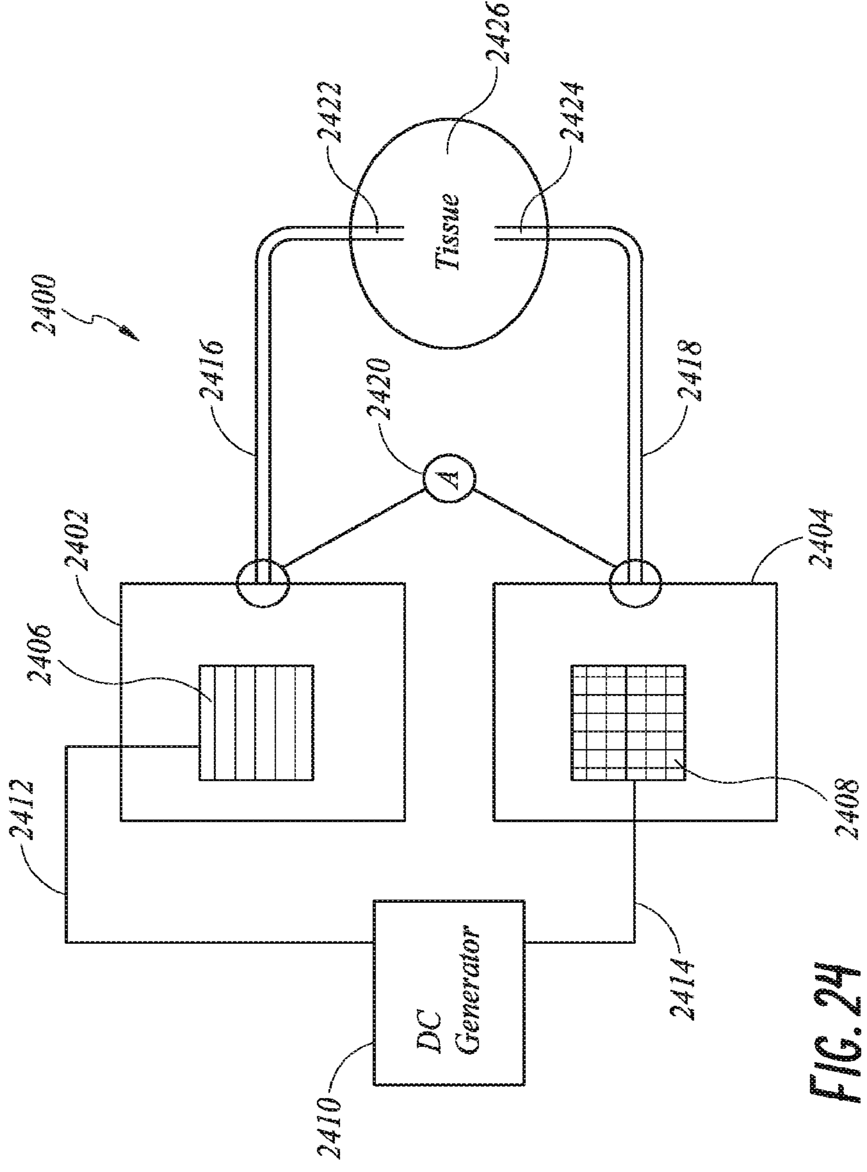

FIG. 24 illustrates that systems and methods can utilize battery-type chemistries to deliver DC current to tissue, such as lead-acid battery, nickel-cadmium, nickel metal hydride, lithium ion, lithium polymer, zinc-carbon, biobatteries, or other types of battery chemistries.

FIG. 24 illustrates that systems and methods can utilize battery-type chemistries to deliver DC current to tissue.

Figure 25:
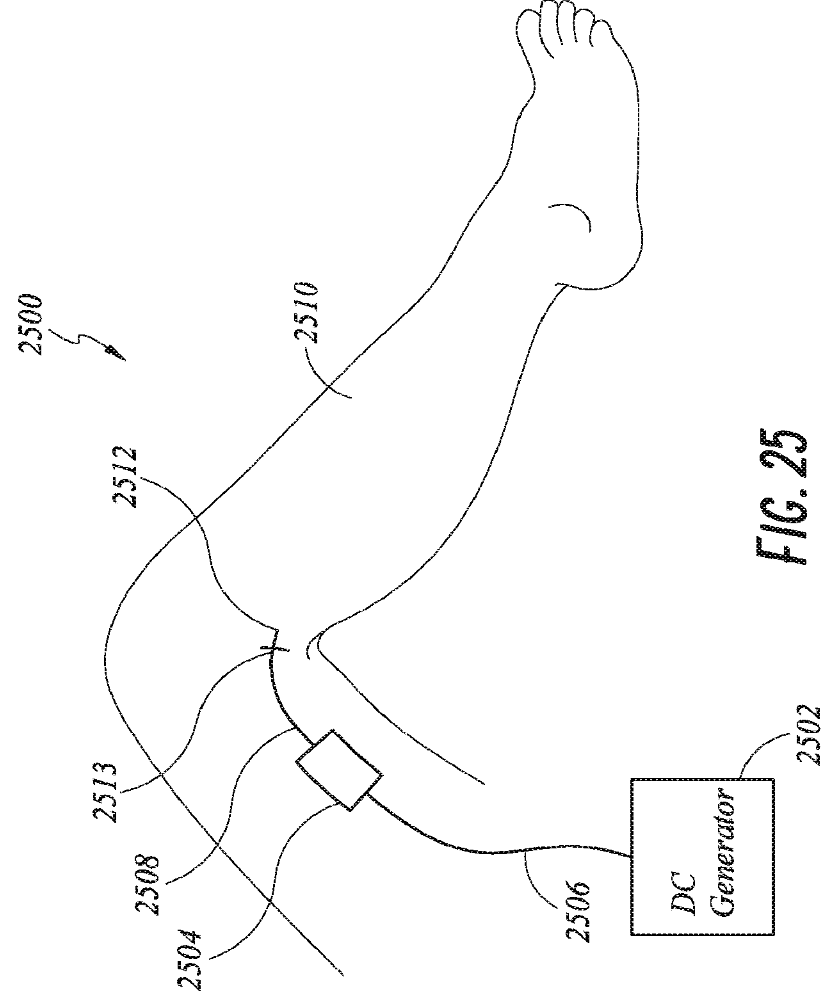

FIG. 25 illustrates schematically a SINE-type electrode modified to allow for attachment at the site of the patient to reduce the length and the impedance of the catheter.

Figure 26B:
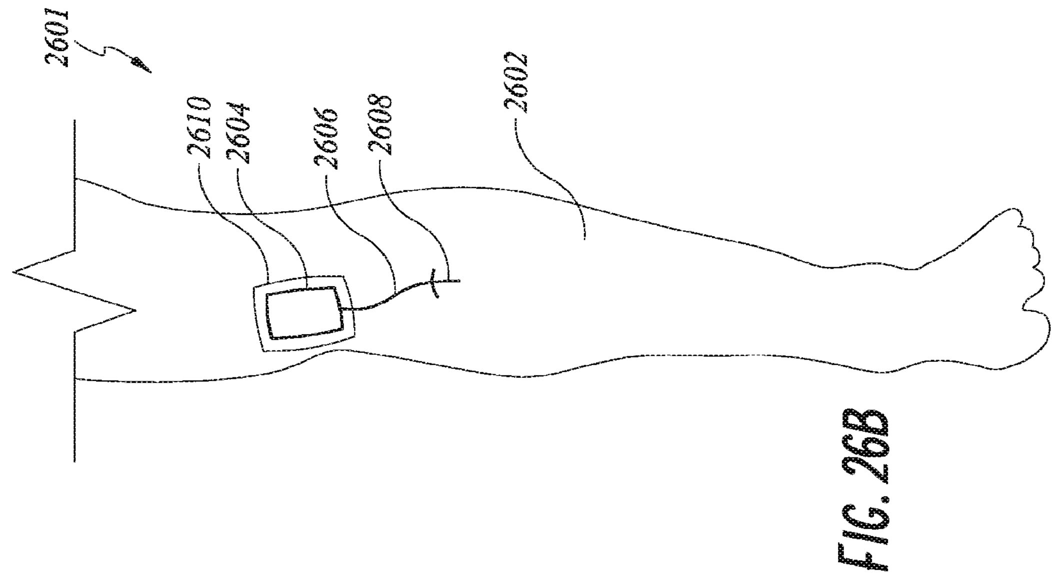
Figure 26A:
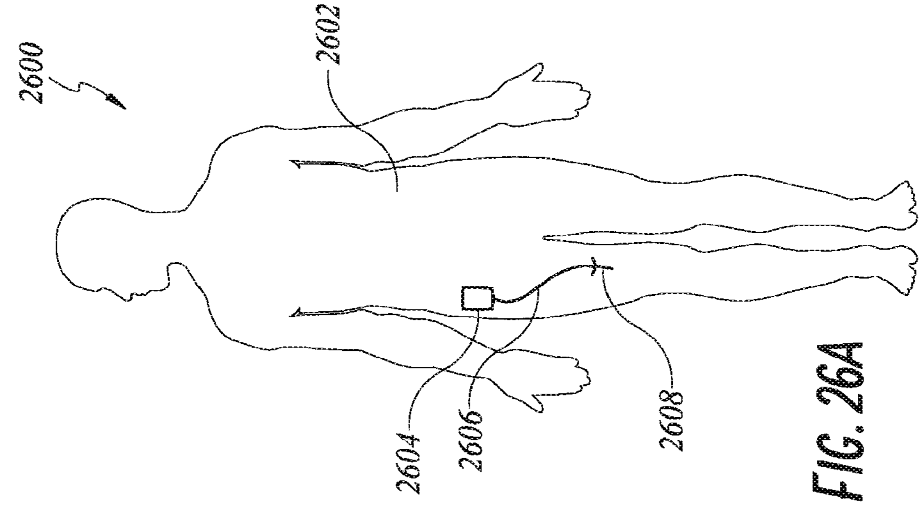
Figure 26C:
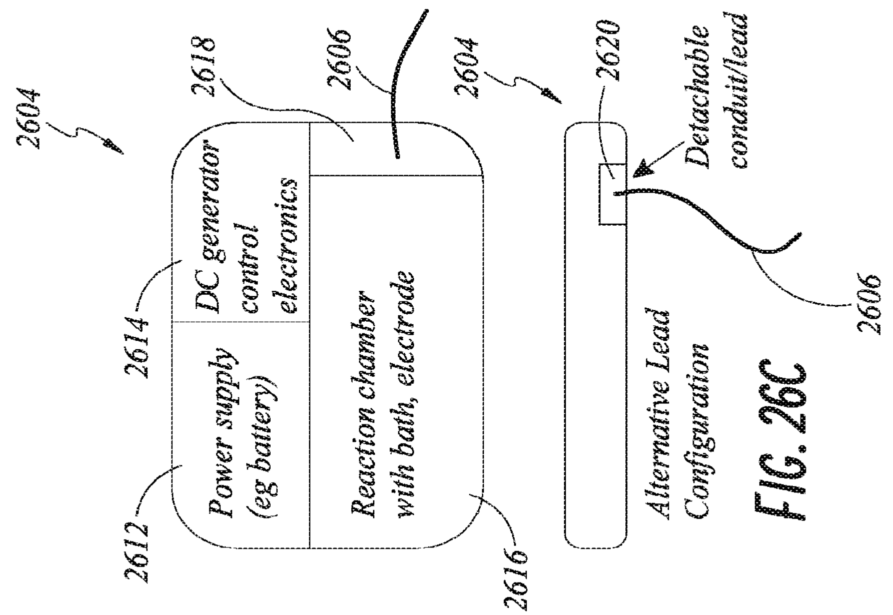

FIG. 26A illustrates a wearable system including a DC generator, wire, and reaction chamber, with a portion of the lead/catheter implanted at the desired anatomical site. FIG. 26B illustrates a bandage-style system that is local to the site of treatment (e.g., nerve block). FIG. 26C shows a schematic embodiment of such a wearable device with two different lead exit configurations.

FIGS. 27A-27D disclose methods of treating pain or other conditions by cycling DC block at a plurality of locations spaced apart from each other.

Figure 28B:
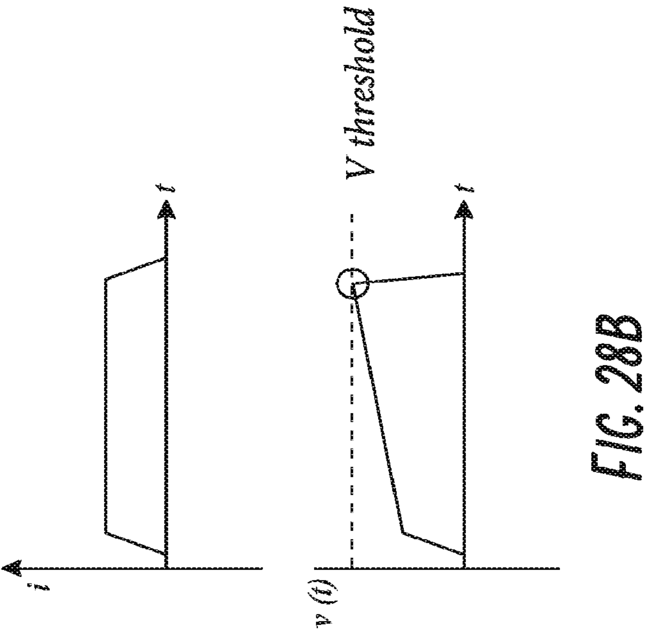
Figure 28A:
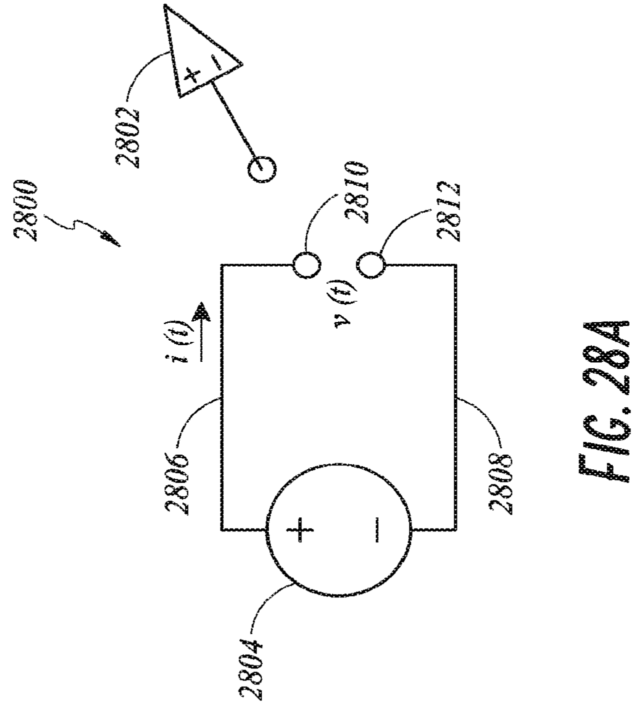

FIG. 28A schematically illustrates a DC current system including an optional reference electrode for voltage monitoring. In the simple example shown in FIG. 28B, electrode voltage increases with continued DC current delivery.

Figure 29:
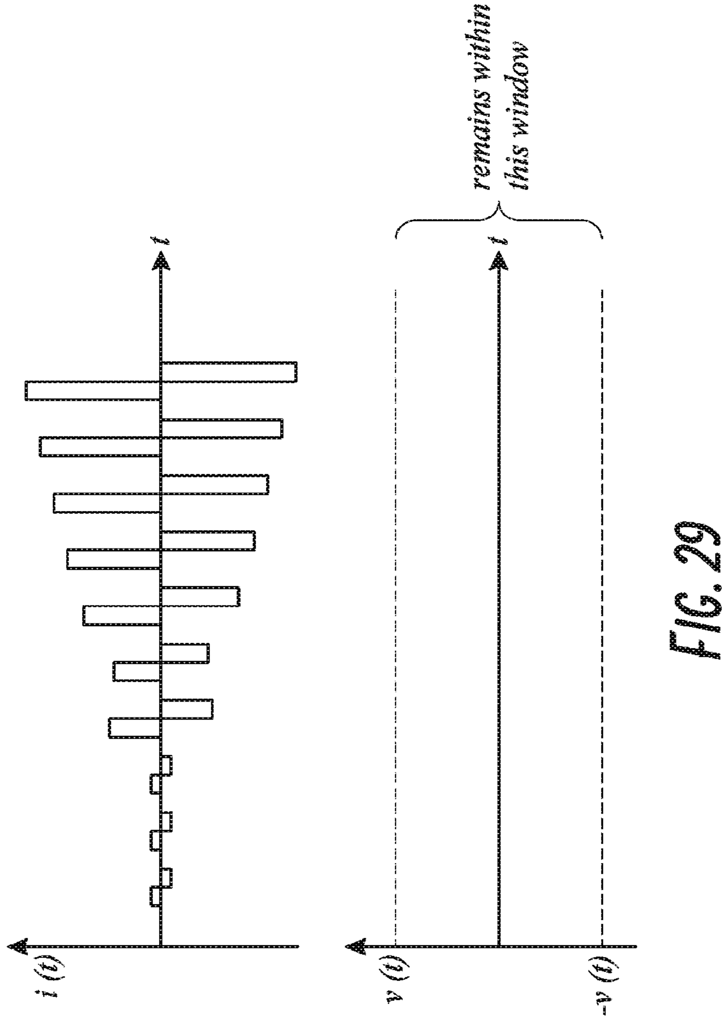

FIG. 29 illustrates that voltage can be kept within a desired range with upper and lower threshold bands, which limits the electrochemistry occurring at the electrode site FIGS. 30A-30C Also disclosed herein in some embodiments are single-fault safe DC systems and methods.

Figure 31:
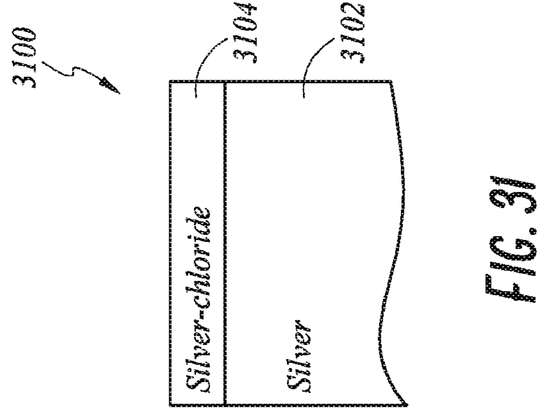

FIG. 31 schematically illustrates a silver-silver chloride electrode.

Figure 32:
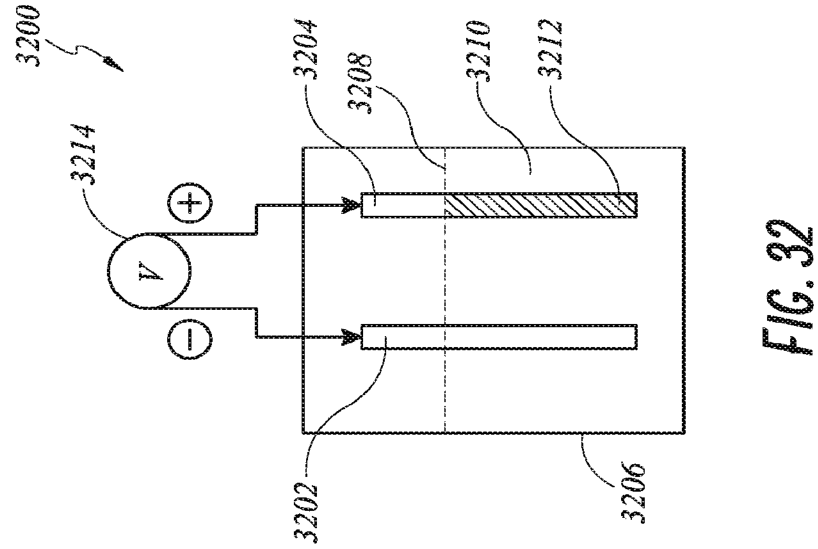

FIG. 32 illustrates a counterelectrode and working electrode are shown immersed in an electrolyte bath and connected to a power supply which drives a potential across the two electrodes.

Figure 33:
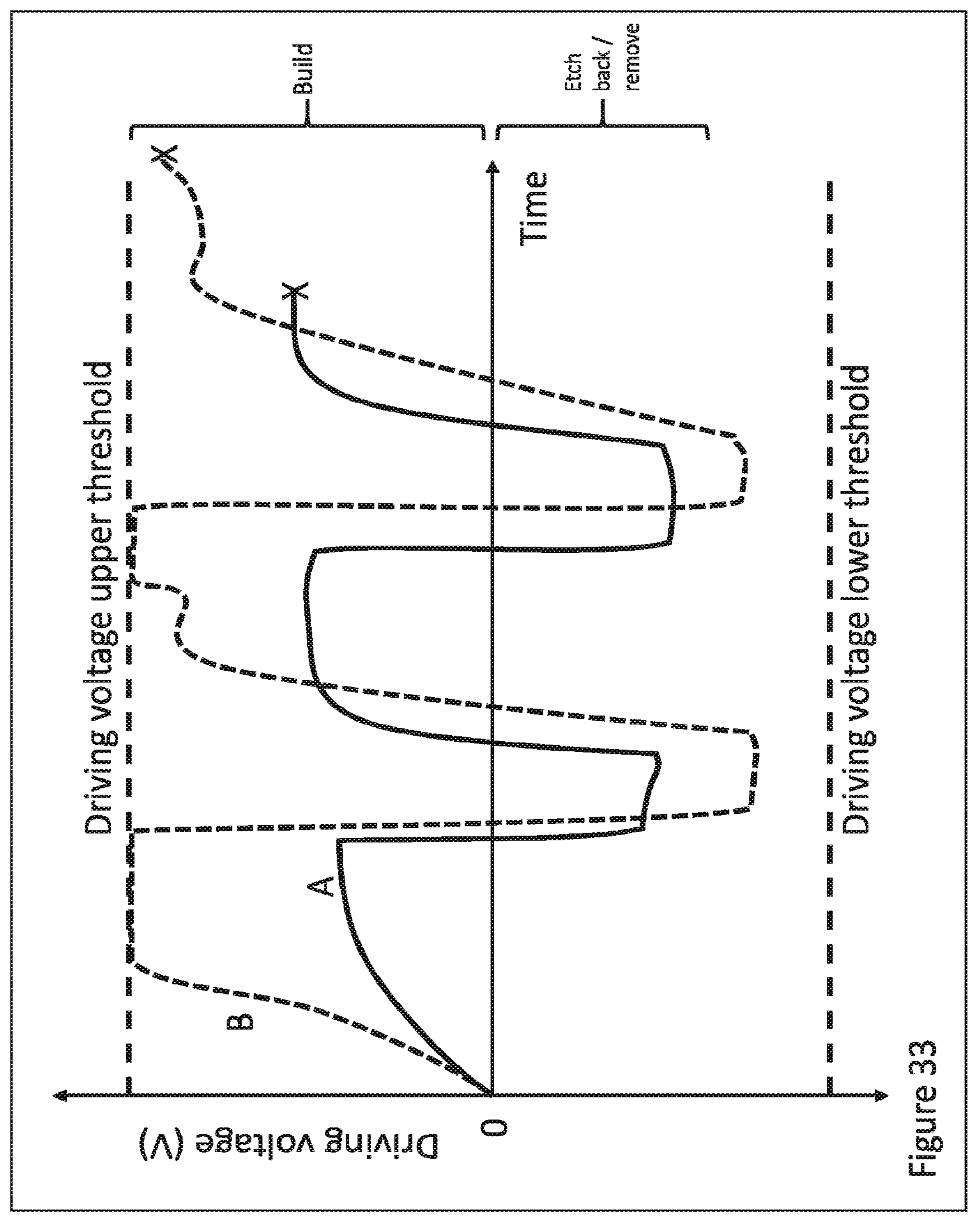

FIG. 33 illustrates driving voltages on a working electrode.

Figure 34:
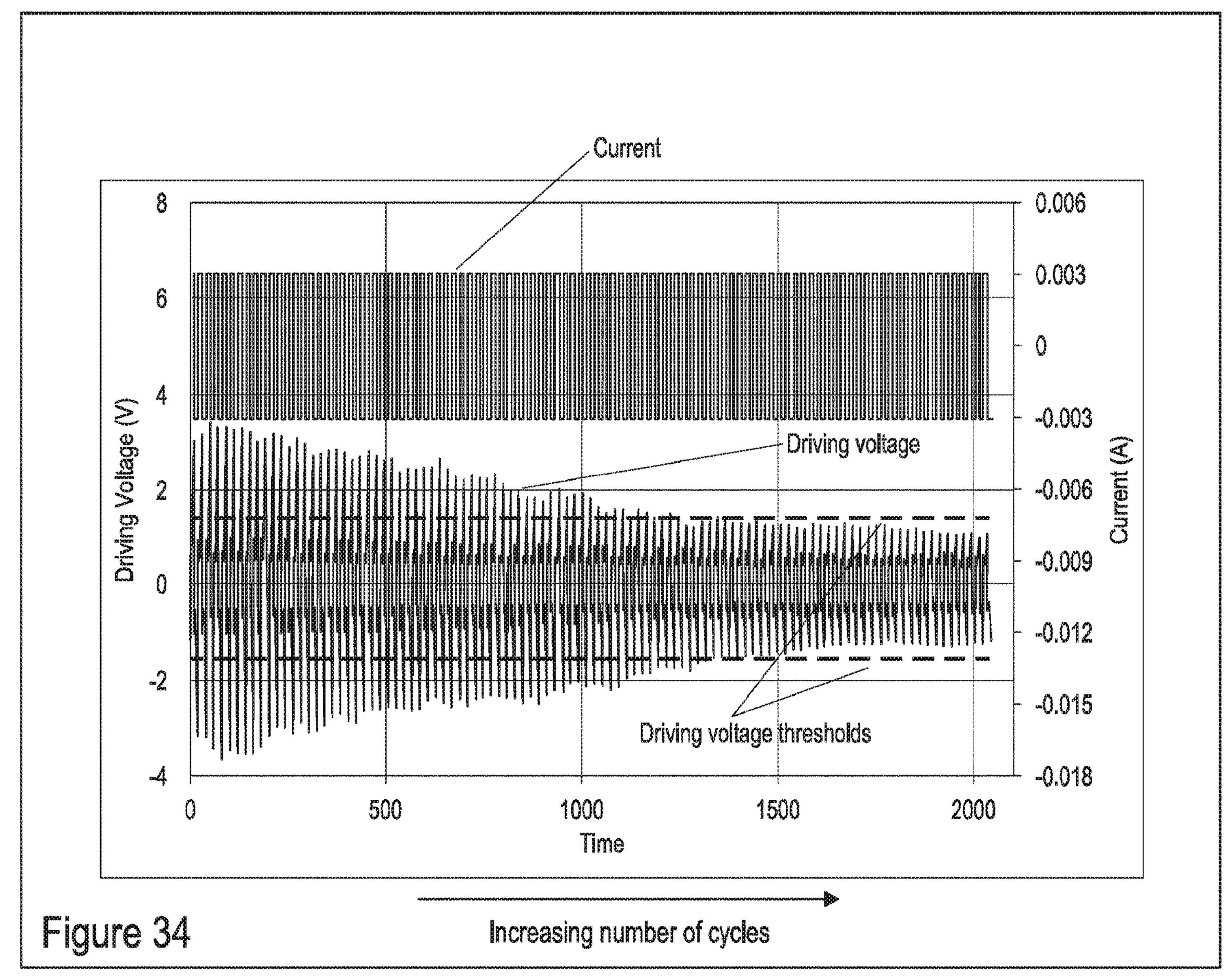

FIG. 34 illustrates that cycling of the silver/silver-chloride reaction at fixed current amplitude and fixed durations has been demonstrated to lead to decreases in peak driving voltages with increasing number of cycles.

Figure 35:
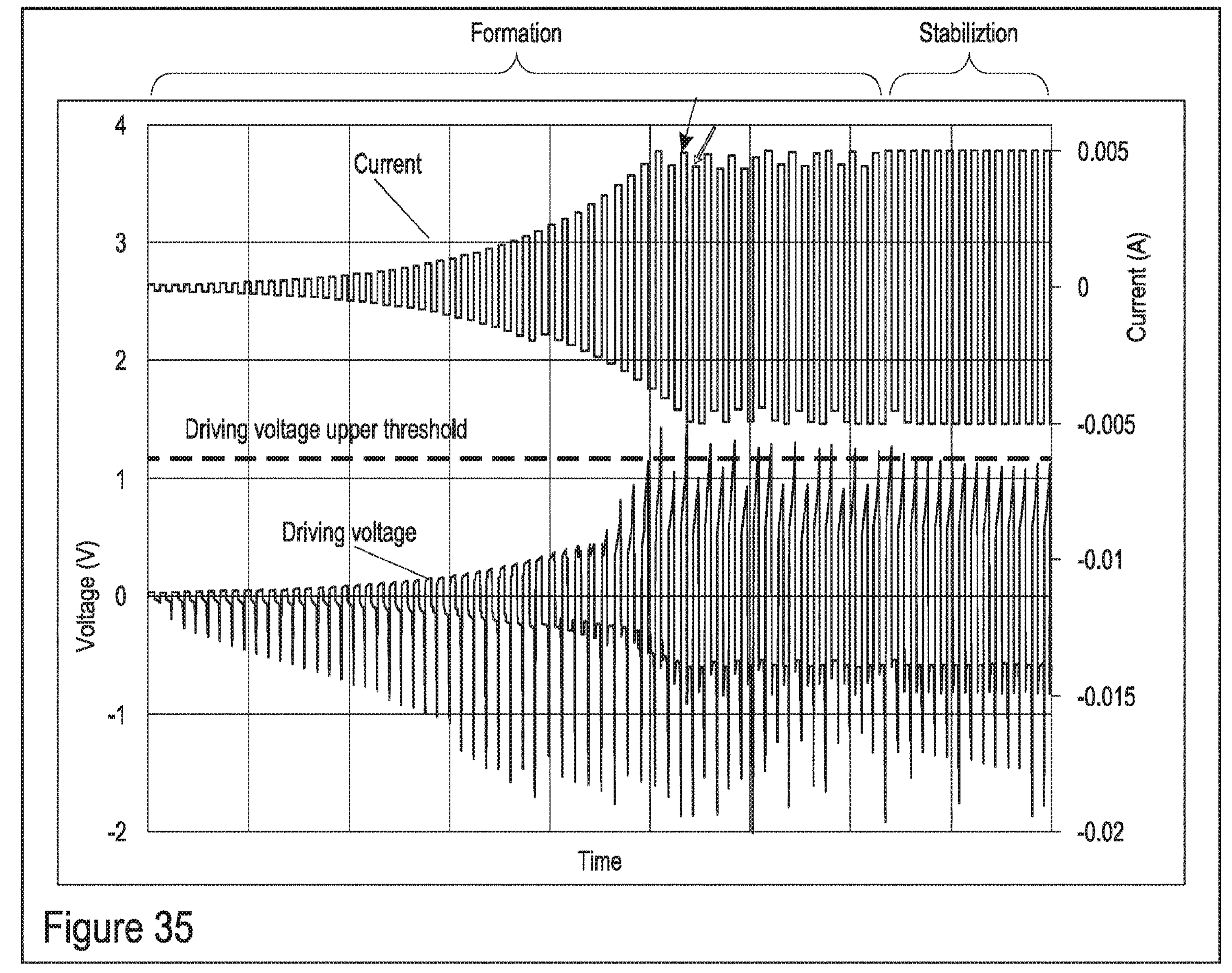

FIG. 35 illustrates that a working electrode and counter-electrode formation are processed in the formation step where the current level starts at a relatively low value and rises with each cycle when the driving voltage upper threshold is not exceeded.

Figure 36:
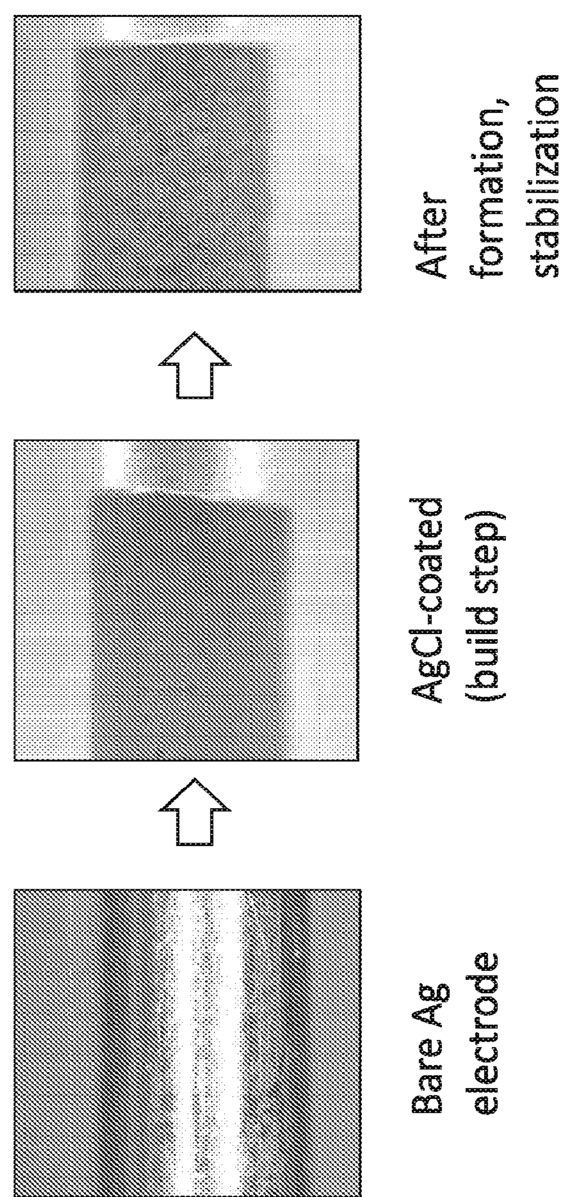

FIG. 36 shows the change in microstructure that can occur after building an AgCl layer on a bare silver electrode and after performing the formation and stabilization steps to condition the AgCl-coated electrode.

Figure 37:
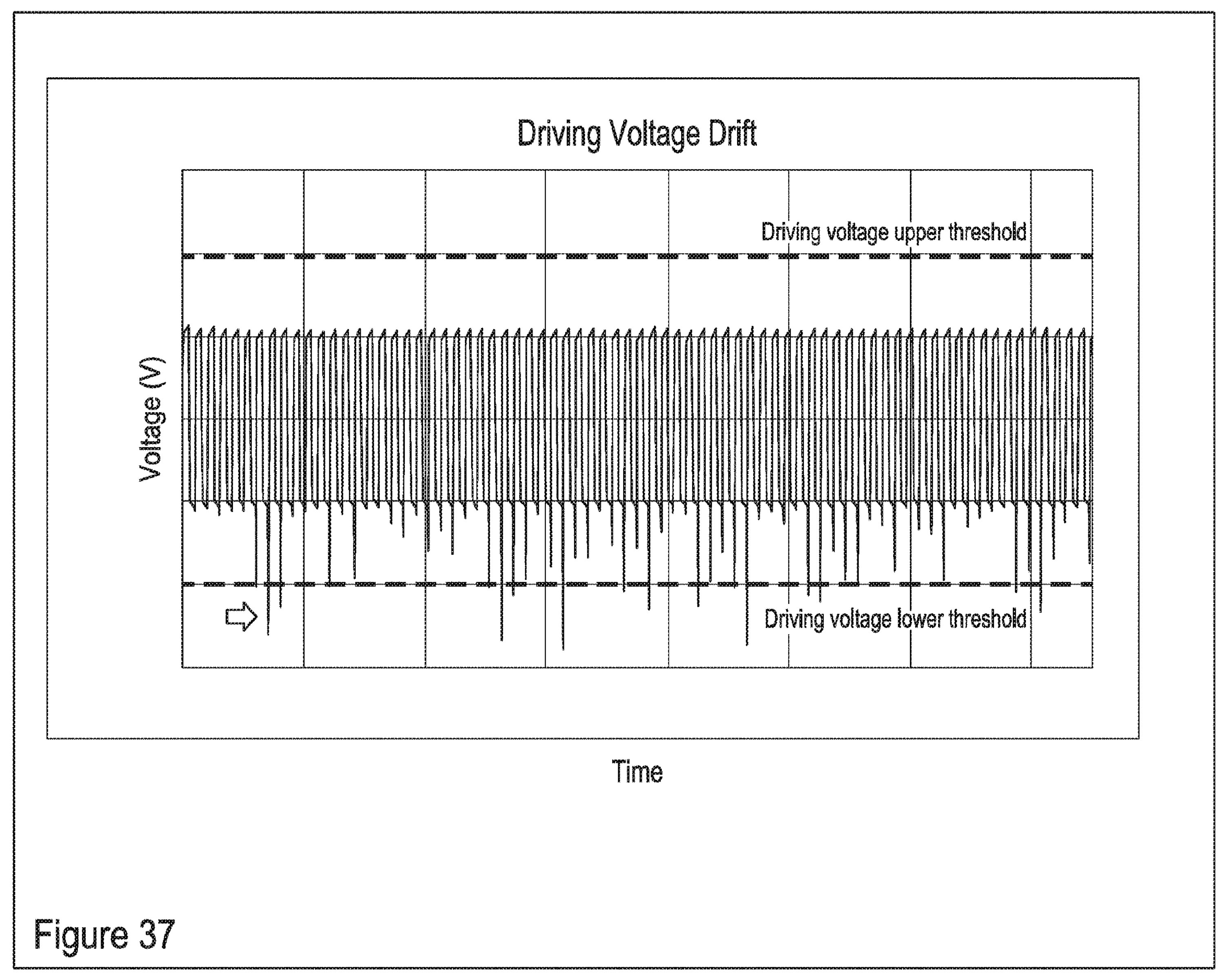

FIG. 37 shows a driving voltage which started to exceed the driving voltage lower threshold over time.

Figure 38:
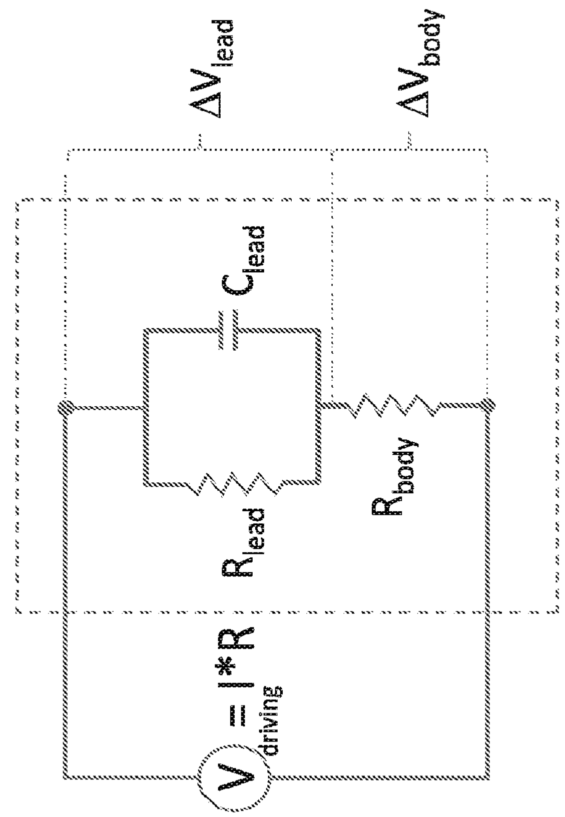
Figure 39:
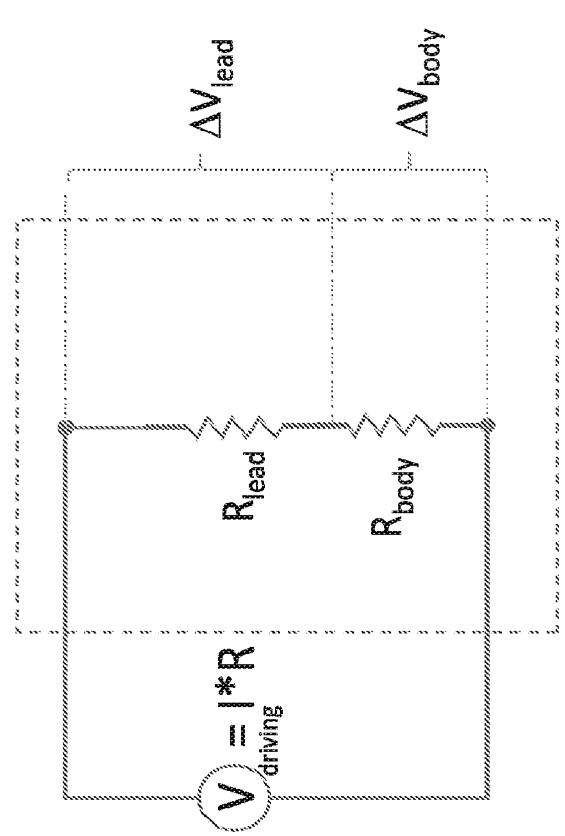
Figure 40:
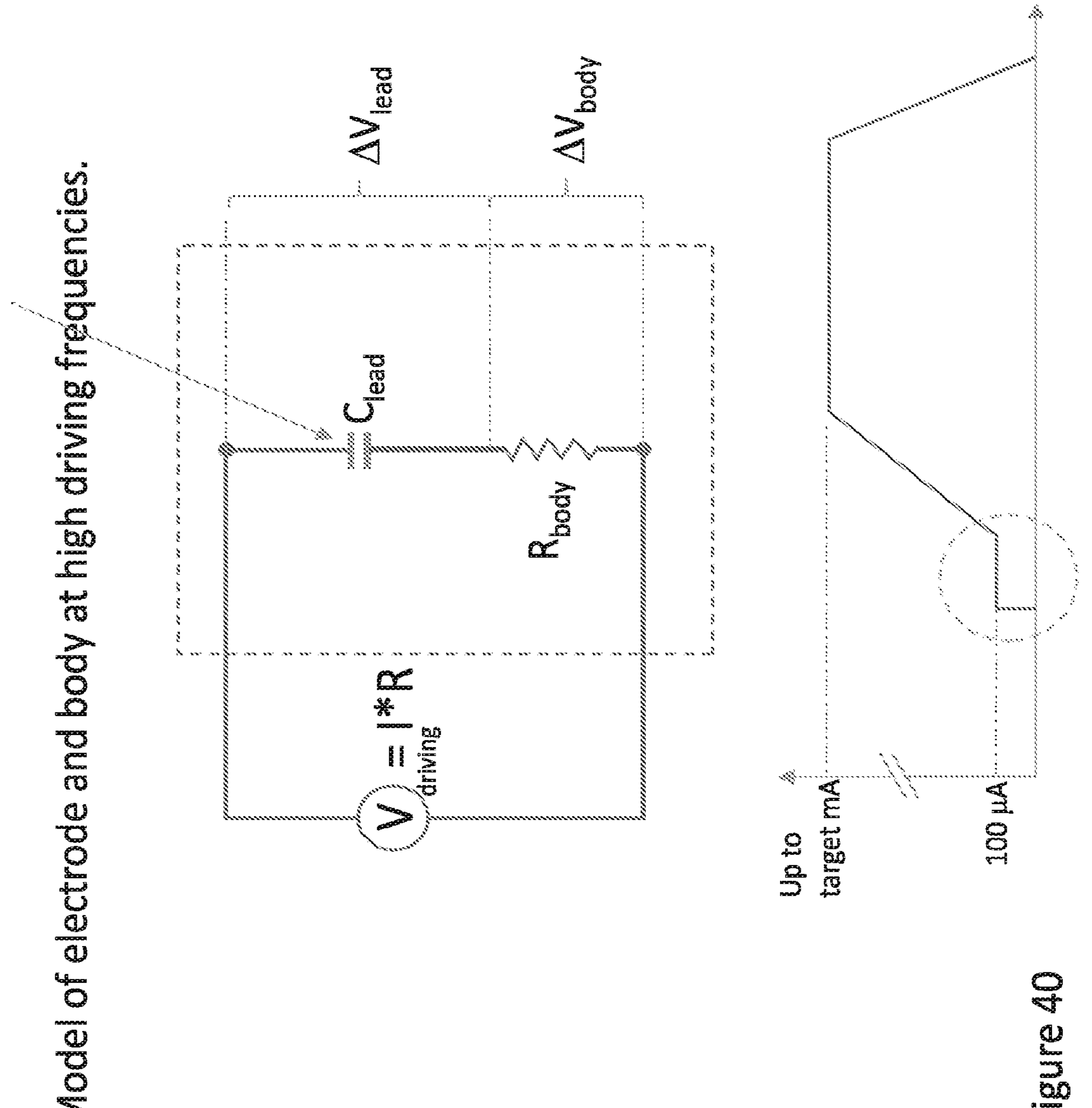

FIG. 38 illustrates that the electrode and body can be modeled as a resistor ($R_{lead}$) and capacitor ($C_{lead}$) in parallel and a body impedance ($R_{body}$) in series with the electrode. At low driving frequencies, the electrode and body can be modeled as shown in FIG. 39 reflective of the equation above. At high driving frequencies the system can be modeled as shown in FIG. 40 where the capacitor behaves like a short and does not have any impedance.

Figure 41:
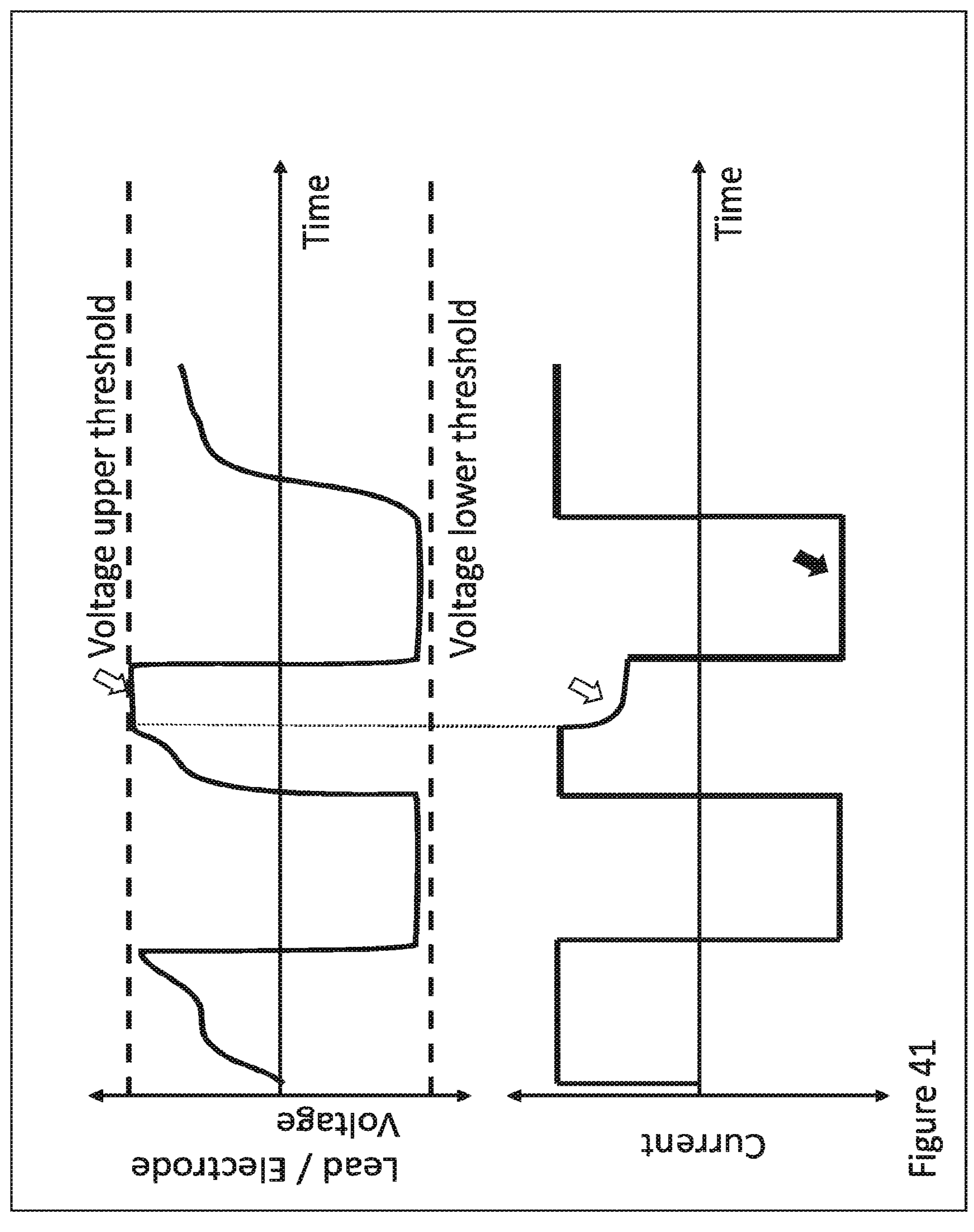

FIG. 41 illustrates a portion of a waveform where the threshold is reached, the current is reduced to stay below the threshold.

Figures 42A, 42B, 42C:
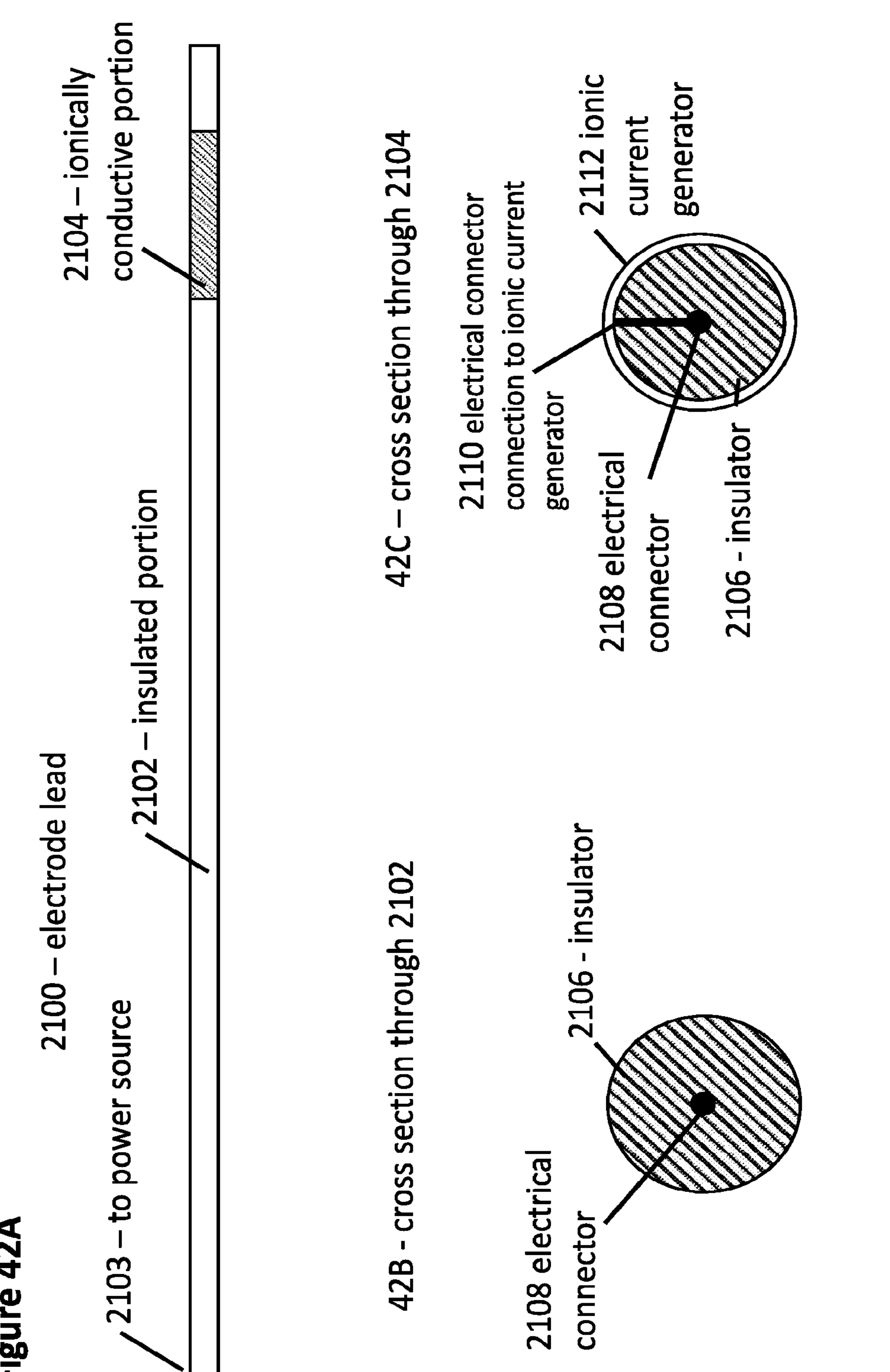

FIGS. 42A-C show schematically an embodiment of an electrode lead configured to deliver ionic direct current to tissue in proximity to the lead.

FIGS. 43A-43D show an embodiment of an electrode lead configured to deliver ionic direct current to tissue in proximity to the lead.

Figures 44A, 44B, 44C:
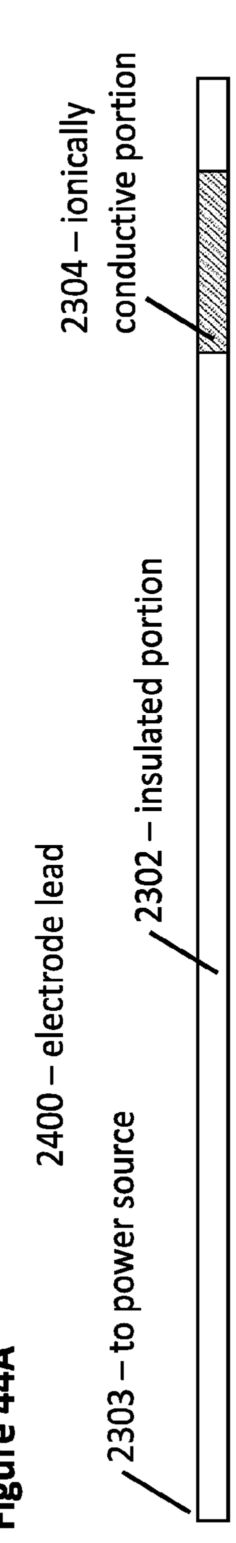

FIGS. 44A-44C illustrate another embodiment of an electrode lead wherein the ionically conductive medium in FIG. 43A-43D is absent, and instead the ionically selective membrane is in direct contact with the ionic current generator and insulator exterior surface.

FIGS. 45A-45C show an embodiment of an electrode lead configured to deliver ionic direct current to tissue in proximity to the lead.

Figure 46:
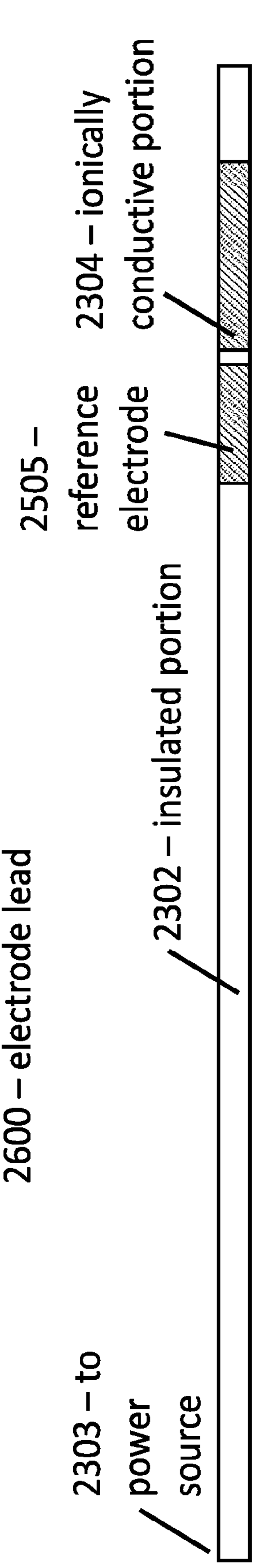

FIG. 46 shows an alternative embodiment to FIGS. 45A-45C in which an electrode lead comprises a portion through which ionic current can pass into the tissue, and an electrically insulated portion.

Figure 47:
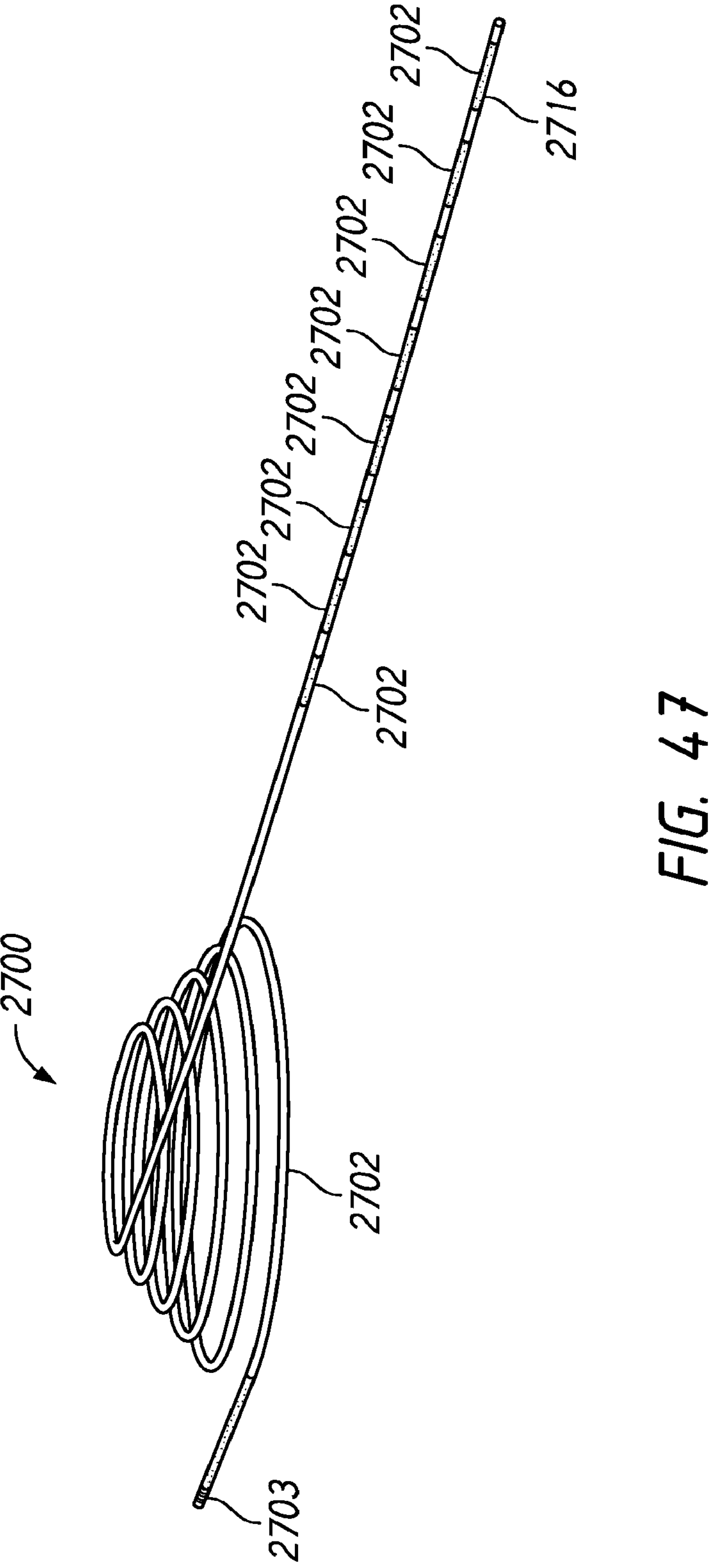

FIG. 47 shows an embodiment of an electrode lead including multiple spaced-apart ionically conductive portions.

Figure 48:
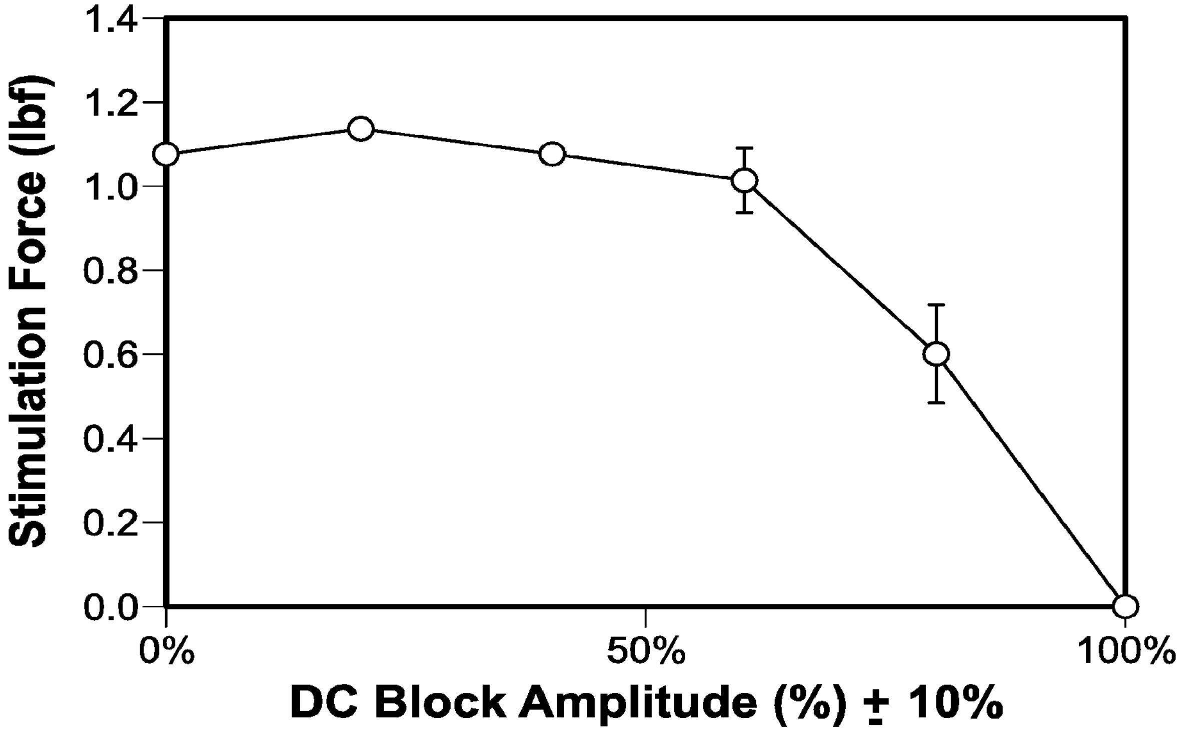

FIG. 48 shows that in a rat model, a stimulation force of the gastrocnemius muscle due to stimulation of the sciatic nerve can be tuned such that the nerve is unblocked (0%) or fully blocked (100%) or tuned to a partial block between 0% and 100%.

Figure 49:
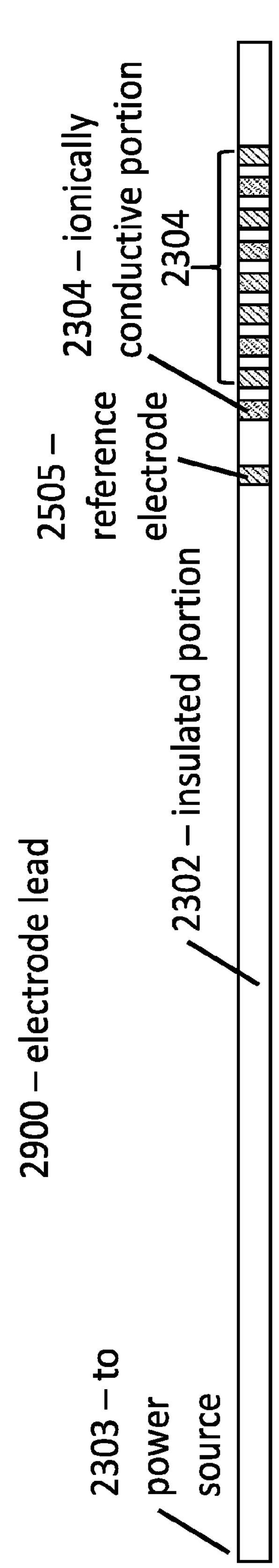

FIG. 49 shows an embodiment of a multi-contact electrode lead configured to deliver ionic direct current to tissue in proximity to the lead.

Figures 50A, 50B:
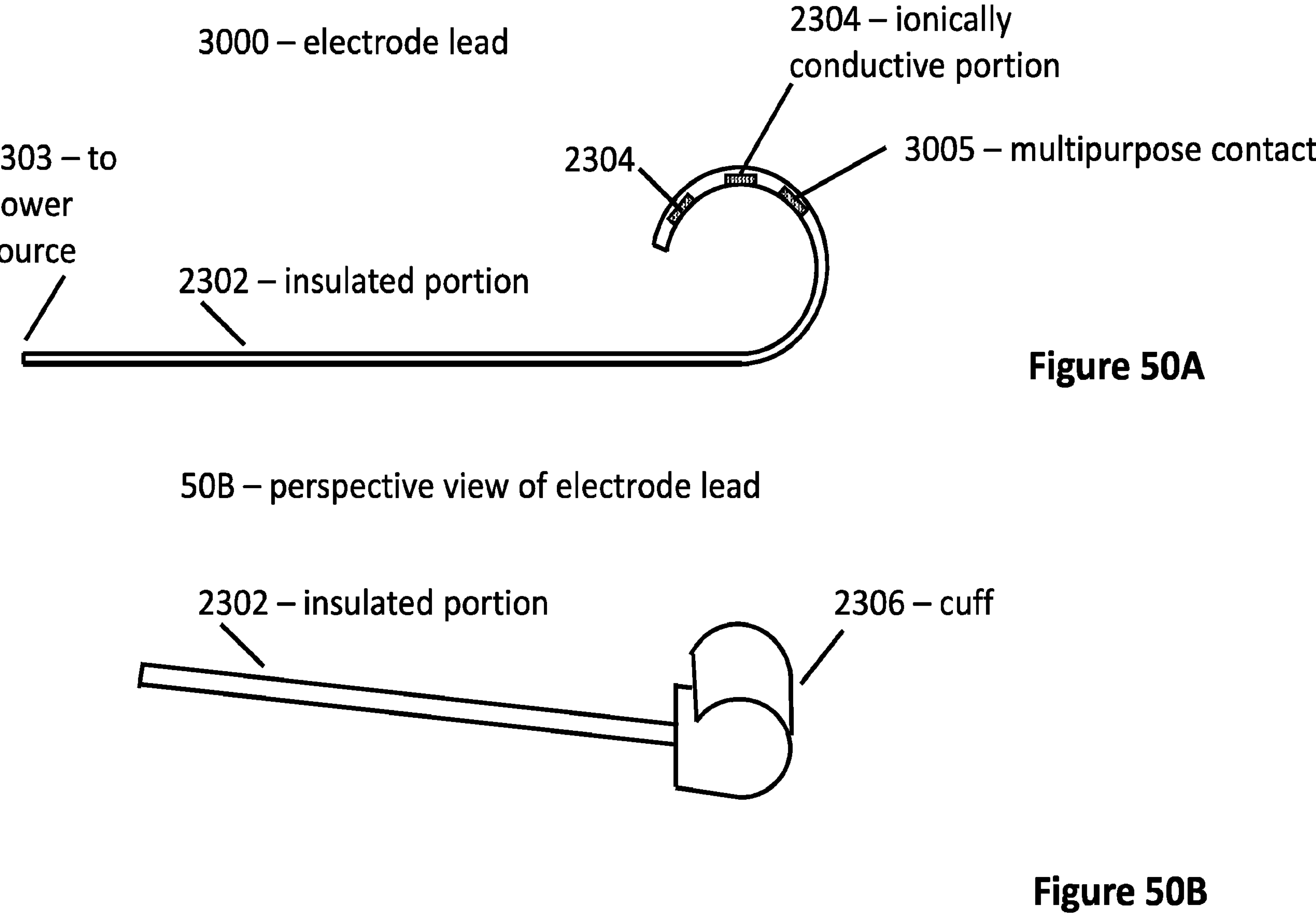

FIGS. 50A-50B illustrate an alternate configuration of a curved multi-contact electrode lead configured to deliver ionic direct current to tissue in proximity to the lead.

Figure 51:
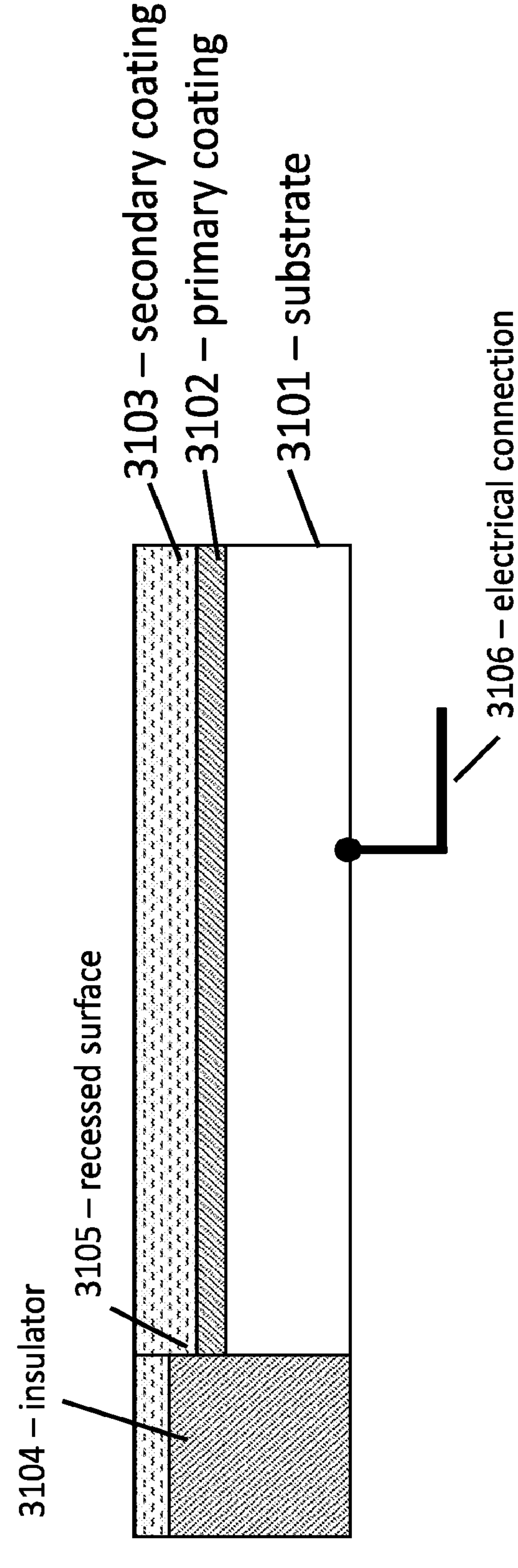

FIG. 51 illustrates that the ionic current generation portion 3 of the electrode may be generalized to having a conversion mechanism from electrical current supplied by the electrical connection to an electrochemical system which convert the electrical current into ionic current.

FIG. 52 illustrates how an ionically conductive portion of the electrode can be configured to generate a more even current density profile along the width of the electrode.

FIGS. 53A-53D illustrates one embodiment of an ionic direct current electrode lead with paired ionic current generation contacts that can be adhered using a helical wire form.

Figure 53A:
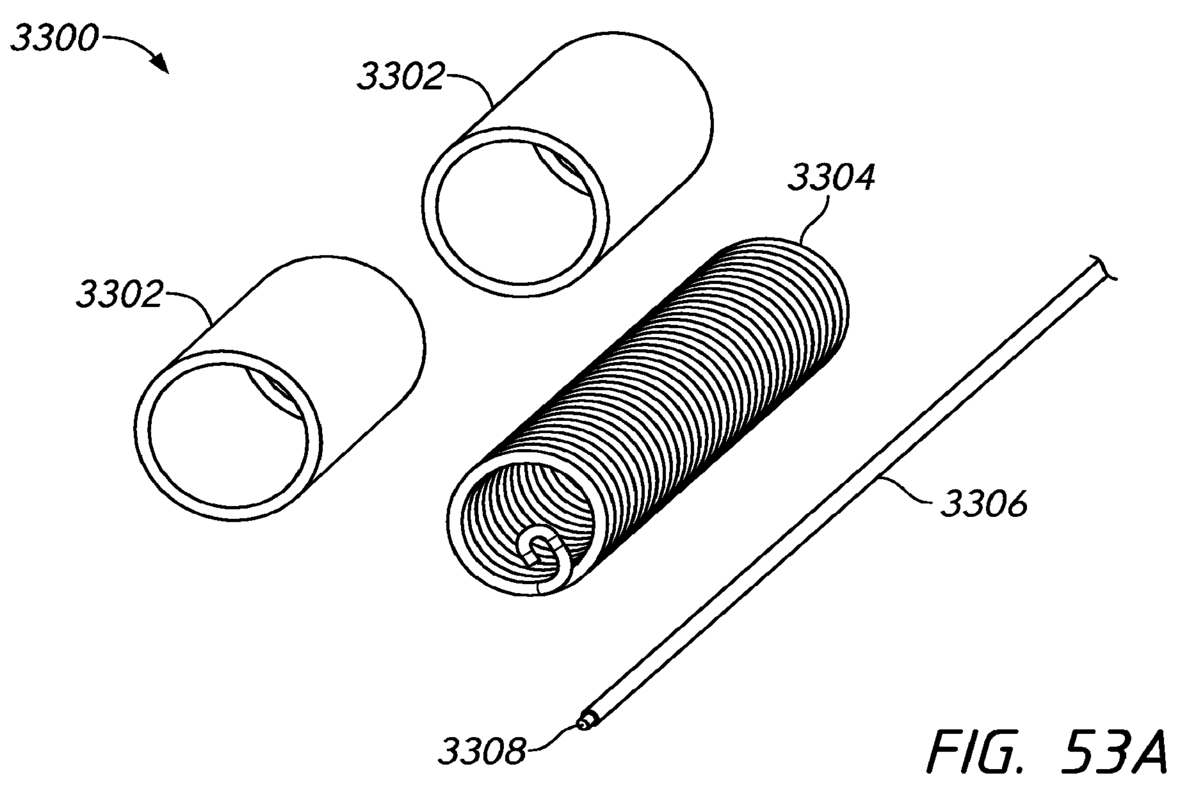
Figure 53B:
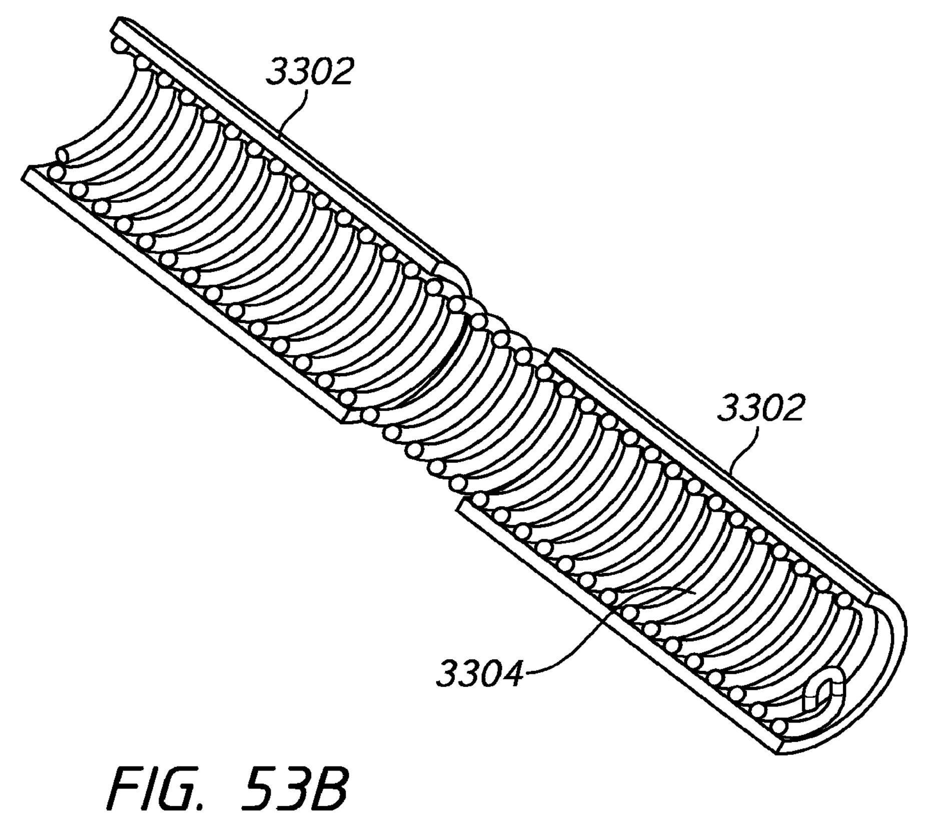
Figure 53C:
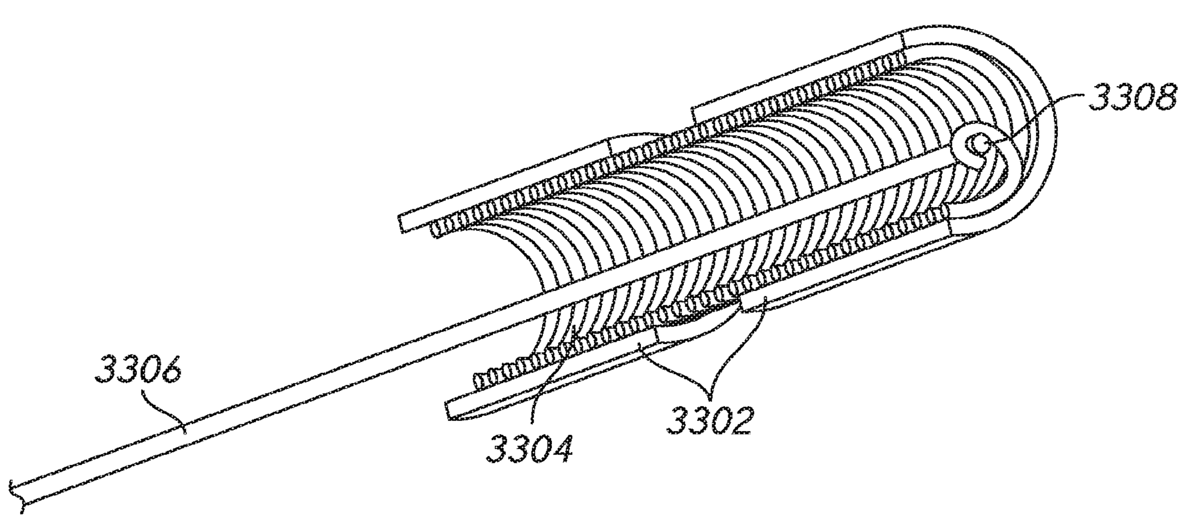
Figure 53D:
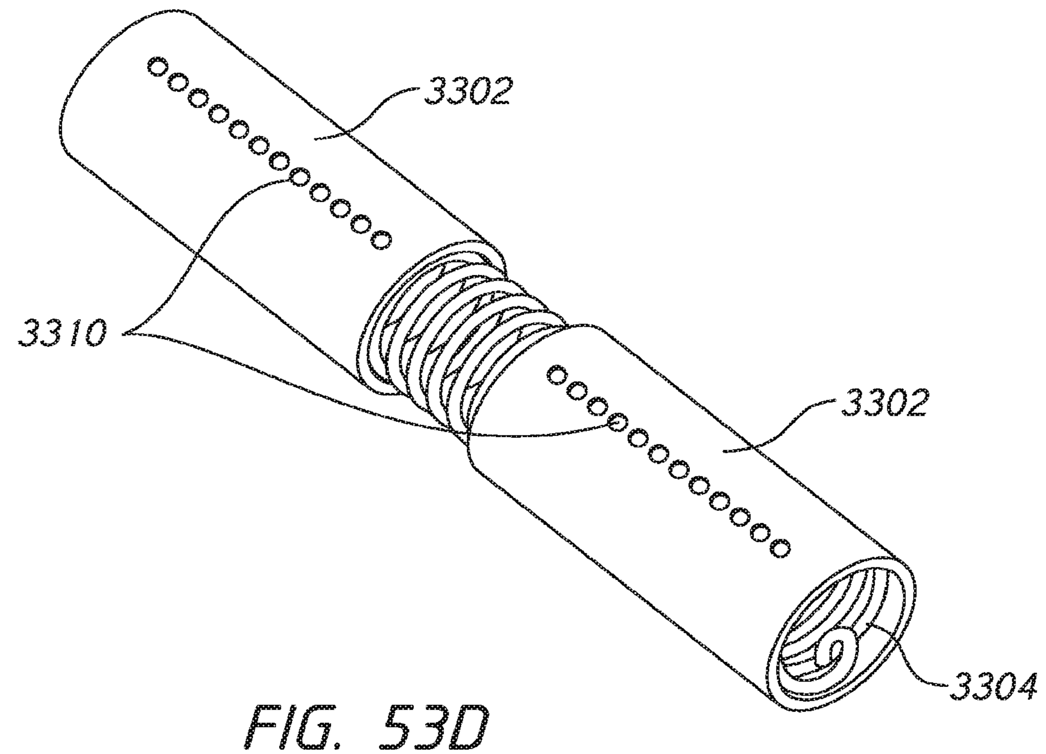
Figure 54A:
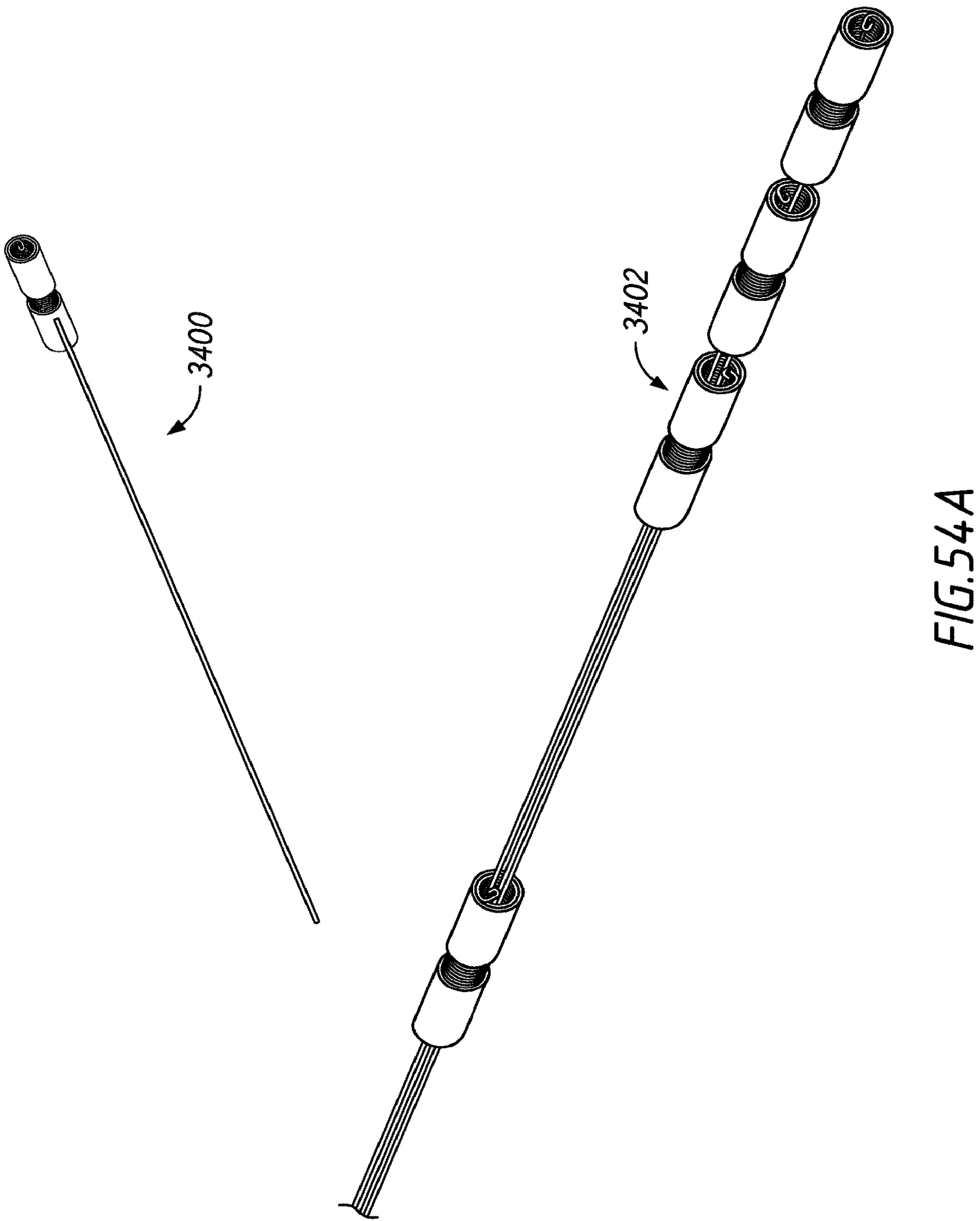
Figure 54B:
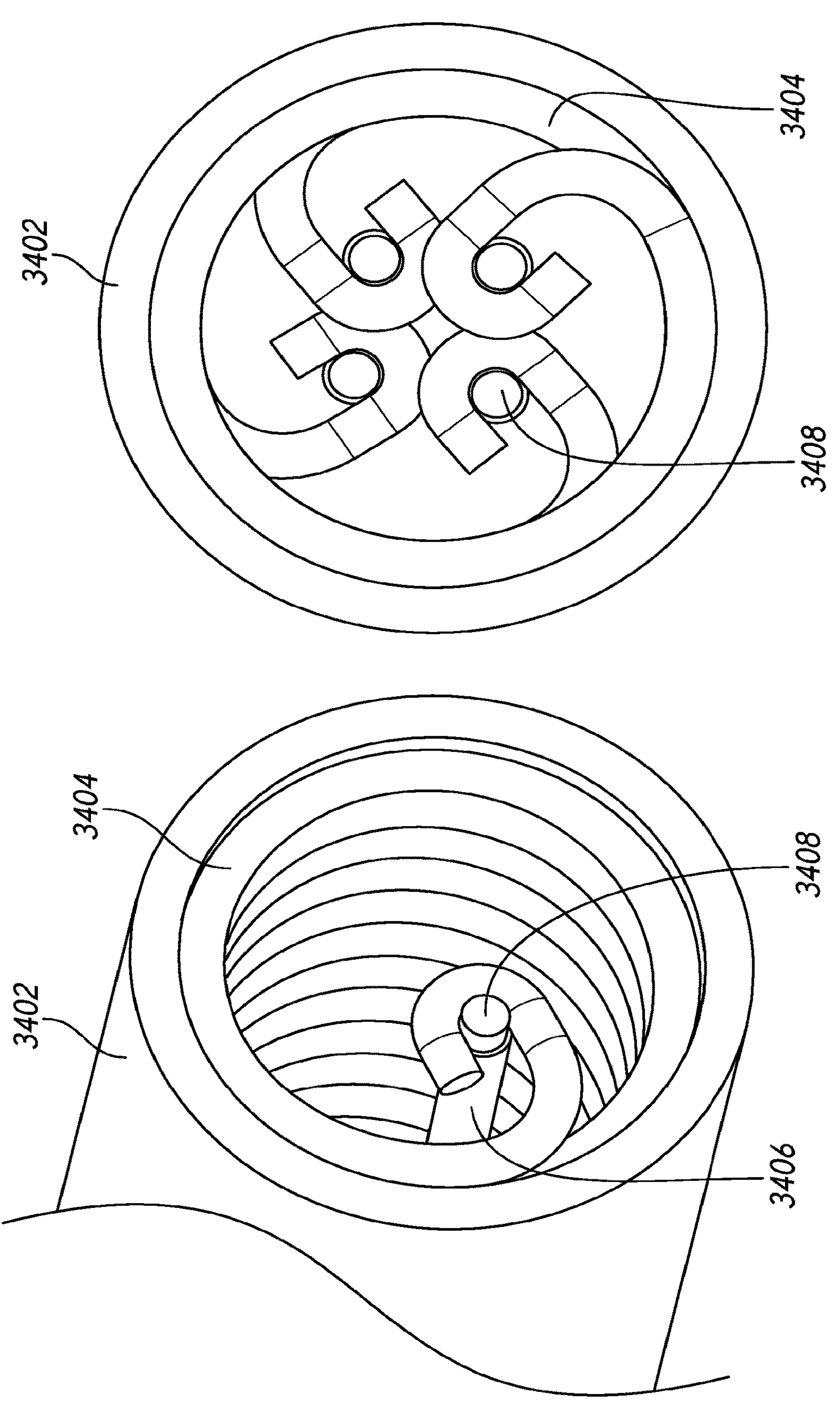

FIGS. 54A and 54B illustrate a lead sub-assembly and a lead with one or a plurality of contacts as previously described in connection with FIGS. 53A-53D above.

FIGS. 55A-55D illustrate further views of electrode leads.

Figure 56A:
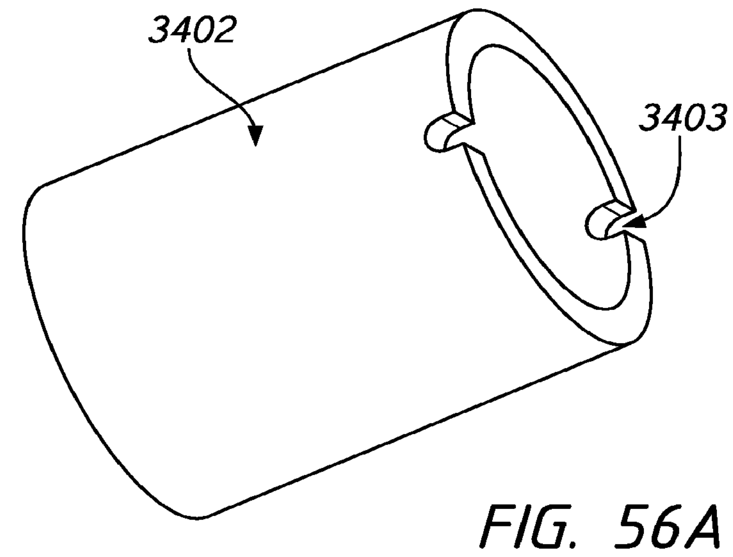
Figure 56B:
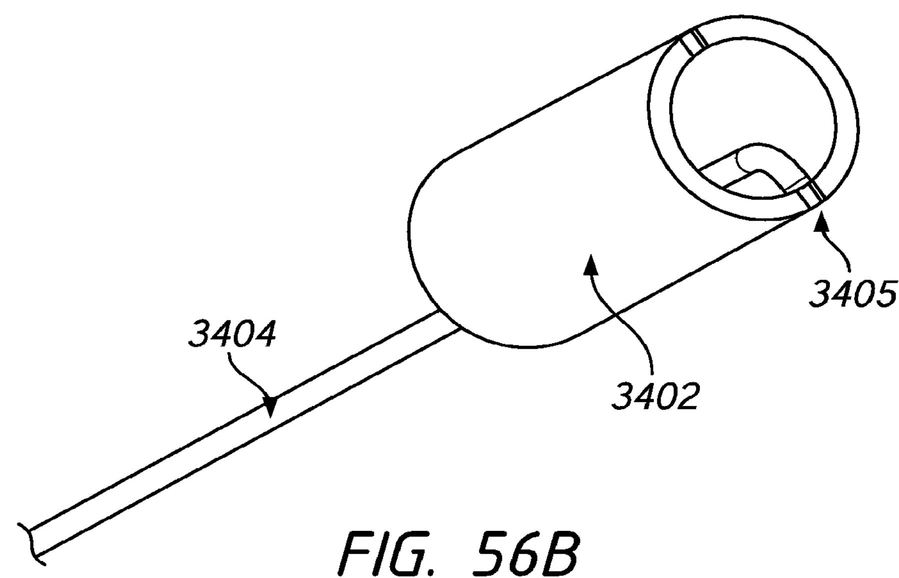
Figure 56C:
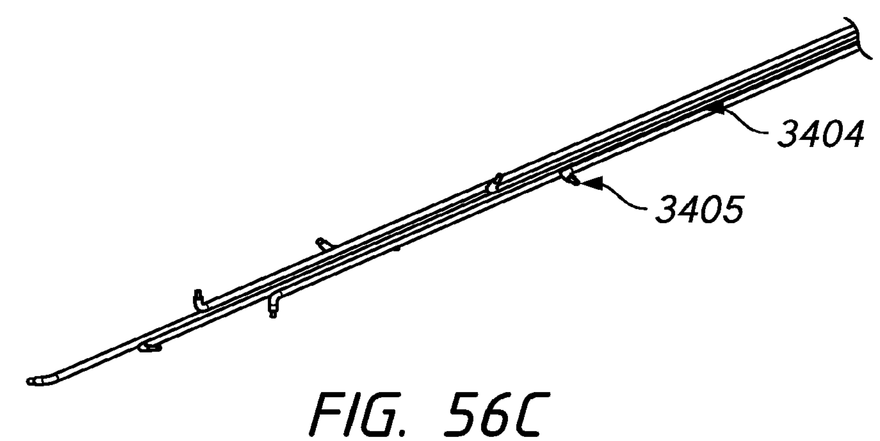

FIGS. 56A-56C schematically illustrate a generally tubular, e.g., cylindrical lead contact that can include a sidewall with distal notches and an interior lumen.

Figure 57A:
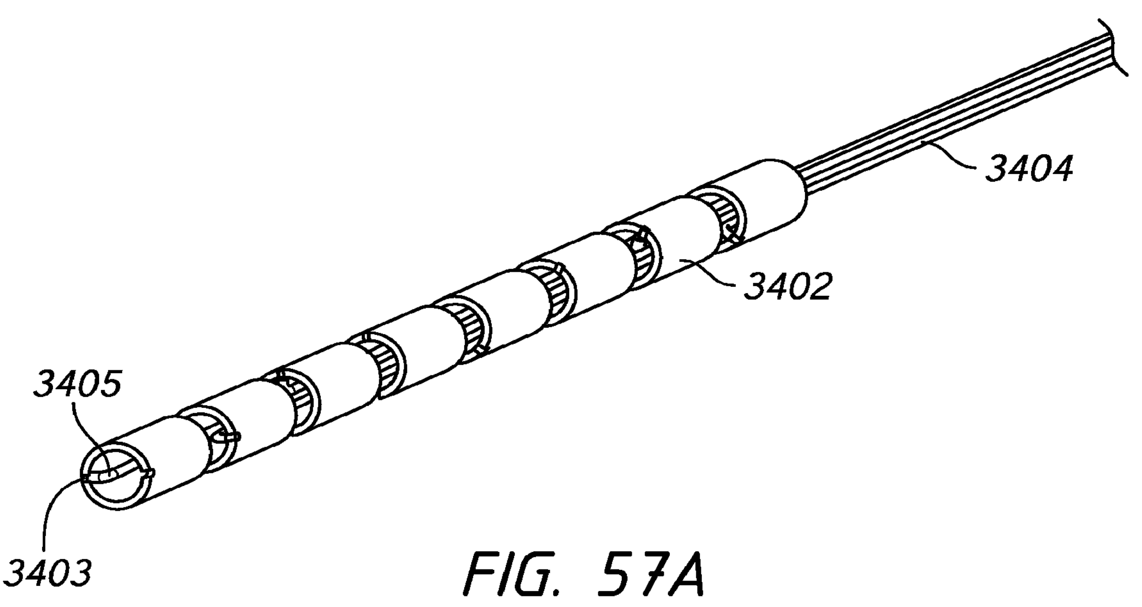
Figure 57B:
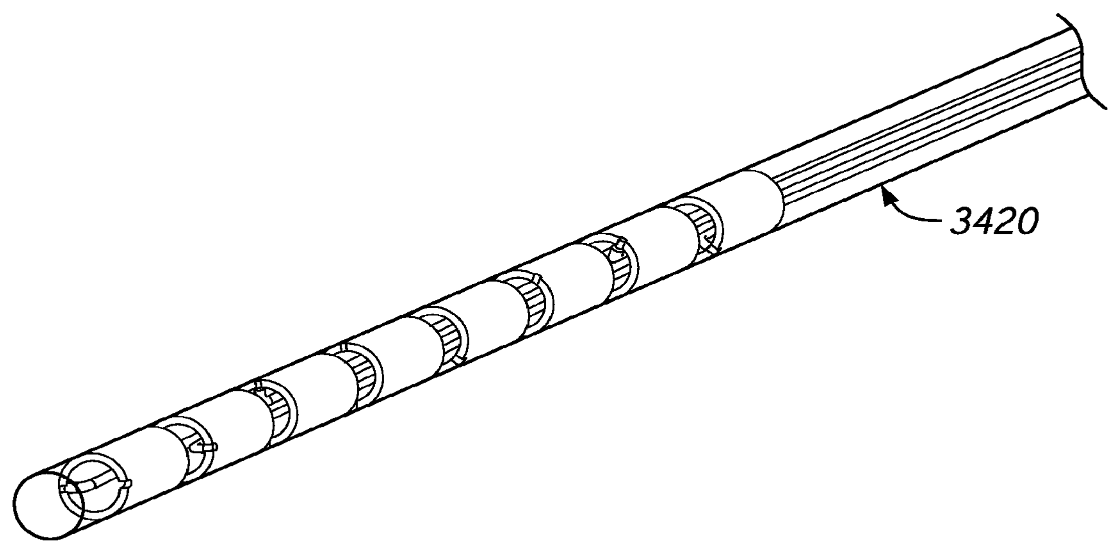
Figure 57C:
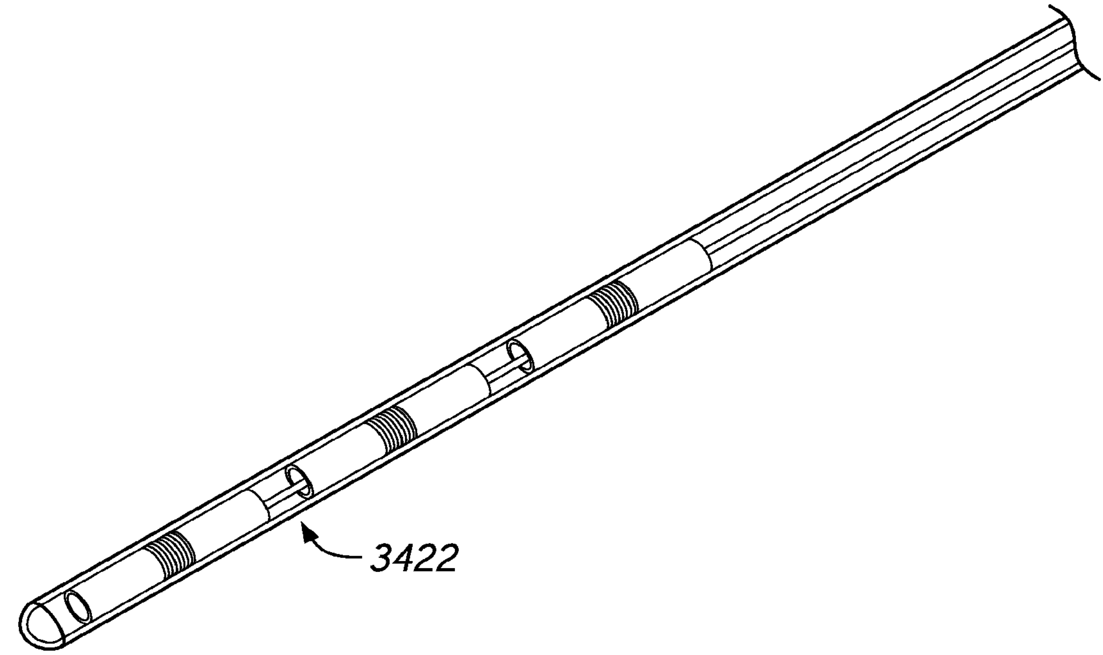

FIGS. 57A-57C schematically illustrate additional lead embodiments, illustrating conduits and spaced-apart lead contacts as previously described.

FIGS. 58A-58D illustrates embodiments of lead electrodes having paddle configurations.

Figure 59:
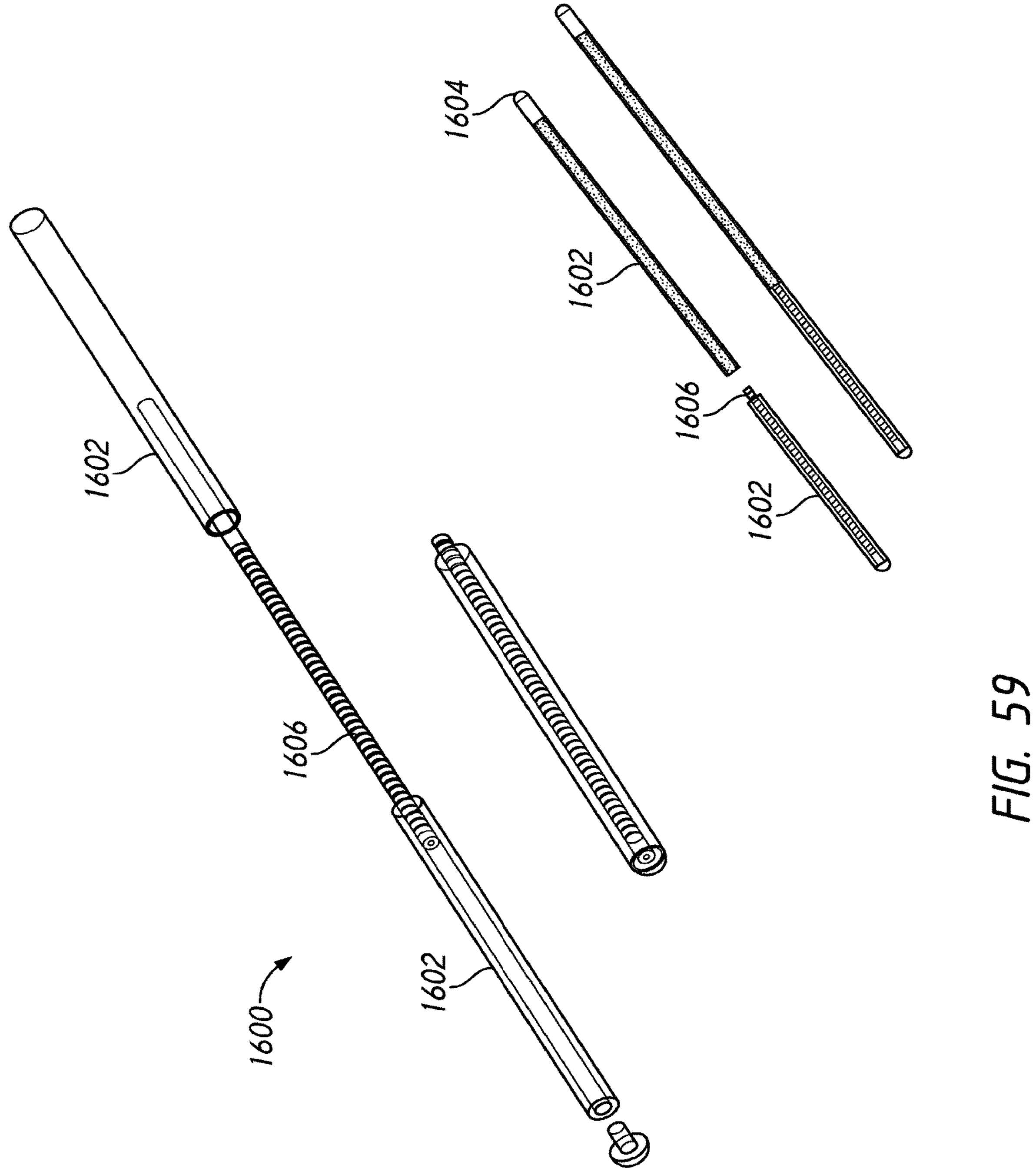

FIG. 59 illustrates an embodiment of a cylindrical lead

Figure 60:
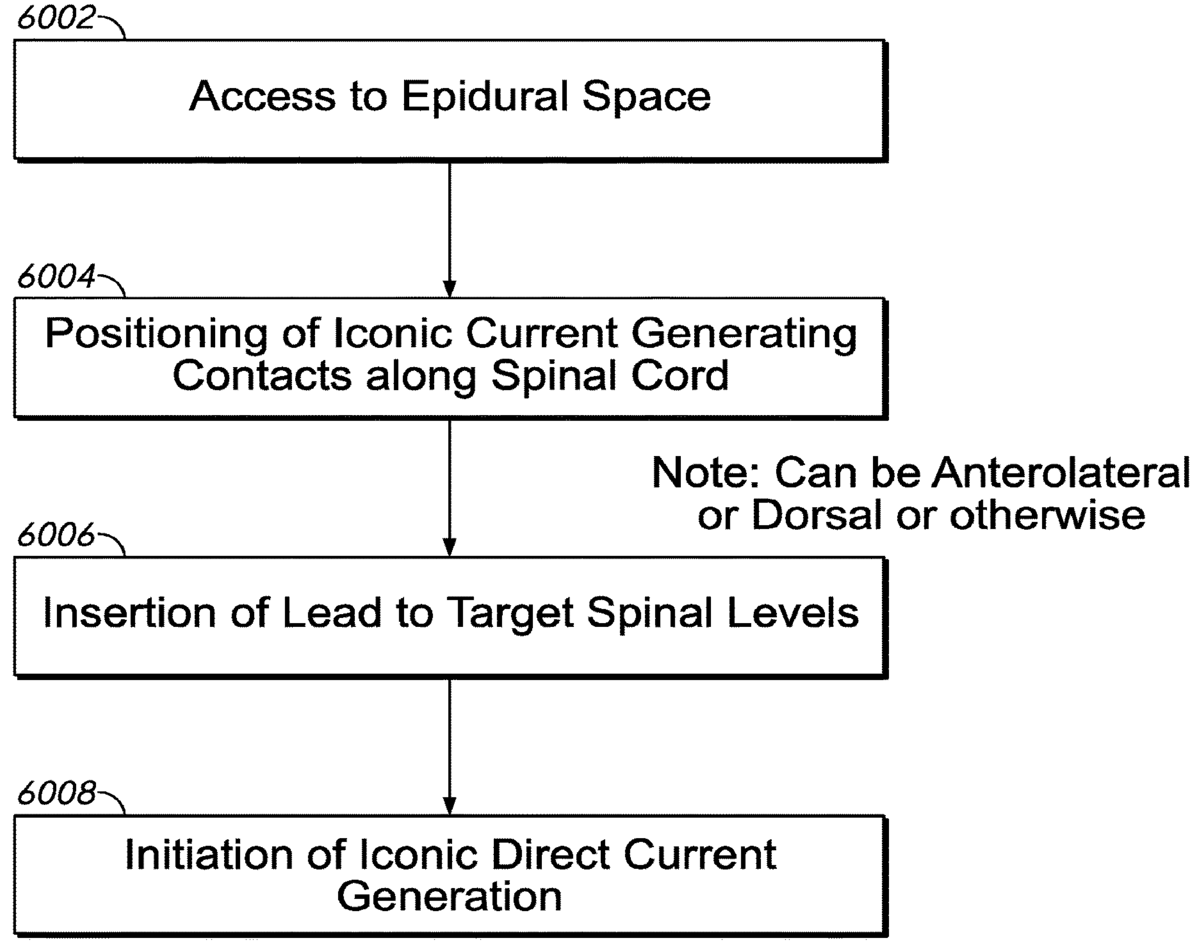
Figure 61:
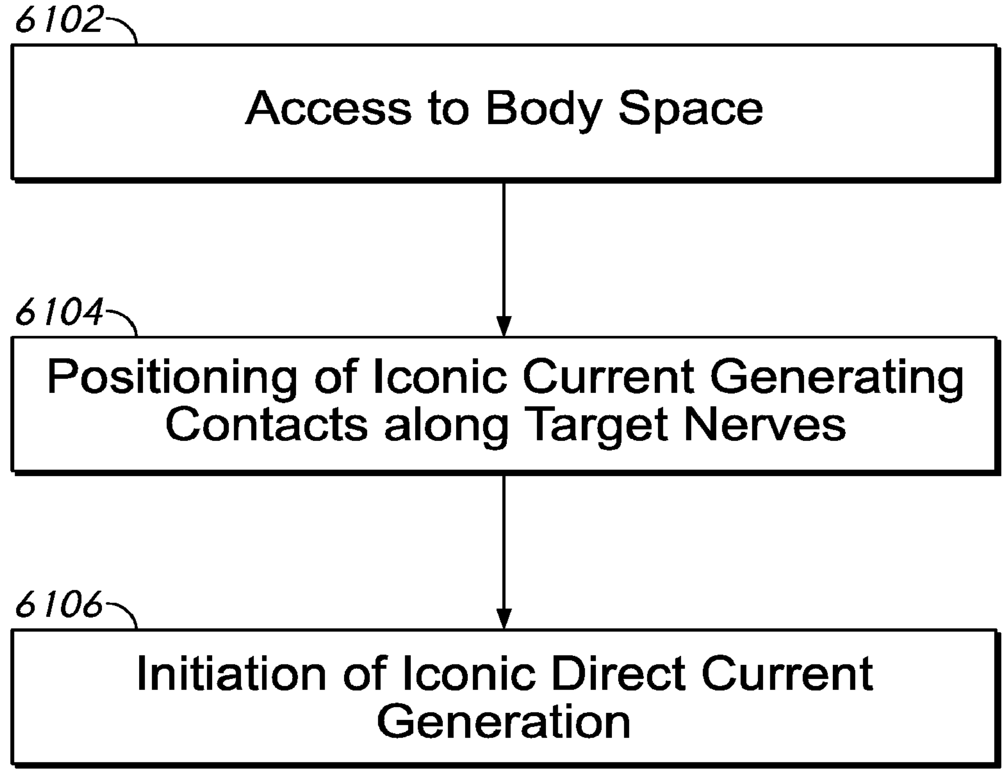
Figure 62:
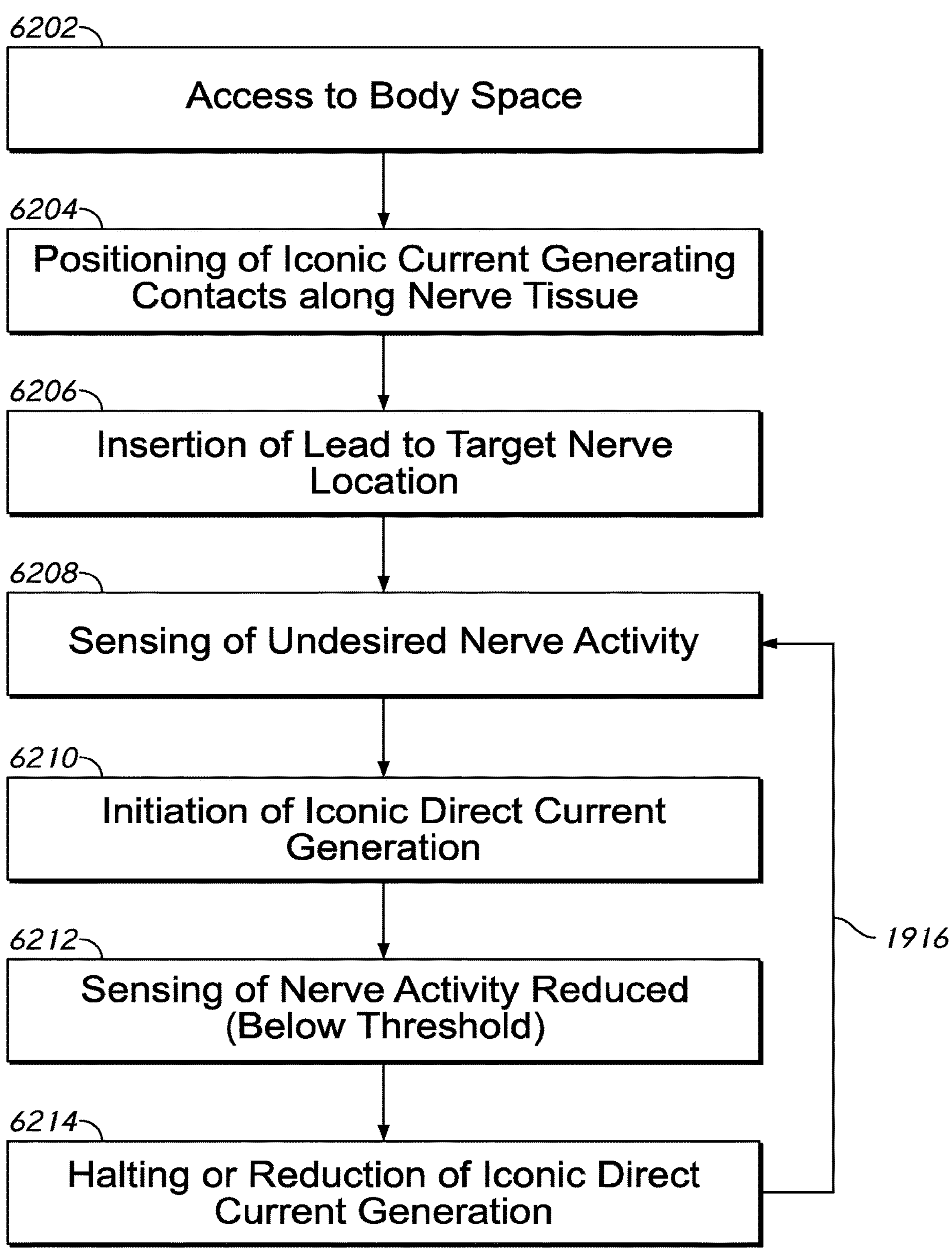

FIGS. 60-62 illustrate various clinical treatment flowchart algorithms including direct current therapy.

Figure 63:
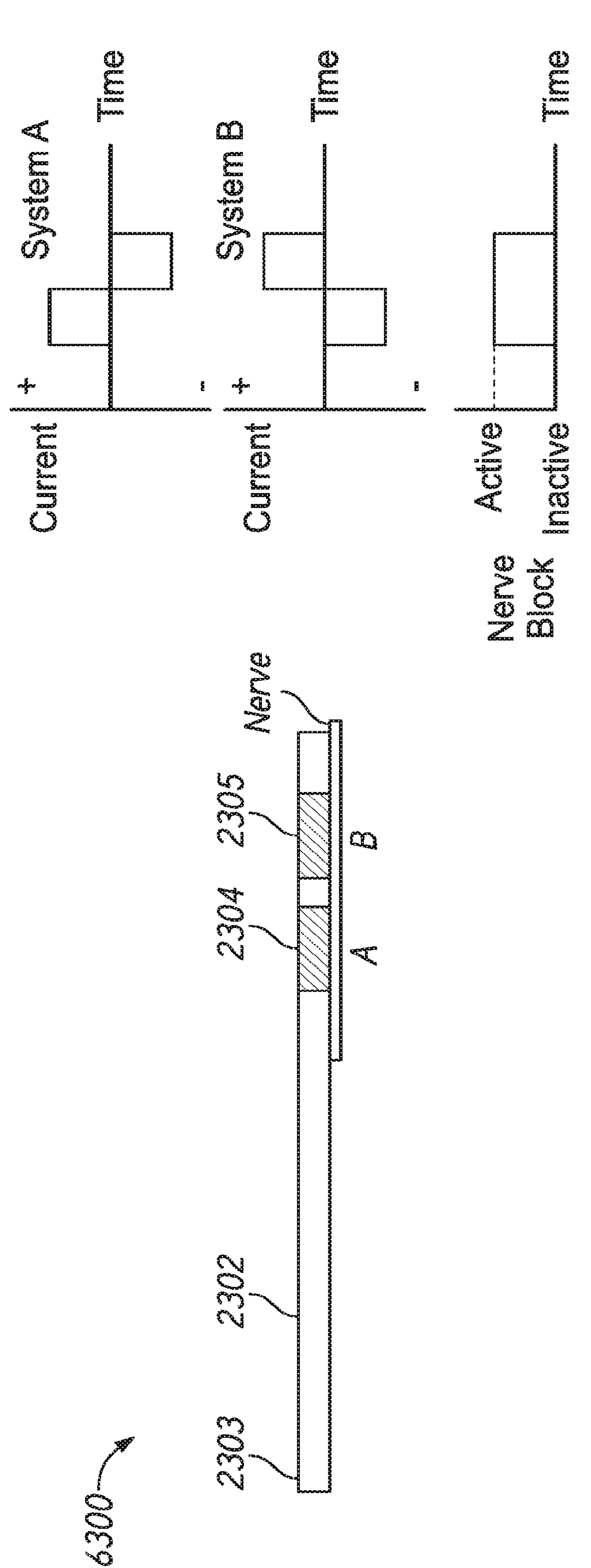

FIG. 63 illustrates an embodiment of an electrode lead system operated in continuous block mode.

FIGS. 64A-64H illustrate various embodiments of separated interface nerve (SINE) electrodes.

Figure 65A:
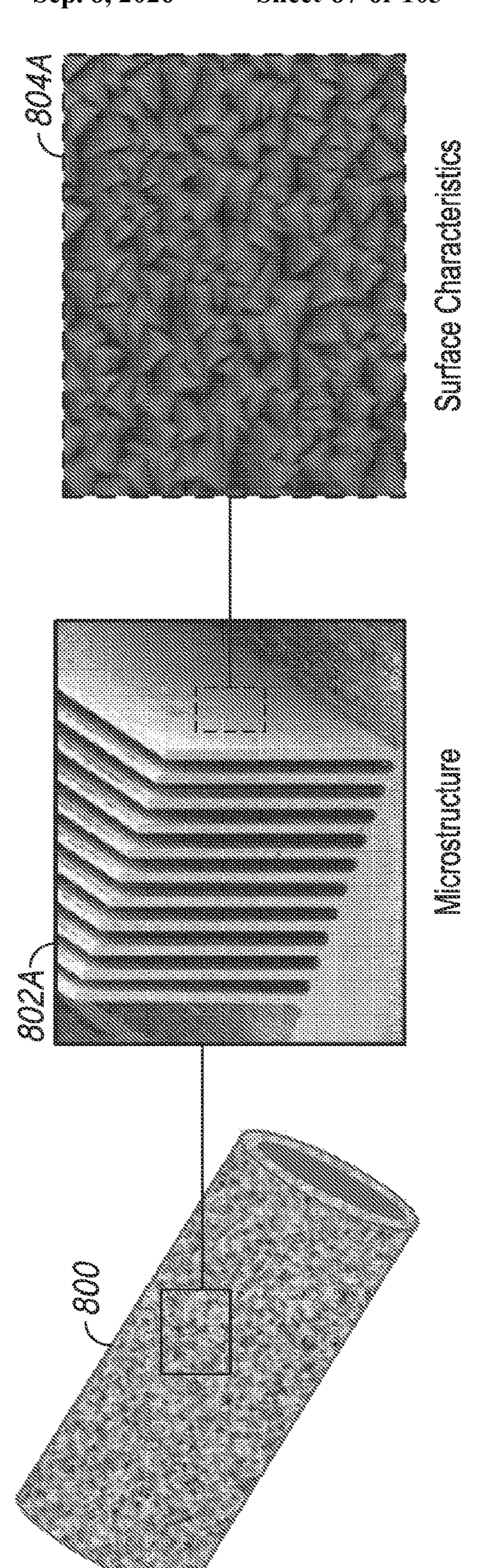

FIGS. 65A-65C illustrate embodiments of high charge density electrodes and electrode leads.

Figure 65D:
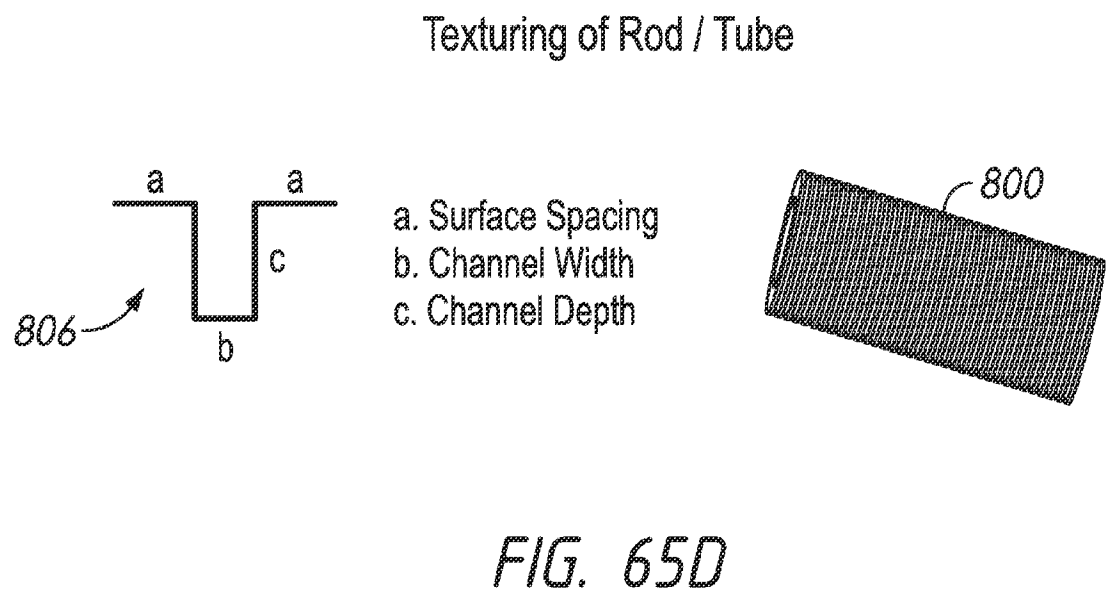
Figure 65E:
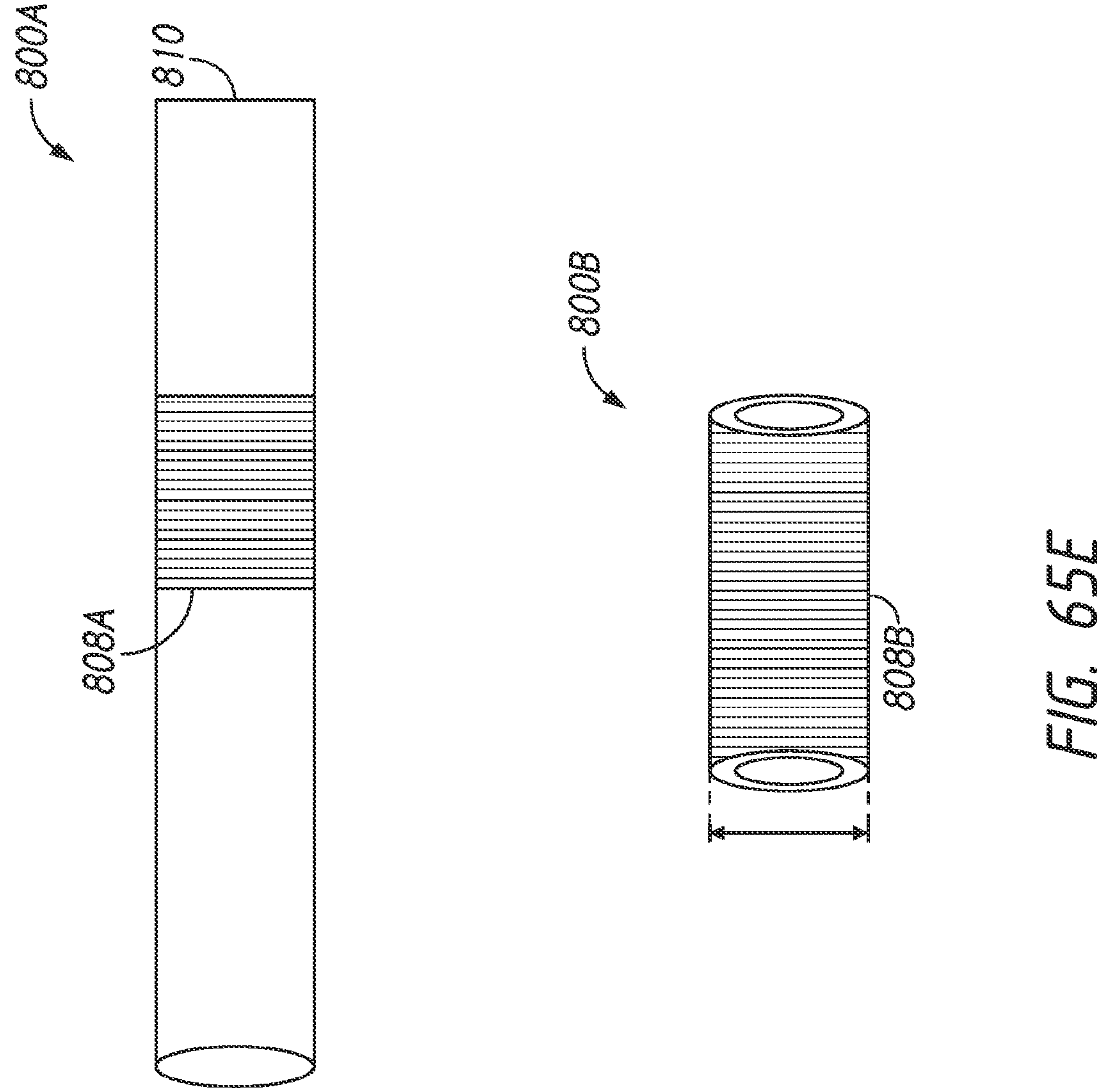
Figure 65F:
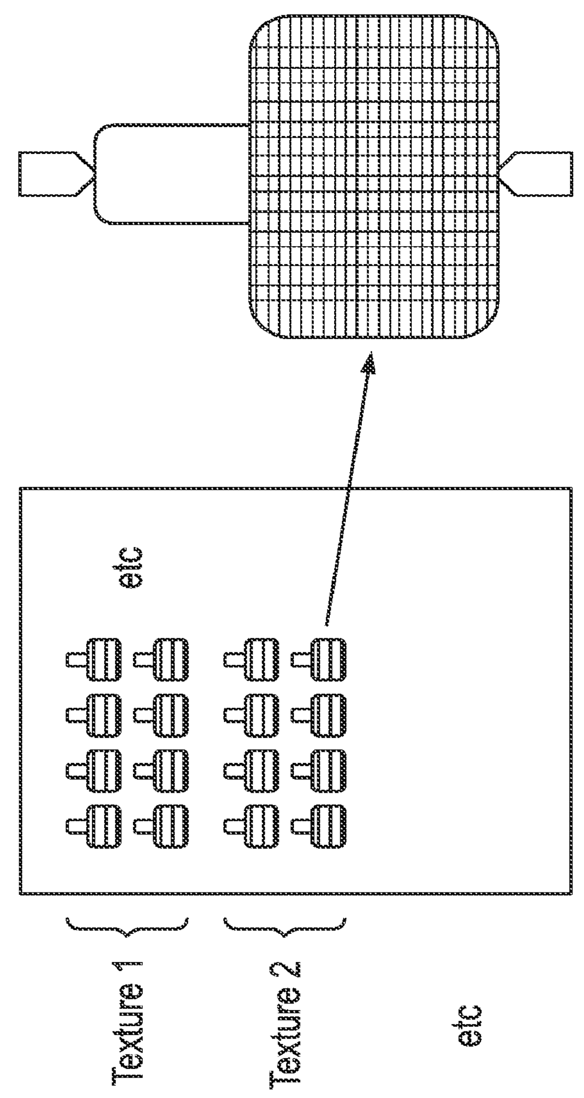
Figure 65G:
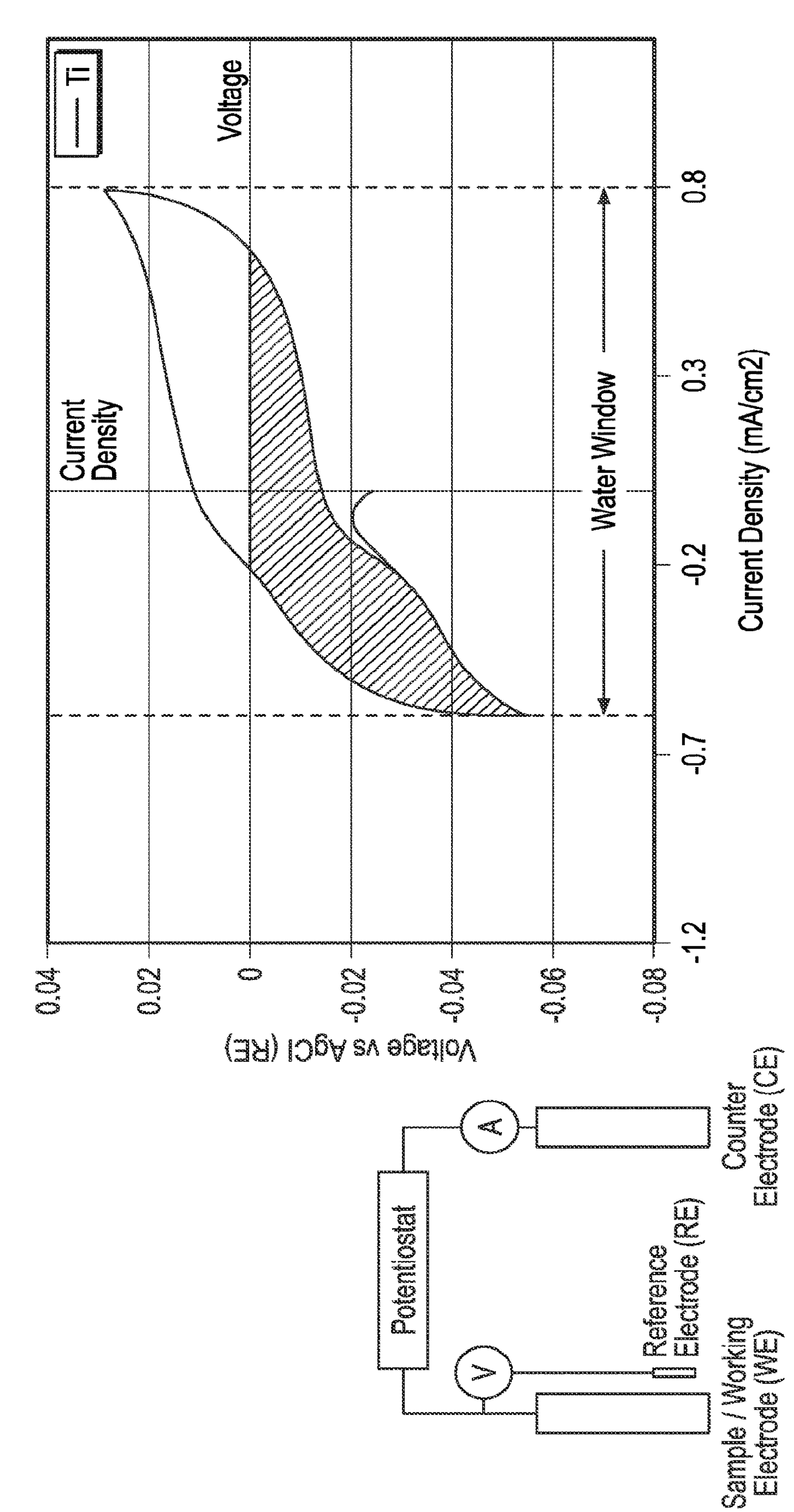

FIGS. 65D-65E illustrate embodiments of a surface area multiplication technology technique that can include texturing of a rod and/or tube. FIG. 65F illustrates an embodiment of a surface area multiplication technology technique that can involve laser texturing of a titanium foil/sheet.

FIGS. 65G-65K illustrate that the cathodic charge storage capacity (shaded regions) can be measured using cyclic voltammetry.

Figure 66A:
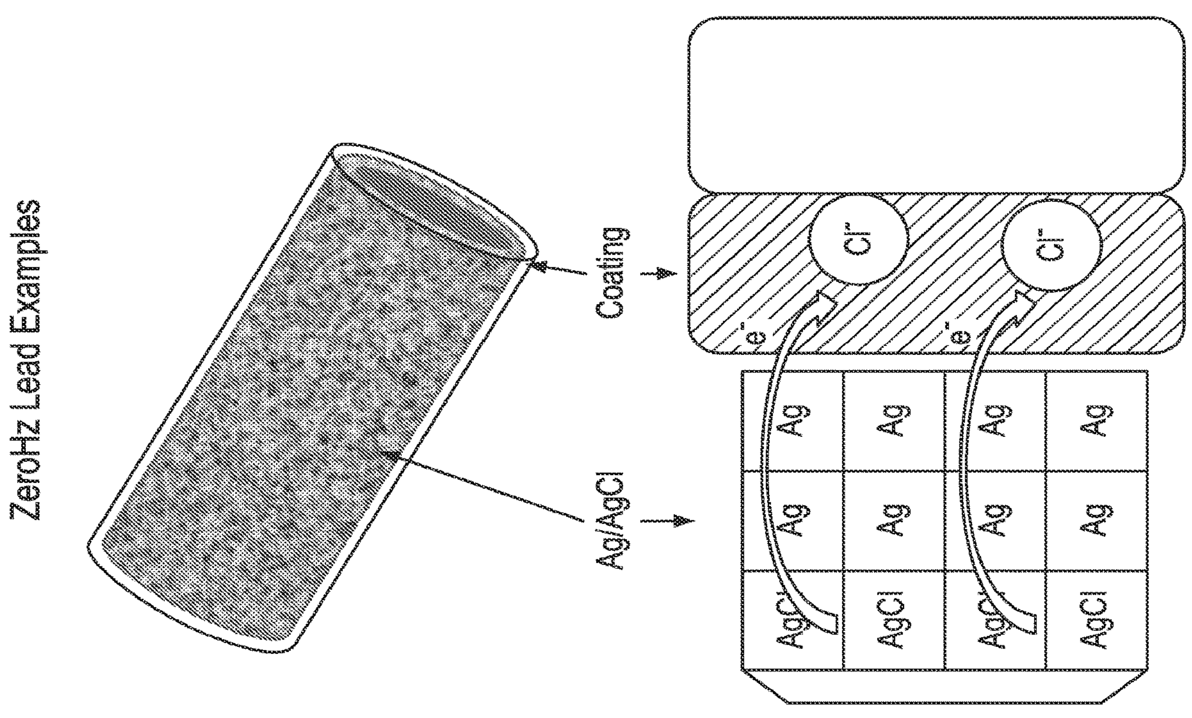
Figure 66B:
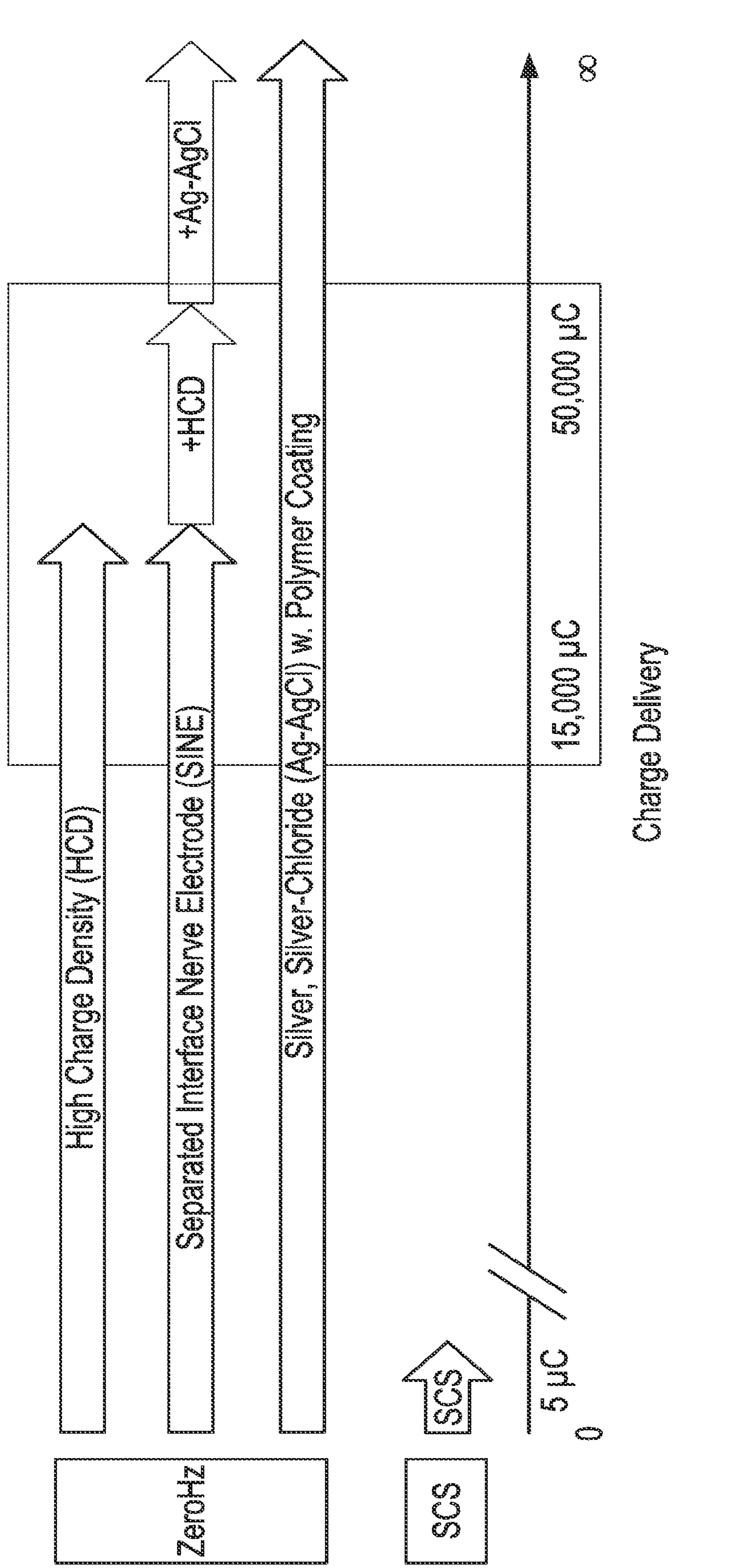

FIGS. 66A-66C schematically illustrate embodiments of various aspects of medical electrical delivery systems and components.

Figure 67A:
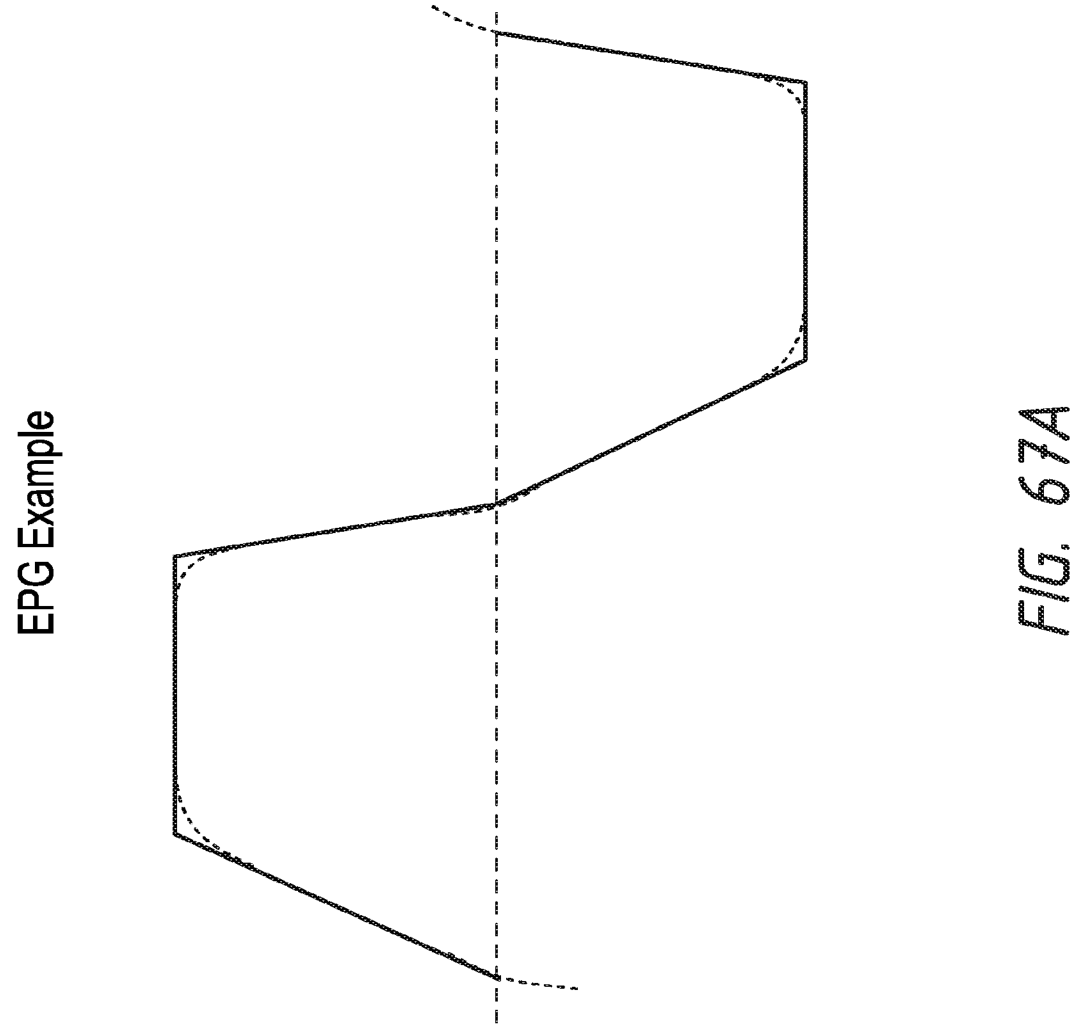
Figure 67B:
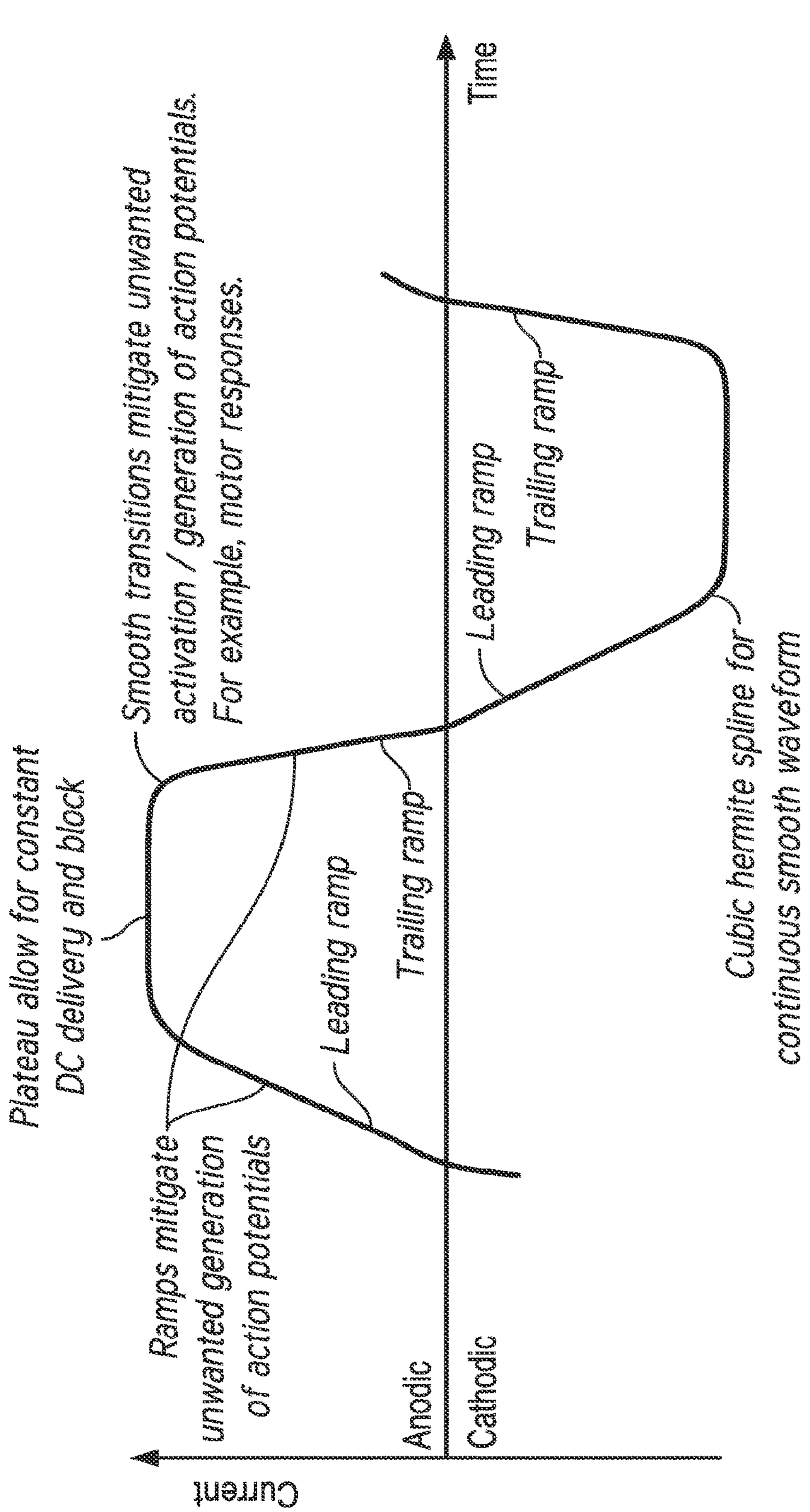
Figure 67C:
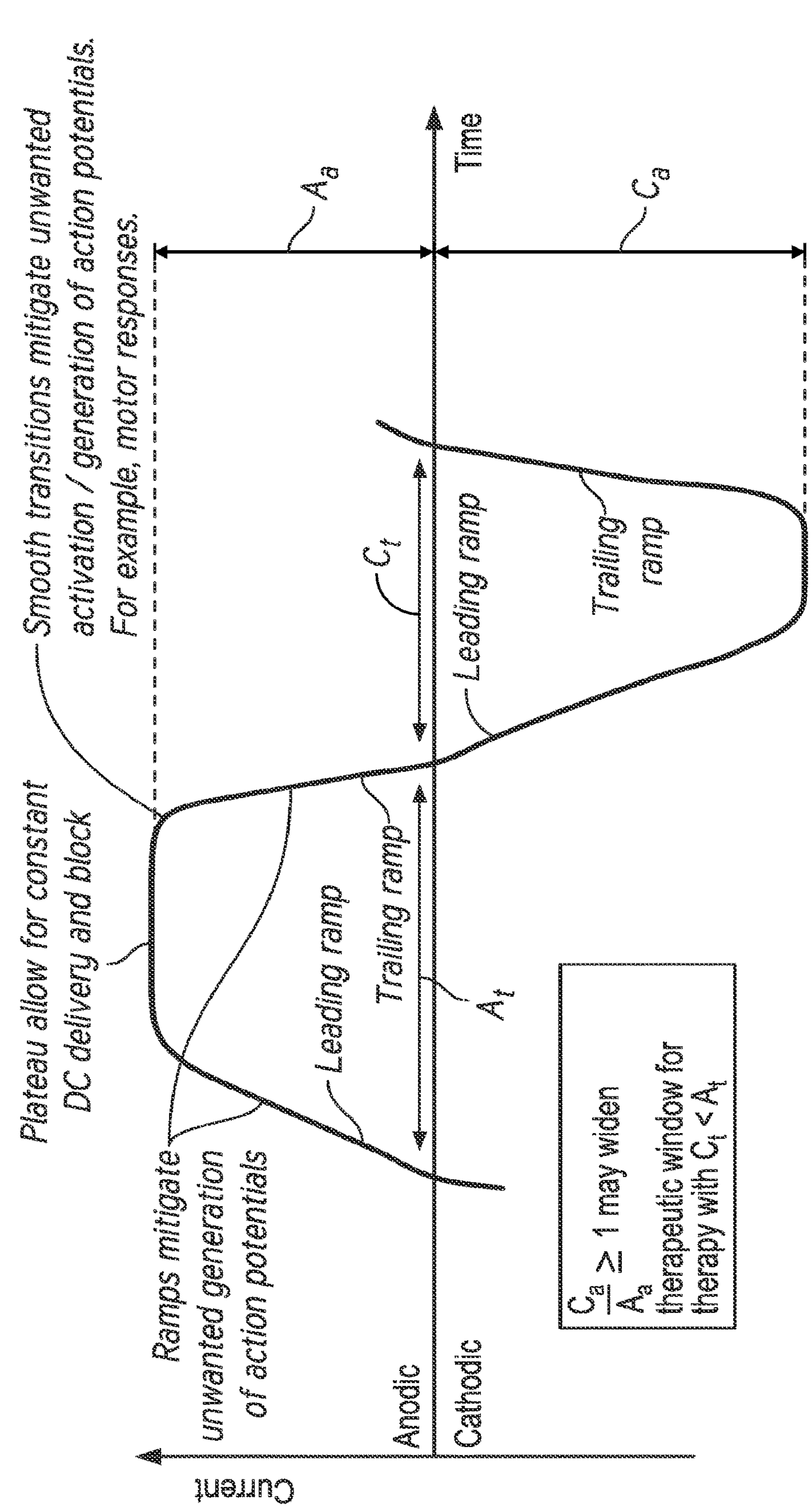

FIGS. 67A-67C illustrate examples of a pulse generator waveform that can advantageously assist in achieving full nerve block quickly without unwanted side effects.

DETAILED DESCRIPTION

This application describes, in some aspects, methods and systems for management of chronic and acute pain states via safe application of direct current (DC) to facilitate nerve block including nerve hypersuppression, or nerve block without rapid reversibility or recovery after direct current application has been removed or stopped. By interfacing with the nerve via ionic conduction pathways instead of conventional electrodes that that do not have an ionic conduction component, an intermittent or continuous short term and long-term nerve block can be generated while reducing risk of damage to the nerve cells. What is disclosed in some embodiments are systems and electrodes for safely delivering blocking direct current (DC) to neural tissue by delivering cycled cathodic and anodic current through a high-charge chemistry. Tissue safety can be maintained by separating the metal interface from the nerve tissue with an ionically conductive element, and by operating the electrode below reaction potentials for undesired reactions, such as electrolysis of water, or oxidation and reduction of water (H2O), which create harmful reactive species such as OH—, H+ or oxygen free radicals.

Not to be limited by theory, the propagation of action potentials in electrically excitable tissue, e.g. neural tissue, leads to refractory periods on the order of milliseconds for sodium channels, typically between about 1 ms and about 20 ms, or between about 2 ms and about 5 ms for the combined absolute and relative refractory periods, thus very low frequency AC current waveforms with half periods meaningfully greater than this refractory period (e.g., greater than about 1 ms, 1.5 ms, 2 ms, 2.5 ms, 3 ms, or more) can also be used to create tissue blockade, and will be perceived by electrically excitable tissue as a direct current stimulus. As such, direct current as defined herein is inclusive of low frequency AC current waveforms that are perceived as and functionally is direct current from the perspective of the tissue whose action potentials are being modulated. The frequency could be, for example, less than about 1 Hz, 0.5 Hz, 0.1 Hz, 0.05 Hz, 0.01 Hz, 0.005 Hz, 0.0001 Hz, or ranges including any two of the foregoing values so long as the direction of current flow is constant over at least the entire refractory period of the target tissue, or at least twice as long as the refractory-causing membrane channel time constant (for example, fast sodium channel inactivation gate time constant)

Chronic pain is a significant burden on individuals and society as a whole. Nearly 50 million adults are estimated to have significant chronic or severe pain in the US alone. (See Nahin, Estimates of Pain Prevalence and Severity in Adults: United States, 2012, The Journal of Pain, 2015 August 16(8): 769-780) Worldwide, chronic pain is estimated to affect more than 1.5 billion people. (Borsook, A Future Without Chronic Pain: Neuroscience and Clinical Research, Cerebrum, 2012 June) While surgical techniques are sometimes applied to remove a specific source of pain, typically due to impingement of a nerve, in many cases the precise cause of pain is not clear and cannot be reliably addressed via a surgical procedure. Pain management can alternatively be addressed by overwhelming the central nervous system with stimulating signals that prevent registration of pain inputs (gate control theory of pain). Typically, this stimulation in the case of spinal cord stimulation (SCS) is performed using metal electrodes and alternating current (AC) stimulation to produce these additional stimulating signals to prevent pain sensation. However, one major drawback is the presence of paresthesia, a sensation of tingling in the innervated region downstream from the stimulated nerve. Methods to eliminate paresthesia which patients can find discomforting have led to different means of stimulation from conventional tonic SCS (~30-120 Hz) stimulation including high frequency stimulation (~10 kHz) and burst stimulation (e.g., five pulses at 500 Hz delivered 40 times per second). (Tjepkema-Cloostermans et al, Effect of Burst Evaluated in Patients Familiar With Spinal Cord Stimulation, Neuromodulation, 2016 July 19(5):492-497).

An alternative means to manage pain signaling to the central nervous system is to prevent conduction of the pain signals from the peripheral signal source by directly blocking the pain signals as compared to masking the pain signals by generating alternative neural inputs to crowd out and inhibit pain signal transmission as in traditional SCS and gate theory. One means to do this is by applying a direct current (DC) to a nerve to prevent action potential (AP) generation and transmission. Because this does not stimulate the nerve as in traditional stimulation, paresthesia can be avoided. The mechanism leading to AP block has been attributed to a depolarization block that deactivates the sodium channels required for an action potential event under the electrode site. (See Bhadra and Kilgore, Direct Current Electrical Conduction Block of Peripheral Nerve, IEEE Transactions on Neural Systems and Rehabilitation Engineering, 2004 September 12(3): 313-324).

Bhadra et al. showed that upon application of DC to nerve tissue, action potential conduction can be blocked (See Bhadra and Kilgore, Direct Current Electrical Conduction Block of Peripheral Nerve, IEEE Transactions on Neural Systems and Rehabilitation Engineering, 2004 September 12(3): 313-324). The authors showed that removal of DC delivery from the same nerve tissue resulted in instantaneous restoration of nerve conduction. However, direct current has long been known to be dangerous to nerve tissue due to creation of toxic species at the electrode-nerve interface (Merrill, Electrical Stimulation of Excitable Tissue: Design of Efficacious and Safe Protocols, Journal of Neuroscience Methods, 2005, 141:171-198). Ackermann et al and Fridman et al have developed systems and methods of safely delivering DC to nerve tissue by separating the toxic species created at the electrode interface from the nerve tissue (U.S. Pat. Nos. 9,008,800 and 9,498,621; Ackermann et al, Separated Interface Nerve Electrode Prevents Direct Current Induced Nerve Damage, J Neurosci Methods, 2011 September 201(1): 173-176; Fridman and Santina, Safe Direct Current Stimulation to Expand Capabilities of Neural Prostheses, IEEE Transaction of Neural Systems and Rehabilitation Engineering, 2013 March 21(2):319-328; Fridman and Santina, Safe Direct Current Stimulator 2: Concept and Design, Conf Proc IEEE Eng Med Bio Soc, 2013: 3126-3129), each of the foregoing of which are incorporated by reference in their entireties. They also teach that rapid reversibility of nerve blockade is desirable and achievable through halting of DC delivery. Ackermann et al. teaches that an undesired, but reversible, suppression of nerve activity occurs with long term direct current delivery (where nerve tissue was shown to be non-conductive for a short period of time following cessation of DC delivery) (U.S. Pat. Nos. 9,008,800 and 9,498,621; Ackermann et al, Separated Interface Nerve Electrode Prevents Direct Current Induced Nerve Damage, J Neurosci Methods, 2011 September 201 (1):173-176), each of which are incorporated by reference in their entireties. Those authors specifically teach methods to reduce this suppression of nerve activity by limiting the duration of DC delivery to allow rapid nerve recovery upon cessation of DC delivery (e.g., within seconds) (U.S. Pat. Nos. 9,008,800 and 9,498,621; Ackermann et al, Separated Interface Nerve Electrode Prevents Direct Current Induced Nerve Damage, J Neurosci Methods, 2011 September 201 (1):173-176). What is invented and described herein in some embodiments are systems and methods for doing the opposite of that which is taught by Ackermann et al: intentionally blocking nerve activity by using periodic DC pulses to intentionally place neural tissue in a state of hypersuppression without rapid reversibility upon cessation of DC delivery (reversibility that occurs in many minutes to hours, as opposed to seconds or less than a minute). Furthermore, what is invented and described herein in some embodiments are systems and methods of treating pain by the aforementioned systems and methods, specifically through selective blockade of antero-lateral column tissue in the spinal cord. Furthermore, what is invented and described herein are systems and methods of treating pain by the aforementioned systems and methods, specifically through selective blockade of dorsal root tissue and/or dorsal root ganglia. Furthermore, what is invented and described herein are systems and methods of treating pain by the aforementioned systems and methods, specifically through blockade of one or more peripheral nerves.

With targeted nerve block, pain from specific dermatomes and pain in regional body sites can be managed. A number of localized targets implicated in moderating pain signal transduction can be addressed. For example, both more centrally located nerve tissues such as the spinothalamic tract and dorsal root ganglion can be targeted to manage lower back pain, sciatica, and complex regional pain syndrome (CPRS) among other pain considerations.

Electrodes where current in the form of ions is generated proximal to the at least one target nerve may comprise an ionically conductive material such as a liquid (e.g., saline or other electrolyte solution), gel, hydrogel, hydrocolloid, polymer, or film. In an alternative embodiment, the ionically conductive materials may be separated by a screen or other filter or membrane material from the nerve tissue. This separating interface may be configured to selectively allow ions through to the nerve to reduce nerve damage such as microporous screens, non-woven screens, ion-exchange membranes (IEM), supported liquid membranes or ionogels, polymer electrolytes such as polyethylene oxide (PEO), polypropylene oxide (PPO), polyvinylidene fluoride-co-hexafluoropropylene copolymer (PVDF-HFP), solid ion conductors, and ion-selective films including cation exchange membranes and anion exchange membranes.

The nerve-interfacing element of the electrode may be further configured to be exposed selectively along the electrode and may be otherwise insulated from the nerve by an ionically impermeable layer. The impermeable layer may also be configured to be electrically insulating to current.

The ionically conducting material may also be separated into multiple regions which may contain different types of ionically conducting material. The interfaces between the different regions may be delineated by semi-permeable membranes or screens that allow for selective or general ionic flow but limit the passage of damaging by products from the conversion of electron current to ionic current. This separating element may be configured to selectively allow ions through to the nerve to reduce nerve damage such as microporous screens, non-woven screens, ion-exchange membranes (IEM), supported liquid membranes or ionogels, polymer electrolytes such as polyethylene oxide (PEO), polypropylene oxide (PPO), polyvinylidene fluoride-co-hexafluoropropylene copolymer (PVDF-HFP), solid ion conductors, and ion-selective films including cation exchange membranes and anion exchange membranes. The different ionically conducting materials may also take different forms. As an example, the nerve may be in contact with a hydrogel which is in contact with a liquid such as an electrolyte solution which then is in contact with a traditional electrical current electrode material.

In some embodiments the traditional electrode may be made from a material such as platinum, platinum-iridium, carbon, titanium nitride, copper, tantalum, silver, silver-chloride or other metals and materials or combinations thereof. In some embodiments, the traditional electrode may be made from carbon, graphite, glassy carbon, dendritic carbon, or other conductive materials. By using high-charge chemistry amplitude and duration of direct current (DC) block can be increased. Candidate chemistries include using a combination of Ag/AgCl electrode in an electrolyte bath (or other suitable ionically conductive material) such as saline that is in ionic contact with neural tissue of interest. In some embodiments the electrode is reversible and can be restored to its initial state. In some embodiments the electrode is sacrificial and the electrochemical reaction that occurs at the electrode cannot be reversed to restore the electrode to its initial state.

Electrodes can be made of a variety of materials. In some embodiments, electrode can be made of silver (Ag) and/or silver chloride (AgCl). In some embodiments, electrode can be made of titanium nitride (TiN). In some embodiments, electrode can be made of carbon (C). In some embodiments, the electrode has an ion-selective coating or membrane. In some embodiments, the electrode does not have an ion-selective coating or membrane.

In some embodiments, an electrode can include a contact comprising a high charge-capacity material. The electrode contact can have in some cases a geometric surface area of between about 1 $mm^2$ and about 10 $mm^2$, or about 1 $mm^2$, 2 $mm^2$, 3 $mm^2$, 4 $mm^2$, 5 $mm^2$, 6 $mm^2$, 7 $mm^2$, 8 $mm^2$, 9 $mm^2$, 10 $mm^2$, 20 $mm^2$, 50 $mm^2$, 100 $mm^2$, or ranges including any two of the foregoing values. The electrode contact itself can be fabricated of a high charge capacity material, such as those described, for example, in U.S. Pat. No. 10,071,241 to Bhadra et al., which is hereby incorporated by reference in its entirety. Alternatively, the electrode contact can comprise a base at least partially, or entirely coated with a high charge capacity material. In some embodiments, a high charge capacity material can have a Q value of at least about 25, 50, 100, 200, 300, 400, 500, 1,000, 2,500, 5,000, 10,000, 50,000, 1000,000, 500,000, or more μC, or ranges including any two of the foregoing values. The Q value of an electrode contact can refer to the total amount of charge that can be delivered through an electrode contact before the electrode contact begins having irreversible chemical reactions, such as oxygen or hydrogen evolution, or dissolution of the electrode materials. Non-limiting examples of high charge capacity materials are platinum black, iridium oxide, titanium nitride, tantalum, silver chloride, poly(ethylenedioxythiophene) and suitable combinations thereof. The electrodes could be fractal coated electrodes in some embodiments. To generate more surface area for the electrochemical reactions to occur, the traditional electrodes may be made from high surface area to volume structures such as roughened surfaces, woven surfaces, patterned surfaces, reticulated foam structures, porous sintered bead structures, nano- or micro-patterned structures to expose additional material surface area. In some embodiments, the electrode can be a SINE (separated-interface nerve electrode) or EICCC (electron to ion current conversion cell) electrode in which an electrode is immersed in an electrolyte solution which is in contact with an ion-conductive material-electrolyte solution interface with an ion-conductive material that electrically contacts the cardiac tissue or area proximal to cardiac tissue, as described, for example, in U.S. Pat. No. 9,008,800 to Ackermann et al., and U.S. Pub. No. 2018/0280691 to Ackermann et al., which is hereby incorporated by reference in their entireties.

The combination of traditional electron-carrying electrode material and ionic conducting material and the conversion mechanism can be collectively characterized as an electron-ion current conversion cell (EICCC). One such example might be a silver/silver chloride (Ag/AgCl) electrode immersed in a saline, e.g., isotonic 0.9% NaCl saline solution fluidly in contact with a saline-containing hydrogel. Upon driving of an electric current through the conventional electrode, reduction of the solid AgCl will drive conversion to solid Ag and Cl— ion formation generating a flow of ions or an ion current. This ionic current flow can be used to modulate the nerve membrane potential and, for example, create a blockade of nerve conduction. The membrane potential may be modulated in such a manner that the potential is ramped up slowly enough to avoid action potential generation as the nerve tissue is depolarized. Upon reversal of the electric current, oxidation of the previously formed Ag or other Ag in the Ag/AgCl electrode will be oxidized to generate AgCl deposits on the electrode, driving the ion current in the opposite direction. Due to the extremely low solubility of Ag and AgCl in saline, the electrode remains mechanically intact during forward and reverse current delivery. In combination, the reduction-oxidation reactions create a fully reversible EICCC. To maintain the preferred reduction-oxidation reaction between Ag and AgCl (or other electrode materials), the amount, e.g., mass, volume, density, or another parameter of the AgCl on the electrode may be maintained within 5%-95%, 10%-90%, 20%-80%, 25%-75%, 30%-70% of its original starting mass on the electrode to ensure that the AgCl is never depleted or saturated, enabling other deleterious reactions from happening at the electrode. In some embodiments, the amount of the electrode can be maintained at least about, or no more than about 5%, 10%, 15%, 20%, 25%, 30%, 35%, 40%, 45%, 50%, 55%, 60%, 65%, 70%, 75%, 80%, 85%, 90%, 95%, 100%, or ranges of between about any two of the foregoing values. In other words, the electrode is reversible and can be restored to its original or substantially to its near-original state. To generate more surface area for the electrochemical reactions to occur, the traditional electrodes may be made from high surface area to volume structures such as roughened surfaces, woven surfaces, patterned surfaces, reticulated foam structures, porous sintered bead structures, nano- or micro-patterned structures to expose additional material surface area. High-charge chemistry electrodes can be biocompatible, or suitably sequestered from body if not. A high surface area electrode material (e.g. Ag/AgCl) in the EICCC may be utilized specifically to decrease the electrode potential drop or to reduce the increase in electrode potential drop which may occur with prolonged current delivery. In some embodiments the EICCC driving current may be between about 0 mA and about 1 mA, between about 1 mA and about 2 mA, between about 2 mA and about 4 mA, between about 4 mA and about 8 mA, higher than about 8 mA, about 0.5 mA, 1 mA, 2 mA, 3 mA, 4 mA, 5 mA, 6 mA, 7 mA, 8 mA, 9 mA, 10 mA, or ranges incorporating any two of the foregoing values. In some embodiments this driving current is then used to generate a corresponding ionic current of similar magnitude, depending on the specific electrochemical reactions.

Another embodiment of the EICCC may comprise a material such as tantalum or titanium nitride to generate a capacitive traditional electrode interface instead of an interface at which an electrochemical reaction occurs. Transparent conducting oxides (TCOs) such as fluorine-doped tin oxide (FTO), nickel titanium dioxide (Ni/TiO2), and other titanium dioxide (TiO2) constructs are also candidate materials that have high charge carrying capacities. In this configuration, charge generation at the traditional electrode surface would attract ionic species from the ionically conductive material until the charge at the traditional electrode interface is passivated. Charging of the capacitive material with an electric current of one polarity can generate current flow in the form of ions. Reversing the polarity of the current flow to the capacitive material can effectively reset the system for a subsequent charging to generate further ionic current flow. To generate more surface area for increased ion current flow capacity to occur, the traditional electrodes may be made from high surface area to volume structures such as roughened surfaces, reticulated foam structures, porous sintered bead structures, nano- or micro-patterned structures to expose additional material surface area. In one embodiment, this capacitive structure is in fluid contact with an electrolyte solution that contacts an electrolyte-saturated hydrogel in contact with target nerve tissue to enable ion current flow to the tissue. In some embodiments, the solution is body fluid such as interstitial fluid that delivers the current to the electrically excitable tissue from the electrode.

In a further embodiment of the EICCC, a combination of both electrochemical and capacitive mechanisms may be used to convert current in the form of electrons to current in the form of ions.

To deliver ionic current to the nerve to facilitate a block, the traditional electrode may be connected via a conductive lead to one or more current sources. A single nerve-electrode interface can provide nerve block when current is applied in one polarity to the EICCC (blocking phase). When the current polarity is reversed to return the electrode to its original state (which may be a non-blocking phase or also a blocking phase), the nerve may or may not continue to block pain stimulus from passing along the nerve. If the nerve has been placed into a state of hypersuppression, the nerve will continue to prevent AP propagation and block pain regardless of the phase state of the electrode. Fridman and Santina have described a means to enable continuous block when current polarity is reversed as driven by an alternating current (AC) using a series of valves to direct current flow direction (Fridman and Santina, Safe Direct Current Stimulation to Expand Capabilities of Neural Prostheses, IEEE Transaction of Neural Systems and Rehabilitation Engineering, 2013 March 21(2):319-328; Fridman and Santina, Safe Direct Current Stimulator 2: Concept and Design, Conf Proc IEEE Eng Med Bio Soc, 2013: 3126-3129). However, in some cases it is desirable to have a more simple system which does not require the use of valves which present additional failure points and add bulk to an implantable system. A simpler, more robust system may be configured without valves and such moving parts by using multiple EICCCs to provide constant stimulation of the nerve tissue itself. In one embodiment to provide continuous block, two nerve-electrode interfaces are present and connected to one or more current sources. The first nerve-electrode interface EICCC is run with the current in one polarity to drive a block while the second nerve-electrode interface EICCC is run with the opposite polarity. After a period of time, the current polarities of the first and second EICCCs are reversed and the second nerve-electrode interface provides a block while the first nerve-electrode interface EICCC state is reversed to its prior state. By cycling the dual-EICCC electrode currents, a continuous block can be maintained at the target nerve. As can be appreciated, more than two, such as 3, 4, 5, 6, 7, 8, 9, 10, or more EICCCs may also be used to facilitate the same continuous block. Electrodes may also be run in either monopolar or bipolar configurations. In some embodiments the EICCC system is configured to not have any mechanically moving parts such as valves or hinges.

Alternatively, nerve activity may be suppressed which means that nerve activity remains blocked even after removal or discontinuation of the blocking current. The nerve may be further put into a state of hypersuppression in which the nerve remains blocked without rapid reversibility after cessation of DC delivery. Modulation of the initial current delivered to the nerve tissue including ramp rate, current amplitude, total charge delivery, and waveform shape can be used to place the nerve in a state of suppression. During the state of suppression, the EICCC may be returned to its initial state by reversing the current polarity used to generate the initial block and suppression state. During the period of reverse current flow, the nerve may remain in a state of hypersuppression. In another configuration the EICCC may deliver subsequent blocking current inputs that extend the suppression duration, with periods of no current delivery, or of reversal current in between blocking current doses. The nerve tissue may remain in a state of hypersuppression during the periods of non-blocking current input. In another configuration, the EICCC may be configured to deliver subsequent current inputs on a schedule. In some embodiments, the DC block waveform may have an amplitude of between 0-250 microamps, 250-500 microamps, 500-1000 microamps, 1000-1500 microamps, or 2000 microamps, or higher, or about, at least about, or no more than about 50, 100, 150, 200, 300, 400, 500, 600, 700, 800, 900, 1,000, 1,100, 1,200, 1,300, 1,400, 1,500, 1,600, 1,700, 1800, 1,900, 2000 microamps or more, or other ranges incorporating any two of the aforementioned values. Placing a nerve into a state of hypersuppression may be facilitated in some embodiments by delivering a charge of 10-50 millicoulombs, 50-100 millicoulombs, 100-500 millicoulombs, 500-1000 millicoulombs, or 1000 millicoulombs or greater, or about, at least about, or no more than about 10, 25, 50, 100, 200, 300, 400, 500, 600, 700, 800, 900, 1,000, or more millicoulombs, or other ranges incorporating any two of the aforementioned values, and depending on nerve size and desired hypersuppression duration. DC block amplitude and current duration may be tuned to enable hypersuppression in the range of, for example, 0-0.5 times the duration of initial DC block, 0.5-1 times the duration of initial DC block, 1-1.5 times the duration of initial DC block, 1.5-2 times the duration of initial DC block, and greater than 2 times the duration of initial DC block, or about, at least about, or no more than about 0.1×, 0.2×, 0.3×, 0.4×, 0.5×, 0.6×, 0.7×, 0.8×, 0.9×, 1×, 1.1×, 1.2×, 1.3×, 1.4×, 1.5×, 1.6×, 1.7×, 1.8×, 1.9×, 2×, 2.5×, 3×, 4×, 5×, or more relative to the duration of initial DC block, or ranges including any two of the aforementioned values.

Sensing the local state of and proximal to the nerve tissue can also provide a useful measure for determining when to provide current inputs to extend nerve suppression as well as to provide a feedback loop for initial current delivery to generate the initial nerve block by modulating the nerve potential such that it cannot transmit action potentials. In one embodiment the nerve's ability to conduct action potentials is monitored such that as direct current is delivered to the nerve tissue, the direct current delivery can be maintained to ensure that the nerve block is maintained, for example. Nerve conduction ability may be monitored by any suitable measure such as delivering a stimulus pulse and measuring compound action potential signal.

In some embodiments sensing is in the form of a reference electrode to measure potential differences relative to the two electrodes which are passing the active current. In some embodiments the active current is modulated in response to one or more measured electrode potentials relative to the reference electrode. In some embodiments the active current is modulated when measured electrode potential indicates that undesired electrochemical reactions may occur at one or more active electrodes. For example, active current may be reduced or ceased upon measurement of an active electrode potential that indicates water electrolysis is occurring or possible. The EICCC may be operated with a direct current input or by applying a potential difference between the working electrode and an auxiliary or counter electrode. In some embodiments, a reference electrode may be located within the EICCC or at the distal end of the EICCC proximal to the nerve tissue.

Figures 1A, 1B:
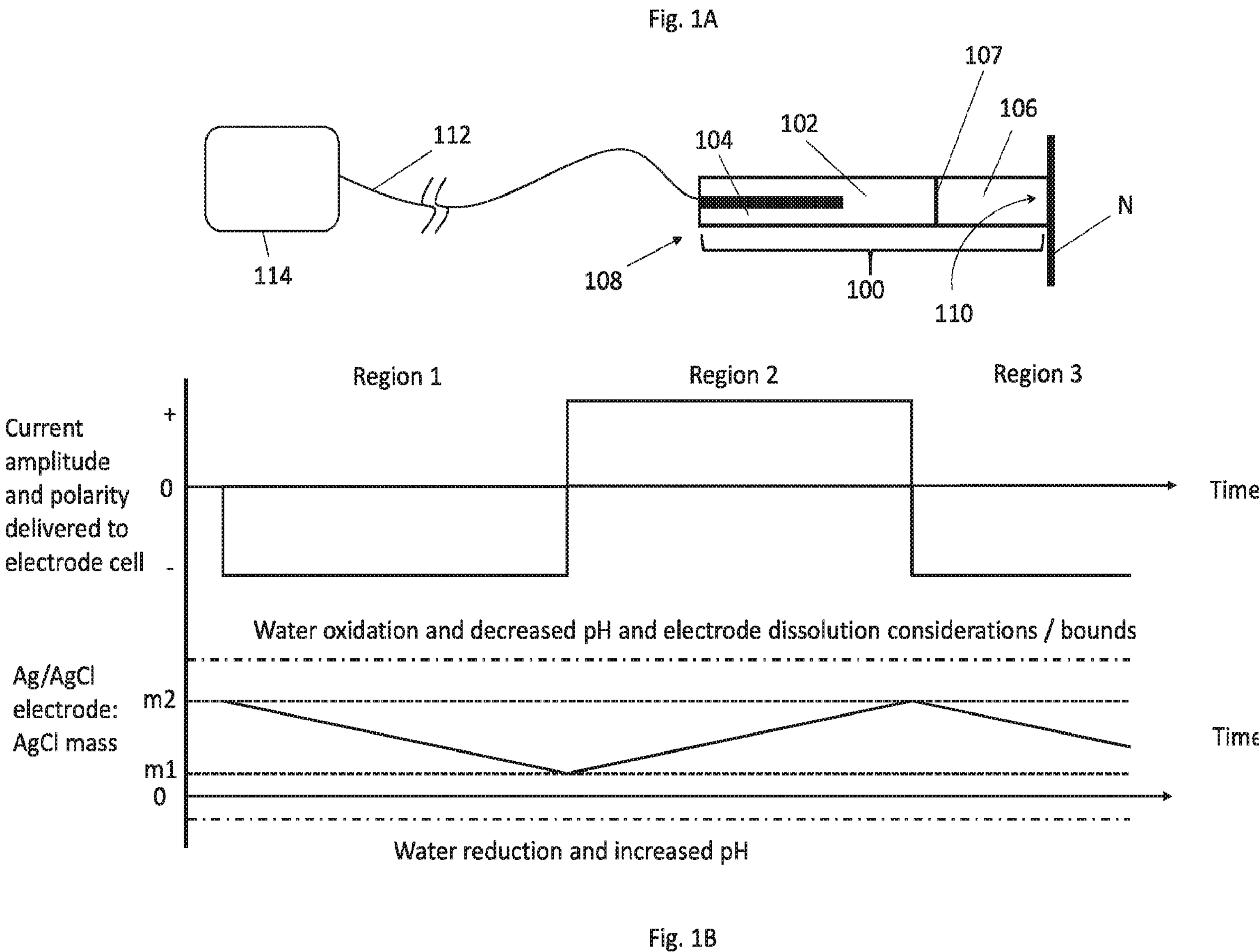
FIG. 1A shows an embodiment of an EICCC electrode in which an electrode is immersed in an electrolyte solution which is in contact with an ion-conductive material-electrolyte solution interface with an ion-conductive material that electrically contacts the nerve tissue N or area proximal to the nerve tissue N.
FIG. 1B is a graph illustrating by pushing a constant current from the current source, the mass of the AgCl electrode can decrease during a cathodic current (reduction reaction) and then increase with an anodic current during an oxidative reaction.

FIG. 1A shows an embodiment of an EICCC electrode 100 in which an electrode 104 is immersed in an electrolyte solution 102 which in is contact with an ion-conductive material—electrolyte solution interface 107 with an ion-conductive material 106 such as a fluid, hydrogel, gel or other polymer that electrically contacts the nerve tissue N or area proximal to the nerve tissue N. The EICCC electrode 100 also comprises an electrically insulated, biocompatible enclosure 108 housing the traditional electrode 104, electrolyte 102, and biocompatible ion conducting material 106 with an aperture (near 110) to enable electrical contact with the nerve N or area proximal to the nerve tissue N. The system further comprises a current delivery lead 112 between the current source 114 and the electrode 104. The current source 114 may be located external or internal to the body depending on the application need. An exemplary non-limiting embodiment of the EICCC 100 comprises a silver, silver-chloride (Ag/AgCl) electrode in a 0.9% saline solution in fluid contact with an electrolyte saturated hydrogel (agar preparation with 0.9% saline).

With an Ag/AgCl electrode used to generate current via reduction of the AgCl on the electrode in a saline solution (NaCl), a sustainable and reversible electrochemical reaction can be achieved to convert current in the form of electrons into current in the form of ions. As seen in Region 1 of FIG. 1B, by pushing a constant current from the current source, the mass of the AgCl electrode will decrease from mass m2 to mass m1 during a cathodic current (reduction reaction) and then increase as seen in Region 2 from mass m1 back to mass m2 with an anodic current during an oxidative reaction. Furthermore, it can be appreciated that by limiting the maximum mass of the AgCl to m2 such that the mass of unreacted Ag is greater than zero helps prevent the Ag/AgCl reaction from depleting available Ag for the electrochemical reaction and provides a reserve safety factor in the event of excess current delivery similar to maintaining m1 above zero. In Region 3, the current polarity is again reversed to match that of Region 1. By not depleting the AgCl mass to zero, the preferred reaction between conversion of solid AgCl to solid Ag with generation of chlorine ions and vice-versa:

$$AgCl(s) + e^- \Leftrightarrow Ag(s) + Cl^-$$

Because water electrolysis or hydrolysis happens at higher reduction potential than AgCl, AgCl dissolution will be preferred preventing undesired reactions and generation of OH—, H+ or oxygen free radicals in the EICCC. Further notable is that the absolute value of the area between the current amplitude and the x-axis (time) can be used to define the total charge delivered (or removed) from the electrode to allow for determination or prediction and/or control of the electrode AgCl mass. It will be appreciated that the current waveform shapes in the different regions need not be perfect square waves but may include finite slopes that ramp from zero amplitude to their final maximum amplitude as well as from their maximum waveform amplitude back to zero current. Waveforms may also be non-linear in pattern and may vary between regions. In a preferred embodiment, the total charge delivered in Region 1 is equivalent to the total charge removed in Region 2. In other words, the magnitude of the area below the current waveform in Region 1 is the same as that of Region 2. Different regions may also be spaced apart in time by a period of zero current (not shown) in which the AgCl electrode mass is conserved while no current is being delivered. Not to be limited by theory, the silver-silver chloride system offers several potential benefits over other electrochemical reactions. For example, the standard potential of the silver-silver chloride reaction is about 0.22 V, which is advantageously well below the voltage at which electrolysis occurs. Electrolysis can occur when the magnitude of potential or voltage used to drive a reaction exceeds about 1.23 volts referenced against the standard hydrogen electrode. Electrolysis of water can be detected via one or more sensors, and cease or modulate (increase or decrease) current delivery and/or driving voltage if electrolysis is detected in some cases. The sensors can also detect in some cases whether the silver-silver chloride reaction is exclusively, substantially exclusively, or predominantly occurring rather than electrolysis, hydrolysis, or a redox water reaction, for example. Furthermore, the amount of charge that can be delivered by such a system is not limited by surface area reactions such as in the case of platinum electrodes which form a monolayer of platinum-hydride on the electrode surface before the available platinum for reaction is exhausted leading to other potentially harmful products forming if the reaction is continued to be driven. In contrast, in an aqueous environment when silver-chloride is reduced it forms solid silver and releases a chloride ion into solution and vice-versa. The reaction in each direction is only limited by the quantity of reactant available so the reaction is in effect limited by the total volume of reactant available compared to being limited to surface area. As such, the reaction can utilize an amount of reactant greater than that of the initial, unreacted surface area of the electrode, such as about or at least about 110%, 120%, 130%, 140%, 150%, 160%, 170%, 180%, 190%, 200%, 250%, 300%, 500%, 1,000%, 5,000%, 10,000%, 25,000%, 50,000%, 100,000%, 500,000%, 1,000,000%, 2,500,000%, 5,000,000%, 10,000,000%, 25,000,000%, 50,000,000%, 100,000,000%, 250,000,000%, 500,000,000%, 1,000,000,000%, or more of the initial total, unreacted surface area of the electrode, or ranges including any two of the aforementioned values and depending on the volume of silver utilized. Therefore, substantially more, and in some cases orders of magnitude more charge can be advantageously delivered to body tissue while remaining below the electrolysis threshold. For example, a platinum or platinum-iridium electrode might deliver 5 microcoulombs per pulse in a 5 mA pulse for 1 millisecond. With embodiment as disclosed herein, it can be possible to achieve about or at least about 1,000×, 5,000×, 10,000×, 50,000×, 100,000×, or more times this charge using DC delivery in the form of a 5 mA pulse with 10 second duration. This may be achieved, for example, by creating a 1 micron coating of AgCl on an electrode of nominal geometry of 3.5 mm length (or between about 1 mm and about 10 mm in length, between about 1 mm and about 5 mm in length, or between about 3 mm and about 4 mm in length) and 1.4 mm diameter (or between about 0.5 mm and about 5 mm in diameter, between about 0.5 mm and about 3 mm in diameter, or between about 1 mm and about 2 mm in diameter) comparable to existing platinum electrodes. One skilled in the art will appreciate that depending on configuration and reservoir of silver-chloride available, the amount of charge delivered can increase to 10,000×, 100,000×, 1,000,000×, 10,000,000×, 100,000,000× or more, or ranges incorporating any two of the aforementioned values, compared to that achievable using a conventional platinum electrode. The silver-silver chloride complex can thus be uniquely situated for use in body environments because the reaction chemistry involves chloride ions which are one of the most readily available ions in and around body tissue.

Figure 1C:
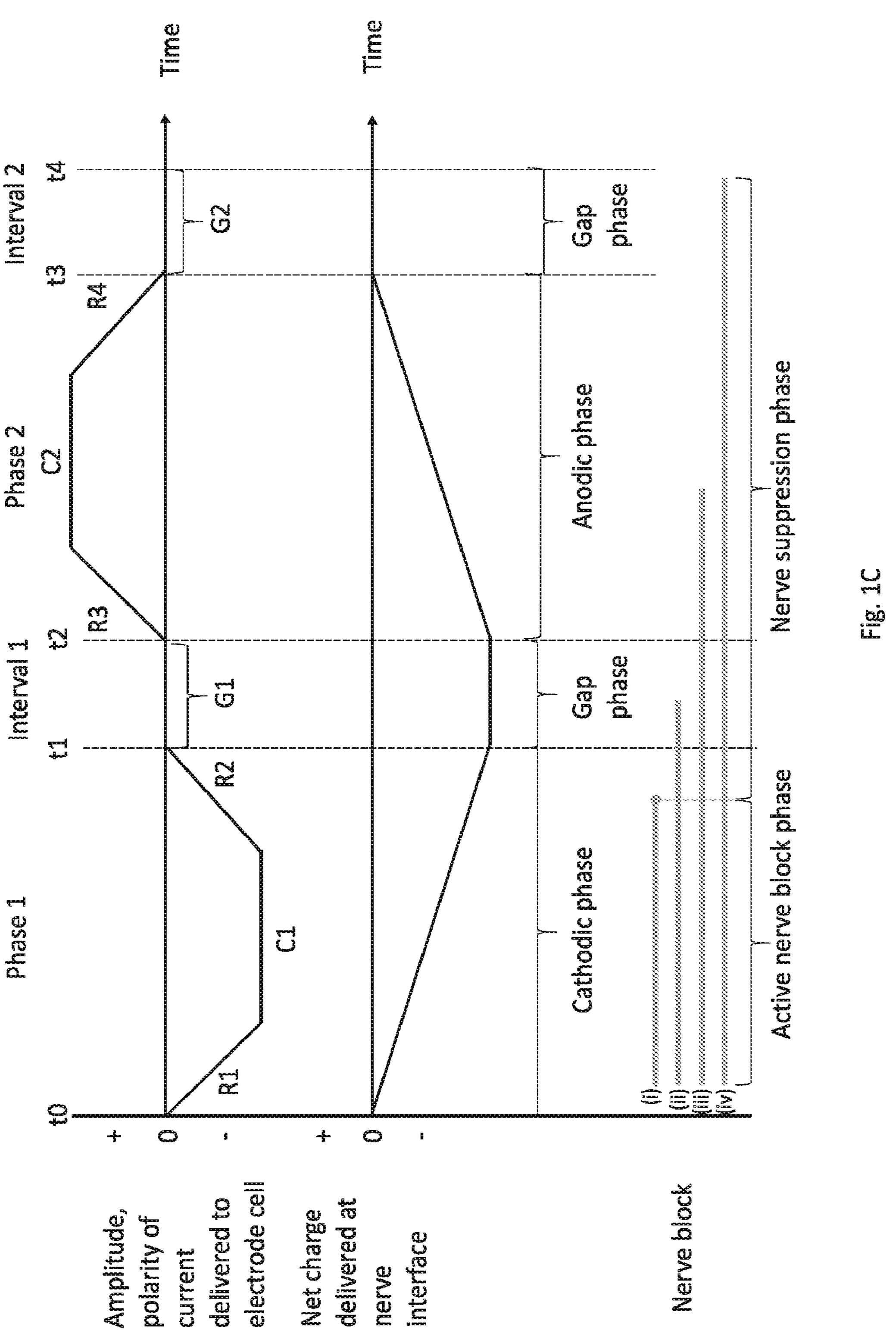
FIG. 1C shows how current being delivered to the electrode cell (EICCC) (top) can be associated with charge delivered to the electrode cell-nerve interface (middle) to provide nerve block (bottom) while enabling zero net charge transfer with long charge phases, according to some embodiments of the invention.

FIG. 1C shows how current being delivered to the electrode cell (EICCC) (top) can be associated with charge delivered to the electrode cell-nerve interface (middle) to provide nerve block (bottom) while enabling zero net charge transfer with long charge phases. In Phase 1, charge can be delivered to the electrode cell with a given polarity and constant or variable ramp rate (R1) to then provide a constant or variable current (C1) with subsequent constant or variable ramp (R2) back to zero current. Phase 1 may be, for example, of duration up to 1 second, 1 minute, 1 hour, 1 day, 1 month, or 1 year, or longer. In some embodiments, Phase 1 average current is non-zero, but instantaneous current may at times be zero. In some embodiments, Phase 1 is either cathodic or anodic but not both. The initial phase, Phase 1, may be followed by an interphase interval (Interval 1) between cathodic and anodic phases that is greater than or equal to zero seconds. Subsequent to this interval, a second current delivery phase (Phase 2) which may be of duration up to 1 second, 1 minute, 1 hour, 1 day, 1 month, or 1 year, or longer can be applied. This second phase is of opposite polarity to Phase 1 where average current is non-zero, but instantaneous current may at times be zero. In Phase 2, charge can be delivered to the electrode cell with a given polarity and constant or variable ramp rate (R3) to then provide a constant or variable current (C2) with subsequent constant or variable ramp (R4) back to zero current. This Phase 2 may then be followed by another interphase interval (Interval 2) that is greater than or equal to zero seconds. The waveform in FIG. 1C may be repeated with identical or differing amplitude and duration parameters as a previous waveform whereby the waveform may be programmed or adjusted by a clinician and/or patient and/or caregiver and/or control system. Adjustments may include adjusting the currents in Phase 1 and Phase 2 such that currents are ramped up and/or down as well as adjusting the durations of the phases t1-t0 and t3-t2, respectively. Interphase intervals can also be adjusted such that their durations t2-t1 and t4-t3 are lengthened or shortened. Any delivery or interphase period could be, for example, at least about, about, or no more than about 1, 5, 10, 15, 20, 25, 30, 35, 40, 45, 50, or 55 seconds; 1, 2, 3, 4, 5, 6, 7, 8, 9, 10, 15, 30, 60, 120 minutes; 3, 4, 5, 6, 7, 8, 9, 10, 12, 16, 18, or 24 hours; 2, 3, 4, 5, 6, 7, 14, 21, 28, 30, 45, 60, 75, 90, or more days; 4, 5, 6, 7, 8, 9, 10, 11, 12, 18, 24 or more months; or ranges including any two of the aforementioned values.

At the nerve interface the current delivered to the electrode cell can generate an increase in charge (positive or negative) delivered to the nerve interface as shown and may be linear as shown or generally increasing in a linear or non-linear fashion in Phase 1. The net charge delivered remains roughly constant during the gap phase or Interval 1 then returns to zero during Phase 2. Initially, the period of nerve block (FIG. 1C bottom) is initiated somewhere during the beginning of Phase 1 and nerve block will remain active (solid line) while charge is being delivered to the nerve interface. However, nerve suppression as defined by continued nerve block after removal of current delivery to the electrode cell may continue after current delivery to the nerve is stopped and may persist into the Interval 1 period (ii), extend into Phase 2 (iii) independent of the opposite polarity current being delivered, or into Interval 2 (iv), or beyond (not pictured). Tuning of these parameters can lead to the placement of the nerve into a state of hypersuppression as seen in FIG. 1C (ii), (iii), (iv) in which nerve suppression may occur for durations greater than one minute after removal of DC delivery.

Figure 1D:
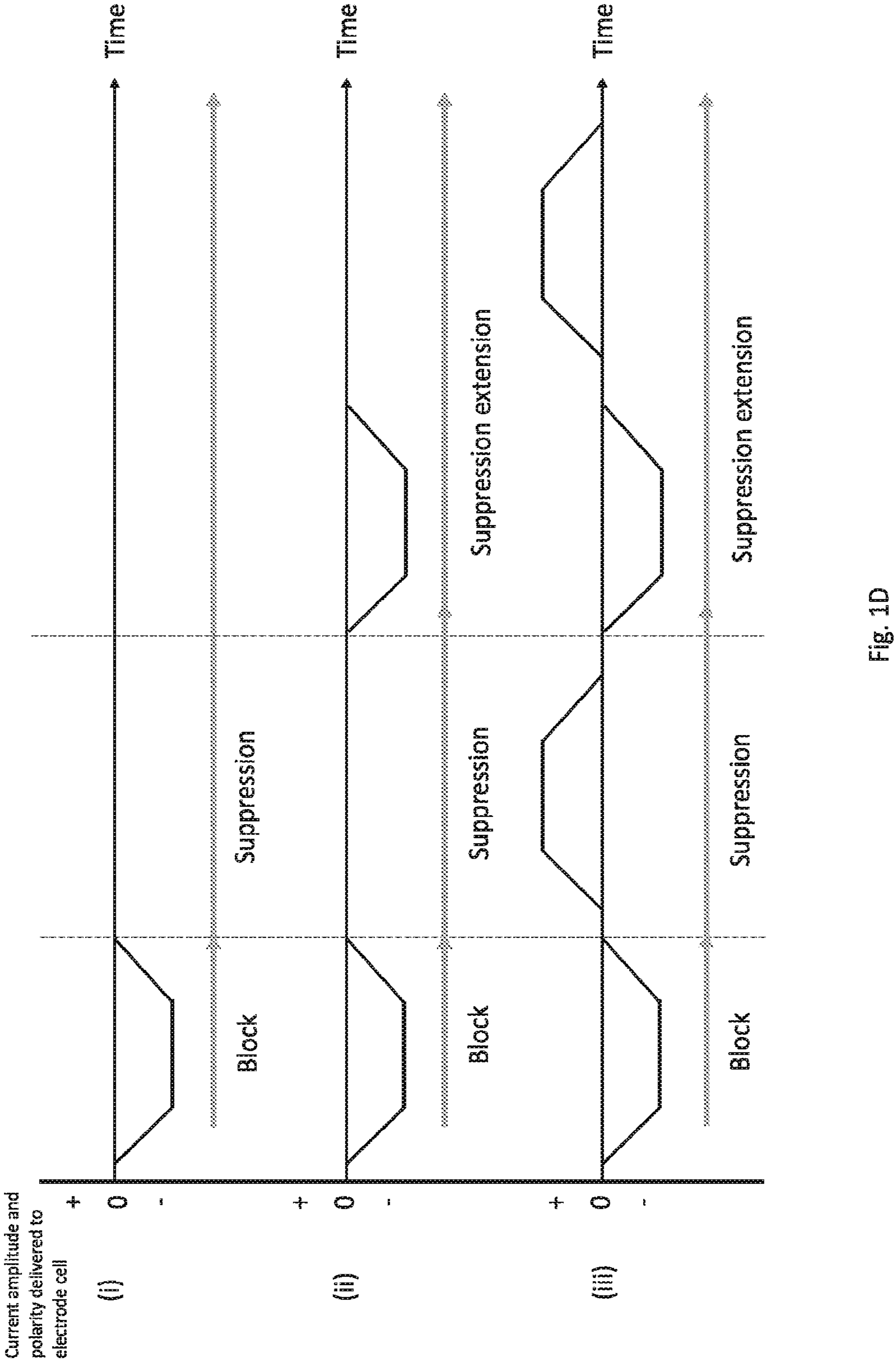
In FIG. 1D waveform patterns delivered to an electrode cell to facilitate nerve block are shown in which current delivered to the electrode cell is shown along with corresponding nerve block periods including hypersuppression regions in which nerve block occurs regardless of current being delivered to the nerve tissue, according to some embodiments of the invention.

In FIG. 1D waveform patterns delivered to an electrode cell to facilitate nerve block are shown in which current delivered to the electrode cell is shown along with corresponding nerve block periods including hypersuppression regions in which nerve block occurs regardless of current being delivered to the nerve tissue. The electrode cell system is designed such that the cathode and/or anode phase is designed to place the neural tissue in a state of not being conductive (or partially conductive) after the cessation of the current for periods longer than one minute (hypersuppression) after current delivery. In FIG. 1D(i) an electron current has been delivered to the electrode cell to generate an ion current at the neural tissue facilitating a nerve block. After this initial current delivery, the neural tissue then enters a state of hypersuppression whereby in the absence of additional current delivery to the neural tissue, the nerve cannot conduct signals or is not fully conductive. The neural tissue suppressed state may also be extended as shown in FIG. 1D(ii) in which a secondary current is delivered to the neural tissue a period of time after the initial current has been delivered where the delivery of the extension current may occur up to one minute after the initial current is delivered or after periods of longer than one minute (hypersuppression). This pattern of suppression extension may be repeated for a defined period of time or indefinitely with constant or variable length intervals between current delivery phases. To maintain the electrode cell in a charge neutral state over repeated uses, current with opposite polarity may be applied after the initial nerve block current is applied and has placed the nerve into a state of hypersuppression (FIG. 1D(iii)). Subsequently, current of the original polarity can be applied to induce additional hypersuppression extension as shown. In this manner the nerve tissue can be repeatedly "dosed" with anodic and/or cathodic safe DC current to maintain the neural tissue in a state of hypersuppression. The hypersuppression duration is longer in duration than a cathodic and/or anodic delivery phase, allowing for complete net charge reversal during hypersuppression. In these examples, the duration and/or amplitude of the cathode and/or anode phase(s) can be programmed to influence the duration and completeness of the nerve block after current delivery has stopped.

Figure 1F:
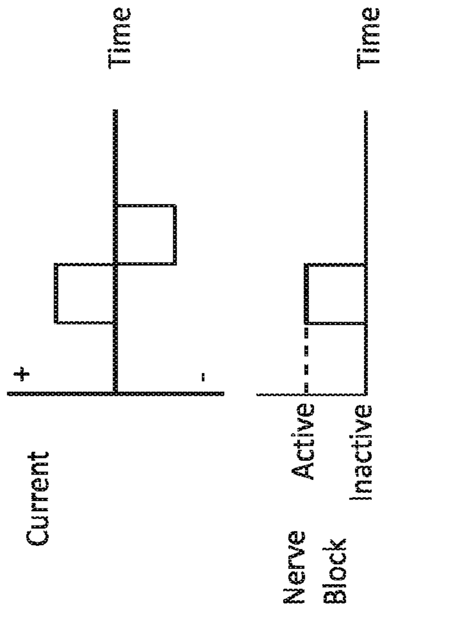
FIG. 1F illustrates a configuration when the electron current is of one polarity as designated by the positive axis, the nerve block is shown to be active and when the polarity of the current is reversed as designated by the negative axis, the nerve block is shown to be inactive.
Figure 1E:
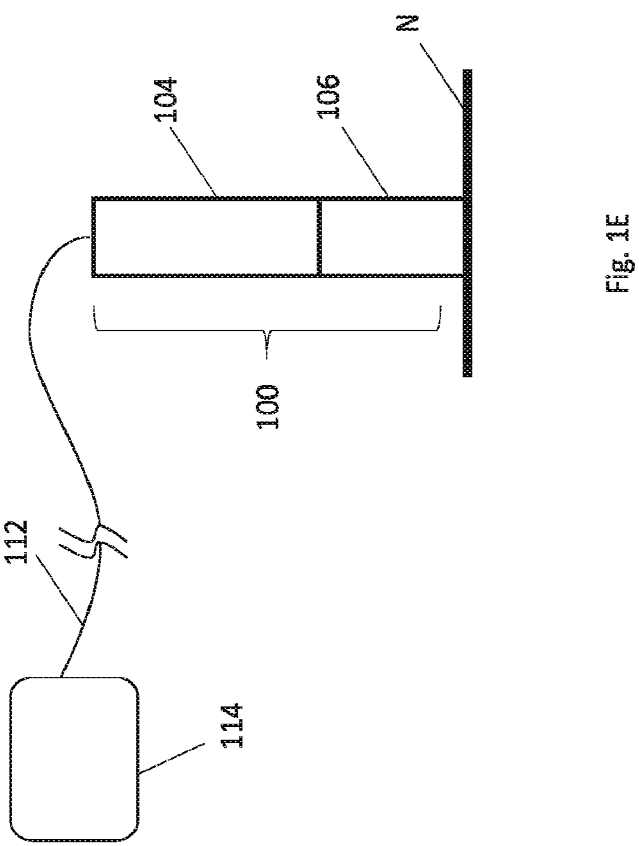
FIG. 1E shows an embodiment of an electron-ion current conversion cell (EICCC) which is connected via an electrically insulated lead to a current source.

FIG. 1E shows an embodiment of an electron-ion current conversion cell (EICCC) 100 which is connected via an electrically insulated lead 112 to a current source 114. The EICCC 100 comprises a traditional electrode (electrode) 104 material (e.g., metal, carbon, etc.) connected to an ionically conductive material (ion conductor 106) which then interfaces with the nerve tissue N, or tissue in proximity to nerve tissue. In some embodiments, the interface can be within about 3 cm, 2.5 cm, 2 cm, 1.5 cm, 1 cm, 5 mm, 2 mm, 1 mm, 0.5 mm, 0.1 mm, or less in proximity to nerve tissue. One skilled in the art will appreciate that the conventional electrode 104 and ionically conductive material 106 may be attached in a multitude of ways such as shown abutting or in an interlocking fashion and the like. The electrode 104 may be inserted within the ion conductor 106 or vice-versa. As shown in FIG. 1F, in one configuration when the electron current is of one polarity as designated by the positive axis, the nerve block is shown to be active and when the polarity of the current is reversed as designated by the negative axis, the nerve block is shown to be inactive. It should be appreciated that in the case in which the initial blocking current is applied to the nerve N in such a manner to induce a state of hypersuppression, the nerve may remain N blocked during the current reversal period. During the current reversal period, the EICCC 100 is in a resetting phase in which the reaction used to generate the ion current is reversed to bring the EICCC 100 components back towards their original state for subsequent blocking current generation.

Figure 1H:
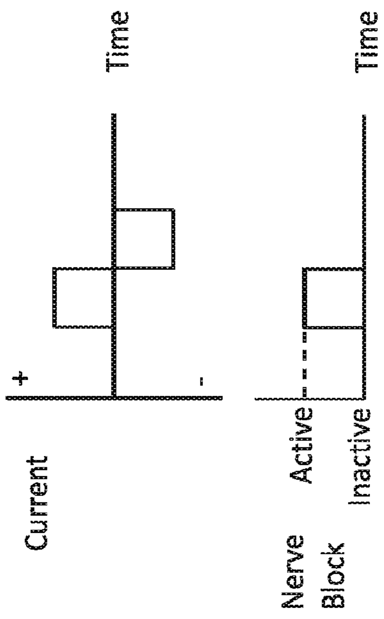
FIG. 1H illustrates current vs. time and nerve block status vs. time charts similar to FIG. 1F.
Figure 1G:
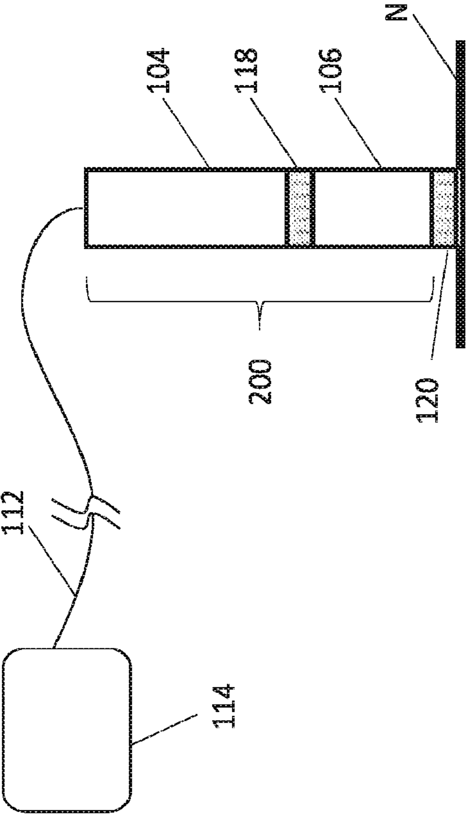
FIG. 1G shows a similar configuration to FIG. 1E but with sequestration screens that respectively separate the traditional electrode from the ion conductor and the ion conductor from the nerve itself.

FIG. 1G shows a similar configuration to FIG. 1E but with sequestration screens 118, 120 that respectively separate the traditional electrode 104 from the ion conductor 106 and the ion conductor 106 from the nerve N itself, or nerve adjacent tissue. One of ordinary skill in the art will appreciate that one, two, or more or no screens may be used, or any combination thereof. The screens 118, 120 are configured to selectively allow certain ions to transfer between the respective materials while restricting the movement of other ions whose movement is not desired, for example to maintain reaction species such as Cl— near the electrode. The screens 118, 120 may be comprised of an ionically selective membrane such as an anion exchange membrane that only allows anions to pass through it. FIG. 1H illustrates current vs. time and nerve block status vs. time charts similar to FIG. 1F.

FIG. 1I shows a similar configuration to FIG. 1G but also includes a feedback sensor 122 that monitors the state of the nerve tissue N and/or region proximal to the nerve N. In some embodiments a sensor 122 may be located proximal or distal to the electrode-nerve interface in order to enable measurement of local compound action potential to provide feedback to the current source 114 and EICCC 210 to enable it to modulate electrode current and nerve interface electrode potential to maintain hypersuppression. In some embodiments the sensor 122 may measure nerve tissue voltage signals and use that information as feedback to modulate the current and electric potential generated at the nerve interface. In some embodiments the electric potential is modulated such that the nerve cells are maintained in a depolarization state in which action potentials cannot propagate along the nerve cells. In some embodiments the sensor 122 comprises a reference electrode whereby the potential difference between one or more working electrodes 104 and the reference electrode can be monitored and used as feedback to the current source 114 to ensure proper operating range of the EICCC 210. The implantable packaging may contain an integrated reference or counter electrode. FIG. 1J illustrates current vs. time and nerve block status vs. time charts similar to FIG. 1H.

Figure 2A:
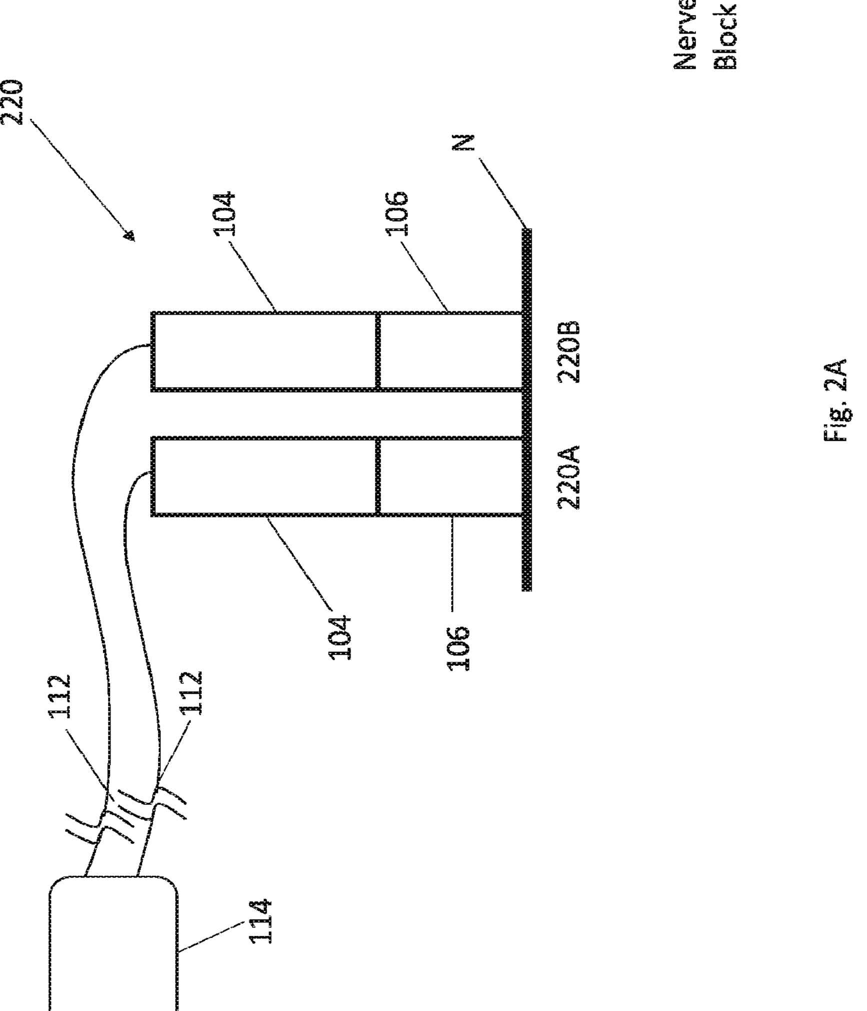

FIG. 2A shows a dual electrode system in which two EICCCs 220A, 220B interface with a nerve N or nerve adjacent tissue. The two electrodes 220A, 220B are driven with currents of opposite polarities as a function of time such that when one is in an active blocking phase, the other is in an inactive non-blocking phase which resets the electrode for blocking once the current polarity is again reversed as shown in FIG. 2B. With this configuration a constant block can be maintained along the nerve N. It should be appreciated that in the case in which a blocking current is applied to the nerve N in such a manner to induce a state of hypersuppression, the nerve block may remain active during the current reversal period of the electrodes 220A, 220B. One skilled in the art will appreciate that the driving currents for the two electrodes 220A, 220B may be spaced apart in time during which no current is driving one or both electrodes 220A, 220B and that during this period block may be maintained if the nerve N is in a state of suppression. Similarly, the driving currents may be of different durations dependent on the electrodes 220A, 220B themselves and any recovery time of the nerve N during which signal remains blocked while no blocking current is being applied. The electrodes 220A, 220B may be oriented as shown in series axially along a nerve N or oriented on opposite sides to the nerve tissue itself.

FIGS. 3A-B show an embodiment where dual traditional electrodes 104A, 104B interface with a nerve N but are driven from a current source via electrically insulated leads 112 with currents of opposite polarities such that when one is in a blocking phase, the other is in a non-blocking phase which resets the electrode for blocking once the current polarity is again reversed. With this configuration a constant block can be maintained along the nerve. The electrodes 104A, 104B may be oriented as shown in series along a nerve N or oriented on opposite sides to the nerve tissue itself.

FIGS. 3C-D show an embodiment where dual EICCCs 230A, 230B interface with a nerve N but are driven with currents of opposite polarities such that when one is in a blocking phase, the other is in a non-blocking phase which resets the electrode for blocking once the current polarity is again reversed. With this configuration a constant block can be maintained along the nerve N as illustrated in FIG. 3D. The electrodes 230A, 230B interface with the nerve N via screens that sequester deleterious byproducts from dangerous electrochemical reactions to protect the nerve N. The screens may include an ionically selective membrane such as an anion exchange membrane that only allows, for example, anions to pass through it (but not cations).

FIG. 4A shows an embodiment of an EICCC electrode 240 in which an electrode 104 is immersed in an electrolyte solution 102 which fluidly in is contact with an ion-conductive material 106 such as a hydrogel, gel or other polymer that electrically contacts the nerve tissue N or area proximal to the nerve tissue. The EICCC 240 electrode also comprises an electrically insulated enclosure 108 housing the traditional electrode 104, electrolyte 102, ion conducting material 106 with an aperture (near 110) to enable electrical contact with the nerve or area proximal to the nerve tissue. The electrolyte-hydrogel 107 interface can alternatively be mediated by an ion selective screen or an ion conductive polymer to sequester by products of any electrochemical reactions to the aqueous region of the cell. The system further optionally comprises a current delivery lead 112 between the current source 114 and the electrode 104. The current source 114 may be located external or internal to the body depending on the application need. An exemplary embodiment of the EICCC 240 comprises a silver, silver-chloride (Ag/AgCl) electrode in a 0.9% saline solution in fluid contact with an electrolyte saturated hydrogel (agar preparation with 0.9% saline). In other examples, the electrode material may comprise metal, carbon, conductive polymers materials and may be configured in a high surface area to volume configuration that may include configurations such as open-celled foam configurations, sintered particle configurations, dendritic configurations or the like.

FIG. 4B shows a system 250 similar to that shown in FIG. 4A with the addition of a reference electrode 111 in proximity to the electrode (working electrode) 104 to monitor voltage drop across the working electrode 104 for EICCC monitoring purposes. For example, to ensure that the electrode 104 is being driven under the desired conditions to ensure that the proper electrochemical reactions are occurring.

FIG. 4C shows a system 260 similar to that shown in FIG. 4A with the addition of a reference electrode 111 in proximity to the nerve tissue interface to monitor voltage drop across the EICCC 260 to the nerve tissue for EICCC monitoring purposes. For example, to ensure that the electrode 104 is being driven under the desired conditions to ensure that the proper electrochemical reactions are occurring.

FIGS. 4D-F show an embodiment of an electrode lead 212 configured to plug into and extend from a current source (not shown, near end 213) that might take the form of conventional IPGs (implantable pulse generators). FIG. 4F is a close-up view of 4E-4E of FIG. 4D. FIG. 4F is a close-up view of 4F-4F in FIG. 4D. This configuration could be similar to as that shown in FIG. 4A except that the nerve interface hydrogel shown in FIG. 4A is removed and the nerve tissue interface comprises a screen or porous frit 404 which contains the electrolyte solution but allows ions to pass to the nerve tissue environment. A connector 213 to the current source is shown with an electrically conductive portion of the electrode lead 213 that extends distal from the connector 213 to the EICCC 400 which couples the electron current to an ionic current via electrochemical reactions. The coiled electrode 402 converts electrical current to ionic current in the EICCC 400 which is then transmitted toward the distal portion of the lead which can be positioned in proximity to the target nerve tissue. Contact with the nerve tissue environment occurs via the ionic current which exits the screen/porous frit 404 that can manipulate the nerve environment.

FIG. 4G shows a schematic embodiment of an EICCC integrated within a hermitically sealed enclosure 410 which contains the current source 412, battery 414 or power supply, and controller 416 to drive the EICCC 280. The EICCC 280 is directly connected to the current source 412 as illustrated and comprises a lead 418 from the current source 412 and an electrode 420 immersed in an electrolyte solution 429 which fluidly is in contact with an ion conductive material 422 such as a hydrogel which in turn contacts the nerve tissue N to be blocked. In this embodiment the electrode element 420 of the EICCC 280 is located relatively proximal to the current source 412 while the nerve contacting lead is located relatively more distally from the current source 412 and extends to the nerve location N. Also illustrated is the ion conductive conduit (e.g. hydrogel connector) 430, connector elementals 432, insulated enclosure 420, and ion conducting electrode lead 428.

FIGS. 5A-B show an embodiment of an electrode configuration 500 in which two electrode contacts are housed within the same electrically insulated enclosure 504. The electrodes 502A, 502B are in ionic contact with ion conducting materials 510/pads 512 that interface with the nerve tissue N and/or area proximal to the nerve. Each electrode 502A, 502B is in electrical communication via its own conductive lead 506 that is driven by the current source 508. The internal electrodes 502A, 502B can be driven cyclically with opposite current polarities to provide a constant nerve block. The current source 508 may be configured to be implantable within the body such that any leads 506 and electrodes 502A, 502B are also fully contained within the body. Alternatively, the current source 508 may be configured to remain outside the body and can be connected via wired or wireless connections in this or other embodiments.

In some embodiments, a system is configured for nerve block at specific nerves. One such nerve is the dorsal root, and/or dorsal root ganglion (DRG) through which pain signals pass (FIG. 6A). The associated dorsal root ganglia from each vertebral level correspond to specific dermatomes in the body (FIG. 7), and blocking pain signals at the DRG level can reduce pain sensation at the innervated dermatome for that specific DRG. Access to the DRG may be facilitated by initial introduction of a needle tip to the DRG. A stylet or obturator in the needle may be used to prevent occlusion of the opening or inadvertent tissue damage due to tissue entrapment by the needle opening. The needle tip may be radiopaque as to be visualized under fluoroscopy or other radiographic means. Removal of the stylet from the needle may also occur in order inject contrast agent to enable visualization of the local structures and to confirm location of the needle tip. A short acting nerve block agent may also be applied to confirm that the targeted DRG body when blocked will provide adequate pain relief. Upon confirmation that the needle is positioned properly and the DRG body is the appropriate target for nerve block, the stylet can be removed if not already removed, and a blocking electrode terminating in an EICCC with a single or multiple electrode-nerve interface contacts can be introduced through the needle. As shown in FIG. 6C the DRG can be accessed with a needle 600, and the needle 600 can be used to penetrate the dura mater as shown. Alternatively, the needle 600 may be positioned just outside the dura mater without puncturing the tissue. The introduced electrode may have radiopaque markers to enable visualization under fluoroscopy. The introduced electrode may also be encased within a secondary sheath that prevents deployment of anchoring elements until the distal end of the sheath is retracted from the distal end of the introduced electrode to expose tissue-anchoring elements. The enclosed electrode may also have stress-relief features such as coils or slack in the electrode body to accommodate bodily motion that might dislodge the electrode without such features. As shown in FIG. 6D and FIG. 6E, the electrode-nerve interface contacts 604 can then be positioned in contact or proximal to the DRG and the introducing needle 600 can be retracted to leave the electrode lead 602 and nerve tissue interface 604 in the desired position. The proximal end of the electrode may be connected to a current source to begin nerve block and ensure proper electrode positioning. Once the appropriate positioning and block have been achieved, the optional electrode sheath can be retracted to expose retention mechanisms such as barbs or frictional elements that prevent dislodging of the electrode from its desired position. Optionally, a conductive gel may be applied between the electrode contact or contacts and nerve interface to further mitigate loss of conduction block if the electrode contacts move relative to the DRG body. In some embodiments, if after deployment of the retention mechanisms, placement must be adjusted, the sheath can be advanced to retract the retention mechanisms and the electrode repositioned before redeploying the retention mechanisms. Once the electrode is properly positioned, the electrode can be disconnected from the current source and the insertion needle removed over the electrode toward its proximal end. The sheath can then be removed in a similar fashion. The current source can then be reconnected to the lead connector to confirm proper placement and that no dislodging has occurred with insertion needle and sheath removal. After an optional evaluative period, the current source may be implanted into the patient body and the electrodes and/or leads may be replaced with permanent electrodes for long-term implantation. The current source may further contain a battery or energy storage unit and electronic circuitry which enables the unit to be programmable from a programming unit that can communicate with the implanted current source when in proximity to the body site close to the current source implantation site. The current source energy source may be optionally rechargeable by the external communication unit such as by inductive charging. FIG. 6B shows an embodiment of a blocking electrode 100 positioned along a DRG to facilitate nerve block along with lead 112 and current source 114. It is understood that nerve block may include hypersuppression of the DRG.

In an alternative embodiment, the current source may be located outside the body of the patient permanently or temporarily to enable nerve block. The electrodes may also be removed once deemed unnecessary thus provided a temporary nerve block as desired. The nerve block may also be turned on and off periodically by modulating the current source as required to enable sensation during procedures that require patient feedback for example.

Block of DRG at specific dermatomes can be used to localize therapeutic pain reduction due to neuralgias, angina, ischemic pain, and complex regional pain syndrome (CRPS). In the case of angina, cervical spinal level nerve roots C6 and C7 have been implicated as frequently involved with the associated pain, and localized DRG block at one or both of these levels (with or without block of additional DRG at other levels) could be used to help manage this pain. (Nakajima et al., Cervical angina: a seemingly still neglected symptom of cervical spine disorder?, Spinal Cord, 2006 44:509-513.) For example, complex regional pain syndrome (CRPS) is often localized to a single limb and generating a localized block can provide more specific pain block for the source of pain. For example, the lumbar dorsal root ganglia at levels L2, L3, L4 have been shown to be able to reduce knee pain on the ipsilateral side of the spine using conventional DRG stimulation techniques. (Bussel et al., Successful Treatment of Intractable Complex Regional Pain Syndrome Type I of the Knee With Dorsal Root Ganglion Stimulation: A Case Report, Neuromodulation, 2015 January 18(1):58-61) Ischemic pain frequently is localized particularly for patients with poor extremity circulation and may be similarly mitigated by targeting the appropriate DRG levels for block.

As described above and illustrated in FIGS. 6A-6D and FIG. 7, an EICCC electrode may be introduced in proximity to a DRG in order to block and/or suppress the nerve tissue in the DRG to prevent distal pain signals from being registered by the individual. Furthermore, multiple dorsal root ganglia may be targeted to generate unilateral and bilateral blocks or to adjust pain coverage based on pain presentation in the body. EICCC electrodes may be placed at the target levels associated with the pain presentation and adjusted to tune the level of pain block and coverage by adjusting the ionic current signal such as by tuning the current amplitude at each DRG level targeted and in contact with an EICCC electrode. Localizing the pain block to specific regions of the body can also help preserve normal sensory function in other regions of the body such that pain signals are not absent and can be used to signal an adverse situation and environmental conditions to the individual.

Compared to traditional SCS in which electrodes are placed along the posterior of the spinal cord in the epidural space, placement of stimulating electrodes 800 in proximity to the lateral spinothalamic tract (LT tract) (FIG. 8A) can leverage an EICCC to generate a nerve block at the desired level (and/or spinal levels distal (away from the head) to the EICCC since pain signals travel in the superior direction) and provide selective pain block depending on unilateral (left or right) or bilateral placement of electrodes 800. Electrode leads 802 may be placed via a laminotomy (FIG. 8A middle, right) to enable access to the epidural space and then the electrodes leads 802 can be introduced and placed into position along the lateral aspect or aspects of the spinal column at the desired level or levels. Leads 802 may also be placed using a percutaneous placement procedure with or without fluoroscopic guidance such as by using a Tuohy or similar needle 808 to introduce the electrode lead 802 into the epidural space (FIG. 8B). The leads 802 can be directed along the spinal column within the epidural space such that the lead 802 is between spinal nerve exit regions and the tissue interface is in proximity to the lateral spinothalamic tract as illustrated in FIGS. 8C-8E. As seen in FIGS. 8C-8E, the electrode lead 802 is positioned laterally to sit outside the lateral spinothalamic tract such that the nerve tract can be blocked with the generated ionic current from the electrode. Leads 802 may also be placed bilaterally to facilitate bilateral block as each lateral spinothalamic tract carries pain information from the contralateral side of the body. The leads 802 may then be connected to a current source to activate the nerve block via tissue interface 804 to ensure proper positioning and signal block. The lead 802 may then be disconnected from the current source and an optional extension cable placed to connect the lead 802 to the implantable current source. The current source may further contain a battery or energy storage unit and electronic circuitry which enables the unit to be programmable from a programming unit that can communicate with the implanted current source when in proximity to the body site close to the current source implantation site. The current source energy source may be optionally wirelessly rechargeable by the external communication unit such as by inductive charging.

In some embodiments multiple electrode leads such as illustrated in FIG. 4D for example may be placed along the spinal cord, targeting the spinothalamic tract as shown in FIG. 8C. Furthermore, the electrodes may be configured to have a multitude of tissue contacting regions whose outputs can be individually adjusted to optimize the nerve tissue block. An embodiment of an EICCC electrode is shown in FIGS. 10A-10C in which multiple tissue interfaces 404A, 404B are present on the electrode 402 and are individually addressable. FIG. 10B is a close-up view of 10B-10B of FIG. 10A. FIG. 10C is a close-up view of 10C-10C of FIG. 10A. In this embodiment a dual system of EICCCs 400 are present and have parallel lumens that are individually associated with each nerve tissue interface region. In FIG. 10 the nerve tissue interface region and associated EICCC are designated by matching letter labels, in this case A and B. Adjusting the current input and corresponding output at the distal end of the electrode can enable electric field shaping to facilitate desired nerve block while minimizing block of undesired structures. An alternative embodiment is captured in FIG. 5 in which individual electrodes are also individually addressable and can be tuned to enable desired block generation.

Using these methods of placement of blocking electrodes along the spinal column to block the spinothalamic tract and the ability to tune the electric field to generate nerve block and/or suppression, specific targets for pain block can be facilitated. For example, trunk pain which is moderated by the thoracic vertebral levels can be modulated by placing leads along the thoracic spine while neck pain may be moderated by providing block and/or suppression in the cervical spine. Upper limb pain may be moderated by providing a combination of cervical and thoracic level block and/or suppression while lower limb pain may be moderated by a combination of lumbar and sacral level block and/or suppression in the spine.

Generation of pain block can be used to facilitate periprocedural pain block where motor control and non-pain sensations are desired. For example in labor and delivery of a child, one of the challenges with pain management particularly with epidural anesthesia is the reduction in ability to be sensate in the lower body. Due to the non-specific nature of the delivered anesthesia in the epidural space sensory, pain, and motor neurons are impacted. The epidural anesthesia can lead to difficulty with generating pushing force during the birthing process and can lead to numbness a few hours after birth impairing motor abilities such as the ability to walk. In some instances, epidurals are further implicated in fetal and newborn health including breastfeeding difficulty. Using the blocking electrodes described above to target the spinothalamic tract and/or dorsal root ganglia, the undesired pain can be targeted without generating the side effects (or reducing side effects) associated with current epidural anesthesia techniques because only the pain tracts are targeted and not any other motor or sensory tracts. Furthermore, in the case in which ionic current is delivered to the nerve tissue in a reversible blocking fashion, the stopping of block can enable the patient to immediately be restored to normal pain sensation if desired and any off-target block can be reversed enabling immediate body function restoration.

Beyond central nervous system interventions, a safe direct current block can also be facilitated in the peripheral nervous system in which EICCC electrodes are placed in contact or in proximity to peripheral nerves to facilitate block. Specific pain targets include focal pain, phantom limb pain, neuroma pain, and neuralgias. Targeting the peripheral nerves proximally (i.e. closer to the spinal cord) from the site of pain for block can suppress pain from the distal site. Specific to neuralgias, postherpetic neuralgia (after shingles) can be targeted based on the presentation of the outbreak which will trace specific dermatomes. For trigeminal neuralgia, the trigeminal nerve (and/or trigeminal ganglion and/or trigeminal nucleus in the brainstem) can be targeted for block to reduce pain that commonly manifests as facial pain. Another target is the glossopharyngeal nerve which produces pain in the neck and throat. Neuralgia in extremities such as the hands, arms, feet, and legs as frequently caused due to diabetes-related neuropathies are also potential targets.

Outside of pain reduction, nerve block and activity suppression can be used to improve cardiovascular health in specific targeted ways. Hypertension which is implicated as a leading cause of cardiovascular disease has been found to be able to be moderated by modulation of the renal nerves to reduce activation of the sympathetic nervous system. Current techniques exist to denervate or ablate these nerves using a variety of energy sources such as ultrasound and radiofrequency energy. (Krum et al., Catheter-based renal sympathetic denervation for resistant hypertension: a multicentre safety and proof-of-principle cohort study. The Lancet. 2009 373(9671): 1275-1281. US Patent Application: 2012/0016226) Using the tools described herein, selective nerve block can be used to facilitate activity reduction in the renal nerves and sympathetic nervous systems to facilitate reduction in hypertension. As shown in FIG. 11, the blocking electrode leads 1100A, 1100B contact the renal nerves to facilitate a block or suppression Also systematically illustrated is EICCC 1104 openly connected at 1106 to current source (not shown). The contact may also be configured in a cuff format to surround the renal artery and provide a circumferential direct current to the outer perimeter of the renal artery and block the nerve tissue surrounding the artery. The delivered blocking current can also be adjusted to fit the individual physiological response to sympathetic nerve block which cannot be done currently with destructive methods such as ablation.

Heart failure is another target disease state with known association with upregulation of the sympathetic nervous system. By using a blocking electrode to moderate the sympathetic ganglia, particularly reducing activity of the cervical sympathetic ganglia, excessive heart activity can be reduced to mitigate overworking of the heart. Similar to dorsal root ganglion access, the cervical ganglia may be accessed for block. As shown in FIG. 12, the relevant sympathetic ganglia including the cervical and stellate (cervicothoracic) ganglia are shown along with their innervation targets in the heart. Methods of access include posterior access as well as through the pleural cavity.

Tachycardia or other tachyarrhythmias such as atrial fibrillation, atrial flutter, multifocal atrial tachycardia, paroxysmal supraventricular tachycardia, ventricular tachycardia, and ventricular fibrillation for example may also be regulated by modulation of the sympathetic nervous system and can be influenced toward a more normal state by targeting the cervical sympathetic ganglia (FIG. 13) to provide a block of the sympathetic ganglia. Methods of access include posterior access as well as through the pleural cavity.

Modulation of the parasympathetic innervation of the heart can be used to regulate cardiac function. Stimulation of the vagus nerve is known to lead to bradycardia, or bradycardia, and suppression of heart rate. Conversely, by creating a vagal nerve block, the heart rate suppressing neural signaling can be reduced or shut down leading to increase in heart rate by reducing the vagal nerve signal. Particularly, the right vagal nerve which innervates the sinoatrial node to help regulate heart rate can be blocked or suppressed to enable increase in heart rate. As seen in FIG. 14, an EICCC electrode 1400 can be placed around or in proximity to the right (and/or left) vagus nerve within the right side of the neck and/or chest with an electrode lead 1402 running down toward an implantable current source 1404 shown in the right pectoral region. The electrode lead 1402 may be placed in the right subclavian region or other desired location and tunneled below the skin to the current source.

In addition to cardiovascular function, the nervous system plays a significant role in regulating gastric processes including satiety (lack of hunger) and satiation (fullness). The vagus nerves innervate the stomach with the majority of signals to the brain reporting state of satiety and satiation. Using the EICCC electrode 1600, a block or nerve suppression of the vagus nerves can be generated to give the individual a heightened sense of satiety and satiation. Gastrointestinal nerves can also be modulated to either increase or decrease GI transit time. As seen in FIGS. 15-16, an exemplary dual EICCC system is shown in which each vagus nerve is wrapped in a cuff-format tissue interface 1606 at which ionic current is deposited at the tissue site from the EICCCs 1600 which are connected via electrode leads 1602 as well as to the current source 1604. The tissue interface may be moderated by a porous frit or other ionically conductive medium such as a conductive hydrogel as previously described herein. FIG. 16 is a close-up view of FIG. 15 near the gastro-esophageal junction region.

Sympathetic nerve suppression or block can also be used to regulate hepatic, gallbladder, and/or pancreatic function and influence glucose and insulin production as shown in FIG. 17. Suppressing or blocking the hepatic nerves can lead to increase insulin production and reduce resistance to insulin enabling management of adult onset or type 2 diabetes in which insulin production is reduced or resistance to insulin function is increased. Using the EICCC electrode 1800, a block or nerve suppression of the hepatic nerves can be generated to increase insulin production and reduce insulin resistance. As seen in FIG. 18, an EICCC system is shown in which the nerves around the hepatic artery and the artery are surrounded by a cuff-format tissue interface 1806 at which ionic current is deposited at the tissue site from the EICCC 1800 connected via an electrode lead 1802 as well as to the current source 1804. The tissue interface 1806 may be moderated by a porous frit or other ionically conductive medium such as a conductive hydrogel as previously described herein. In other embodiments, splenic neuromodulation could either improve depressed immune function, or reduce inflammation or hyperimmune function (e.g., in autoimmune conditions such as SLE, rheumatoid arthritis, Crohn's, ulcerative colitis), or other conditions.

Movement disorders including Tourette's syndrome, dystonia, Parkinson's disease (and associated rigidity), essential tremor, spasticity, and epilepsy can also be influenced by moderating neural tissue activity. These disorders and diseases are characterized by neural hyperactivity in specific parts of the brain, which can lead to the symptomatic presentation. Targeting specific regions of the brain for block including those captured in Table 1 below can be used to help manage a patient's symptoms. It is recognized that blocking of these targets could be either unilateral or bilateral.

TABLE 1

Movement disorders and brain region targets for nerve tissue block for symptom reduction.

| Disease, Disorder | Region of the Brain |
|---|---|
| Tourette's syndrome | 1. anteromedial globus pallidus<br>2. Ventral anterior thalamus<br>3. Ventrolateral motor part of thalamus |
| Dystonia | 1. Internal segment of the globus pallidus (GPi) |
| Parkinson's disease | 1. Internal segment of the globus pallidus (GPi)<br>2. Subthalamic nucleus (STN),<br>3. Pedunculopontine nucleus (PPN),<br>4. Vim (ventro-intermediate nucleus) (a subdivision of the thalamus) |
| Essential Tremor | 1. Thalamus (Vim: ventro-intermediate nucleaus)<br>2. posterior subthalamic area (PSA) |
| Epilepsy | 1. Anterior nucleus of the thalamus<br>2. Other identified epileptogenic foci |

Similarly, psychiatric disorders including treatment resistant depression (TRD), anxiety, obsessive compulsive disorder (OCD), and post-traumatic stress disorder (PTSD) have are targets for neural block to reduce symptoms from these conditions. Targeting specific regions of the brain for block including those captured in the Table 2 below can be used to help manage a patient's symptoms. It is recognized that blocking of these targets could be either unilateral or bilateral. Other disorders that can be treated can include, for example, schizophrenia, schizoaffective disorder, bipolar disorder, mania, alcoholism, substance abuse, and others.

TABLE 2

Psychiatric disorders and brain region targets for nerve block for symptom reduction.

| Disease, Disorder | Region of the Brain |
| --- | --- |
| Treatment Resistant Depression | 1. Subgenual cingulate cortex, 2. Inferior thalamic peduncle, and 3. Nucleus accumbens |
| Anxiety | 1. Nucleus accumbens |
| OCD | 1. Ventral internal capsule 2. Ventral striatum |
| PTSD | 1. Basolateral amygdala |

Chronic pain is another target in which specific regions in the brain have been implicated in affecting chronic pain. One such region is the thalamus which is the entry point for pain signaling to the brain. Specific regions in the thalamus have been identified as targets for neural activity reduction to reduce chronic pain as shown in Table 3 below. It is recognized that blocking of these targets could be either unilateral or bilateral

TABLE 3

Brain region targets for nerve block for pain reduction.

| Disease, Disorder | Region of the Brain |
| --- | --- |
| Chronic pain | 1. Ventromedial thalamic nuclei 2. Intralaminar thalamic nuclei |

In some embodiments a system is configured for generation of nerve block for disorders and diseases that can be addressed by reducing neural activity in specific regions of the brain responsible for the specific disorder. Neural activity reduction can be facilitated by directly blocking and reducing activity of specific neurons as well as by blocking pathways along which excessive neural signaling is occurring. In some embodiments, this system for deep brain block (DBB) comprises all or some of the steps of identification of the anatomic target site for block, creating an access site to the exterior of the brain tissue, creating a path through the brain tissue to the target site, evaluating the suitability of the target site for block, adjusting or refining the location of the target site, providing nerve block at the target site, and adjusting the nerve tissue block strength or location. Practically, this process may be implemented using techniques known in the field of deep brain stimulation (DBS) in which a target anatomic site is identified using a combination of imaging techniques such as but not limited to magnetic resonance imaging (MRI) including functional MRI (fMRI), computed tomography (CT), PET scanning, and/or x-rays. This site can then be accessed using stereotactic techniques to register an identified region from imaging to the physical anatomy on the patient. A frame may be fixed to the patient's head and skull to allow for spatial registration during the procedure. An access site to the brain tissue in the form of a burr hole or craniotomy can be formed with or without additional access tools fixed to the skull such as insertion cannula and advancement/retraction equipment to access the target site. Advancement of a nerve tissue activity measurement probe through the brain tissue to the target site may be used to enable evaluation of the suitability of the brain region. This probe may record neural activity to determine that the measured signals are consistent with that of tissue requiring block. If the signal characteristics indicate that the location is not optimal or appropriate for block, the probe may be adjusted until the correct location is identified. The measurement probe may be exchanged with the blocking electrode which can then be inserted with the active portion of the electrode positioned within the target site. Activation of the blocking signal can then be used to assess efficacy of the block as well as to tune the strength of the signal. The blocking electrode can then be fixed to the skull to maintain the active portion's (e.g., region delivering ionic current) position at the target site. An extension lead can be connected to the affixed blocking electrode and connected to an implantable current source, similar to an implantable pulse generator (IPG), whose output signal can be adjusted to facilitate optimal symptom reduction. Blocking electrodes may be implanted unilaterally or bilaterally as the contralateral side of the body is affected by specific anatomic target sites.

FIG. 9A shows an electron-ion current conversion cell (EICCC) electrode 900 configured to interface with a deep brain block (DBB) target in the thalamus. The nerve tissue interface 904 contacts and provides block to the target site in the thalamus while an electrode lead 902 provides a conduit between the thalamus and the exterior of the skull. An extension port in the skull anchor 910 allows for communication between the current source 908 and the electrode lead 902 via an electrode extension 906 which can connect electrically with the port and current source 908. Within the lead 902 itself the EICCC blocking electrode comprises an internal electrode 916 such as an Ag/AgCl wire which converts electron current to ionic current in an ion conductive medium 918 such as saline and generates ionic current at the nerve tissue interface 904 via an ionically conductive material such as a porous frit 920 designed to allow ions to flow through it to generate a block at the nerve tissue site. The ionically conductive medium 918 and/or tissue interface material may also comprise a hydrogel or other ionically conductive material as described elsewhere herein.

Specific to epilepsy, electrocorticography (ECoG) may be performed to identify the epileptic focus or foci for targeting of electrode placement and nerve block in that location. The implanted blocking electrode may be used to block or suppress nerve tissue activity on demand by the user during an epileptic fit or when sensing the onset of an epileptic fit. Moreover, the system including the blocking electrode may be configured to alternatively lower the field potential of a cluster of neurons prone to causing epileptic fits such that epileptic fits may be prevented instead of being reacted to when they are about to occur or when they are occurring. In another embodiment, the blocking electrode is combined with a measurement or sensing electrode such that the activity of the neuron cluster or clusters comprising the epileptic focus or foci are monitoring and when activity indicative of onset of an epileptic episode is measured, the system can automatically generates a block to reduce activity of the target cells in a closed-loop fashion. In FIG. 9B an embodiment of a blocking/suppressing electrode 950 with an integrated sensing electrode 922 is shown in which a sensing electrode 922 is in proximity to the nerve tissue interface 904 such that sensing of the target neuron activity can occur and the signal from the sensing electrode 922 feeds back to the current source 908 which can be activated based on the sensing electrode signal to generate an ionic current at the nerve tissue 904 interface to disrupt or prevent onset of an epileptic fit. The sensing electrode 922 can include an insulated conductive path to electrode extension 924. In other embodiments, the blocking electrode may also serve as the sensing electrode 922 (e.g. when blocking current is not being applied). An electrode for blocking tissue to treat epilepsy may be configured as straight probe which is implanted deeper than the cortical surface, or may be configured as a epi-cortical electrode (e.g., by having a planar or conformal element).

Disclosed herein in some embodiments are systems and methods to maintain desired electrochemical reactions by monitoring signals indicative of the reactions occurring to modify the reaction generation conditions. Not to be limited by theory, traditional alternating current stimulation of neural tissue typically delivers a relatively low amount of charge through conventional electrodes (e.g., platinum electrodes). However, in some embodiments, high charge density electrodes including those described elsewhere herein deliver relatively greater amounts of charge closer to and beyond, and in some cases far beyond, the Shannon limit. Control systems and methods such as those disclosed herein can surprisingly and advantageously allow for the safe delivery of such current to tissue.

In some embodiments, a system which delivers ionic current driven by an electrochemical reaction can include a monitoring system, e.g., including a hardware and/or software controller configured to measure the voltage required to generate the electric current to drive the electrochemical reaction. If the voltage crosses a threshold, e.g., a predetermined threshold, the controller can adjust (e.g., increase or decrease) the current output to bring the voltage level into an acceptable range relative to the threshold voltage level. For example, if the voltage required to maintain a specific current level becomes too high, the current level may be reduced to the point that the voltage falls below the defined threshold. In some embodiments, if the voltage required to maintain a specific current level becomes too high, the current level may be set to zero. In yet another alternative system, if the voltage required to maintain a specific current level becomes too high the current level may be reversed.

In some embodiments, the current may take the form of a waveform such as, for example, a square wave or similar waveform between a first electrode (e.g., a working electrode) and a second electrode (e.g., a counter electrode) in which current is passed between the two electrodes with opposite polarity relative to a single electrode depending on the position within the waveform cycle. The voltage waveform required to drive the current between the electrodes may fall within an upper and lower voltage threshold limit. Over time, if the underlying electrochemical reaction is found to drift because of various conditions, the driving voltage waveform required to maintain the target current waveform may also drift. If the excursions/deviations from the target thresholds are significant enough, this may be indicative of undesired electrochemical reactions occurring. The voltage threshold limits and associated voltages may alternatively or additionally be measured between the working electrode and reference electrode to directly assess the voltage drop across the working electrode—electrolyte interface to assess the electrochemical reactions and potentials across that interface. To prevent these excursions into undesirable zones, the current delivered may be adjusted to reduce the driving voltages as described above. Alternatively, the voltage excursions may be due to changes in electrochemistry. For example in a system in which a reaction occurs where the same target amount of charge is transferred from one electrode to a second electrode and back to the first electrode, the net charge over time may drift from zero (e.g., become unbalanced) due to imperfect charge accounting. This in turn may lead to changes in voltage required to generate the desired current and be indicative of undesired electrochemical reactions occurring. The drift in net charge transfer from a target level may be countered in some embodiments by monitoring the driving voltage, and generating a control loop that generates additional charge on an electrode which has been detected via its driving voltage characteristics to be deficient in reactants. For example for a Ag—AgCl system, depletion of available AgCl on the working electrode can present as a negative dip in voltage when driving it cathodically as the lower reaction potential $AgCl(s)+e^- \leftrightarrow Ag(s)+Cl^-$ reaction is no longer available and other higher reaction potential reactions take place requiring higher driving voltages. In this case, if a higher voltage is detected during the cathodic phase of the waveform, additional charge may be imparted to the working electrode during a subsequent anodic phase by increasing the duration, amplitude, or both, of the current delivered to the working electrode.

FIG. 19 illustrates a driving voltage waveform and positive and negative thresholds over a period of time. As shown, the negative threshold is crossed/breached due to negative voltage dips before time point 2600. After 2600, the negative dips are no longer present and can be addressed by adjusting the target current level, and/or by adjusting distribution of charge transfer between the working and counter electrodes. For example, additional charge to generate more reactant material can be transferred during the anodic phase of the cycle for the working electrode.

FIG. 20 illustrates a driving voltage waveform, and positive and negative thresholds over a period of time. As shown, the negative threshold is crossed/breached due to negative voltage dips which may present characteristically as dips or spikes on top of a more monotonically increasing or generally flat voltage waveform, and may be indicative of undesired reactions taking place.

FIG. 21 illustrates schematically a voltage and current versus time graph illustrating an electrode annealing process in which the current amplitude is being ramped to a set target while the driving voltage is held below a set threshold. If the driving voltage is not exceeded for a given current amplitude, the current can be incrementally increased upward to the target current. If the driving voltage is exceeded for a given current amplitude, the current can similarly be incrementally decreased until the voltage threshold is no longer exceeded. Multiple cycles at a given current amplitude can be used to determine whether or not the system is stable at that current level and duration as assessed by staying within the voltage thresholds before incrementing the current up toward the target current. In some embodiments, at least about, about, or no more than about 2, 3, 4, 5, 6, 7, 8, 9, 10, 15, 20, 25, 30, 35, 40, 45, 50, 60, 70, 80, 90, 100, 150, 200, 250, 500, 1,000, or more or less cycles can be utilized, or ranges incorporating any two of the foregoing values. The voltage threshold for a series of cycles at a target current may also be set to fall within a driving voltage tolerance to be deemed stable to determine whether or not the annealing process has been successful.

Also disclosed here are systems and methods for blocking neural tissue with direct current. The systems can allow for indefinite direct current delivery (e.g., without requiring recharge reversal of current). Water or other suitable media such as normal saline can be used as the primary redox reactant in some cases; the reservoir can be refilled with water or other media as needed. In some embodiments, one, two, or more vents can be present to allow the venting of gas generated by the redox reaction. In some embodiments the vent may comprise a gas permeable by liquid impermeable membrane to enable venting of gas but retention of liquid within the container. The DC generator may have voltage sufficient to drive potentially large lead/catheter impedance. The system can also include one, two, or more pumps to cycle media, such as water, through a pH neutralizer to maintain a desired, e.g., neutral pH of the bath. The system can also include pH sensors to detect the pH of the bath, and allow for modifications, e.g., buffering if needed. The bath may further comprise a pH-buffered solution to maintain a nominally constant bath pH. FIG. 22 illustrates a system that can include a nerve-tissue interface operably connected to a catheter configured to hold a liquid. Also shown is a reaction chamber including a reaction electrode that can have a high surface area, which can be partially or entirely surrounded by a redox reactant (e.g., water) as previously noted. The chamber can also include a pH sensor. The chamber can be operably connected to a pump and reservoir of pH neutralizer that can be sealed from the chamber normally, and a valve or other reversible passageway opened when the pH falls outside of a pre-determined threshold value. The chamber can also include an agitator (e.g., an ultrasonic probe) to promote release of bubbles from the electrode. The bath may also include a surfactant to reduce the adhesion of bubbles to the electrode when formed. The reaction electrode can be operably connected to a DC generator. The DC generator can also be connected to a potential second unit to facilitate return current.

In some embodiments, a DC blocking electrode tissue system can include replaceable electrode material. Spent reacting metal (or other material) can be optionally removed over time, and fresh reactant material supplied to the reaction chamber. This can advantageously allow for one-way delivery of DC current without requiring a reversal/recharge phase. FIG. 23A illustrates a system including a reaction chamber including a reaction material. A rotatable member such as a spool with a tether (including or operably attached to reaction material), conveyor belt, or other mechanism can move fresh reactant material into (and spent reactant material out of) the reaction chamber as shown. Also illustrated is a catheter configured to convey the DC current to a tissue interface. Also illustrated is DC generator operably connected to the reaction chamber and/or the spool.

In some embodiments, disclosed herein is a separated interface nerve electrode that can include an integrated sensor for detecting the electrochemical status of a reaction/working electrode as shown schematically in FIG. 23B. A sensor can measure one, two, or more variables indicative of the working electrode state such as, for example, pH, mass, or voltage. In some embodiments the sensor may be a reference electrode such as an Ag—AgCl reference electrode or platinum reference electrode to enable measurement of the potential between the working electrode and the reference electrode to probe the electrochemical reactions occurring at the working electrode—electrolyte interface. Such leads/electrodes can have a relatively short length to reduce impedance. The lead lengths may range in length from 0 to 2 cm, 2 to 4 cm, 4 to 8 cm, or 8 to 12 cm in length, or ranges incorporating any two of the aforementioned values. Furthermore the combination of the lead geometry and ionically conductive media within the lead may be configured to have an impedance value less than 1 kOhm/cm length or between 1-3 kOhm/cm or above 3 kOhm/cm.

FIG. 24 illustrates that systems and methods can utilize battery-type chemistries to deliver DC current to tissue, such as lead-acid battery, nickel-cadmium, nickel metal hydride, lithium ion, lithium polymer, zinc-carbon, biobatteries, or other types of battery chemistries. Systems can include a DC generator operably connected to one, two, or more reaction chambers that can include battery chemistry-type reactants. For example, the reactant could be lead/lead oxide and the redox reactant could be sulfuric acid and/or water as illustrated. A membrane or other unit denoted at A can prevent passage of deleterious components into the catheter/lead connected to tissue (e.g., a cation or anion-selective membrane).

FIG. 25 illustrates schematically a SINE-type electrode modified to allow for attachment at the site of the patient to reduce the length and the impedance of the catheter. For example, a DC generator is operably connected to a wire connected to a reaction chamber (e.g., electrode system/charge generator including an electrode and electrode bath), in turn connected to a liquid catheter/tube configured to deliver DC current to a target tissue location. While one or more of the aforementioned components could be external or internal to the patient, in some embodiments as shown only a small length of liquid catheter/tube sits between the electrode system and target tissue location in the patient to reduce length and impedance. In some embodiments the majority, or at least about 50%, 60%, 70%, 80%, 90%, or more of the length of the liquid catheter/tube may sit internal to the patient's body. In some embodiments, less than about 5 cm, 4 cm, 3 cm, 2 cm, 1 cm, or less of the length of the liquid catheter/tube are internal to the patient.

In some embodiments, the system could be completely wearable to promote mobility of the patient. The system could include a strap, adhesive, band, or other element for attachment to the desired body surface, such as the scalp, neck, upper or lower extremities, torso, or abdomen for example. The lead/catheter could interface percutaneously as shown at the desired anatomical site, or transcutaneously in other embodiments. FIG. 26A illustrates a wearable system including a DC generator, wire, and reaction chamber, with a portion of the lead/catheter implanted at the desired anatomical site. FIG. 26B illustrates a bandage-style system that is local to the site of treatment (e.g., nerve block). FIG. 26C shows a schematic embodiment of such a wearable device with two different lead exit configurations where the lead exits the narrow aspect of the system and where the lead exits the wider aspect of the system and can be directly inserted into the patient body. The lead may be configured to be detachable from the rest of the system to enable case of insertion into the patient body prior to connecting to the rest of the wearable system.

Figures 27A, 27B, 27C, 27D:
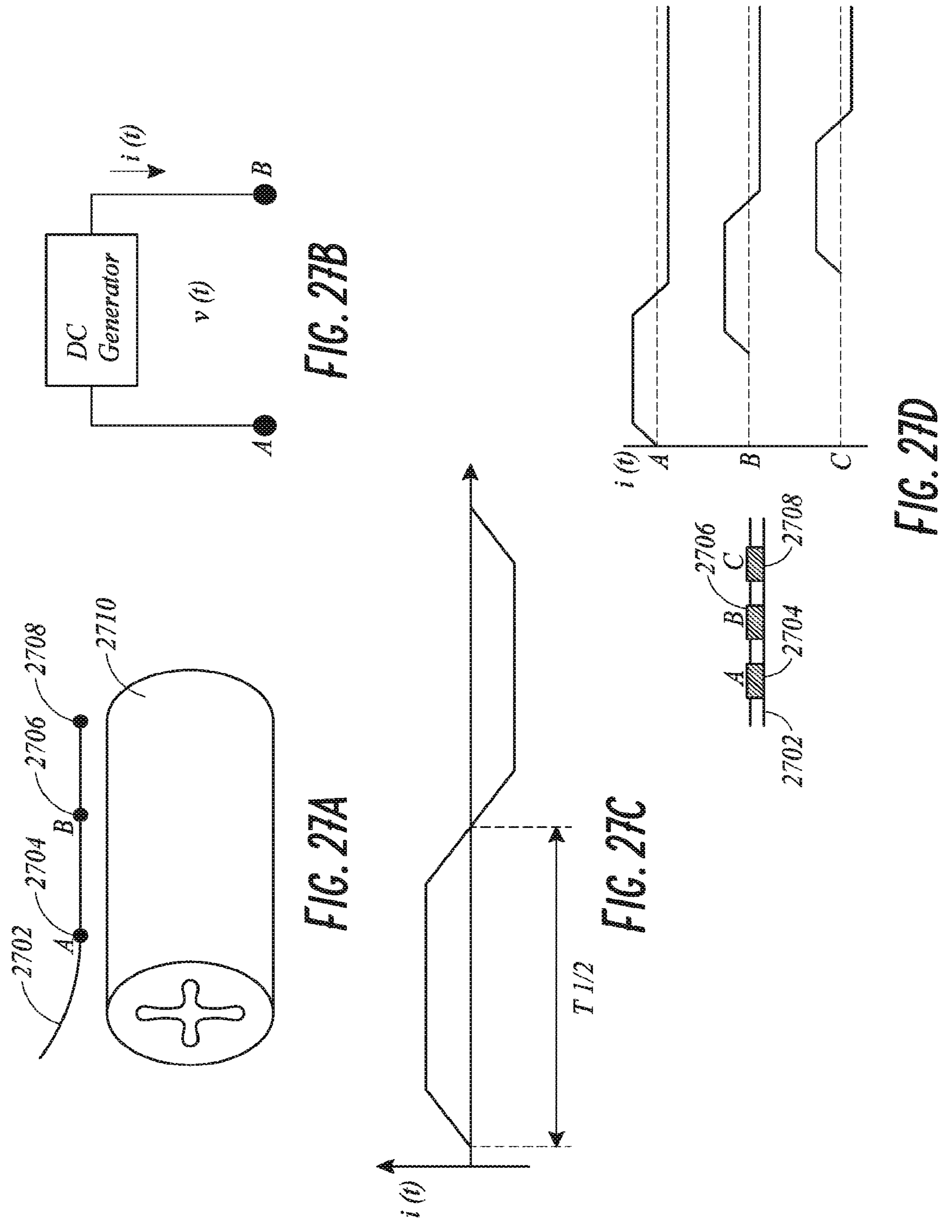

In some embodiments, disclosed herein are methods of treating pain or other conditions by cycling DC block at a plurality of locations spaced apart from each other. For example, electrodes could be present at sites A and B shown schematically in FIG. 27A, supplied by a DC generator. Variables v(t) (voltage over time) or i(t) (current over time) as shown in FIG. 27B could have very long biphasic cycles. As illustrated in FIG. 27C the time of each phase of the biphasic wave $t_{1/2}$ could be, for example, at least about 0.1 sec. 1 sec, 5 sec, 10 sec, 20 sec, 50 sec, 100 sec, 500 sec, 1000 sec, 5000 sec, or longer, or ranges incorporating any two of the foregoing values. Blocking tissue part of the time can involve an electrode directly beneath or proximate target tissue to be therapeutically beneficial in a person in need thereof. The DC current block can in some embodiments, be in the vicinity of electrodes A or B, thus providing continuous or near-continuous block in the tissue. In some embodiments, 3, 4, 5, or more spaced apart electrodes with overlapping charge waveforms can be utilized to advantageously promote continuous nerve blockade as shown in FIG. 27D.

Also disclosed herein are systems and methods of controlling DC output current amplitude based on measuring a variable indicative of electrochemical state for a DC blocking electrode system. This can advantageously promote safe use of DC current to ensure operation only in the electrochemical range (e.g., reaction types) that are safe for the health of the tissue as well as the electrode. The variable could be, for example, one, two, or more of: voltage, pH, temperature, or others. FIG. 28A schematically illustrates a DC current system including an optional reference electrode for voltage monitoring. In the simple example shown in FIG. 28B, electrode voltage increases with continued DC current delivery. Current can be halted once the voltage reaches a threshold maximal value indicating that a different chemistry (e.g., electrolysis of water) may be possibly occurring. In some embodiments, the system can be more complex to allow less interrupted delivery by decreasing or otherwise modulating output current to keep the voltage within a desired operating window. Output can be controlled, for example, with a Proportional-Integral-Derivative (PID) controller. Net-imbalanced charge delivery can be desirable in some cases to keep operating voltage within the desired window.

Some embodiments can also include an annealing process for an electrode, e.g., a silver-silver chloride electrode without or without a coating, operably connected to a DC generator. The output current can be gradually increased in a cyclical fashion, while monitoring the voltage. The voltage can be kept within a desired range with upper and lower threshold bands as shown in FIG. 29 which limits the electrochemistry occurring at the electrode site (e.g., to a silver-silver chloride reaction as opposed to water electrolysis).

Also disclosed herein in some embodiments are single-fault safe DC systems and methods. The systems can methods can involve very large series capacitors, such as about or at least about 5,000, 7,500, 10,000, or more microfarads (mfd), as shown schematically in FIG. 30A. Charge accounting can be performed so a known value is delivered in each direction, such as utilizing any number of the following: programmed amplitude and duration of delivery; measured delivery using voltage across a sense resistor; monitoring voltage out (with or without additional (e.g., third or fourth) reference electrodes as shown schematically in FIG. 30B; monitoring circuits to have control of switches to halt or slow current delivery as shown schematically in FIG. 30C; and/or performing monitoring by an independent microcontroller or logic device to promote tolerance to single (or multiple) fault conditions.

Additionally disclosed are electrode systems and methods for making these systems which can deliver direct current safely to tissue. Specifically, a silver-silver chloride electrode configuration is disclosed comprising a silver (Ag) substrate with an attached silver-chloride (AgCl) layer (FIG. 31). The AgCl layer may be deposited on the surface through a chemical deposition process. Alternatively or in addition, the AgCl layer may also be grown on the silver substrate through an electrochemical process of immersing the silver substrate in an electrolyte solution containing chloride ions (Cl—) and driving current through the substrate to facilitate a chemical reaction oxidizing the silver atoms in the substrate allowing them to bind to the chloride ions to generate silver chloride as previously described:

$$Ag(s) + Cl^- \Leftrightarrow AgCl(s) + e^-$$

In some embodiments, the electrodes may be in any desired shape, including but not limited to generally flat, or rounded, such as in a cylindrical shape. In one non-limiting embodiment, the electrode can include dimensions of about 1.4 mm in outer diameter with a length of about 3.5 mm. In another embodiment, the electrode may comprise a flat disk, with a diameter of about 3.6 mm. The electrode may also have an oblong or pill shape. The electrode surface area may be, for example, in the range of less than about 5 $mm^2$, about 5 to 10 $mm^2$, about 10-15 $mm^2$, about 15-20 $mm^2$, greater than 20 $mm^2$, or ranges including any two of the aforementioned values (e.g., between about 5 $mm^2$ and about 20 $mm^2$). A layer of silver chloride on the silver substrate may be generated with, for example, a thickness of less than about 1 micron, about 1 to 3 microns, about 3 to 5 microns, about 5-10 microns, or about 10 microns and greater, or ranges including any two of the aforementioned values (such as between about 1 micron and 10 microns), to enable sufficient direct current and charge delivery as therapeutically necessary. In one configuration, a cylindrical electrode of diameter about 1.4 mm and length about 3.5 mm is prepared with an about 10 micron thick layer of silver-chloride to enable delivery of up to about 5000 mA-seconds of charge such as a specific setting of about 5 mA of current for about 10 seconds. When the reaction is run in reverse with an appropriate counter-electrode, the electrode may be regenerated to enable prolonged cycling and use of the direct current in the body.

Silver chloride can be created on pure Ag by the application of direct current through an electrolyte bath (FIG. 32). As seen in FIG. 32 a counterelectrode and working electrode are shown immersed in an electrolyte bath and connected to a power supply which drives a potential across the two electrodes. In one configuration, the electrolyte bath includes chloride ions such as a saline solution, for example 0.9 wt % saline. The counterelectrode and working electrode may both be silver, or just the working electrode may be silver. With application of a driving voltage, a current is generated and silver on the working electrode can be converted to silver chloride creating a layer of silver chloride on the silver substrate.

A simplistic approach could apply direct current and calculate, by means of coulometric measurement, the total charge needed to produce enough AgCl on the electrode such that the longest cathodic pulse at therapeutic current levels would not deplete the electrode. However, the simplistic approach fails to address the properties of AgCl which affect both its ability to easily participate in the symmetric electrochemical reaction while remaining with a safe driving voltage range below the electrolysis potential threshold. It can be important in some embodiments that the electrode system keeps the ionic current flow isolated to the Ag to AgCl electrochemical reaction to substantially prevent the production of potential harmful byproducts. Controlling the voltage potential applied to the electrodes can be the primary means of selecting the electrochemical reaction as different reactions take place at different potentials. An AgCl electrode which does not have the correct properties can require voltage potentials higher than an allowable threshold value to maintain the prescribed current flow and duration. As a result, the electrochemical reaction can become uncontrolled, leading to the generation of potentially harmful byproducts.

One initial step can be to generate a layer of silver chloride on the silver substrate. To do this in a controlled fashion that does not cause electrolysis of the aqueous solution, a maximum current may be specified which may be the target current for therapeutic operation of the electrode or the maximum therapeutic current for the electrode. The maximum current may be in the range of, for example, about 0 to 3 mA, about 3 to 5 mA, about 5 to 7.5 mA, about 7.5 to 10 mA, or about 10 mA and higher, or ranges including any two of the aforementioned values. A driving voltage can then be applied between the counterelectrode and working electrode to generate a silver chloride layer on the working electrode. A target total charge can be specified to generate the target amount of silver chloride on the electrode surface. The build period of the electrode can be specified as well as an etch back period wherein the current is driven in reverse to remove some of the formed silver chloride to generate a more robust formation of silver chloride on the electrode surface. One configuration could include a 60 second build period with a 10% etch back period, for example, wherein 10% of the built AgCl layer is then removed prior to the next build period. Other combinations of build and etch back or removal periods can be used to generate the AgCl on the silver substrate.

As shown in FIG. 33 for trace A (solid line), the driving voltage applied can be positive corresponding to building of AgCl on the working electrode. After the prescribed build period a removal or etch back period occurs, then the next build cycle occurs until the total charge and target AgCl layer has been deposited at which the build process terminates as denoted by the 'X'. Because the absolute values of driving voltage thresholds were not reached in trace A, the driving voltage did not need to be adjusted during the AgCl generation process. However, in FIG. 33 for trace B (dotted line), the driving voltage upper threshold was reached and an algorithm stored in the controller can cap the driving voltage at an upped threshold level by reducing the current used to build the AgCl. The build period can be followed by a removal or etch back period as described and this process continues until the target charge is deposited in the form of AgCl on the working electrode.

Once the silver chloride has been generated on the electrode, the driving voltages to convert the AgCl to silver and vice versa may still exceed the electrolysis potential leading to potentially dangerous conditions if used in proximity to tissue. To condition the electrode such that it can operate in a safe range with driving voltages maintained below the electrolysis potential, the electrode can be cycled in a specific manner.

Cycling of the silver/silver-chloride reaction at fixed current amplitude and fixed durations has been demonstrated to lead to decreases in peak driving voltages with increasing number of cycles as shown in FIG. 34 and can result in driving voltages below the electrolysis threshold. However, the approach of fixing the current amplitude and duration can in some cases lead to generation of undesired and unsafe byproducts if the driving voltages exceed the electrolysis threshold as seen by the peak voltages which exceed or cross the driving voltage threshold upper and lower limits, potentially leading to generation of undesirable reaction by products. In some embodiments, the electrode can be prepared in a manufacturing bath and then the electrode is removed from that bath prior to use in the target device bath or in the body directly at which time the driving voltages can be reduced and within the desired range.

To mitigate generation of undesirable byproducts, cycling algorithms have been developed that can be executed by a hardware or software processor, which cycles the electrode in a build and removal cycle to obtain the desired current amplitude and duration that can be repeatedly cycled without exceeding set driving voltage thresholds which may be the electrolysis potential or otherwise. The process occurs through, for example, two steps, a formation step and a stabilization step.

The formation step involves the repeated cycling of current which builds a layer of AgCl for a specific period then removes the added AgCl. The amount of AgCl deposited is limited by the current level which is in turn limited by the maximum voltage limit or driving voltage upper threshold. There may also be a minimum voltage limit or driving voltage lower threshold. As the AgCl is repeatedly added and removed the underlying structure of the AgCl is transformed allowing it to sustain more current at the fixed driving voltage level. Under certain processes, these changes can be observed as microstructural changes visible on the surface of the electrode. The formation phase continues until the current level that can be sustained meets the prescribed value.

One embodiment of an algorithm is as follows:

a. Apply anodic current to the electrode for the prescribed period. During this time, measure the peak positive voltage over the duration.
b. Apply cathodic current to the electrode until the total charge applied during the anodic phase has been removed. During this time, measure the peak negative voltage over the duration.
c. Analyze the peak voltages and adjust the current to be applied on both the anodic and cathodic phases. If the magnitude of the peak voltage is below the voltage limit, then the current magnitude is increased by a fixed proportion up to the prescribed current limit. If the peak voltage magnitude exceeds the voltage limit then the current magnitude is decreased by a proportional amount.
d. If the anodic current has reached the prescribed current value then move to the stabilization phase. Otherwise continue to repeat the cycling process.

In FIG. 35 a working electrode and counterelectrode formation are processed in the formation step where the current level starts at a relatively low value and rises with each cycle when the driving voltage upper threshold is not exceeded. As seen by the solid arrows, when the driving voltage upper threshold is exceeded for a given current level, the applied current level for the next cycle is reduced as shown with the open arrow. The duration of the positive current for the working electrode is set to the target duration and the final amplitude is the target amplitude. Both may be configured to vary in other embodiments of the algorithm.

The stabilization step can also involve the repeated cycling of current which builds a layer of AgCl for a specific period, then removes the added AgCl. The amount of AgCl deposited is fixed and determined by the current and duration. As the AgCl is repeatedly added and removed, the underlying structure of the AgCl is transformed, reducing the voltage potential required to pass the prescribed current for the duration. The stabilization phase continues until the cycle-to-cycle voltage variation falls below a preconfigured value. As seen in FIG. 35 the stabilization phase may include a substantially consistent current amplitude with each cycle and driving voltages whose peak levels are consistent within a pre-defined variation value.

One embodiment of an algorithm is as follows:

e. Apply anodic current to the electrode for the prescribed period. During this time measure the peak positive voltage over the duration.

f. Apply cathodic current to the electrode until the total charge applied during the anodic phase has been removed. During this time measure the peak negative voltage over the duration.

g. Maintain (e.g., in a memory) a list of the previous N peak voltages. The number of samples, N, is the configured stability period.

h. If the variation in peak anodic voltages is below a configured value the electrode formation process is complete. Otherwise, continue to cycle current. Alternatively, the magnitude of the peak anodic voltages are below a configured value until or when the electrode formation process is complete.

In some embodiments, the electrode could have a working surface area of, for example, about, less than about, or no more than about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 90, 100 $mm^2$, or more or less, or ranges including any two of the foregoing values.

In some embodiments, the maximum current limit could be, for example, about, less than about, or no more than about 0.1, 0.2, 0.3, 0.4, 0.5, 1, 2, 3, 4, 5, 6, 7, 8, 9, 10 mA, or more or less, or ranges including any two of the foregoing values.

In some embodiments, the voltage limit could be, for example, about, less than about, or no more than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.5, 3, 3.5, 4, 4.5, 5V, or more or less, or ranges including any two of the foregoing values.

In some embodiments, the voltage variation limit could be, for example, about, less than about, or no more than about 0.1, 0.5, 1, 5, 10, 15, 20, 25, 50, 75, 100, 125, 150, 175, 200, 225, 250 mV, or more or less, or ranges including any two of the foregoing values.

In some embodiments, the time period limit could be, for example, about, less than about, or no more than about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 seconds or more or less, or ranges including any two of the foregoing values.

In some embodiments, the stability period could be, for example, at least about, about, or no more than about 2, 3, 4, 5, 6, 7, 8, 9, 10, 15, 20, 25, 30, 35, 40, 45, 50, 60, 70, 80, 90, 100, 150, 200, 250, 500, 1,000 cycles, or more or less, or ranges incorporating any two of the foregoing values.

In some embodiments, the build period could be, for example, at least about, about, or no more than about 2, 3, 4, 5, 6, 7, 8, 9, 10, 15, 20, 25, 30, 35, 40, 45, 50, 60, 70, 80, 90, 100, 150, 200, 250, 500, 1,000 seconds, or more or less, or ranges incorporating any two of the foregoing values.

In some embodiments, the build etch-back period could be, for example, at least about, about, or no more than about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 60%, 70%, 80%, 90%, or more or less, or ranges incorporating any two of the foregoing values.

In alternative embodiments, the build charge might be up to about 2500, 3000, 3500, 4000, 4500, or 5000 mA-seconds or higher than 5000 mA-seconds, such as 5500, 6000, 7000, 8000, 9000, 10000 mA-seconds, or more, or ranges including any two of the aforementioned values.

In some embodiments, such as in the algorithms disclosed, for example, the electrode can be conditioned in a manner that allows for delivery of the target current amplitude for the desired duration with a driving voltage below a set threshold such as the electrolysis potential, for example. The algorithm also limits the amount of time the electrode is exposed to voltages above the driving voltage upper threshold which can lead to generation of deleterious by products that can damage tissue.

FIG. 36 shows the change in microstructure that can occur after building an AgCl layer on a bare silver electrode and after performing the formation and stabilization steps to condition the AgCl-coated electrode. These microstructural changes can include formation of Ag—AgCl "islands" that readily transition between the Ag and AgCl forms and increase surface area for electrochemical reaction.

While embodiments have been described for building and conditioning an electrode so that the driving voltage remains below a set threshold which can be a safety threshold such as the electrolysis potential or another threshold set as desired such as by incorporating safety factors, the system may still encounter scenarios that tend to push the driving voltage out of the desired target range. For example, the charge exchanged between the working and counter electrodes may be slightly biased such that more charge is being deposited on the counter electrode than on the working electrode with each cycle. Over many cycles this may strip the working electrode of active, conditioned AgCl or another substrate causing the magnitude of the driving voltage to rise. FIG. 37 shows a driving voltage which started to exceed the driving voltage lower threshold over time. Furthermore, in the body the impedance of the system is not only dictated by the reaction potentials across the electrode-body interfaces but also by the impedance of the body tissue itself and the voltage drop that occurs through the tissue. The tissue impedance may change due to capsule formation (e.g., fibrosis) around the electrodes, movement, weight gain or loss, or other factors that cause the body impedance to vary (increase or decrease) over time. At low frequencies because the driving voltage comprises the voltage drop across the lead immediately surrounding tissue ($\Delta V_{lead}$) and the body ($\Delta V_{body}$) as shown below:

$$V_{driving} = \Delta V_{lead} + \Delta V_{body} = I * (R_{lead} + R_{body})$$

It can be advantageous in some cases to ensure that the voltage drop across the lead does not exceed the safety threshold, because that voltage drop is dictated by electrochemical reactions. If one can calculate the body resistance ($R_{body}$), then $\Delta V_{body}$ can be determined for a set current value (I) and the voltage drop across the lead ($\Delta V_{lead}$) can be calculated and adjusted by adjusting the driving voltage ($V_{driving}$) to ensure that $\Delta V_{lead}$ remains in a safe range.

In FIG. 38 the electrode and body can be modeled as a resistor ($R_{lead}$) and capacitor ($C_{lead}$) in parallel and a body impedance ($R_{body}$) in series with the electrode. At low driving frequencies, the electrode and body can be modeled as shown in FIG. 39 reflective of the equation above. At high driving frequencies the system can be modeled as shown in FIG. 40 where the capacitor behaves like a short and does not have any impedance. Referring to FIG. 40 in this scenario, the system can be defined by the following equation where $\Delta V_{lead}=0$ because $R_{lead}=0$:

$$V_{driving} = \Delta V_{lead} + \Delta V_{body} = I * (R_{lead} + R_{body}) = I * R_{body}$$

By knowing $V_{driving}$ and the current (I), the body impedance ($R_{body}$) can be calculated:

$$R_{body} = V_{driving}/I$$

Therefore, the lead or electrode voltage drop can be calculated (e.g., via a processor) and controlled by adjusting the overall driving voltage:

$$\Delta V_{lead} = V_{driving} - \Delta V_{body}$$

This can allow the system to maintain the voltage below a set threshold.

$$\Delta V_{lead} < V_{threshold}$$

Referring again to FIG. 40 the ability to simulate the short across the lead or electrode-body interface can be implemented by generating a short current input as seen circled in the figure. In some embodiments, the current input include a current amplitude on the order of up to about 10 microseconds, from about 10 to about 20 microseconds, from about 20 to about 50 microseconds, from about 50 to about 100 microseconds, from about 100 microseconds to about 200 microseconds, more than about 200 microseconds, or ranges including any two of the aforementioned values. This current input can occur at the beginning of the DC cycle, during the DC cycle, or after the DC cycle in order to determine the body impedance to allow for adjustment of the driving voltage in order to maintain the lead or electrode voltage below a set threshold. The set threshold may be a safety threshold such as the electrolysis potential. The current input may be performed each cycle or every other cycle or periodically or on demand as desired to allow for determination of the lead or electrode voltage drop. This voltage drop knowledge can then be used to adjust the driving voltage in an automated control loop or manually. After the initial high frequency current input, the DC current waveform may be applied based on the adjusted driving voltage as determined in the prior high frequency current input.

If the lead or electrode voltage is determined to be in excess of a threshold value it can also be adjusted by adjusting the delivered current by reducing the current amplitude as shown in FIG. 41 wherein the portion of the waveform where the threshold is reached, the current is reduced to stay below the threshold. In a silver-silver chloride electrode application with both as the counter electrode and the working electrodes, controllers implementing the algorithm described can advantageously enable self-balancing of charge. The silver-silver chloride system can exhibit higher voltages during the anodic phase (positive voltage) for the working electrode when the amount of available AgCl on the corresponding counter electrode partially depletes such that less easily reacted AgCl leads to higher potentials to drive the reaction. By reducing the amount of charge pulled from the counter electrode during the anodic phase (open arrows) but having a full amplitude current during the cathodic phase (solid arrow), net charge is added to the counter electrode helping to rebalance the charge distribution between the electrodes.

It should be noted that the systems and algorithms described above can also be used to maintain voltages within specific target driving voltage and lead voltage ranges as desired and set by the end user within the algorithm.

FIGS. 42A-C show schematically an embodiment of an electrode lead 2100 configured to deliver ionic direct current to tissue in proximity to the lead 2100. The lead 2100 can include a portion 2104 through which ionic current can pass into the tissue and an electrically insulated portion 2102. The portion 2104 through which ionic current can pass is in proximity to an ionic current generation source 2112. The system further can comprise an electric current connection 2103 to a power source. The current source may be located external or internal to the body depending on the application need. Some embodiments comprise an ionic current generation source comprising a silver cylindrical ring with a silver chloride layer on its exterior surface as generated by techniques such as by oxidizing silver in a saline solution. An electrical connection between the silver and power source is facilitated by electrically connecting a conductive conduit such as a wire to the silver cylindrical ring such as by welding, mechanical fusing or other techniques known in the art. As shown in the cross-sectional views FIG. 42B (cross section through the insulated portion) and FIG. 42C (cross section through the ionically conductive portion), this electrical connector 2108 may be preferentially situated in the interior of the silver cylindrical ring and within the external diameter of the insulated portion 2106 of the lead 2100. The insulated portion 2106 of the lead 2100 is molded around the silver/silver chloride ring and electrical connector 2108 comprising an electrically insulating material such as silicone or polyurethane. Additionally shown in FIG. 42C is ionic current generator 2112 and electrical connection to the ionic current generator 2110. A molding process leaves the cylindrical outer surface exposed. Another embodiment comprises a silver ring with external diameter in the range of about 1.0 to 1.5 mm with wall thickness of about 0.08-0.14 mm. In the embodiment described above, ionic current in the form of chloride ions may be generated by driving a cathodic current through the silver chloride to convert the silver chloride to silver that is redeposited on the silver cylindrical ring and free chloride ions. The end of the lead may also be blunt or tapered or rounded to facilitate improved insertion and navigation through the body. In other embodiments, the silver cylindrical ring may be replaced by alternative substrates including platinum, stainless steel, titanium, gold, platinum-iridium. To increase the available electrochemical surface area (ESA), the substrate may comprise microstructural features that increase the available surface area. In some embodiments, the substrate may comprise an open porosity sintered component. In some embodiments, the substrate may comprise an open porosity foam component such as a reticulate foam structure. In some embodiments, the substrate may comprise surface texturing from micromachining to generate features such as grooves or roughness to increase the overall ESA. These micromachining tools may comprise laser ablation to generate channels or grooves or general surface roughness. Additional micromachining techniques which can accomplish these goals are electric discharge machining (EDM), material etching techniques, pattern masking and etching techniques, bead or grit blasting, and surface sanding. The alternative substrate ring material may further be coated with a high charge capacity material such as sputtered iridium oxide (SIROF), Poly(3,4-ethylenedioxythiophene)-poly(styrene-sulfonate) (PEDOT), titanium nitride (TiN), fractal titanium nitride, porous titanium nitride, or some combination thereof.

FIGS. 43A-43D show an embodiment of an electrode lead 2300 configured to deliver ionic direct current to tissue in proximity to the lead similar to FIGS. 42A-42C in which the lead has been covered in an ionically conductive medium 2314 to facilitate transmission of ionic current from the ionic current generator 2312 to the target tissue. As shown in FIG. 43A, the electrode lead 2300 includes an insulated portion 2302, ionically conductive portion 2304, and a portion 2303 operably connected to a power source (not shown). FIG. 43B is a cross-section through the insulated portion 2302 of FIG. 43A illustrating electrical connector 2308 within insulator 2306. FIG. 43C is a cross-section through the ionically conductive portion 2304 of FIG. 43A illustrating electrical connector 2308 within insulator 2306, as well as ionic current generator 2312, ionically conductive medium 2314, ionically selective membrane 2316, and electrical connection 2301 to the ionic current generator 2312. The ionically selective membrane 2316 is shown to enable passage of ions but limiting passage of other materials through the membrane. In some embodiments the ionically conductive medium 2314 and ionically selective membrane 2316 are restricted to the ionic current generator 2312 portion of the lead 2300, as shown in the longitudinal cross-section of FIG. 43D. In some embodiments, the ionically conductive medium 2314 comprises a high salt content hydrogel with an anion exchange membrane as the ionically selective membrane 2316 allows transmission of anions, e.g., chloride ions, but limits transmission of cations and uncharged particles.

FIGS. 44A-44C illustrate another embodiment of an electrode lead wherein the ionically conductive medium 2314 in FIG. 43A-43D is absent, and instead the ionically selective membrane 2316 is in direct contact with the ionic current generator 2312 and insulator 2306 exterior surface. FIG. 44B is a cross-section through the insulated portion 2302 of FIG. 44A illustrating electrical connector 2308 within insulator 2306. FIG. 44C is a cross-section through the ionically conductive portion 2304 of FIG. 44A. In some embodiments the ionically selective membrane 2316 is localized only to the ionic current generator 2312 portion of the lead 2400. In other embodiments the membrane 2316 covers both the ionically conductive portion 2304 and the insulated portion 2306 of the lead 2400. In some embodiments, the ionically selective membrane 2316 comprises an anion exchange membrane. This membrane 2316 can be formed on the lead 2400 in a variety of ways including dip-coating the lead 2400 in a bath of solvated anion exchange membrane ionomer and driving off the solvent by heating or another chemical process to yield the final coating on the lead. The coating may be preferentially bonded to the insulated portion of the lead. The coating may also be configured to have gas permeable properties such as if gaseous species are generated below the coating, the gas can escape or dissolve into the surrounding tissue and be evacuated by the body. In another embodiment small channels in the coating are present to enable any gas formed below the coating to vent and escape from the region between the coating and the electrode surface.

FIGS. 45A-45C show an embodiment of an electrode lead 2500 configured to deliver ionic direct current to tissue in proximity to the lead. As illustrated in FIG. 45A, the lead 2500 comprises a portion 2304 through which ionic current can pass into the tissue and an electrically insulated portion 2302 as previously described. The electrode lead 2500 also comprises a reference electrode 2505 used to provide a representative measurement of the potential difference across the ionically conductive portion 2304 of the lead 2300 and the immediately adjacent tissue. In this embodiment an ionically selective membrane 2316 is situated over the lead 2500 and is preferentially an anion exchange membrane. A direct measurement between the ionically conductive portion 2304 of the lead 2500 and the distal counterelectrode would be less accurate due to current flow between the two electrodes leading to ohmic potential drops that can obscure the true potential difference as well as the potential drop due to body resistance between the working and counterelectrodes. The reference electrode 2505 can be configured to be a high-impedance electrode which limits current flow through the electrode limiting potential difference measurements from being skewed due to ohmic potential drops across the electrode-environment interface. In one embodiment the reference electrode 2505 comprises a silver cylindrical ring with a silver chloride coating on its exterior surface. In an alternative embodiment the reference electrode 2505 may be made from a platinum or platinum-iridium alloy. FIG. 45B is a cross-section through the insulated portion 2302 of FIG. 45A illustrating electrical connector 2308 within insulator 2306. FIG. 45C is a cross-section through the ionically conductive portion 2304 of FIG. 44A.

FIG. 46 shows an alternative embodiment to FIGS. 45A-45C in which an electrode lead 2600 comprises a portion 2304 through which ionic current can pass into the tissue, and an electrically insulated portion 2302. The electrode lead also comprises a reference electrode 2505 as previously described and used to provide a representative measurement of the potential difference across the electrochemically active portion of the ionically conductive portion 2304 of the lead 2600 and immediately surrounding tissues. The reference electrode 2505 is located in proximity to the ionically conductive portion 2304 of the lead 2600 but remains electrically isolated and spaced apart from the ionically conductive portion 2304 of the lead 2600.

FIG. 47 shows an embodiment of an electrode lead 2700 comprising a connector 2703 for the connection to an electrical power source (not shown), an insulated portion of the lead 2702 and multiple spaced-apart ionically conductive portions 2702 of the lead along with an ionically selective membrane 2716 or coating applied over the ionically conductive portions 2702 of the lead. The multiple ionically conductive contacts 2702 may be operated independently, in pairs, or in alternating patterns to deliver current to the proximal tissue. Furthermore, the contacts may be operated not only in a current delivery mode but may be run in a high impedance mode as reference electrodes to measure the potential difference between the working electrodes (ionically conductive portions passing current) and the counter electrode which can be the body of the power supply unit. In some embodiments, the working electrodes may be configured such that they deliver different ionic DC levels to optimize the nerve block desired. Some embodiments can include about or at least about 2, 3, 4, 5, 6, 7, 8, 9, 10, 11, 12, 13, 14, 15, 16, 20, 25, 32 or more ionically conductive portions, or ranges including any two of the aforementioned values.

FIG. 48 shows that in a rat model, a stimulation force of the gastrocnemius muscle due to stimulation of the sciatic nerve can be tuned such that the nerve is unblocked (0%) or fully blocked (100%) or tuned to a partial block between 0% and 100%, such as about 10%, 20%, 30%, 40%, 50%, 60%, 70%, 80%, 90%, or ranges including any two of the aforementioned values. As seen, increasing the DC block amplitude decreases the stimulation force in a gradual manner so that this nerve block tuning and current field tuning is possible similar to what is performed with current spinal cord stimulators that use AC stimulation signals.

FIG. 49 shows an embodiment of a multi-contact electrode lead 2900 configured to deliver ionic direct current to tissue in proximity to the lead 2900. The lead 2900 comprises a plurality of contacts 2304 through which ionic current can pass into the tissue and an electrically insulated portion 2302. The electrode lead 2900 can also comprise a reference electrode or electrodes 2505 used to provide a representative measurement of the potential difference between the ionically conductive portion of the lead 2900 and immediately adjacent tissue as previously described. By having a relatively high-density configuration of ionically conductive contacts 2304, the current field as referenced in FIG. 48 can be configured and customized with high level of precision by individually addressing and controlling the contacts. Furthermore, a reference electrode or multitude of electrodes can help ensure that the electrochemical reaction of the ionically conductive contacts operate within the desired operating parameters.

FIGS. 50A-50B illustrate an alternate configuration of a curved multi-contact electrode lead 3000 configured to deliver ionic direct current to tissue in proximity to the lead. FIG. 50A is a side view, and FIG. 50B is a perspective view. The system can be designed to be wrapped around a nerve as a nerve cuff 2306 and may have a plurality of ionic current conductive contacts 3005 along the length of the nerve cuff 2306 as illustrated. The long axis of the electrode can run substantially perpendicular to the long axis of the nerve which is captured in the interior portion of the curved aspect of the electrode. Alternatively or in combination, the cuff 2306 may extend along the length of the nerve and had discrete contacts that run along the width of the cuff 2306 (running along the length of the nerve). The contacts may be used independently or together to generate ionic DC block. Contacts 3005 may also be used as reference electrodes in some embodiments.

As shown in FIG. 51 the ionic current generation portion 3100 of the electrode may be generalized to having a conversion mechanism from electrical current supplied by the electrical connection 3106 to an electrochemical system (3101 and 3102) which convert the electrical current into ionic current. The electrochemical system may be optionally covered with an ionically selective membrane or ionically conductive medium 3103 to facilitate transport of the ions from the ion generation system to nearby tissues. The surface of the ion generation system 3100 may also include a recessed surface 3105 relative to adjacent insulating surfaces 3104 to generate a more even current field profile along the ionically conductive electrode surface to facilitate even ion generation along the electrode. In some embodiments, the ion generation system 3100 comprises a substrate made of silver 3101 with a primary coating of silver chloride 3102 adhered to the exterior surface of the substrate 3101. An anion exchange membrane can be optionally adhered to the surface of the electrode and insulator to enable chloride ions to pass but to prevent cations and uncharged particles from passing through the coating 3103. In other embodiments, the substrate 3101 may comprise alternative substrates including platinum, stainless steel, titanium, gold, platinum-iridium. To increase the available electrochemical surface area (ESA), the substrate may comprise microstructural features that increase the available surface area. In some embodiments, the substrate may comprise an open porosity sintered component. In some embodiments, the substrate may comprise an open porosity foam component such as a reticulate foam structure. In some embodiments, the substrate may comprise surface texturing from micromachining to generate features such as grooves or roughness to increase the overall ESA. These micromachining tools may comprise laser ablation to generate channels or grooves or general surface roughness. Additional micromachining techniques which can accomplish these goals are electric discharge machining (EDM), material etching techniques, pattern masking and etching techniques, bead or grit blasting, and surface sanding. The substrate 3101 may further be coated with a coating 3102 such as high charge capacity material such as sputtered iridium oxide (SIROF), Poly(3,4-ethylenedioxythiophene)-poly(styrenesulfonate) (PEDOT), titanium nitride (TiN), fractal titanium nitride, porous titanium nitride, or some combination thereof. In some embodiments, the primary coating 3101 may comprise an adhesion layer to promote adhesion between the substrate 3101 and the secondary coating 3103. An exemplary embodiment is deposition of a titanium adhesion layer 3101 to promote adhesion of a secondary coating 3103 of titanium nitride to different substrate 3101 surfaces.

FIG. 52 illustrates how an ionically conductive portion of the electrode can be configured to generate a more even current density profile along the width 3206 of the electrode. As shown in the graph, recessing the surface 3210 of the conductive electrode 3204 at a depth 3208 in between insulated portions 3202 can help make the current density of the edges of the electrode approach that of the center of the electrode. The current generating surface 3210 may also be configured to be covered with one or more coatings as previously described that enable transport of ions such as an ion exchange membrane but restrict passage of other particles.

FIGS. 53A-53D illustrates one embodiment of an ionic direct current electrode lead 3300 with paired ionic current generation contacts 3302, which can be silver contacts (or titanium nitride, or other material including those disclosed elsewhere herein), that can be adhered using a helical wire form 3304, which can be made of silver. FIG. 53A illustrates an exploded view of various components of the ionic direct current electrode lead 3300, including ionic current generation contacts 3302, helical wire form 3304, insulated wire 3306, and end of insulated wire 3308. As shown in FIG. 53B, the helical wire form 3304 is shown connecting the current generation contacts 3302 along the interior aspect of the ionic current generation contacts 3302. The helical wireform 3304 may be fused or placed in electrical contact with the current generation contacts 3302 via laser welding, spot welding, physical contact, ultrasonic welding or other means of providing electrical contact between the two objects, as shown in FIG. 53D along fixation points 3310. As shown in FIG. 53C a lead contact assembly cross section, an insulated wire 3306, which can be a 16 strands PTFE coated lead, is then connected electrically to the helical wireform 3304. The end of the insulated wire 3308 is stripped such as by laser ablation to expose the conductive core and may comprise a solid core or multistranded configuration. The laser ablated section may be a variety of sizes, such as 0.15-0.25 mm or other suitable sizes such as less than 0.15 mm or greater than 0.25 mm. The insulated wire 3306 can comprise a variety of configurations, which can include at least 16-22 strands of MP35 or Med. SS 0.1 mm overall diameter. The insulated wire 3306 can comprise a coating of different thicknesses and materials, which can at least include PTFE coatings of 15-20 microns thick. The exposed conductive aspect 3308 of the wire 3306 can then be crimped and/or fused to the helical wire form 3304 to create an electrode pair unit. It can be appreciated that the number of connected current generation contacts 3302 may be fewer or greater than that shown for each helical wire form 3304.

For example, each helical wire form may have a single current generation contact in electrical contact with it and an associated insulated wire to provide electrical connectivity to the electric power supply. The current generation contact may be configured to have electrochemical properties such that when provided with electrical current, a portion of the contact can transform that electrical current into ionic current. In one embodiment the current generation contact comprises a silver cylindrical body with silver chloride on the outer cylindrical surface of the contact that can release chloride ions when driven with a cathodic current. These lead contact constructions of ionic current generating contacts, helical wire form, and insulated wire may be combined to generate electrodes with multiple leads that can be space in proximity with an even spacing or uneven spacing as desired for the specific application. Specific lead contacts may be used as working electrodes to generate ionic current or reference electrodes to measure the potential difference between the electrode lead and a counter electrode or between the electrode lead and immediately adjacent tissue or may be used as both by switching them between different states. The plurality of lead contacts may then be positioned and physically connected by a binding material that can be molded around and through the lead contacts to create an elongated lead structure. This binding material may be a flexible polymer and is preferentially biocompatible. Example materials include silicone and polyurethanes. This binding material may preferentially be an electrical insulator. This binding material in preferentially insulating to ionic current. A coating may further be situated around the electrode lead to allow passage of ions from the electrode into the target tissue. The coating may comprise an anion exchange membrane which allows anions such as chloride ions to pass through from the ionic current generation portion to tissue in proximity to the lead.

FIG. 54A illustrates a lead sub-assembly 3400 (top) and a lead with one or a plurality of contacts 3402 as previously described in connection with FIGS. 53A-53D above. The contacts 3402 can allow for ionic current generation as previously described. FIG. 54B illustrates a plurality of contacts 3402 coupled to a plurality of ends of insulated wires 3308.

Figure 55A:
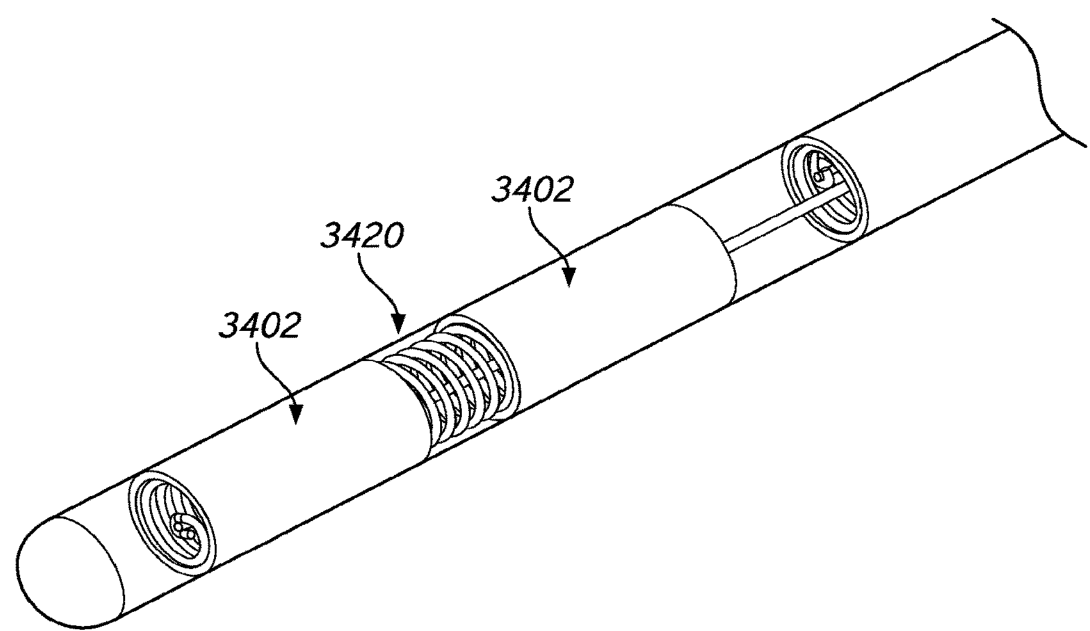
Figure 55B:
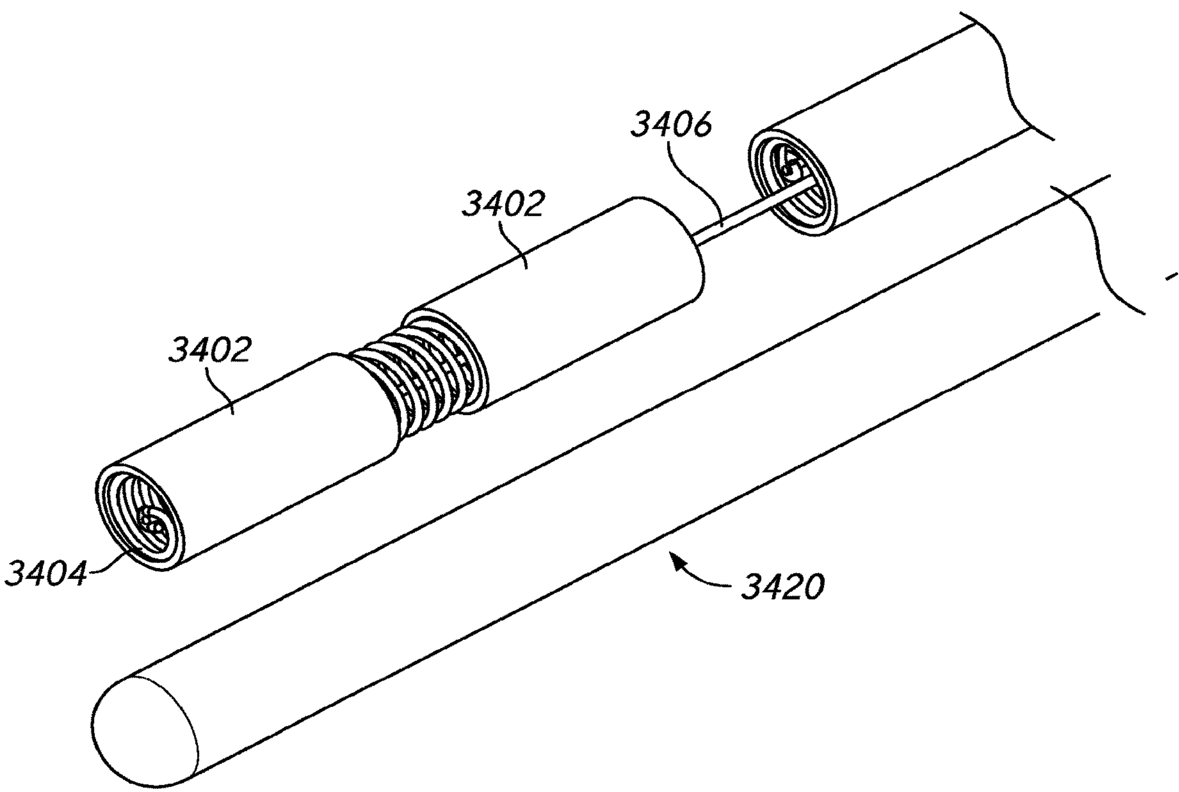
Figures 55C, 55D:
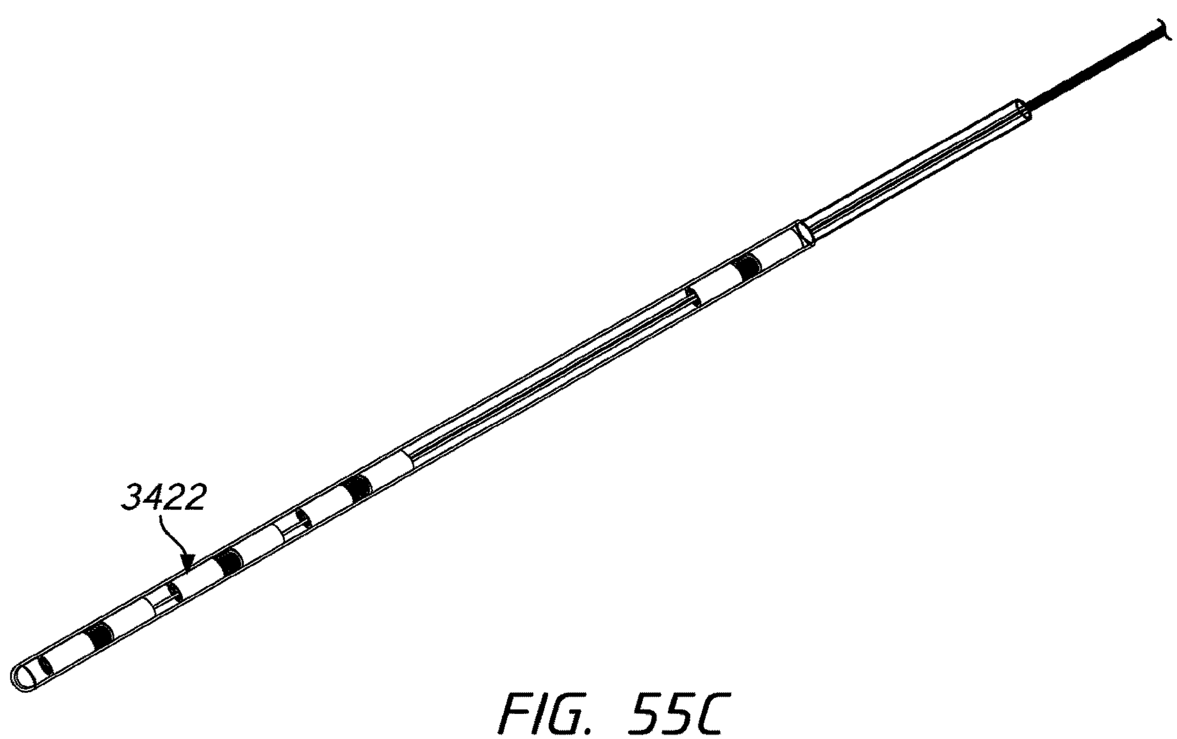

FIGS. 55A-55D illustrate further views of electrode leads. The lead contacts 3402 can be connected by a binding material 3420, and/or have a coating 3422 as noted elsewhere herein. The system can be designed to designate particular working as well as reference electrodes. FIG. 55B illustrates a binding material 3420, which can be a silicone overmold having the shape depicted, prepared to connect and/or cover the lead contacts 3402, and FIG. 55A illustrates the binding material 3420 applied to the lead contacts 3402. FIG. 55D illustrates the coating 3422, which can be an ion exchange coating, prepared to coat the lead contracts 3402, and FIG. 55C illustrates the coating 3422 coating the lead contacts 3402.

FIGS. 56A-56C schematically illustrate a generally tubular, e.g., cylindrical lead contact 3402 that can include a sidewall with distal notches 3403 and an interior lumen. One, two, or more conduits 3404 can be housed at least partially within each lead contact 3402 with conductive end portions 3405 in electrical communication with the lead contact 3402. As illustrated in FIG. 56B, the conductive end portion 3405 can be positioned, which can include retained, within the distal notch 3403. As shown in FIG. 56C, a plurality of conduits 3404 can be grouped together with each having a conduct end portion 3405 extending outward.

FIGS. 57A-57B schematically illustrate additional lead embodiments, illustrating conduits and spaced-apart lead contacts as previously described. FIG. 57A illustrates contacts 3402 without binding material or a coating layer, while FIG. 57B illustrates contacts connected with a binding material 3420 which may, for example, comprise silicone that has been overmolded onto and throughout the other components except where excluded such as along the outer electrode contact surfaces. Optionally a coating layer 3422 may be situated as a surface layer over the lead embodiment as shown in FIG. 57C. In some embodiments this coating layer may comprise an ionically conductive polymer such as an anion exchange membrane.

Figures 58A, 58B, 58C, 58D:
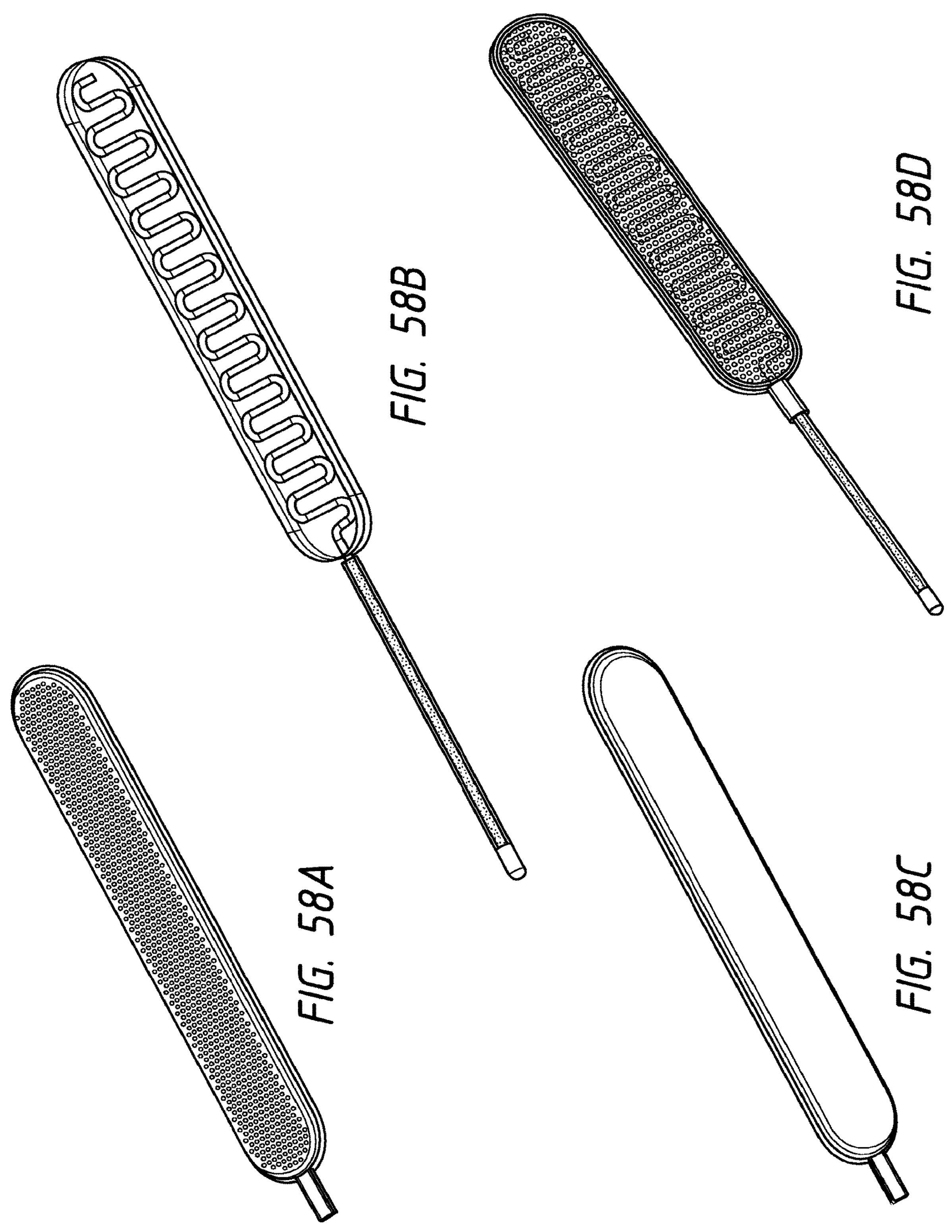

FIGS. 58A-58D illustrates embodiments of lead electrodes having paddle configurations. The electrodes could include an ionic current generation element (e.g., Ag/AgCl) generally in electrical continuity along the paddle that can include a serpentine shape as shown in FIG. 58B, or another shape. The paddle could have an ionically permeable covering on both sides as shown in FIG. 58A, an ionically permeable covering on one side only as shown in FIG. 58D, or an ionically impermeable covering on at least one side as shown in FIG. 58C.

FIG. 59 illustrates an embodiment of a cylindrical lead 1600, that can include a fluid conduit 162 configured for filling of an enclosed volume with ionically conductive medium including saline, electrolyte, gels, etc. Also illustrated is a proximal connector and endcap 1604, that can allow for connection to the proximal end of the system, and can allow for electrical contact to the interior coiled electrode 1606.

FIG. 60 illustrates a clinical treatment flowchart algorithm in which the lead is placed into a desired target anatomical location, e.g., the epidural space 6002 and positioned along the spinal cord 6004 and inserted to the desired spinal column level 6006. Subsequently, the lead can be connected to a power supply whether for permanent implant or external use and initiation of ionic direct current generation can begin 6008. In some instances the spinal cord region being accessed is the anterolateral aspect of the cord including the region closest to the spinothalamic tract. In some instances the positioning comprises positioning the lead or leads along the dorsal aspect of the spinal column. Once the lead or leads have been positioned in the appropriate locations, ionic direct current can be generated to initiate block of the nerve tissue proximal to the ionic current generating contacts. Current generation may lead to a constant block or intermittent block of the nerve tissue. In some clinical treatment algorithms the nerve tissue is dosed with ionic direct current for a period of time and then stopped such that the residual pain is significantly lower than the initial pain even without active nerve block, such that the device can provide a reduced or pain free treatment-free period or holiday.

FIG. 61 illustrates a clinical treatment flowchart algorithm in which the lead is placed into the body 6102 and ionic current generating contacts of the lead are positioned along a target nerve (or peripherally in other embodiments) for nerve block 6104. Subsequently, the lead can be connected to a power supply whether for permanent implant or external use and initiation of ionic current generation can begin 6106. Once the lead or leads have been positioned in the appropriate locations, ionic direct current can be generated to initiate block of the nerve tissue proximal to the ionic current generating contacts. Current generation may lead to a constant block or intermittent block of the nerve tissue. In some clinical treatment algorithms the nerve tissue is dosed with ionic direct current for a period of time and then stopped such that the residual pain is significantly lower than the initial pain even without active nerve block, such that the device can provide a reduced or pain free treatment-free period or holiday.

FIG. 62 illustrates a clinical treatment flowchart algorithm in which the body space is accessed 6202, and ionic current delivery lead contacts are positioned within the body proximate target nerve tissue 6204. The lead can then be positioned to a precise target location 6206 as needed. The lead may then be put into a sensing mode to measure activity along the target nerve 6208. The lead can then be connected to a power source, and/or the connected power source activated. Once undesired nerve activity is detected, the system can initiate ionic direct current generation to reduce activity of the nerve or completely block the nerve signal 6210. In some embodiments, the system continues to sense activity on the nerve for example by using a contact positioned distal to the central nervous system direction to see if undesired activity is still being transmitted along the nerve. Once the system determines that the nerve activity is falls below a target threshold 6212, the ionic current may be modulated and reduced 6214. A complementary sensing configuration involves the system described above but also incorporates a contact positioned proximal to the central nervous system direction to monitor transmission of the undesired signal through the nerve tissue. The direct current may be modulated to bring the transmitted signal sensed by the proximal contact below a target threshold. This feedback can provide a means for creating patient-specific therapeutic thresholds by taking in patient inputs to determine these initial target thresholds. By applying machine learning algorithms, the system can improve its ability to recognize undesired nerve activity that requires blocking (partial or complete) from activity that does not lead to the undesired sensations experienced by the patient. Over time by monitoring patterns in undesired nerve activity, blocking current delivery, and proximal signal transmission, the system may be better able to anticipate and more quickly or automatically address undesired nerve activity.

FIG. 63 illustrates an embodiment of an electrode lead system 6300 operated in continuous block mode, where dual ionic direct current generating electrodes 2304, 2305 interface with a nerve but are driven from a current source via electrically insulated leads 2302 with currents of opposite polarities such that when one is in a blocking phase, the other is in a non-blocking phase which resets the electrode for blocking once the current polarity is again reversed. With this configuration, a constant block can be advantageously maintained along the nerve. The electrodes may be oriented as shown in series along a nerve or oriented on opposite sides to the nerve tissue itself.

Figure 64A:
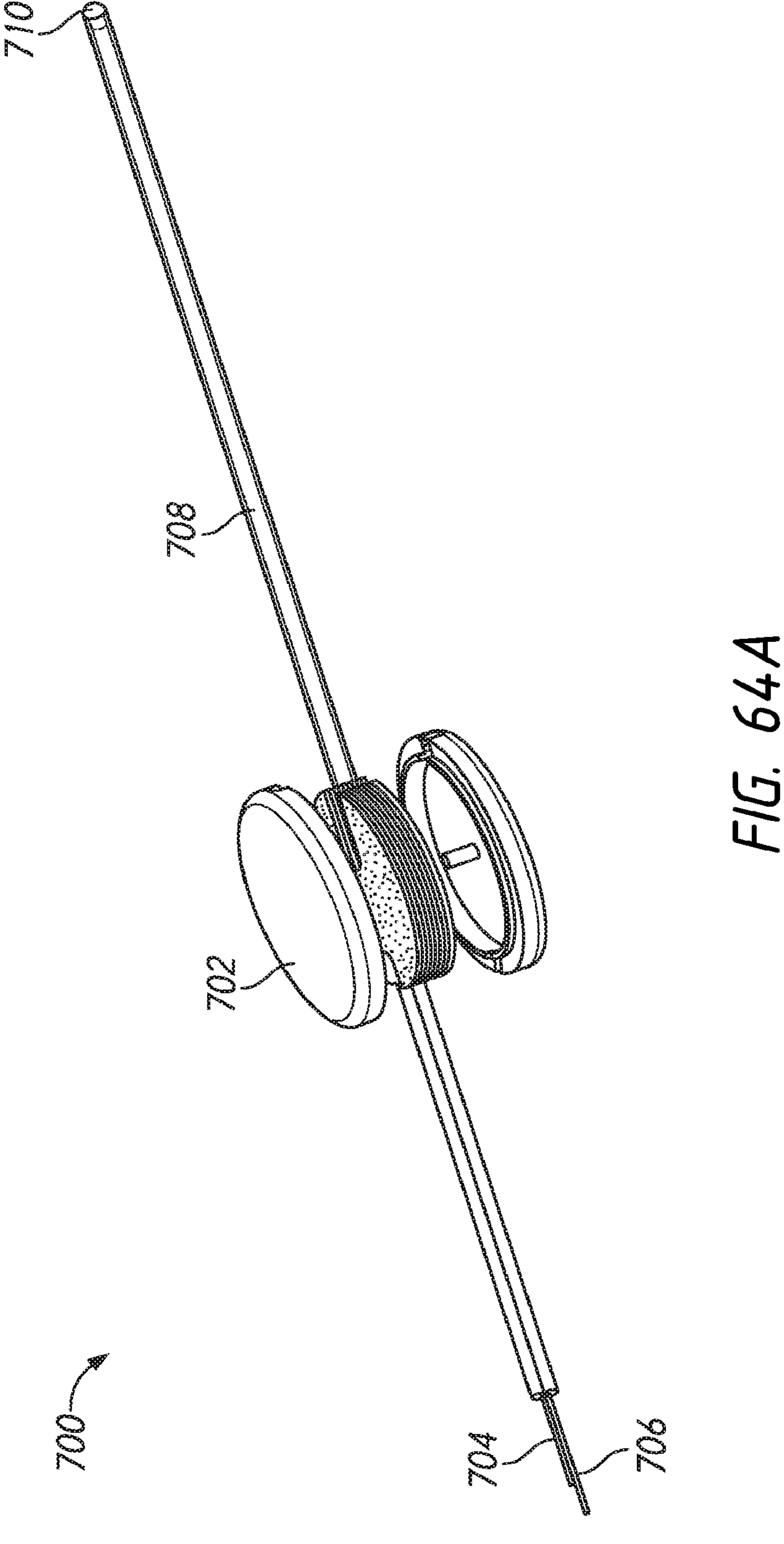
Figure 64B:
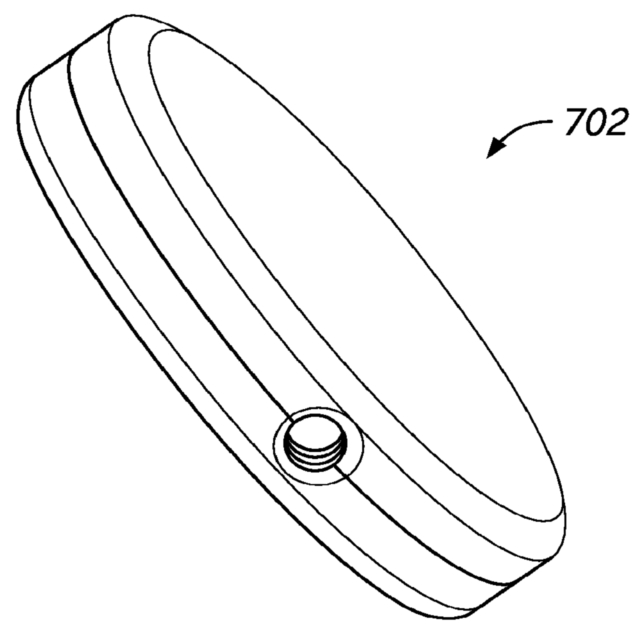
Figure 64C:
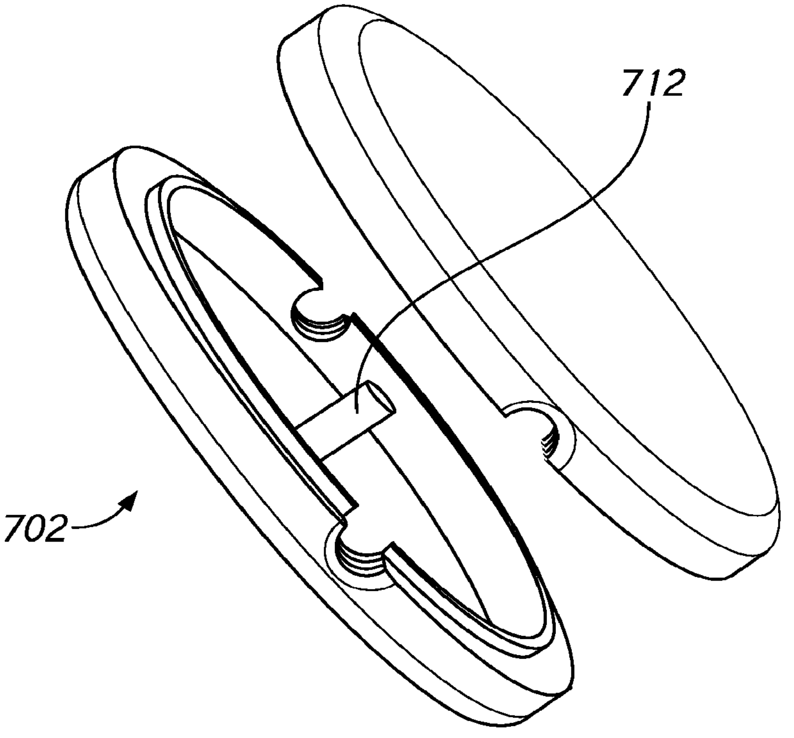
Figure 64D:
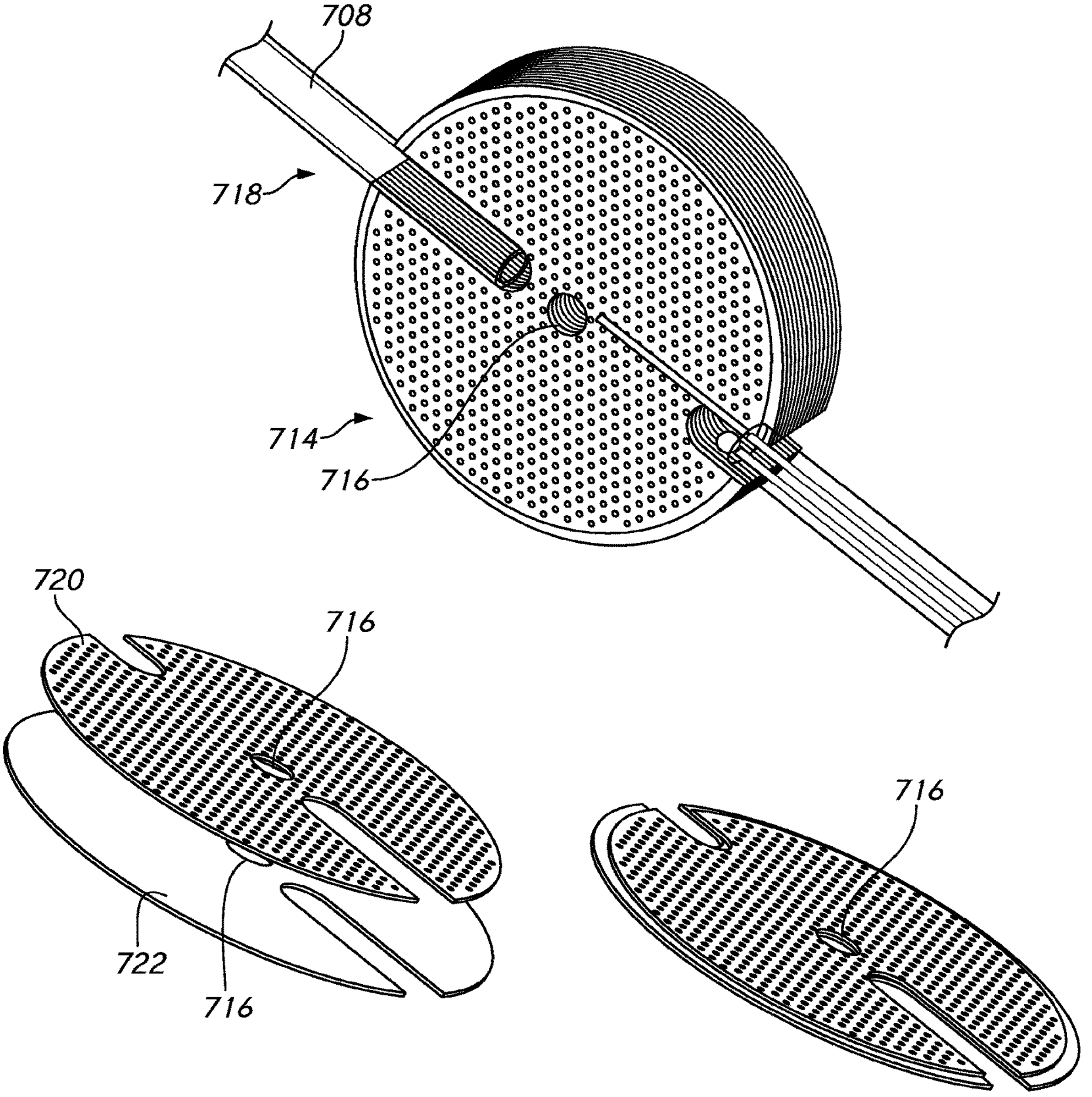

FIGS. 64A-64H illustrate various embodiments of separated interface nerve (SINE) electrodes. FIG. 64A illustrates an embodiment of a SINE electrode 700 that can include a casing 702, which can be disc-shaped and hermetically sealed in some embodiments. Also shown is a stimulation electrode 704 configured to drive charge generation in electrodes to generate ionic current. The current can also be reversed to generate a waveform. A reference electrode 706 is also illustrated, that can allow for measurement of potential drop across an electrode interface. The reference electrode 706 could include silver/silver-chloride, or platinum. Also illustrated is an ion conduit 708 that can be filled with ion transmissive material, such as saline, an electrolyte, or an ionically conducting gel or polymer. An electrode contact region 710 is also illustrated with a distal end and/or a sidewall port. A microporous filter, ionically transmissive material, and ionic exchange membrane are also illustrated. FIGS. 64B through 64D illustrate non-limiting additional features of the disc-shaped casing, any number of which can be utilized in some embodiments. FIG. 64B illustrates a casing 702 in a assembled configuration, while FIG. 64C illustrates the casing 702 in an unassembled configuration. As shown in FIG. 64C, the casing 702 has an alignment feature 712 that is configured to interface with a corresponding alignment opening 716 in an electrode stack 714, shown in FIG. 64D, configured to generate charge and ionic current. FIG. 64D further illustrates a fluid conduit to electrode contact region 718 at which the ion conduit interfaces with the electrode stack 714. The electrode stack 714 has disks or electrode surface(s) 720, which can be metal plates that are configured to generate charge, and a disk(s) or spacer(s) 722 that is configured to hold fluid for ion conduction and contact an electrode. The electrode surface(s) 720 can be perforated to enable fluid and ion flowing through the electrode surfaces(s) 720 and between the spacer(s) 722. The electrode surface(s) 720 can be made of a variety of materials, such as titanium, titanium coated in titanium nitride, titanium with sputtered iridium oxide film (SIROF), and/or others. The electrode surface(s) 720 can include a substrate of 304 or 316 stainless steel, platinum or titanium nitride coated Pt, SIROF coated Pt, and/or PEDOT coated Pt. The spacer(s) 722 can be made of a variety of materials, which can include porous or fluid passing polymer or nonconductive material, polyester, nylon, PEEK, polycarbonate, and/or others. The material of the spacer(s) 722 can be knitted, non-woven, meshed, perforated, and/or other configurations.

Figure 64E:
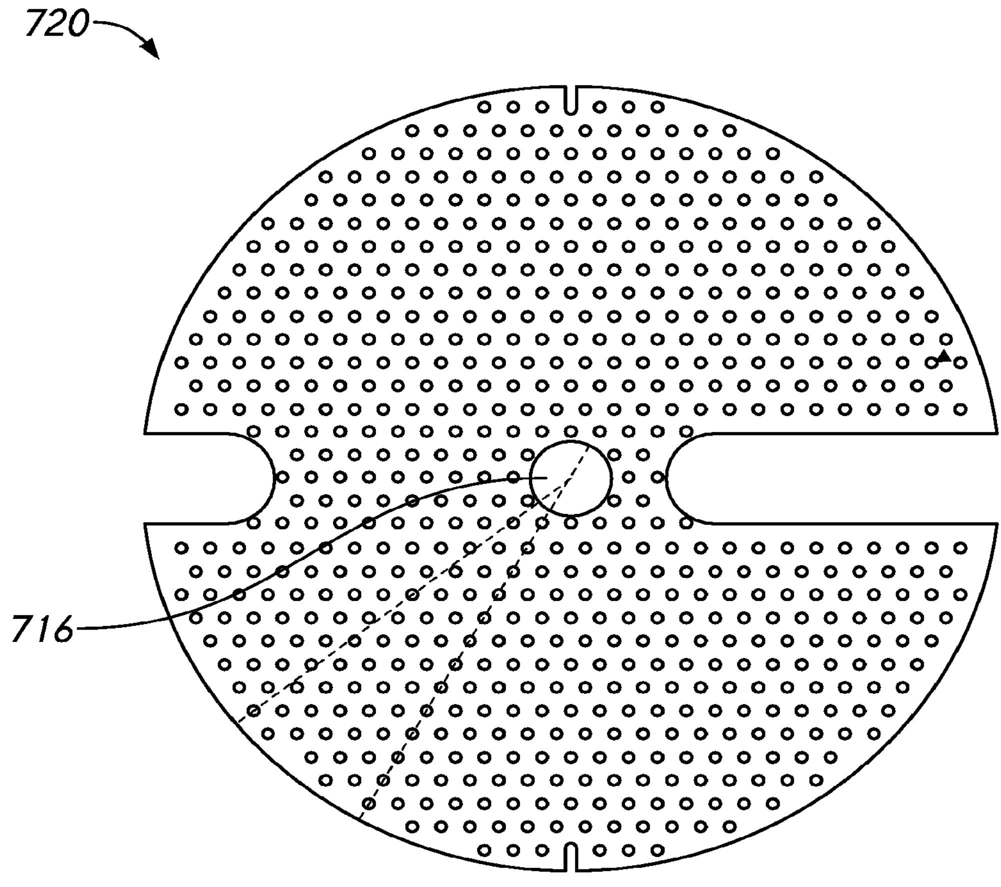
Figure 64F:
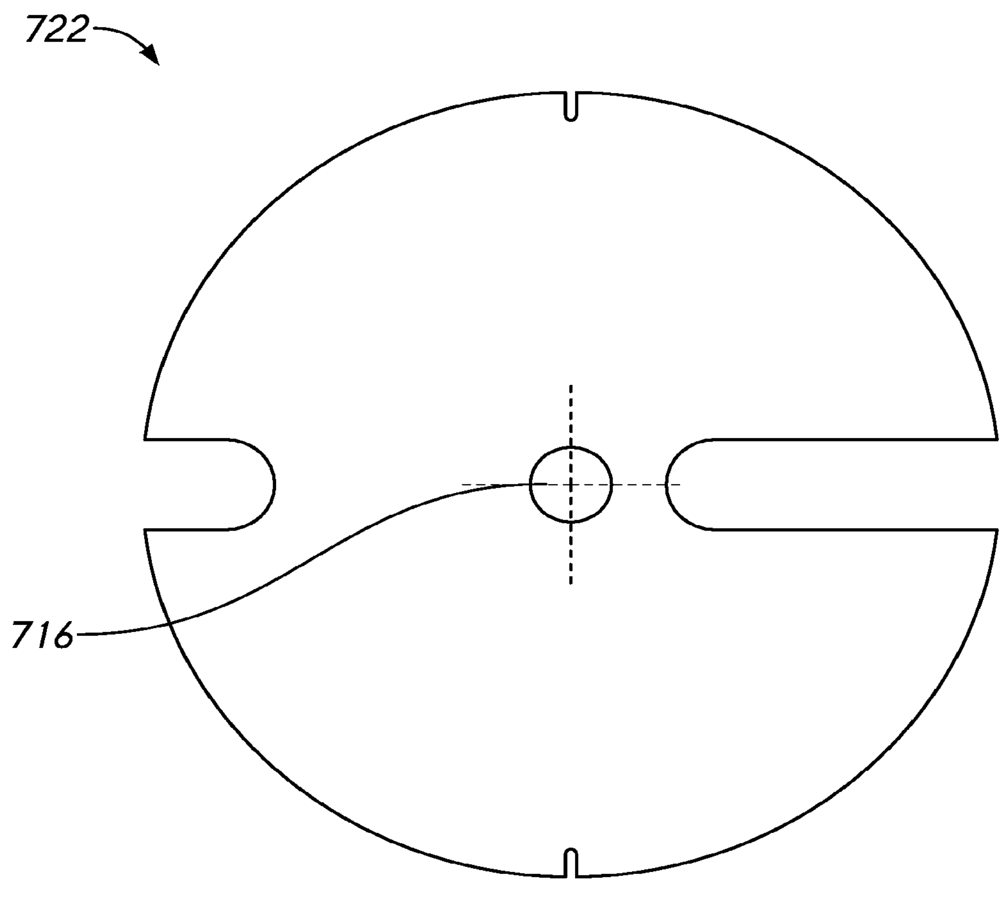
Figure 64G:
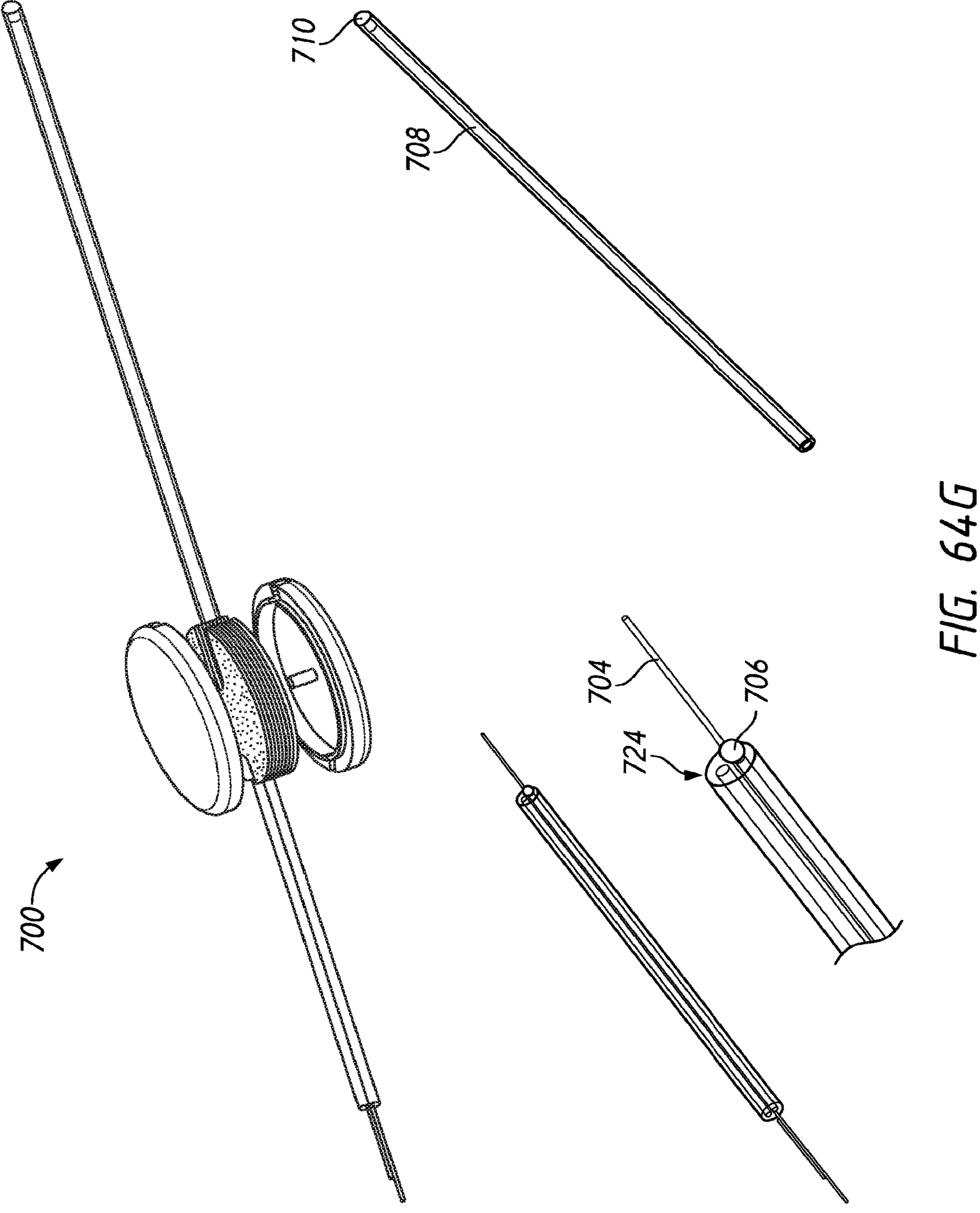
Figure 64H:
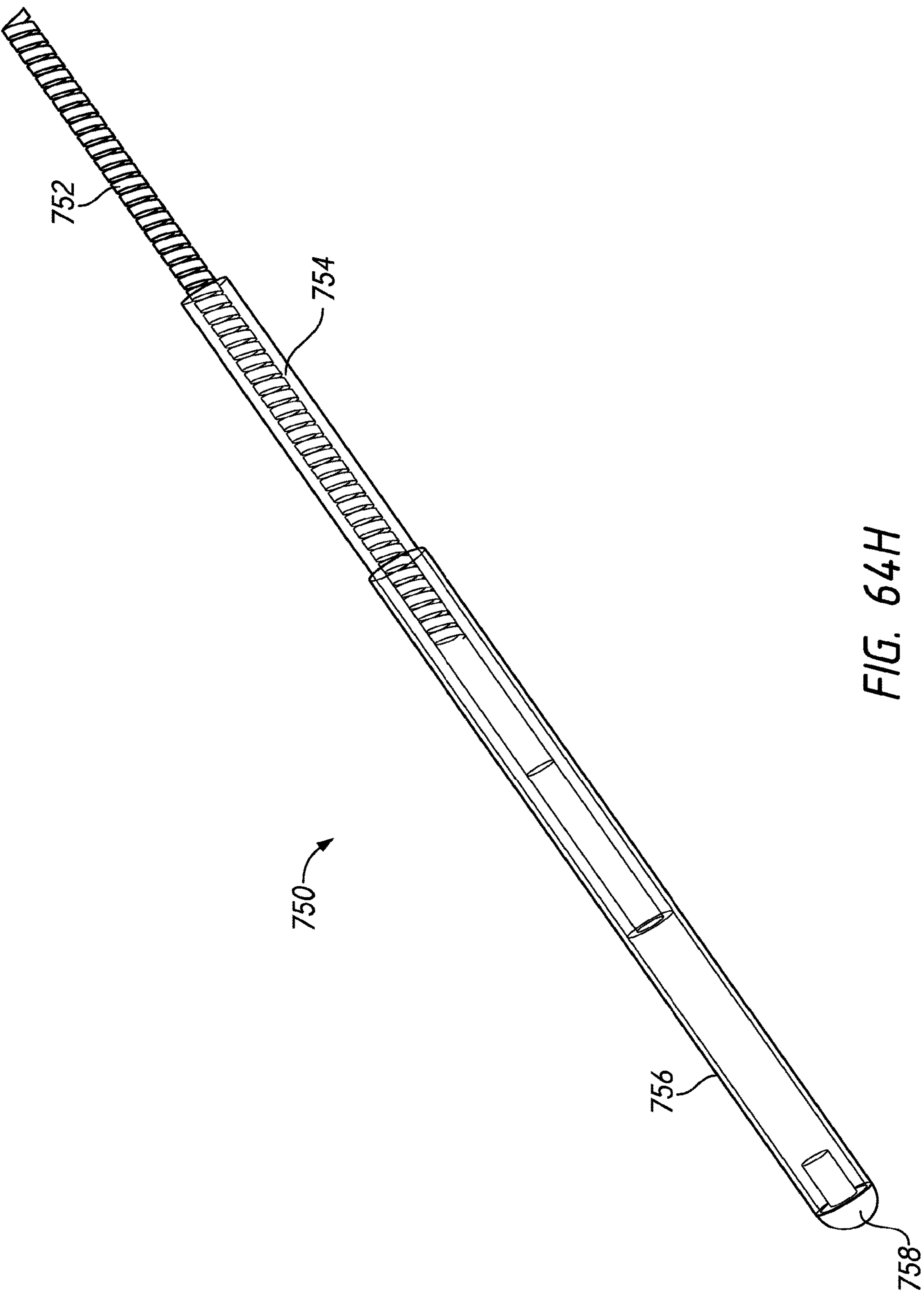

FIG. 64E describes embodiments of disks or electrode surfaces 720, with non-limiting example dimensions in millimeters of various features, that can be made of titanium material and perforated, and configured to be positioned within the disc-shaped casing. Base geometry example of the textured region of the disk 720 is a 0.1 or 0.13 mm thick grade 2 titanium foil/sheet. FIG. 64F describes embodiments of disks or spacers 722, with non-limiting example dimensions in millimeters of various features, that can be made of a polymer material such as a 0.2 mm thick polyester woven like Dacron, and configured to be positioned within the disc-shaped casing. Other materials can also be used. FIG. 64G illustrates embodiments of the SINE electrode 700 and, more particularly, features of the fluid conduit 724, that can be filled with an ionically conductive medium such as saline, electrolyte, and/or a gel, as well as a reference electrode 706. FIG. 64H illustrates another embodiment of a SINE electrode 750 that can include a generally cylindrical geometry, coiled electrode surface 752, fluid retention spacer 754, insulating conduit 756, and electrode contact region 756. The coiled electrode surface 752 can include characteristics that are the same or similar to the disks or electrode surface(s) 720. The fluid retention spacer 754 can be configured to be ionically conductive. The fluid retention spacer 754 can enable filing of an enclosed volume with ionically conductive medium (such as saline, electrolyte, etc.) such that the fluid is held in proximity to the coiled electrode surface 752 to enable electrochemical reactions to occur. The fluid retention spacer 754 can physically retained an electrode centered and positioned. The fluid retention spacer 754 can include cylindrical felt, porous hydrophilic polymer material, ionically conductive gel, and/or other suitable materials. The electrode contact region 758 can be positioned on a distal end, or side port, of the SINE electrode 750. The electrode contact region 758 can include a microporous filter or frit, an ionically transmissive material, and/or ion exchange membrane.

FIGS. 65A-65D illustrate embodiments of high charge density electrodes and electrode leads. As shown in FIG. 65A, increasing the charge-carrying surface area via surface area multiplication technology can advantageously and surprisingly increase the efficacy of the high charge density electrodes and leads. For example, the lead 800, which can be an electrode, can have a microstructure 802A, which can include a plurality of plate-like structures. The microstructure 802A can include surface characteristics 804A that increase the surface area of the microstructure 804A. Other microstructures and/or surface treatment technologies can be used to increase surface area. The high charge density electrodes and leads can be made of a variety of materials, which can include solder thermal interface materials (STIM) and/or implant-compatible materials. FIG. 65B illustrates non-limiting examples of high charge density materials and associated characteristics that can be utilized in some embodiments. FIG. 65C illustrates non-limiting examples of surface area multiplication technology techniques. For example, sintering, packed filament (e.g. wire/("fuzz button")/"steel wool"), laser patterning/etching, micromachining, foaming, and/or other techniques may be used at a microscale. An example of micromachining is shown with microstructure 802A. An example of laser texturing with pulse technologies is shown with microstructure 802B. An example of metallic foam trabecular is shown with microstructure 802C. An example of packed filament (e.g. wire/"fuzz button"/"steel wool") is shown with microstructure 802D. Surface treatments alone or with the microstructures detailed above can be used to increase surface area. For example, fractal deposition shown with surface 804A can increase surface area, which may include TiN. Surface activation is another surface treatment that can increase surface area, which may include IrOx. In some embodiments, creating a microstructure within the high charge density substrate material to increase an available electrochemical surface area of the high charge density substrate material can increase the available electrochemical surface area by about or at least about 2×, 3×, 4×, 5×, 6×, 7×, 8×, 9×, 10×, 15×, 20×, 25×, or more or ranges including any two of the foregoing values.

FIGS. 65D-65E illustrate embodiments of a surface area multiplication technology technique that can include texturing of a rod and/or tube. A target rod or tube can have a variety of diameters which can include 1.5 mm or other suitable diameters such as less than 1, 1-1.25, 1.25-1.5, 1.5-1.75, 1.75-2, or greater than 2 mm, or ranges including any two of the foregoing values. The textured region on a target rod or tube can be a variety of lengths, which can include 3.5-4 mm or other suitable diameters such as less than 3, 3-3.5, 3.5-4, 4-4.5, 4.5-5, or greater than 5 mm. The inner diameter of a target tube can be a variety of sizes, which can include 1-1.1 mm or other suitable inner diameters such as less than 0.8, 0.8-0.9, 0.9-1, 1.1-1.2, 1.2-1.3, 1.3-1.4, 1.4-1.5, or greater than 1.5 mm. The rod can be made of a variety of stock materials, which can include Grade 2 Ti solid rod with an outer diameter of 0.0625" and length of 12." The tube can be made of a variety of stock materials, which can include as one non-limiting example SS316 HypoTubing, 17 Gauge, 0.058" outer diameter, 0.042" inner diameter, 0.008" wall, and 12" length.

FIG. 65D illustrates a rod or tube 800 that is textured to increase surface area. The rod or tube 800 can include a plurality of channels 806. The plurality of channels 806 can be circumferential and/or spiral (including having multiple parallel spirals). In some aspects, the plurality of channels 806 may include channels that run perpendicular to the circumferential direction of the tube or rod 800 that create texture. Each of the plurality of channels 806 can be spaced apart by "a" microns or micrometers, have a channel width of "b" microns or micrometers, and have a channel depth of "c" microns or micrometers. The channel can have varying aspect ratios where a, b, and c have different values. For example, {a, b, c} can equal {25, 25, 25}, {25, 25, 50}, {25, 25, 75}, {25, 25, 100}, {50, 50, 50}, {50, 50, 100}, {50, 50, 150}, {50, 100, 150}, {100, 100, 100}, {100, 100, 150}, or other suitable combinations.

FIG. 65E illustrates an embodiment of a rod 800A and tube 800B with texturing. The rod 800A includes a textured region 808A. In some aspects, the textured region 808A is 3.5 mm in length and is positioned 4-5 mm from a first end 810 of the rod 800A but other sizes can be implemented. The rod 800A can be a length of 25 mm and have a diameter of about 1.5 mm but other sizes can be implemented. The tube 800B has a textured region 808B covering the entire outer periphery. In some aspects, the textured region 808B covers a portion of the outer periphery. The tube 800B and textured region 808B are both 3.5 mm but other sizes can be implemented, including when the length of the tube 800B and the textured region 808B are not the same length. The tube 800B can have an outer diameter of about 1.5 mm but other sizes can be implemented.

FIG. 65F illustrates an embodiment of a surface area multiplication technology technique that can involve laser texturing of a titanium foil/sheet. The base geometry of the Ti foil/sheet can be, in some embodiments, a 0.1-0.2 mm thick Grade 2 Ti foil/sheet or other suitable thicknesses such as less than 0.1 mm or greater than 0.2 mm. A variety of stock materials can be used for the Ti foil/sheet, which can include Grade 2 Ti/foil that is 0.13 mm, 0.1 mm, or other suitable thicknesses.

Figure 65H:
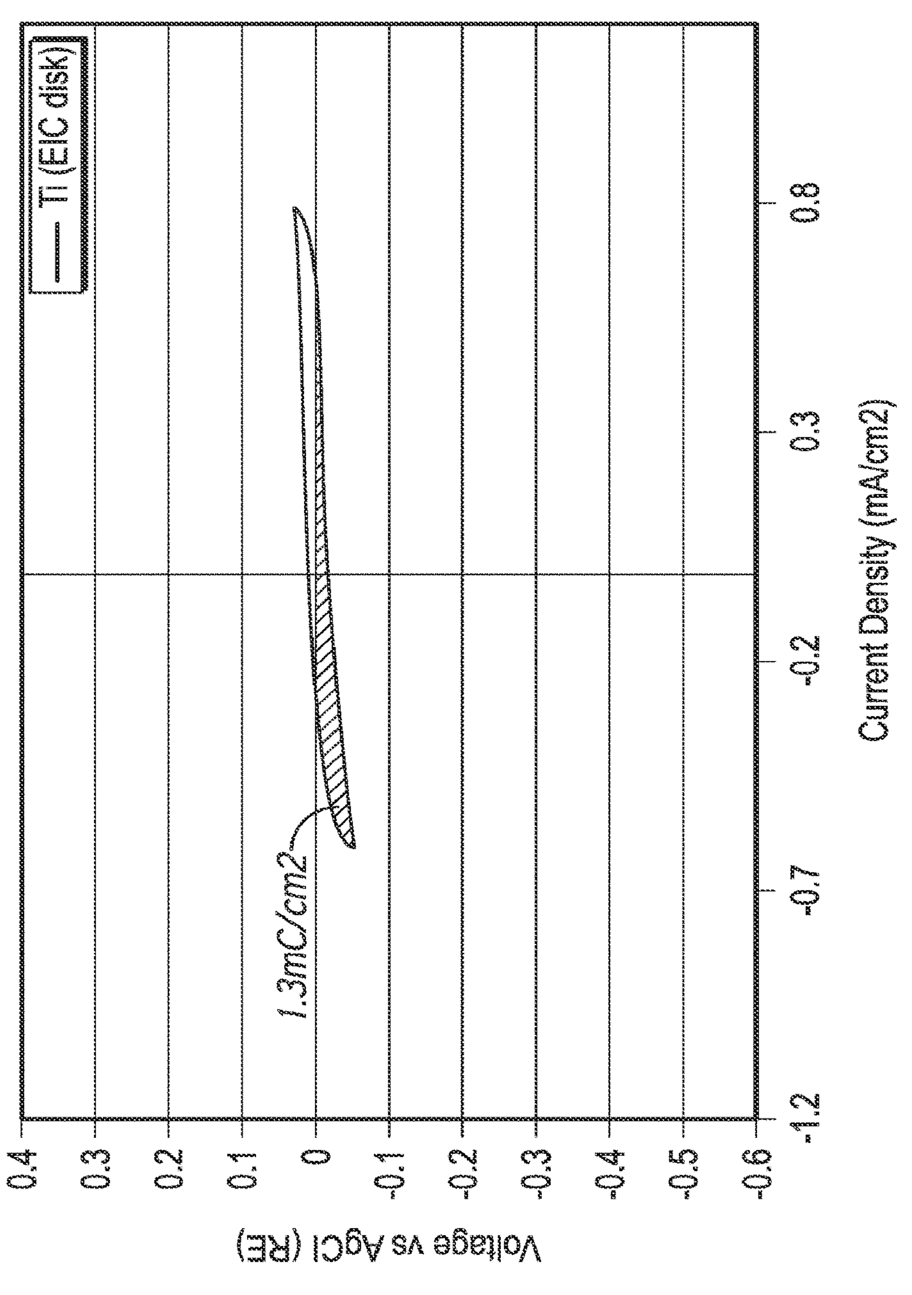
Figure 65I:
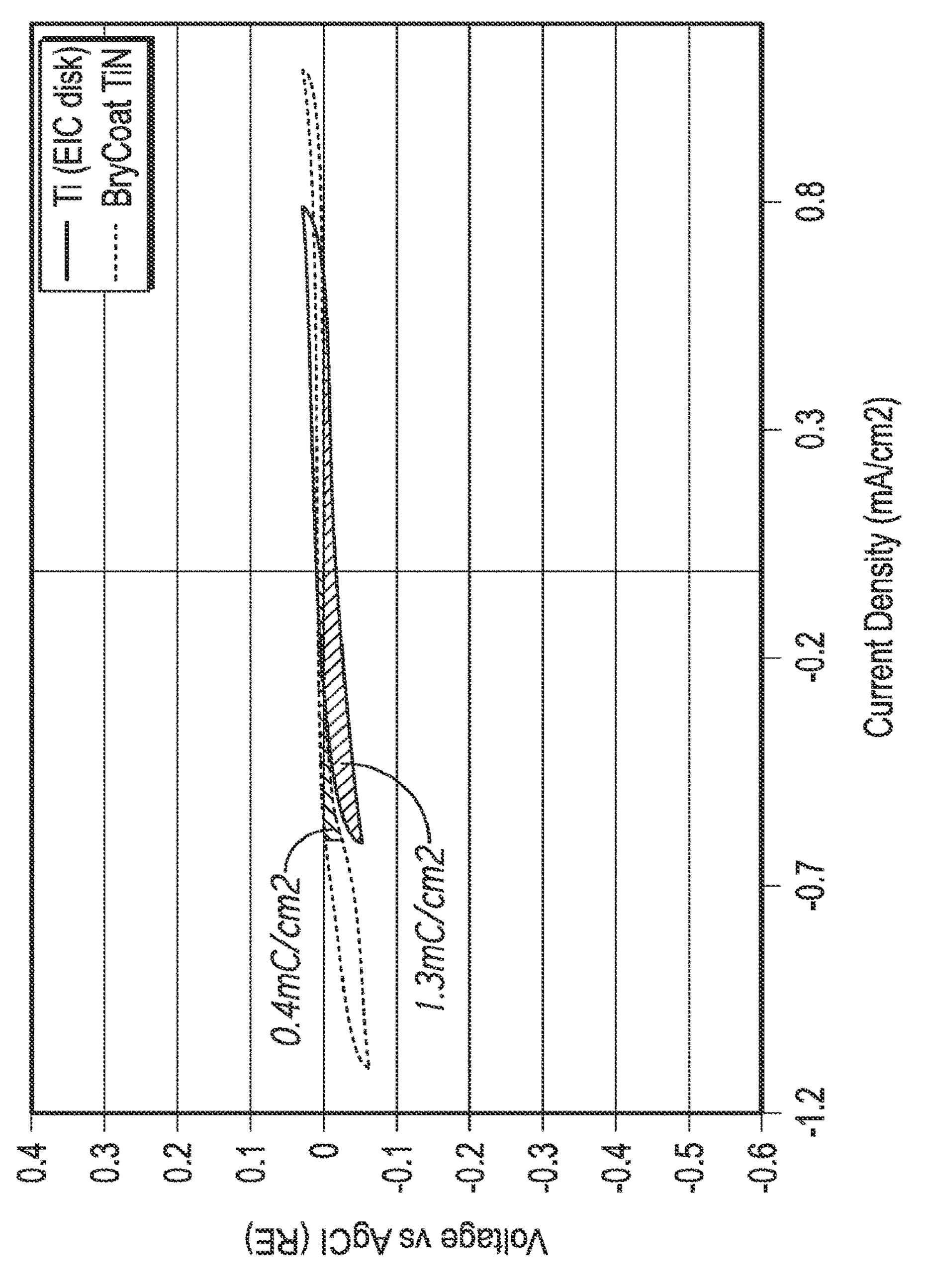
Figure 65J:
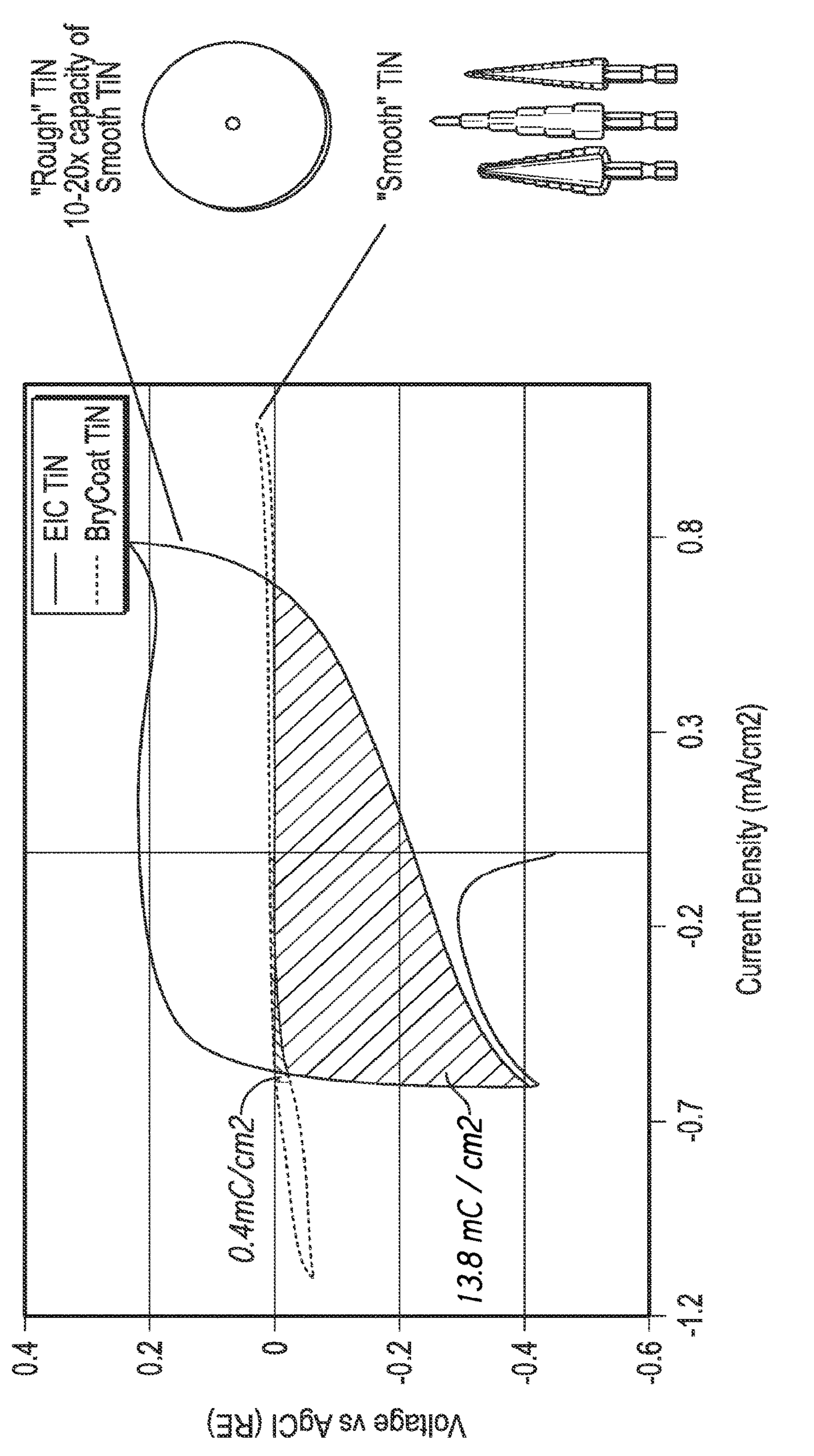
Figure 65K:
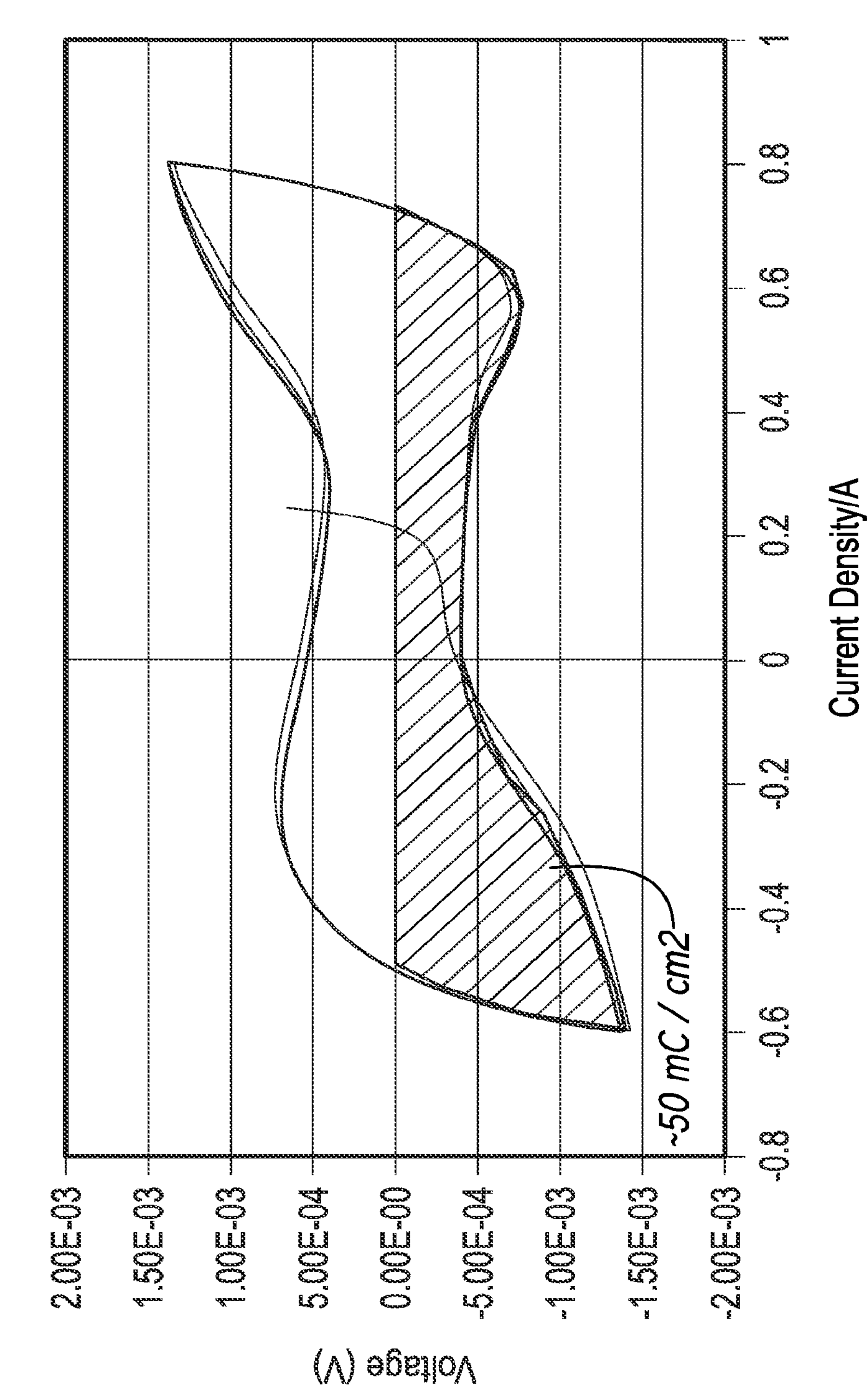

FIGS. 65G-65K illustrate that the cathodic charge storage capacity (shaded regions) can be measured using cyclic voltammetry by sweeping the voltage across the electrode interface for that material's water window or voltage range within which electrolysis will not occur to see how much charge can be generated by the material without generating deleterious by-products that can be harmful to surrounding tissue during in vivo use. For a given material type and surface area and voltage sweep rate the charge storage capacity can be measured. For example, as shown in FIG. 65H, the charge storage capacity of titanium (Ti) over the −0.6 to 0.8 voltage range is 1.3 mC/cm$^2$. Notably, even for a given material, its particular form and structure can be important for dictating its charge storage and charge injection capacity. For example, as seen in FIG. 65I comparing titanium (Ti) and smooth titanium nitride (TiN) over the −0.6 to 0.8 voltage range, the charge storage capacity of the titanium (Ti) at 1.3 mC/cm$^2$ is greater than that of the smooth titanium nitride (TiN) at 0.4 mC/cm$^2$. However, as seen in FIG. 65J when comparing smooth titanium nitride (TiN) to "rough" porous titanium nitride (TiN) at 13.8 mC/cm$^2$ the charge storage capacity increases substantially in large part due to the additional surface area available on the porous titanium nitride (TiN). As highlighted in FIG. 65K, the impact of material properties on charge storage capacity can be highly dependent on composition and preparation as the desired material, e.g., sputtered iridium oxide film (SIROF)

coated material shows very high charge storage capacities at about 50 mC/cm$^2$ compared to titanium nitride.

FIGS. 66A-66C schematically illustrate embodiments of various aspects of medical electrical delivery systems and components. FIG. 66A schematically describes examples of electrode types that can be utilized in combination with other embodiments described herein, including high charge capacity material electrodes, separated interface nerve electrodes, and silver/silver-chloride with polymer coatings. FIG. 66B compares examples of charge delivery properties of various electrode types, including high charge density (HCD), separated interface nerve electrode (SINE), silver/silver-chloride (Ag—AgCl) with polymer coating, and SCS. FIG. 66C illustrates one embodiment of a percutaneous silver/silver-chloride lead 812 and paddle silver/silver-chloride lead 814. In some embodiments, a silver/silver-chloride electrode can include an ion (e.g., anion) exchange resin configured to sequester silver within the polymer itself.

FIGS. 67A-67C illustrate examples of a pulse generator waveform that can advantageously assist in achieving full nerve block quickly without unwanted side effects. In some embodiments, having higher cathodic amplitude than anodic amplitude (e.g., disproportionate cathodic-anodic phase duty cycles) can potentially widen the therapeutic window for therapy. By using a smoothed trapezoidal waveform with ramps up to target anodic and cathodic current magnitudes, unwanted generation of activation potentials is avoided by more gradually increasing the current and electric field compared to a more abrupt transition in electric field potential as might be facilitated with a square wave waveform. Furthermore, making the transitions from ramp region to plateau a smooth function with a continuous derivative of $D_{current}/D_{time}$ instead of an abrupt transition can further increase the therapeutic range of the therapy prior to generating unwanted activation potentials. The smoothing function may comprise a cubic hermite spline or other continuous waveform with at least first derivative continuity. In some embodiments the leading ramp rate is lower than the trailing ramp rate with a leading ramp rate that may be in the range of, e.g., 1 to 2 times slower or 2 to 4 times slower or 5 or more times slower than the trailing ramp rate. In other embodiments, the leading and trailing ramp rate may be the same or the trailing ramp rate may be slower than the leading ramp rate. In some embodiments the magnitude of the leading ramp rate may be in the range of up to about 0.1 milliamperes/s (mA/s) or about 0.1 to about 0.5 mA/s or about 0.5 to about 1.0 mA/s or about 1.0 to about 3.0 mA/s or about 3.0 to about 5.0 mA/s or about 5.0 mA/s and higher, or ranges incorporating any two of the foregoing values. In some embodiments the magnitude of the trailing ramp rate may be in the range of about 0 to about 1 milliamperes/second (mA/s) or about 1.0 to about 2.0 mA/s or about 2.0 to about 5.0 mA/s or about 5.0 to about 10.0 mA/s or about 10 to about 20 mA/s or 20 mA/s and higher, or ranges incorporating any two of the foregoing values. Furthermore having a higher cathodic amplitude (Ca) than anodic amplitude (Aa) with a disproportionate cathodic<anodic phase duty cycles (Ct<At) where total charge (area under each respective curve) remains balanced can advantageously widen the therapeutic window for therapy.

In some embodiments, direct current (DC) delivery amplitudes for any therapy disclosed herein could be, for example, in the range of about 0 to about 0.5 mA, about 0.5 to about 1.5 mA and about 1.5 to about 2.5 mA, or ranges incorporating any two of the foregoing values. In some embodiments, about 2.5 mA to about 5 mA and about 5 mA and above can be utilized both for anodic and cathodic current levels for block. Response has been seen, for example at about 0-1.5 mA range in animal studies as well as paresthesia onset in peripheral human nerves at about 1.5 mA (cathodic and anodic) with complete block at about 2.5 mA and current delivery up to about 5.5 mA.

In some embodiments, direct current delivery to a patient can be targeted to any number of anatomical locations, including but not limited to: the dorsal root ganglion; dorsal roots; dorsal columns; dorsal horn; Lissauer's tract; and/or the antero-lateral pain tracts. In some embodiments, direct current delivery can be directed to a peripheral nerve, or other target locations as described elsewhere herein. Not to be limited by theory, in some embodiments DC delivery can potently modulate small diameter fibers in the spinal cord and depolarize spinal cord neurons. DC delivery may not necessarily be sensitive to fiber size, and may have a wide therapeutic window. DC delivery can be utilized for a wide variety of indications, including but not limited to cardiac mapping for arrhythmias, epilepsy, and movement disorders, as well as a variety of other conditions disclosed elsewhere herein.

The systems and methods described in the figures above may be used to generate DC nerve block. Depending on the specific direct current application of nerve block, nerve suppression, or continued block after removal or stopping of the current may occur, and hypersuppression may result for continued nerve blockade in excess of one minute after removal of the DC source to delay nerve conduction recovery. The nerve block and suppression may be generated in an intermittent or continuous manner depending on the desired application. Means for continuous nerve block have been described that provide for safe delivery of nerve block via ionic current utilizing multiple electrodes or sequenced electrode contact activation enabling a means to modulate nerve conduction safely without necessitating complex mechanical systems. The system may be fully or partially implantable, or completely non-implantable (e.g., transcutaneous) with all tissue contacting materials biocompatible for tissue contact and implantation compatibility.

In some embodiments, systems and methods as disclosed herein can be used or modified for use as part of alternating current stimulation systems, including but not limited to spinal cord stimulation (SCS) systems for treatment of chronic pain, such as for example the SENZA system by Nevro Corporation; the PRECISION systems including PRECISION PLUS and PRECISION SPECTRA by Boston Scientific Corporation, and the INTELLIS system from Medtronic PLC. As one example, systems and methods as disclosed herein can increase efficacy of an alternating current delivery system including delivering alternating current via an electrode and electrode lead to a target tissue of a patient utilizing a DC-offset waveform generated by a pulse generator and facilitated by a controller. The alternating frequency could be any desired frequency, including high frequency systems of about 10 kHz or higher, from about 1.5 kHz to about 100 kHz, from about 1.5 kHz to about 50 kHz, from about 3 kHz to about 20 kHz, from about 3 kHz to about 15 kHz, from about 5 kHz to about 15 kHz, or from about 3 kHz to about 10 kHz, or other ranges incorporating any two of the aforementioned values. The electrode and/or electrode lead can include one or more of: high density charge materials, a SINE electrode, and/or a silver-silver chloride material. Such systems and methods can in some cases advantageously increase the excitability of target neurons, thereby decreasing thresholds and widening the therapeutic window of the target tissue stimulation.

The foregoing description and examples has been set forth to illustrate the disclosure according to various embodiments and are not intended as being unduly limiting. The headings provided herein are for organizational purposes only and should not be used to limit embodiments. Each of the disclosed aspects and examples of the present disclosure may be considered individually or in combination with other aspects, examples, and variations of the disclosure. In addition, unless otherwise specified, none of the steps of the methods of the present disclosure are confined to any particular order of performance. References cited herein are incorporated by reference in their entirety.

While the methods and devices described herein may be susceptible to various modifications and alternative forms, specific examples thereof have been shown in the drawings and are herein described in detail. It should be understood, however, that the embodiments disclosed should cover modifications, equivalents, and alternatives falling within the spirit and scope of the various embodiments described herein and the appended claims.

Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some examples, acts or events can be performed concurrently, e.g., through multi-threaded processing, interrupt processing, or multiple processors or processor cores or on other parallel architectures, rather than sequentially.

The use of sequential, or time-ordered language, such as "then," "next," "after," "subsequently." and the like, unless specifically stated otherwise, or otherwise understood within the context as used, is generally intended to facilitate the flow of the text and is not intended to limit the sequence of operations performed.

The various illustrative logical blocks, modules, processes, methods, and algorithms described in connection with the embodiments disclosed herein can be implemented as electronic hardware, computer software, or combinations of both. To clearly illustrate this interchangeability of hardware and software, various illustrative components, blocks, modules, operations, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The blocks, operations, or steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, an optical disc (e.g., CD-ROM or DVD), or any other form of volatile or non-volatile computer-readable storage medium known in the art. A storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that some examples include, while other examples do not include, certain features, elements, and/or states. Thus, such conditional language is not generally intended to imply that features, elements, blocks, and/or states are in any way required for one or more examples or that one or more examples necessarily include logic for deciding, with or without author input or prompting, whether these features, elements and/or states are included or are to be performed in any particular embodiment.

The methods disclosed herein may include certain actions taken by a practitioner; however, the methods can also include any third-party instruction of those actions, either expressly or by implication. For example, actions such as "positioning an electrode" include "instructing positioning of an electrode."

The ranges disclosed herein also encompass any and all overlap, sub-ranges, and combinations thereof. Language such as "up to," "at least," "greater than." "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 hour" includes "1 hour." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure. The phrase "at least one of" is intended to require at least one item from the subsequent listing, not one type of each item from each item in the subsequent listing. For example, "at least one of A, B, and C" can include A, B, C, A and B, A and C, B and C, or A, B, and C.

What is claimed is:

1. A method for nerve block of a patient utilizing a rechargeable implanted electrode, comprising:

generating a first current of a first polarity through the rechargeable implanted electrode proximate a nerve sufficient to at least partially block conduction in the nerve;

wherein the first current comprises a first waveform, wherein a slope of a leading ramp of the first waveform is less steep than a trailing ramp of the first waveform; and generating a second current of a second polarity opposite the first polarity through the rechargeable implanted electrode proximate the nerve sufficient to at least partially block conduction in the nerve, wherein the second current comprises a second waveform, wherein a slope of a leading ramp of the second waveform is less steep than a trailing ramp of the second waveform, and wherein the first waveform and the second waveform each form a trapezoidal shape when viewed on a time axis.

2. The method of claim 1, further comprising sensing an amount of stored charge in the rechargeable implanted electrode while delivering the first current;

and ceasing delivery of the first current when the amount of the stored charge is sensed to reach a pre-determined threshold value.

3. The method of claim 1, further comprising discontinuing at least one of the first current or the second current when an amount of water is being electrolyzed.

4. The method of claim 1, wherein the rechargeable implanted electrode generates current to increase or decrease an amount of stored charge on the rechargeable electrode, wherein the decrease and increase in amount of stored charge on the rechargeable implanted electrode are not equal.

5. The method of claim 1, wherein the rechargeable implanted electrode generates current to increase or decrease an amount of stored charge on the rechargeable implanted electrode, wherein the decrease and increase in amount of stored charge on the rechargeable implanted electrode is equal.

6. The method of claim 1, wherein the rechargeable implanted electrode is housed in an insulated enclosure.

7. The method of claim 1, wherein the rechargeable implanted electrode is a titanium nitride rechargeable implanted electrode comprising porous or fractal titanium nitride.

8. The method of claim 1, wherein the rechargeable implanted electrode generates current sufficient to deliver at least about 5,000 uC of charge into excitable tissue without damaging the excitable tissue.

9. The method of claim 1, wherein the rechargeable implanted electrode generates current sufficient to deliver at least about 25,000 uC of charge into excitable tissue without damaging the excitable tissue.

10. A method for nerve block of a patient utilizing an implanted electrode, comprising:

generating a first current of a first polarity proximal to the implanted electrode comprising a high charge density material proximate a nerve sufficient to at least partially block conduction in the nerve, wherein the first current decreases an amount of stored charge in the implanted electrode;

dynamically sensing the amount of the stored charge in the implanted electrode while delivering the first current;

ceasing delivery of the first current when the amount of the stored charge is sensed to reach a pre-determined threshold value; and generating a second current of a second polarity opposite the first polarity through the implanted electrode, wherein the second current increases the amount of the stored charge of the implanted electrode to recharge the implanted electrode, wherein the first current comprises a first waveform, wherein a slope of a leading ramp of the first waveform is less steep than a trailing ramp of the first waveform, wherein the second current comprises a second waveform, wherein a slope of a leading ramp of the second waveform is less steep than a trailing ramp of the second waveform, and wherein the first waveform and the second waveform each form a trapezoidal shape when viewed on a time axis.

11. The method of claim 10, wherein the implanted electrode is created by providing a substrate comprising a high charge density coating material on a surface thereof; and creating a microstructure within the substrate to increase an available electrochemical surface area of the high charge density coating material.

12. The method of claim 11, wherein the substrate comprises titanium or platinum-iridium, and wherein the high charge density coating material comprises porous titanium nitride.

13. The method of claim 11, wherein the high charge density coating material is selected from the group consisting of: iridium oxide, Poly(3,4-ethylenedioxythiophene)-poly(styrenesulfonate) (PEDOT), titanium nitride (TiN), fractal titanium nitride, porous titanium nitride, or a combination thereof.

14. The method of claim 11, wherein the high charge density coating material comprises titanium nitride.

15. The method of claim 11, wherein creating a microstructure comprises micromachining the substrate material.

16. The method of claim 11, wherein micromachining comprises electric discharge machining.

17. The method of claim 11, wherein creating the microstructure comprises using one or more of: material etching techniques, pattern masking and etching techniques, bead or grit blasting, and surface sanding.

18. The method of claim 11, wherein creating a microstructure comprises laser texturing.

19. The method of claim 11, wherein laser texturing comprises creating spaced-apart channels or grooves in a tubular member.

20. The method of claim 19, wherein the spaced-apart channels or grooves comprise a spiral or circumferential geometry with respect to a long axis of the tubular member.

21. The method of claim 11, wherein the substrate comprises a tubular member.

22. The method of claim 11, wherein the substrate comprises a material sheet.

23. The method of claim 10, wherein creating a microstructure comprises foaming.

24. The method of claim 10, wherein creating a microstructure comprises sintering.

25. The method of claim 10, wherein creating a microstructure comprises increasing an available electrochemical surface area by at least about 2×.

26. The method of claim 25, wherein creating the microstructure comprises increasing an available electrochemical surface area by at least about 5×.

27. The method of claim 26, wherein creating the microstructure comprises increasing an available electrochemical surface area by at least about 10×.

* * * * *